US012508262B2

(12) United States Patent
Seehra et al.

(10) Patent No.: US 12,508,262 B2
(45) Date of Patent: Dec. 30, 2025

(54) METHODS OF USING ALK2 INHIBITORS

(71) Applicant: Keros Therapeutics, Inc., Lexington, MA (US)

(72) Inventors: Jasbir S. Seehra, Lexington, MA (US); Jennifer Lachey, Lincoln, MA (US); Elissa Furutani, Belmont, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 156 days.

(21) Appl. No.: 17/246,577

(22) Filed: Apr. 30, 2021

(65) Prior Publication Data

US 2022/0401445 A1 Dec. 22, 2022

Related U.S. Application Data

(60) Provisional application No. 63/161,288, filed on Mar. 15, 2021, provisional application No. 63/156,823, filed on Mar. 4, 2021, provisional application No. 63/121,370, filed on Dec. 4, 2020, provisional application No. 63/111,403, filed on Nov. 9, 2020, provisional application No. 63/109,848, filed on Nov. 4, 2020, provisional application No. 63/018,243, filed on Apr. 30, 2020.

(51) Int. Cl.

| | |
|---|---|
| ***A61K 31/5025*** | (2006.01) |
| ***A61K 9/00*** | (2006.01) |
| ***A61K 31/496*** | (2006.01) |
| ***A61K 31/517*** | (2006.01) |
| ***A61P 7/06*** | (2006.01) |

(52) U.S. Cl.

CPC ........ *A61K 31/5025* (2013.01); *A61K 9/0053* (2013.01); *A61K 31/496* (2013.01); *A61K 31/517* (2013.01); *A61P 7/06* (2018.01)

(58) Field of Classification Search

CPC .................................................. A61K 31/5025

See application file for complete search history.

(56) References Cited

U.S. PATENT DOCUMENTS

| | | | |
|---|---|---|---|
| 7,534,764 | B2 | 5/2009 | Ganz et al. |
| 7,820,163 | B2 | 10/2010 | Leung et al. |
| 7,968,091 | B2 | 6/2011 | Woolf et al. |
| 8,163,711 | B2 | 4/2012 | Nakayama et al. |
| 8,268,799 | B2 | 9/2012 | Nakayama et al. |
| 8,329,174 | B2 | 12/2012 | Leung et al. |
| 8,338,377 | B2 | 12/2012 | Seehra |
| 8,455,428 | B2 | 6/2013 | Grinberg et al. |
| 8,470,799 | B2 | 6/2013 | Nakayama et al. |
| 8,507,501 | B2 | 8/2013 | Yu et al. |
| 8,609,817 | B2 | 12/2013 | Leung et al. |
| 8,629,250 | B2 | 1/2014 | Sasu et al. |
| 8,637,023 | B2 | 1/2014 | Lin et al. |
| 8,765,129 | B2 | 7/2014 | Leung et al. |
| 8,791,250 | B2 | 7/2014 | Nakayama et al. |
| 8,796,199 | B2 | 8/2014 | Grinberg et al. |
| 8,841,431 | B2 | 9/2014 | Sell et al. |
| 8,895,002 | B2 | 11/2014 | Lin et al. |
| 9,045,484 | B2 | 6/2015 | Yu et al. |
| 9,051,382 | B2 | 6/2015 | Trentmann et al. |
| 9,228,188 | B2 | 1/2016 | Bettencourt et al. |
| 9,315,577 | B2 | 4/2016 | Foltz et al. |
| 9,556,251 | B2 | 1/2017 | Lin et al. |
| 9,610,356 | B2 | 4/2017 | Hohlbaum et al. |
| 9,636,398 | B2 | 5/2017 | Beligere et al. |
| 9,657,098 | B2 | 5/2017 | Westerman et al. |
| 9,682,983 | B2 | 6/2017 | Alimardanov et al. |
| 9,708,379 | B2 | 7/2017 | Lin et al. |
| 9,914,762 | B2 | 3/2018 | Seehra |
| 9,950,034 | B2 | 4/2018 | Hohlbaum et al. |
| 9,988,627 | B2 | 6/2018 | Baryza et al. |
| 10,017,516 | B2 | 7/2018 | Alimardanov et al. |
| 10,023,621 | B2 | 7/2018 | Kumar et al. |
| 10,118,958 | B2 | 11/2018 | Mueller et al. |
| 10,233,186 | B2 | 3/2019 | Brooijmans et al. |
| 10,260,068 | B2 | 4/2019 | Hino et al. |
| 10,323,088 | B2 | 6/2019 | Westerman |
| 10,428,148 | B2 | 10/2019 | Katagiri et al. |
| 10,513,521 | B2 | 12/2019 | Lee et al. |
| 10,669,277 | B2 | 6/2020 | Wilson et al. |
| 10,765,626 | B2 | 9/2020 | Kumar et al. |
| 10,822,403 | B2 | 11/2020 | Mueller et al. |
| 10,934,359 | B2 | 3/2021 | Roy et al. |
| 11,026,947 | B2 | 6/2021 | Yu et al. |
| 11,654,147 | B2 | 5/2023 | Yu et al. |
| 12,071,438 | B2 | 8/2024 | Bethune et al. |

(Continued)

FOREIGN PATENT DOCUMENTS

| | | | |
|---|---|---|---|
| CN | 101094853 | A | 12/2007 |
| WO | WO-02/18382 | A1 | 3/2002 |

(Continued)

OTHER PUBLICATIONS

Asshoff et al., “Momelotinib inhibits ACVR1/ALK2, decreases hepcidin production, and ameliorates anemia of chronic disease in rodents”, Blood, Feb. 10, 2017 (Year: 2017).*

Brittenham, “Iron-Chelating Therapy for Transfusional Iron overload”, N English J Med., Jan. 13, 2011 (Year: 2011).*

“Beta Thalassemia (Cooley’s Anemia)”, Children’s Hospital of Philadelphia, Jan. 20, 2012 (Year: 2012).*

“Hemolytic Anemia”, Cincinnati Children’s, Oct. 8, 2011 (Year: 2011).*

“7 Risk Factors that could lead to Anemia”, Lendenberg Cancer and Hematology Center, Feb. 19, 2019 (Year: 2019).*

“Myeloproliferative Disorders Causes, Symptoms, and Treatment Options”, UPMC Hillman Cancer Center, Apr. 29, 2020 (Year: 2020).*

“Myelodysplastic/myeloproliferative neoplasm, unclassifiable”, NIH, 2020 (Year: 2020).*

(Continued)

*Primary Examiner* — Andrew D Kosar
*Assistant Examiner* — Gillian A Hutter
(74) *Attorney, Agent, or Firm* — Clark & Elbing LLP

(57) ABSTRACT

The invention relates to methods of treating multiple osteochondroma and anemia resulting from iron imbalance using small molecule ALK2 inhibitors.

2 Claims, 15 Drawing Sheets

(56) References Cited

U.S. PATENT DOCUMENTS

| | | | |
|---|---|---|---|
| 2004/0096990 | A1 | 5/2004 | Geacintov et al. |
| 2007/0004618 | A1 | 1/2007 | Ganz et al. |
| 2010/0062001 | A1 | 3/2010 | Reiter et al. |
| 2011/0182904 | A1 | 7/2011 | Zimmerman et al. |
| 2012/0030780 | A1 | 2/2012 | Ma |
| 2012/0196853 | A1 | 8/2012 | Durrenberger et al. |
| 2012/0202806 | A1 | 8/2012 | Durrenberger et al. |
| 2012/0214798 | A1 | 8/2012 | Durrenberger et al. |
| 2012/0214803 | A1 | 8/2012 | Buhr et al. |
| 2013/0089560 | A1 | 4/2013 | Chartier-Courtaud et al. |
| 2014/0057970 | A1 | 2/2014 | Schwobel et al. |
| 2015/0291675 | A1 | 10/2015 | Trentmann et al. |
| 2016/0046633 | A1 | 2/2016 | Alimardanov et al. |
| 2016/0075772 | A1 | 3/2016 | Hatsell et al. |
| 2016/0115167 | A1 | 4/2016 | Yu et al. |
| 2016/0115209 | A1 | 4/2016 | Knopf et al. |
| 2016/0186172 | A1 | 6/2016 | Bettencourt et al. |
| 2016/0257958 | A1 | 9/2016 | Sell et al. |
| 2017/0183411 | A1 | 6/2017 | Lin et al. |
| 2018/0057586 | A1 | 3/2018 | Westerman et al. |
| 2018/0118835 | A1 | 5/2018 | Katagiri et al. |
| 2018/0171005 | A1 | 6/2018 | Cong et al. |
| 2018/0180614 | A1 | 6/2018 | Crowe, Jr. et al. |
| 2019/0055192 | A1 | 2/2019 | Dalton et al. |
| 2019/0218262 | A1 | 7/2019 | Rajasekhar Suragani et al. |
| 2020/0040054 | A1 | 2/2020 | Du et al. |
| 2020/0095250 | A1 | 3/2020 | Vechorkin et al. |
| 2020/0179389 | A1 | 6/2020 | Yu et al. |
| 2020/0199131 | A1 | 6/2020 | Pan et al. |
| 2020/0331908 | A1 | 10/2020 | Brubaker et al. |
| 2021/0154195 | A1 | 5/2021 | Chen et al. |
| 2021/0238185 | A1 | 8/2021 | Bethune et al. |
| 2021/0253720 | A1 | 8/2021 | Seehra et al. |
| 2021/0393605 | A1 | 12/2021 | Seguy et al. |
| 2023/0000869 | A1 | 1/2023 | Yu et al. |
| 2023/0372390 | A1 | 11/2023 | Seehra et al. |
| 2023/0398118 | A1 | 12/2023 | Seehra et al. |
| 2023/0406956 | A1 | 12/2023 | Seehra et al. |
| 2025/0034148 | A1 | 1/2025 | Seehra et al. |

FOREIGN PATENT DOCUMENTS

| | | | | | |
|---|---|---|---|---|---|
| WO | WO-2006/052913 | A1 | | 5/2006 | |
| WO | WO-2007/028212 | A1 | | 3/2007 | |
| WO | WO-2008/097461 | A2 | | 8/2008 | |
| WO | WO-2008/124768 | A1 | | 10/2008 | |
| WO | WO-2009/058797 | A1 | | 5/2009 | |
| WO | WO-2009/114180 | A1 | | 9/2009 | |
| WO | WO-2010017047 | A1 | * | 2/2010 | ........... A61K 31/535 |
| WO | WO-2010/091150 | A1 | | 8/2010 | |
| WO | WO-2010/124874 | A1 | | 11/2010 | |
| WO | WO-2011/023722 | A1 | | 3/2011 | |
| WO | WO-2011/029832 | A1 | | 3/2011 | |
| WO | WO-2012/022742 | A1 | | 2/2012 | |
| WO | WO-2012/064805 | A1 | | 5/2012 | |
| WO | WO-2012/065059 | A2 | | 5/2012 | |
| WO | WO-2012/065852 | A2 | | 5/2012 | |
| WO | WO-2012/150973 | A1 | | 11/2012 | |
| WO | WO-2013/016452 | A2 | | 1/2013 | |
| WO | WO-2013/090635 | A2 | | 6/2013 | |
| WO | WO-2013/187416 | A1 | | 12/2013 | |
| WO | WO-2014/071015 | A1 | | 5/2014 | |
| WO | WO-2014/138088 | A1 | | 9/2014 | |
| WO | WO-2014/160203 | A2 | | 10/2014 | |
| WO | WO-2015/051135 | A2 | | 4/2015 | |
| WO | WO-2015/148654 | A1 | | 10/2015 | |
| WO | WO-2015/152183 | A1 | | 10/2015 | |
| WO | WO-2015/187977 | A1 | | 12/2015 | |
| WO | WO-2016/011019 | A1 | | 1/2016 | |
| WO | WO-2016/039796 | A2 | | 3/2016 | |
| WO | WO-2016/054406 | A1 | | 4/2016 | |
| WO | WO-2016/121908 | A1 | | 8/2016 | |
| WO | WO-2016/130897 | A1 | | 8/2016 | |
| WO | WO-2016/165808 | A1 | | 10/2016 | |
| WO | WO-2017/184942 | A1 | | 10/2017 | |
| WO | WO-2018/067873 | A2 | | 4/2018 | |
| WO | WO-2018/209242 | A1 | | 11/2018 | |
| WO | WO-2018200855 | A1 | * | 11/2018 | ........... A61K 31/519 |
| WO | WO-2018/232094 | A1 | | 12/2018 | |
| WO | WO-2019/102256 | A1 | | 5/2019 | |
| WO | WO-2019/191204 | A1 | | 10/2019 | |
| WO | WO-2020/068729 | A1 | | 4/2020 | |
| WO | WO-2020/086730 | A1 | | 4/2020 | |
| WO | WO-2020/086736 | A1 | | 4/2020 | |
| WO | WO-2020/086963 | A1 | | 4/2020 | |
| WO | WO-2020/118011 | A1 | | 6/2020 | |
| WO | WO-2020/201038 | A1 | | 10/2020 | |
| WO | WO-2021/030386 | A1 | | 2/2021 | |
| WO | WO-2021/062171 | A1 | | 4/2021 | |
| WO | WO-2021/067670 | A1 | | 4/2021 | |
| WO | WO-2021/163170 | A1 | | 8/2021 | |
| WO | WO-2022/240948 | A1 | | 11/2022 | |
| WO | WO-2023/081212 | A1 | | 5/2023 | |

OTHER PUBLICATIONS

International Search Report and Written Opinion for PCT/US2021/030362, mailed Sep. 16, 2021 (17 pages).

Ensan et al., "Targeting ALK2: An Open Science Approach to Developing Therapeutics for the Treatment of Diffuse Intrinsic Pontine Glioma," J Med Chem. 63(9):4978-4996 (2020).

International Search Report and Written Opinion for Patent Application No. PCT/US2019/058062, mailed Dec. 24, 2019 (9 pages).

Berge et al., "Pharmaceutical salts," J Pharm Sci. 66(1):1-19 (1977).

Stieger et al., "Recrystallization of Active Pharmaceutical Ingredients," Crystallization—Science and Technology. 183-201 (Sep. 2012) (23 pages).

Saal et al., "Pharmaceutical salts: a summary on doses of salt formers from the Orange Book," Eur J Pharm Sci. 49(4):614-23 (Jul. 2013).

International Search Report and Written Opinion for PCT/US2021/058529, dated Feb. 23, 2022 (12 pages).

Morrell et al., "Targeting BMP signalling in cardiovascular disease and anaemia," Nat Rev Cardiol. 13(2):106-20 (with supplemental material) (2016) (32 pages).

Saeed et al., "Remnant-Like Particle Cholesterol, Low-Density Lipoprotein Triglycerides, and Incident Cardiovascular Disease," J Am Coll Cardiol. 72(2):156-169 (with supplemental material) (Jul. 2018) (31 pages).

Ali et al., "Bone morphogenetic proteins and their antagonists: current and emerging clinical uses," Br J Pharmacol. 171(15):3620-32 (2014).

Vela, Driton, "Balance of cardiac and systemic hepcidin and its role in heart physiology and pathology," Lab Invest. 98(3):315-326 (Mar. 2018).

Abdelmahmuod et al., "Iron Deficiency Anemia-Induced Lymphocytopenia in a Young Female," Case Rep Oncol. 13(2):793-797 (Jul. 2020) (5 pages).

International Search Report and Written Opinion for PCT/US2021/057985, dated Mar. 30, 2022 (9 pages).

Barton et al., "Iron overload and prolonged ingestion of iron supplements: clinical features and mutation analysis of hemochromatosis-associated genes in four cases," Am J Hematol. 81(10):760-7 (2006).

International Search Report and Written Opinion for PCT/US2021/057974, dated Mar. 2, 2022 (8 pages).

"Sideroblastic anemia," Wikipedia, <https://en.wikipedia.org/w/index.php?title=Sideroblastic_anemia&oldid=1056240400>, retrieved May 12, 2023 (Nov. 20, 2021) (6 pages).

International Search Report and Written Opinion for PCT/US2022/048703, dated Mar. 20, 2023 (10 pages).

Singer et al., "Comparative phenotypic profiling of the JAK2 inhibitors ruxolitinib, fedratinib, momelotinib, and pacritinib reveals distinct mechanistic signatures," PLoS ONE. 14(9): e0222944 (Sep. 2019) (14 pages).

U.S. Appl. No. 18/289,039, filed Oct. 31, 2023, Seehra et al.

U.S. Appl. No. 19/207,888, filed May 14, 2025, Seehra et al.

(56) References Cited

OTHER PUBLICATIONS

Akinc et al., "Targeting the Hepcidin Pathway with RNAi Therapeutics for the Treatment of Anemia," Blood. 118(21):688 (Abstract) (Nov. 2011) (2 pages).
Angmo et al., "Identification of Guanosine 5'-diphosphate as Potential Iron Mobilizer: Preventing the Hepcidin-Ferroportin Interaction and Modulating the Interleukin-6/Stat-3 Pathway," Sci Rep. 7:40097 (Jan. 2017) (12 pages).
Asshoff et al., "Momelotinib inhibits ACVR1/ALK2, decreases hepcidin production, and ameliorates anemia of chronic disease in rodents," Blood. 129(13):1823-1830 (Mar. 2017).
Aykul et al. "Anti-ACVR1 antibodies exacerbate heterotopic ossification in fibrodysplasia ossificans progressiva (FOP) by activating FOP-mutant ACVR1," J Clin Invest. 132(12): (14 pages) (Published Jun. 15, 2022).
Babitt et al., "Modulation of bone morphogenetic protein signaling in vivo regulates systemic iron balance," J Clin Invest. 117(7):1933-1939 (Jul. 2007) (7 pages).
Benjamini et al., "Immunology: A Short Course," Second Edition. John Wiley & Sons, Inc., p. 40 (1991) (3 pages).
Boergermann et al., "Dorsomorphin and LDN-193189 inhibit BMP-medated Smad, p38 and Akt signalling in C2C12 cells." The International Journal of Biochemistry & Cell Biology, 42(11): 1802-1807 (2010).
Casset et al., "A peptide mimetic of an anti-CD4 monoclonal antibody by rational design," Biochem Biophys Res Commun. 307(1):198-205 (2003).
Cooke et al., "A fully human anti-hepcidin antibody modulates iron metabolism in both mice and nonhuman primates," Blood. 122(17):3054-3061 (Oct. 2013) (8 pages).
Ferrara et al., "Recombinant renewable polyclonal antibodies," MAbs. 7(1):32-41 (2015) (10 pages).
Fujimoto, Mai, et al. "Establishment of a novel model of chondrogenesis using murine embryonic stem cells carrying fibrodysplasia ossificans progressiva-associated mutant ALK2." Biochemical and biophysical research communications 455.3-4 (2014): 347-352.12.12.2014.
Harth et al. "A Selection Fit Mechanism in BMP Receptor IA as a Possible Source for BMP Ligand-Receptor Promiscuity," PLoS One. 5(9): 1-13 (Published Sep. 28, 2010).
Hixon et al., "DISC-0974, a Novel, First-in-Class, Anti-Hemojuvelin Monoclonal Antibody Is Predicted to be Efficacious at Low Doses in Humans as Determined By Pharmacokinetic/Pharmacodynamic (PK/PD) Modeling in Non-Clinical Studies," Blood. 136(Supplement 1):14-15 (Nov. 2020) (2 pages).
Hohlbaum et al., "Discovery and Preclinical Characterization of a Novel Hepcidin Antagonist with Tunable PK/PD Properties for the Treatment of Anemia in Different Patient Populations," Blood. 118(21):687 (Abstract) (Nov. 2011) (2 pages).
Holm et al., "Functional mapping and single chain construction of the anti-cytokeratin 8 monoclonal antibody TS1," Mol Immunol. 44(6):1075-84 (2007).
Hong et al., "Applications of Small Molecule BMP Inhibitors in Physiology and Disease," Cytokine and Growth Factor Reviews, 20(5-6): 409-418 (2009).
Hopkins, "Inhibitors of the bone morphogenetic protein (BMP) signaling pathway: a patent review (2008-2015)," Expert Opin Ther Pat. 26(10):1115-28 (2016) (15 pages).
Kaplan et al., "From mysteries to medicines: drug development for fibrodysplasia ossificans progressiva," Expert Opin Orphan Drugs. 1(8):637-649 (Aug. 2013).
Katagiri et al., "Development of blocking monoclonal antibodies against ALK2, which is a type I receptor for BMPs," Annual Meeting of the American Society for Bone and Mineral Research, Colorado Convention Center, Denver, CO, USA—Sep. 8-11, 2017, Abstract 1094. 32(S1):S33 (2017).
Kovac et al., "Anti-hemojuvelin antibody corrects anemia caused by inappropriately high hepcidin levels," (Letters to the Editor) haematologica. 101:e173-176 (May 2016) (4 pages).
Mueller et al., "3NH7: Crystal structure of the neutralizing Fab fragment AbD1556 bound to the BMP type I receptor IA," RCSB PDB, < https://www.rcsb.org/structure/3NH7>, Released Oct. 27, 2010, (Revised Nov. 1, 2023) (5 pages).
Olsen et al., "BMPR2 inhibits activin- and BMP-signaling via wild type ALK2," J Cell Sci 131(11):jcs213512 (2018) (39 pages).
Pang et al., "ACVR1-Fc suppresses BMP signaling and chondro-osseous differentiation in an in vitro model of Fibrodysplasia ossificans progressiva," Bone. 92:29-36 (Aug. 2, 2016).
Rudikoff et al., "Single amino acid substitution altering antigen-binding specificity," Immunology, 79, pp. 1979-1983 (1982) (5 pages).
Sanchez-Duffhues et al., "Bone morphogenetic protein receptors: Structure, function and targeting by selective small molecule kinase inhibitors," Bone. 138:115472 (Sep. 2020) (13 pages).
Santa Cruz Biotechnology, Inc., Datasheet for "ACTR-I (C-5): sc-374523," <https://datasheets.scbt.com/sc-374523.pdf>, retrieved on May 25, 2018 (1 page).
Santa Cruz Biotechnology, Inc., Datasheet for "ACTR-IA (Y0311): sc-73676," <https://datasheets.scbt.com/sc-73676.pdf>, retrieved on May 23, 2018 (1 page).
Sanvitale et al., "A new class of small molecule inhibitor of BMP signaling," PLoS One. 8(4):e62721 (2013) (11 pages).
Sasu et al., "Antihepcidin antibody treatment modulates iron metabolism and is effective in a mouse model of inflammation-induced anemia," Blood. 115(17):3616-3624 (Apr. 2010) (9 pages).
Steinbicker et al., "Inhibition of bone morphogenetic protein signaling attenuates anemia associated with inflammation," Blood. 117(18):4915-4923 (May 2011) (9 pages).
Sun et al., "Mucus binding protein [Lactobacillus kitasatonis DSM 16761 = JCM 1039]," <www.ncbi.nlm.nih.gov/protein/KRM05866, retrieved Jan. 29, 2020 (2 pages).
Vadhan-Raj et al., "A first-in-human phase 1 study of a hepcidin monoclonal antibody, LY2787106, in cancer-associated anemia," Journal of Hematology & Oncology. 10:73 (Mar. 2017) (12 pages).
Van Eijk et al., "Randomized double-blind placebo-controlled PK/PD study on the effects of a single intravenous dose of the anti-hepcidin Spiegelmer NOX-H94 on serum iron during experimental human endotoxemia," Crit Care. 17(Supplement 2):P352 (Mar. 2013) (4 pages).

* cited by examiner

**** P < 0.0001 via unpaired two-tail t-test

** P < 0.01 via unpaired two-tail t-test

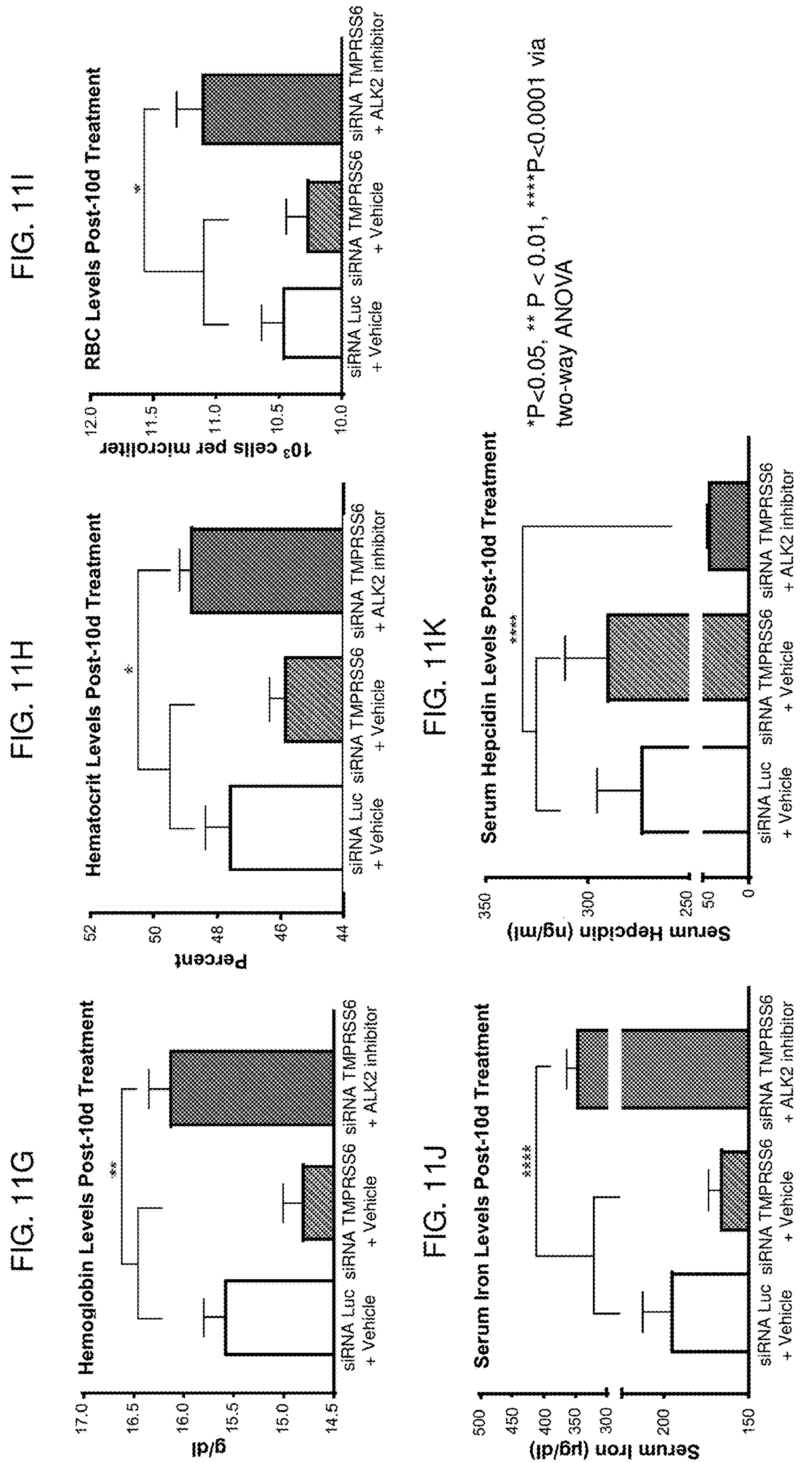
FIG. 11G
Hemoglobin Levels Post-10d Treatment
g/dl
17.0
16.5
16.0
15.5
15.0
14.5
**
siRNA Luc + Vehicle
siRNA TMPRSS6 + Vehicle
siRNA TMPRSS6 + ALK2 inhibitor
FIG. 11H
Hematocrit Levels Post-10d Treatment
Percent
52
50
48
46
44
*
siRNA Luc + Vehicle
siRNA TMPRSS6 + Vehicle
siRNA TMPRSS6 + ALK2 inhibitor
FIG. 11I
RBC Levels Post-10d Treatment
10³ cells per microliter
12.0
11.5
11.0
10.5
10.0
*
siRNA Luc + Vehicle
siRNA TMPRSS6 + Vehicle
siRNA TMPRSS6 + ALK2 inhibitor
FIG. 11J
Serum Iron Levels Post-10d Treatment
Serum Iron (µg/dl)
500
450
400
350
300
200
150
****
siRNA Luc + Vehicle
siRNA TMPRSS6 + Vehicle
siRNA TMPRSS6 + ALK2 inhibitor
FIG. 11K
Serum Hepcidin Levels Post-10d Treatment
Serum Hepcidin (ng/ml)
350
300
250
50
0
****
siRNA Luc + Vehicle
siRNA TMPRSS6 + Vehicle
siRNA TMPRSS6 + ALK2 inhibitor
*P<0.05,  P < 0.01, **P<0.0001 via two-way ANOVA

METHODS OF USING ALK2 INHIBITORS

BACKGROUND

The BMP signaling family is a diverse subset of the TGF-β superfamily. Over twenty known BMP ligands are recognized by three distinct type II (BMPRII, ActRIIa, and ActRIIb) and at least four type I (ALK1, ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner. Soluble BMP inhibitors, such as noggin, chordin, gremlin, and follistatin, limit BMP signaling by ligand sequestration.

A role for BMP signals in regulating expression of hepcidin, a peptide hormone and central regulator of systemic iron balance, has also been suggested. Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes. The link between BMP signaling and iron metabolism represents a potential target for therapeutics.

Given the tremendous structural diversity of the BMP and TGF-β superfamily at the level of ligands (>25 distinct ligands at present) and receptors (four type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas receptors heterotetramers exhibit more specificity for particular ligands. Neutralizing antibodies which are specific for particular ligands or receptors have been previously described and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF THE INVENTION

The present invention features methods of treating diseases or conditions involving BMP signaling using small molecule ALK2 inhibitors. For example, the small molecule ALK2 inhibitors may be used to increase serum iron, increase transferrin saturation, increase iron bioavailability (e.g., by mobilizing iron from storage tissue), increase reticulocyte hemoglobin, promote the formation of hemoglobin-rich red blood cells, reestablish iron homeostasis, and/or reduce hepcidin in a subject in need thereof, such as a subject having anemia resulting from iron imbalance. The small molecule ALK2 inhibitors can also be used to treat multiple osteochondroma (MO).

In a first aspect, the invention provides a method of treating a subject having or at risk of developing anemia resulting from iron imbalance by administering to the subject a therapeutically effective amount of a small molecule ALK2 inhibitor or a pharmaceutically acceptable salt thereof.

In another aspect, the invention provides a method of increasing serum iron in a subject in need thereof by administering to the subject a therapeutically effective amount of a small molecule ALK2 inhibitor or a pharmaceutically acceptable salt thereof.

In another aspect, the invention provides a method of increasing transferrin saturation in a subject in need thereof by administering to the subject a therapeutically effective amount of a small molecule ALK2 inhibitor or a pharmaceutically acceptable salt thereof.

In another aspect, the invention provides a method of increasing iron bioavailability in a subject in need thereof (e.g., mobilizing iron from storage tissue) by administering to the subject a therapeutically effective amount of a small molecule ALK2 inhibitor or a pharmaceutically acceptable salt thereof.

In another aspect, the invention provides a method of increasing reticulocyte hemoglobin in a subject in need thereof by administering to the subject a therapeutically effective amount of a small molecule ALK2 inhibitor or a pharmaceutically acceptable salt thereof.

In another aspect, the invention provides a method of increasing or promoting the formation of hemoglobin-containing red blood cells (e.g., hemoglobin-rich red blood cells) in a subject in need thereof by administering to the subject a therapeutically effective amount of a small molecule ALK2 inhibitor or a pharmaceutically acceptable salt thereof.

In another aspect, the invention provides a method of re-establishing iron homeostasis in a subject in need thereof by administering to the subject a therapeutically effective amount of a small molecule ALK2 inhibitor or a pharmaceutically acceptable salt thereof.

In another aspect, the invention provides a method of reducing serum hepcidin in a subject in need thereof by administering to the subject a therapeutically effective amount of a small molecule ALK2 inhibitor or a pharmaceutically acceptable salt thereof.

In some embodiments of any of the above aspects, the small molecule ALK2 inhibitor is a compound of any one of Formulas I-III, Compounds 1-7, BCX9250, or INCB00928, or a pharmaceutically acceptable salt thereof.

In some embodiments of any of the foregoing aspects, the subject has or is at risk of developing anemia.

In some embodiments of any of the foregoing aspects, the subject has or is at risk of developing anemia resulting from iron imbalance.

In some embodiments of any of the foregoing aspects the anemia is iron deficiency anemia (IDA), iron-refractory iron deficiency anemia (IRIDA), anemia associated with myelofibrosis, anemia associated with myelofibrosis treatment (e.g., treatment with a JAK inhibitor, such as ruxolitinib or fedratinib), aplastic anemia, vitamin deficiency anemia (e.g., vitamin B-12 deficiency or folate deficiency), anemia of inflammation (also called anemia of chronic disease), anemia associated with bone marrow disease, hemolytic anemia, sickle cell anemia, microcytic anemia, hypochromic anemia, sideroblastic anemia (e.g., congenital sideroblastic anemia or acquired sideroblastic anemia), Diamond Blackfan anemia, Fanconi anemia, Pearson syndrome, dyskeratosis congenita, congenital dyserythropoietic anemia, anemia of prematurity, refractory anemia with excess of blasts, anemia associated with a bone marrow defect (e.g., paroxysmal nocturnal hemoglobinuria), anemia associated with adverse reaction to medication (e.g., to an anti-retroviral HIV drug), anemia associated with a myelodysplastic syndrome, anemia associated with a gastrointestinal condition (e.g., Crohn's disease or ulcerative colitis, celiac disease, gastric bypass surgery, *Helicobacter pylori* infection, or autoimmune gastritis), anemia associated with bone marrow transplantation, anemia associated with cancer (e.g., a solid tumor, such as breast cancer, lung cancer, colon cancer; a tumor of the lymphatic system, such as chronic lymphocyte leukemia, non-Hodgkin's lymphoma, Hodgkin's lymphoma; or a tumor of the hematopoietic system, such as leukemia or multiple myeloma), anemia associated with cancer treatment (e.g., radiation or chemotherapy, e.g., chemotherapy with a platinum-containing agent), anemia associated with dialysis, anemia associated with an inflammatory or autoimmune disease (e.g., rheumatoid arthritis, other inflammatory arthritides, ankylosing spondylitis, systemic lupus erythematosus (SLE), an acute or chronic skin disease (e.g. psoriasis), or inflammatory bowel disease (e.g., Crohn's disease or ulcerative colitis), cystitis, or gastritis), anemia associated with acute or chronic renal disease (e.g., chronic kidney disease) or failure, anemia associated with diabetes, anemia associated with acute or chronic liver disease, anemia associated with acute or chronic bleeding, anemia associated with infection (e.g., malaria, osteomyelitis), anemia associated with splenomegaly, anemia associated with *Porphyria*, anemia associated with vasculitis, anemia associated with hemolysis, anemia associated with urinary tract infection, anemia associated with hemoglobinopathy (e.g., sickle cell disease), anemia associated with thalassemia (e.g., α- or β-thalassemia), anemia associated with Churg-Strauss syndrome, anemia associated with Felty syndrome, anemia associated with graft versus host disease, anemia associated with hematopoietic stem cell transplantation, anemia associated with pancytopenia, anemia associated with pure red-cell aplasia, anemia associated with purpura Schoenlein-Henoch, anemia associated with Shwachman syndrome (also called Shwachman-Diamond syndrome), anemia associated with drug use or abuse (e.g., alcohol abuse), or anemia associated with contraindication to transfusion (e.g., anemia in a patient of advanced age, a patient with allo- or auto-antibodies, a pediatric patient, a patient with cardiopulmonary disease, or a patient who objects to transfusion for religious reasons (e.g., some Jehovah's Witnesses)). In some embodiments, the anemia is IDA. In some embodiments, the anemia is IRIDA. In some embodiments, the anemia is anemia of inflammation. In some embodiments, the anemia is associated with myelofibrosis. In some embodiments, the anemia is associated with myelofibrosis treatment. In some embodiments, the anemia is anemia associated with cancer. In some embodiments, the anemia is anemia associated with cancer treatment. In some embodiments, the anemia is anemia associated with acute renal disease or failure. In some embodiments, the anemia is anemia associated with chronic renal disease (e.g., chronic kidney disease). In some embodiments, the anemia is associated with a gastrointestinal condition. In some embodiments, the anemia is aplastic anemia. In some embodiments, the anemia is anemia associated with bone marrow disease. In some embodiments, the anemia is hemolytic anemia. In some embodiments, the anemia is sickle cell anemia. In some embodiments, the anemia is microcytic anemia. In some embodiments, the anemia is hypochromic anemia. In some embodiments, the anemia is sideroblastic anemia. In some embodiments, the sideroblastic anemia is congenital sideroblastic anemia. In some embodiments, the sideroblastic anemia is acquired sideroblastic anemia. In some embodiments, the anemia is Diamond Blackfan anemia. In some embodiments, the anemia is Fanconi anemia. In some embodiments, the anemia is Pearson syndrome.

In some embodiments, the anemia is dyskeratosis congenita. In some embodiments, the anemia is congenital dyserythropoietic anemia. In some embodiments, the anemia is anemia of prematurity. In some embodiments, the anemia is refractory anemia with excess of blasts. In some embodiments, the anemia is anemia associated with a bone marrow defect. In some embodiments, the anemia is anemia associated with adverse reaction to medication. In some embodiments, the anemia is anemia associated with a myelodysplastic syndrome. In some embodiments, the anemia is anemia associated with bone marrow transplantation. In some embodiments, the anemia is anemia associated with dialysis. In some embodiments, the anemia is anemia associated with an inflammatory or autoimmune disease. In some embodiments, the anemia is anemia associated with diabetes. In some embodiments, the anemia is anemia associated with acute or chronic liver disease. In some embodiments, the anemia is anemia associated with infection. In some embodiments, the anemia is anemia associated with splenomegaly. In some embodiments, the anemia is anemia associated with *Porphyria*. In some embodiments, the anemia is anemia associated with vasculitis. In some embodiments, the anemia is anemia associated with hemolysis. In some embodiments, the anemia is anemia associated with urinary tract infection. In some embodiments, the anemia is anemia associated with hemoglobinopathy. In some embodiments, the anemia is anemia associated with thalassemia. In some embodiments, the anemia is anemia associated with Churg-Strauss syndrome. In some embodiments, the anemia is anemia associated with Felty syndrome. In some embodiments, the anemia is anemia associated with graft versus host disease. In some embodiments, the anemia is anemia associated with hematopoietic stem cell transplantation. In some embodiments, the anemia is anemia associated with pancytopenia. In some embodiments, the anemia is anemia associated with pure red-cell aplasia. In some embodiments, the anemia is anemia associated with purpura Schoenlein-Henoch. In some embodiments, the anemia is anemia associated with Shwachman syndrome. In some embodiments, the anemia is anemia associated with drug use or abuse. In some embodiments, the anemia is anemia associated with contraindication to transfusion. In some embodiments, the anemia is anemia associated with acute or chronic bleeding. In some embodiments, the acute or chronic bleeding is due to surgery, trauma, a wound, an ulcer, urinary tract bleeding, digestive tract bleeding, frequent blood donation, or heavy menstrual bleeding.

In some embodiments of any of the foregoing aspects, the compound, or pharmaceutically acceptable salt thereof, is administered in an amount sufficient to increase serum iron, increase transferrin saturation, increase iron bioavailability, increase reticulocyte hemoglobin, promote the formation of hemoglobin-containing red blood cells (e.g., hemoglobin-rich red blood cells), reestablish iron homeostasis, and/or reduce serum hepcidin.

In another aspect, the invention provides a method of treating a subject having multiple osteochondroma (MO) by administering to the subject a therapeutically effective amount of a small molecule ALK2 inhibitor or a pharmaceutically acceptable salt thereof.

In another aspect, the invention provides a method of preventing or reducing the formation of an osteochondroma in a subject having MO by administering to the subject a therapeutically effective amount of a small molecule ALK2 inhibitor or a pharmaceutically acceptable salt thereof.

In another aspect, the invention provides a method of reducing the size of an osteochondroma in a subject having MO by administering to the subject a therapeutically effective amount of a small molecule ALK2 inhibitor or a pharmaceutically acceptable salt thereof.

In another aspect, the invention provides a method of slowing or inhibiting the growth of an osteochondroma in a subject having MO by administering to the subject a therapeutically effective amount of a small molecule ALK2 inhibitor or a pharmaceutically acceptable salt thereof.

In another aspect, the invention provides a method of reducing the number of osteochondromas in a subject having MO by administering to the subject a therapeutically effective amount of a small molecule ALK2 inhibitor or a pharmaceutically acceptable salt thereof.

In some embodiments of any of the foregoing aspects, the small molecule ALK2 inhibitor is compound of any one of Formulas I-III, Compounds 1-7, BCX9250, or INCB00928, or a pharmaceutically acceptable salt thereof.

In some embodiments of any of the foregoing aspects, the MO is hereditary MO.

In some embodiments of any of the foregoing aspects, the MO is spontaneous MO.

In some embodiments of any of the foregoing aspects, the subject has not yet developed an osteochondroma.

In some embodiments of any of the foregoing aspects, the subject has already developed one or more osteochondroma.

In some embodiments of any of the foregoing aspects, the osteochondroma is formed on a long bone.

In some embodiments of any of the foregoing aspects, the osteochondroma is formed on a flat bone.

In some embodiments of any of the foregoing aspects, the osteochondroma is formed on the growing end of a bone.

In some embodiments of any of the foregoing aspects, the subject is an adult.

In some embodiments of any of the foregoing aspects, the subject is a child.

In some embodiments of any of the foregoing aspects, the subject is an adolescent.

In some embodiments of any of the foregoing aspects, the compound, or a pharmaceutically acceptable salt thereof is administered in an amount sufficient to treat MO, prevent the formation of an osteochondroma, reduce the formation of an osteochondroma, reduce the size of an osteochondroma, reduce the growth of an osteochondroma, or reduce the number of osteochondromas in a subject having MO.

In some embodiments of any of the foregoing aspects, the method reduces the need of the subject for surgical intervention to treat MO (e.g., the subject no longer requires surgery to treat MO or the subject requires fewer, less frequent, or less invasive surgical procedures to treat MO).

In some embodiments of any of the foregoing aspects, the small molecule ALK2 inhibitor or a pharmaceutically acceptable salt thereof is a compound of Formula I:

(Formula I)

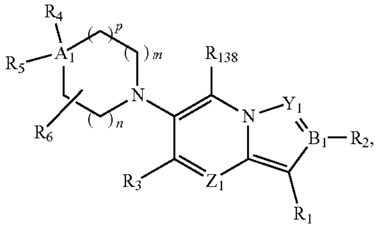

or a pharmaceutically acceptable salt thereof, wherein:

$R_1$ is hydrogen or an optionally substituted substituent;

$R_2$ is optionally absent, hydrogen, or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen or an optionally substituted substituent;

$R_6$ is independently one or more of hydrogen or an optionally substituted substituent; $B_1$, is C or N; $Y_1$ is N or $CR_{139}$, wherein $R_{139}$ is hydrogen or an optionally substituted substituent; $Z_1$ is N or $CR_{140}$, wherein $R_{140}$ is hydrogen or an optionally substituted substituent; $A_1$ is C, N, O, C(O), S, SO, or $SO_2$; m is 0, 1, 2, or 3; n is 0, 1, 2, or 3; and p is 0 or 1; wherein optionally any two or more of $R_4$, $R_5$, or $R_6$ may be joined together to form one or more rings.

In some embodiments, the compound of Formula I has a structure of Formula I-a:

(Formula I-a)

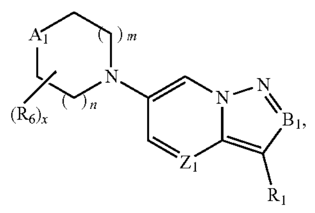

or a pharmaceutically acceptable salt thereof, wherein:

$A_1$ is $NR_{4a}$ or $CR_{4b}R_5$;

$B_1$ is N or $CR_2$;

$Z_1$ is N or $CR_3$;

$R_1$ is selected from cycloalkyl, aryl, heteroaryl, and heterocyclyl;

$R_2$ is H, CN, $NO_2$, alkyl, or amino;

$R_3$ is selected from H, CN, $NO_2$, alkyl, alkoxy, heterocyclyloxy, heteroaryloxy, aryloxy, cycloalkyloxy, carbonyl, amino, amido, sulfonyl, sulfonamido, cycloalkyl, aryl, heterocyclyl, and heteroaryl;

$R_{4a}$ is selected from alkyl, alkenyl, alkynyl, carbonyl, $O^-$, alkoxycarbonyl, cycloalkyl, aryl, heterocyclyl, and heteroaryl;

$R_{4b}$ is selected from halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl;

$R_5$ is selected from H, halo, hydroxy and alkyl, or $R_{4b}$ and $R_5$ together with $A_1$ form a ring selected from cycloalkyl and heterocyclyl;

each $R_6$ is independently selected from H, halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl and oxo;

n is 0 or 1;

m is 0 or 1; and x is 0, 1, 2, 3, or 4.

In some embodiments of the compound of Formula I-a, $A_1$ is $NR_{4a}$ or $CR_{4b}R_5$;

$B_1$ is N or $CR_2$;

$Z_1$ is N or $CR_3$;

$R_1$ is selected from aryl, heteroaryl, and heterocyclyl;

$R_2$ is H or amino;

$R_3$ is H or heterocyclyloxy;

$R_{4a}$ is selected from alkyl, $O^-$, aryl, heterocyclyl, and heteroaryl;

$R_{4b}$ is selected from alkyl, alkoxy, amino, aryl, heterocyclyl, and heteroaryl;

$R_5$ is selected from H and alkyl, or $R_{4b}$ and $R_5$ together with $A_1$ form a ring selected from cycloalkyl and heterocyclyl;

each $R_6$ is independently selected from H, halo, alkyl and oxo;

n is 0 or 1;

m is 0 or 1; and x is 0, 1, 2, 3, or 4.

In some embodiments of the compound of Formula I-a, $R_{4a}$ is selected from alkyl, $O^-$, heterocyclyl, and heteroaryl;

$R_{4b}$ is selected from alkyl, alkoxy, amino, amido, heterocyclyl, and heteroaryl;

$R_5$ is selected from H and alkyl, or $R_{4b}$ and $R_5$ together with $A_1$ form a heterocyclyl; and each $R_6$ is independently selected from H, halo, and alkyl; and x is 0 or 1.

In some embodiments of the compound of Formula I-a, $R_1$ is selected from H, aryl, 5-6 membered heteroaryl,

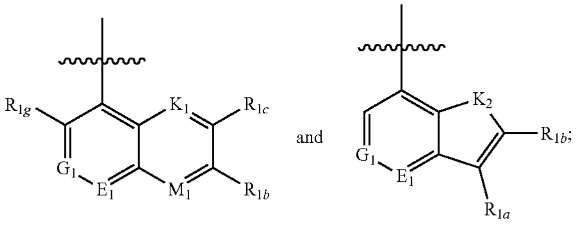

wherein:

each $E_1$ is independently selected from N and $CR_{1d}$;

each $G_1$ is independently selected from N and $CR_{1e}$;

$K_1$ is N or CH;

$K_2$ is NH or S;

$M_1$ is N or $CR_{1a}$;

$R_{1a}$ is selected from H, halo, alkyl, haloalkyl, and amido;

$R_{1b}$ is selected from H, halo, CN, alkyl, haloalkyl, hydroxy, alkoxy, and haloalkoxy;

$R_{1c}$ is selected from H, halo, CN, alkyl, haloalkyl, hydroxy, alkoxy, haloalkoxy, amino and amido, or $R_{1b}$ and $R_{1c}$ together with the carbon atoms to which they are attached form a heterocyclyl;

$R_{1d}$ is selected from H, CN, alkyl, haloalkyl, hydroxy, amido and sulfonamido;

$R_{1e}$ is selected from H, alkyl and amino; and $R_{1g}$ is H or halo.

In some embodiments of the compound of Formula I-a, $R_{4a}$ is selected from alkyl, $O^-$, heterocyclyl, and heteroaryl;

$R_{4b}$ is selected from alkyl, alkoxy, amino, amido, heterocyclyl, and heteroaryl;

$R_5$ is selected from H and alkyl, or $R_{4b}$ and $R_5$ together with $A_1$ form a heterocyclyl; and each $R_6$ is independently selected from H, halo, and alkyl; and x is 0 or 1.

In some embodiments, $R_1$ is selected from H, aryl, 5-6 membered heteroaryl,

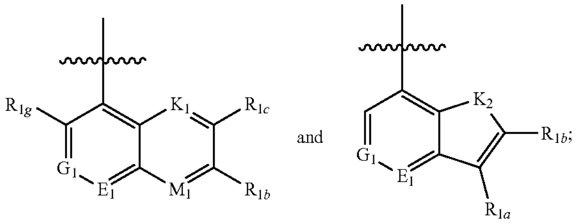

wherein:

each $E_1$ is independently selected from N and $CR_{1d}$;

each $G_1$ is independently selected from N and $CR_{1e}$;

$K_1$ is N or CH;

$K_2$ is NH or S;

$M_1$ is $CR_{1a}$;

$R_{1a}$ is selected from H and amido;

$R_{1b}$ is selected from H, halo, alkyl, and alkoxy;

$R_{1c}$ is selected from H, alkyl, and alkoxy, or $R_{1b}$ and $R_{1c}$ together with the carbon atoms to which they are attached form a heterocyclyl;

$R_{1d}$ is selected from H, alkyl, hydroxy, amido and sulfonamido;

$R_{1e}$ is selected from H, alkyl and amino;

$R_{1f}$ is H; and $R_{1g}$ is H.

In some embodiments, the compound of Formula I has a structure of any one of Formulas I-1 to I-104 or a pharmaceutically acceptable salt thereof. In some embodiments, the compound of Formula I has the structure of Formula I-1. In some embodiments, the compound of Formula I has the structure of Formula I-2. In some embodiments, the compound of Formula I has the structure of Formula I-3. In some embodiments, the compound of Formula I has the structure of Formula I-4. In some embodiments, the compound of Formula I has the structure of Formula I-5. In some embodiments, the compound of Formula I has the structure of Formula I-6. In some embodiments, the compound of Formula I has the structure of Formula I-7. In some embodiments, the compound of Formula I has the structure of Formula I-8. In some embodiments, the compound of Formula I has the structure of Formula I-9. In some embodiments, the compound of Formula I has the structure of Formula I-10. In some embodiments, the compound of Formula I has the structure of Formula I-11. In some embodiments, the compound of Formula I has the structure of Formula I-12. In some embodiments, the compound of Formula I has the structure of Formula I-13. In some embodiments, the compound of Formula I has the structure of Formula I-14. In some embodiments, the compound of Formula I has the structure of Formula I-15. In some embodiments, the compound of Formula I has the structure of Formula I-16. In some embodiments, the compound of Formula I has the structure of Formula I-17. In some embodiments, the compound of Formula I has the structure of Formula I-18. In some embodiments, the compound of Formula I has the structure of Formula I-19. In some embodiments, the compound of Formula I has the structure of Formula I-20. In some embodiments, the compound of Formula I has the structure of Formula I-21. In some embodiments, the compound of Formula I has the structure of Formula I-22. In some embodiments, the compound of Formula I has the structure of Formula I-23. In some embodiments, the compound of Formula I has the structure of Formula I-24. In some embodiments, the compound of Formula I has the structure of Formula I-25. In some embodiments, the compound of Formula I has the structure of Formula I-26. In some embodiments, the compound of Formula I has the structure of Formula I-27. In some embodiments, the compound of Formula I has the structure of Formula I-28. In some embodiments, the compound of Formula I has the structure of Formula I-29. In some embodiments, the compound of Formula I has the structure of Formula I-30. In some embodiments, the compound of Formula I has the structure of Formula I-31. In some embodiments, the compound of Formula I has the structure of Formula I-32. In some embodiments, the compound of Formula I has the structure of Formula I-33. In some embodiments, the compound of Formula I has the structure of Formula I-34. In some embodiments, the compound of Formula I has the structure of Formula I-35. In some embodiments, the compound of Formula I has the structure of Formula I-36. In some embodiments, the compound of Formula I has the structure of Formula I-37. In some embodiments, the compound of Formula I has the structure of Formula I-38. In some embodiments, the compound of Formula I has the structure of Formula I-39. In some embodiments, the compound of Formula I has the structure of Formula I-40. In some embodiments, the compound of Formula I has the structure of Formula I-41. In some embodiments, the compound of Formula I has the structure of Formula I-42. In some embodiments, the compound of Formula I has the structure of Formula I-43. In some embodiments, the compound of Formula I has the structure of Formula I-44. In some embodiments, the compound of Formula I has the structure of Formula I-45. In some embodiments, the compound of Formula I has the structure of Formula I-46. In some embodiments, the compound of Formula I has the structure of Formula I-47. In some embodiments, the compound of Formula I has the structure of Formula I-48. In some embodiments, the compound of Formula I has the structure of Formula I-49. In some embodiments, the compound of Formula I has the structure of Formula I-50. In some embodiments, the compound of Formula I has the structure of Formula I-51. In some embodiments, the compound of Formula I has the structure of Formula I-52. In some embodiments, the compound of Formula I has the structure of Formula I-53. In some embodiments, the compound of Formula I has the structure of Formula I-54. In some embodiments, the compound of Formula I has the structure of Formula I-55. In some embodiments, the compound of Formula I has the structure of Formula I-56. In some embodiments, the compound of Formula I has the structure of Formula I-57. In some embodiments, the compound of Formula I has the structure of Formula I-58. In some embodiments, the compound of Formula I has the structure of Formula I-59. In some embodiments, the compound of Formula I has the structure of Formula I-60. In some embodiments, the compound of Formula I has the structure of Formula I-61. In some embodiments, the compound of Formula I has the structure of Formula I-62. In some embodiments, the compound of Formula I has the structure of Formula I-63. In some embodiments, the compound of Formula I has the structure of Formula I-64. In some embodiments, the compound of Formula I has the structure of Formula I-65. In some embodiments, the compound of Formula I has the structure of Formula I-66. In some embodiments, the compound of Formula I has the structure of Formula I-67. In some embodiments, the compound of Formula I has the structure of Formula I-68. In some embodiments, the compound of Formula I has the structure of Formula I-69. In some embodiments, the compound of Formula I has the structure of Formula I-70. In some embodiments, the compound of Formula I has the structure of Formula I-71. In some embodiments, the compound of Formula I has the structure of Formula I-72. In some embodiments, the compound of Formula I has the structure of Formula I-73. In some embodiments, the compound of Formula I has the structure of Formula I-74. In some embodiments, the compound of Formula I has the structure of Formula I-75. In some embodiments, the compound of Formula I has the structure of Formula I-76. In some embodiments, the compound of Formula I has the structure of Formula I-77. In some embodiments, the compound of Formula I has the structure of Formula I-78. In some embodiments, the compound of Formula I has the structure of Formula I-79. In some embodiments, the compound of Formula I has the structure of Formula I-80. In some embodiments, the compound of Formula I has the structure of Formula I-81. In some embodiments, the compound of Formula I has the structure of Formula I-82. In some embodiments, the compound of Formula I has the structure of Formula I-83. In some embodiments, the compound of Formula I has the structure of Formula I-84. In some embodiments, the compound of Formula I has the structure of Formula I-85. In some embodiments, the compound of Formula I has the structure of Formula I-86. In some embodiments, the compound of Formula I has the structure of Formula I-87. In some embodiments, the compound of Formula I has the structure of Formula I-88. In some embodiments, the compound of Formula I has the structure of Formula I-89. In some embodiments, the compound of Formula I has the structure of Formula I-90. In some embodiments, the compound of Formula I has the structure of Formula I-91. In some embodiments, the compound of Formula I has the structure of Formula I-92. In some embodiments, the compound of Formula I has the structure of Formula I-93. In some embodiments, the compound of Formula I has the structure of Formula I-94. In some embodiments, the compound of Formula I has the structure of Formula I-95. In some embodiments, the compound of Formula I has the structure of Formula I-96. In some embodiments, the compound of Formula I has the structure of Formula I-97. In some embodiments, the compound of Formula I has the structure of Formula I-98. In some embodiments, the compound of Formula I has the structure of Formula I-99. In some embodiments, the compound of Formula I has the structure of Formula I-100. In some embodiments, the compound of Formula I has the structure of Formula I-101. In some embodiments, the compound of Formula I has the structure of Formula I-102. In some embodiments, the compound of Formula I has the structure of Formula I-103. In some embodiments, the compound of Formula I has the structure of Formula I-104. In some embodiments, the compound of Formula I has the structure of Formula I-105. In some embodiments, the compound of Formula I has the structure of Formula I-106. In some embodiments, the compound of Formula I has the structure of Formula I-107. In some embodiments, the compound of Formula I has the structure of Formula I-108. In some embodiments, the compound of Formula I has the structure of Formula I-109. In some embodiments, the compound of Formula I has the structure of Formula I-110. In some embodiments, the compound of Formula I has the structure of Formula I-111. In some embodiments, the compound of Formula I has the structure of Formula I-112. In some embodiments, the compound of Formula I has the structure of Formula I-113. In some embodiments, the compound of Formula I has the structure of Formula I-114. In some embodiments, the compound of Formula I has the structure of Formula I-115. In some embodiments, the compound of Formula I has the structure of Formula I-116. In some embodiments, the compound of Formula I has the structure of Formula I-117. In some embodiments, the compound of Formula I has the structure of Formula I-118. In some embodiments, the compound of Formula I has the structure of Formula I-119. In some embodiments, the compound of Formula I has the structure of Formula I-120. In some embodiments, the compound of Formula I has the structure of Formula I-121. In some embodiments, the compound of Formula I has the structure of Formula I-122. In some embodiments, the compound of Formula I has the structure of Formula I-123. In some embodiments, the compound of Formula I has the structure of Formula I-124. In some embodiments, the compound of Formula I has the structure of Formula I-125. In some embodiments, the compound of Formula I has the structure of Formula I-126. In some embodiments, the compound of Formula I has the structure of Formula I-127. In some embodiments, the compound of Formula I has the structure of Formula I-128. In some embodiments, the compound of Formula I has the structure of Formula I-129. In some embodiments, the compound of Formula I has the structure of Formula I-130. In some embodiments, the compound of Formula I has the structure of Formula I-131. In some embodiments, the compound of Formula I has the structure of Formula I-132. In some embodiments, the compound of Formula I has the structure of Formula I-133. In some embodiments, the compound of Formula I has the structure of Formula I-134. In some embodiments, the compound of Formula I has the structure of Formula I-135. In some embodiments, the compound of Formula I has the structure of Formula I-136. In some embodiments, the compound of Formula I has the structure of Formula I-137. In some embodiments, the compound of Formula I has the structure of Formula I-138. In some embodiments, the compound of Formula I has the structure of Formula I-139. In some embodiments, the compound of Formula I has the structure of Formula I-140. In some embodiments, the compound of Formula I has the structure of Formula I-141. In some embodiments, the compound of Formula I has the structure of Formula I-142. In some embodiments, the compound of Formula I has the structure of Formula I-143. In some embodiments, the compound of Formula I has the structure of Formula I-144. In some embodiments, the compound of Formula I has the structure of Formula I-145. In some embodiments, the compound of Formula I has the structure of Formula I-146. In some embodiments, the compound of Formula I has the structure of Formula I-147. In some embodiments, the compound of Formula I has the structure of Formula I-148. In some embodiments, the compound of Formula I has the structure of Formula I-149. In some embodiments, the compound of Formula I has the structure of Formula I-150. In some embodiments, the compound of Formula I has the structure of Formula I-151. In some embodiments, the compound of Formula I has the structure of Formula I-152. In some embodiments, the compound of Formula I has the structure of Formula I-153. In some embodiments, the compound of Formula I has the structure of Formula I-154. In some embodiments, the compound of Formula I has the structure of Formula I-155. In some embodiments, the compound of Formula I has the structure of Formula I-156. In some embodiments, the compound of Formula I has the structure of Formula I-157. In some embodiments, the compound of Formula I has the structure of Formula I-158. In some embodiments, the compound of Formula I has the structure of Formula I-159. In some embodiments, the compound of Formula I has the structure of Formula I-160. In some embodiments, the compound of Formula I has the structure of Formula I-161. In some embodiments, the compound of Formula I has the structure of Formula I-162. In some embodiments, the compound of Formula I has the structure of Formula I-163. In some embodiments, the compound of Formula I has the structure of Formula I-164. In some embodiments, the compound of Formula I has the structure of Formula I-165. In some embodiments, the compound of Formula I has the structure of Formula I-166. In some embodiments, the compound of Formula I has the structure of Formula I-167. In some embodiments, the compound of Formula I has the structure of Formula I-168. In some embodiments, the compound of Formula I has the structure of Formula I-169. In some embodiments, the compound of Formula I has the structure of Formula I-170. In some embodiments, the compound of Formula I has the structure of Formula I-171. In some embodiments, the compound of Formula I has the structure of Formula I-172. In some embodiments, the compound of Formula I has the structure of Formula I-173. In some embodiments, the compound of Formula I has the structure of Formula I-174. In some embodiments, the compound of Formula I has the structure of Formula I-175. In some embodiments, the compound of Formula I has the structure of Formula I-176. In some embodiments, the compound of Formula I has the structure of Formula I-177. In some embodiments, the compound of Formula I has the structure of Formula I-178. In some embodiments, the compound of Formula I has the structure of Formula I-179. In some embodiments, the compound of Formula I has the structure of Formula I-180. In some embodiments, the compound of Formula I has the structure of Formula I-181. In some embodiments, the compound of Formula I has the structure of Formula I-182. In some embodiments, the compound of Formula I has the structure of Formula I-183. In some embodiments, the compound of Formula I has the structure of Formula I-184. In some embodiments, the compound of Formula I has the structure of Formula I-185. In some embodiments, the compound of Formula I has the structure of Formula I-186. In some embodiments, the compound of Formula I has the structure of Formula I-187. In some embodiments, the compound of Formula I has the structure of Formula I-188. In some embodiments, the compound of Formula I has the structure of Formula I-189. In some embodiments, the compound of Formula I has the structure of Formula I-190. In some embodiments, the compound of Formula I has the structure of Formula I-191. In some embodiments, the compound of Formula I has the structure of Formula I-192. In some embodiments, the compound of Formula I has the structure of Formula I-193. In some embodiments, the compound of Formula I has the structure of Formula I-194. In some embodiments, the compound of Formula I has the structure of Formula I-195. In some embodiments, the compound of Formula I has the structure of Formula I-196. In some embodiments, the compound of Formula I has the structure of Formula I-197. In some embodiments, the compound of Formula I has the structure of Formula I-198. In some embodiments, the compound of Formula I has the structure of Formula I-199. In some embodiments, the compound of Formula I has the structure of Formula I-200.

In some embodiments of any of the foregoing aspects, the small molecule ALK2 inhibitor or a pharmaceutically acceptable salt thereof is a compound of Formula II:

Formula II

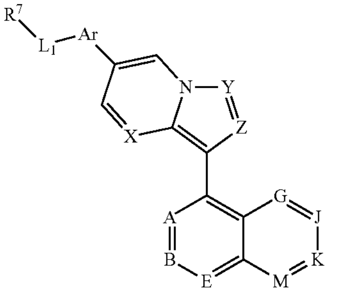

or a pharmaceutically acceptable salt thereof, wherein

X and Y are independently selected from $CR^{15}$ and N, preferably both N;

Z is selected from $CR^{3'}$ and N, preferably $CR^{3'}$, most preferably CH;

Ar is a substituted or unsubstituted aryl ring or a substituted or unsubstituted heteroaryl ring;

$L_1$ is absent or selected from substituted or unsubstituted alkyl, substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclylheteroalkyl, and substituted or unsubstituted heteroalkyl; and J and K are both absent or, independently for each occurrence, are each $CR^{16}$;

A is $CR^{16}$;

B and E are each independently $CR^{17}$;

if J and K are absent, then G is $R^{16}$ and M is $R^{17}$; if J and K are not absent, then G is $CR^{16}$ and M is $CR^{17}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from

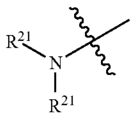

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido, preferably H;

$R^{16}$, independently for each occurrence, is selected from H, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and $—R^{22}$, $—NH_2$, $—NHR^{22}$, $—N(R^{22})_2$, halogen, $—CO_2H$, $—CO_2R^{22}$, $—CONH_2$, $—CONHR^{22}$, $—CON(R^{22})_2$, $—C(NH_2)═N(OH)$, $—C(NHR^{22})═N(OH)$, $—C(N(R^{22})_2)═N(OH)$, $—C(NH_2)═NH$, $—C(NHR^{22})═NH$, $—C(NHR^{22})═NR^{22}$, $—C(N(R^{22})_2)═NH$, $—C(N(R^{22})_2)═NR^{22}$, —CN, $—CH_2CH_2OH$, $—CH_2OH$, $—CH_2SO_2NH_2$, $—CH_2SO_2NHR^{22}$, $—CH_2SO_2N(R^{22})_2$, $—SO_2NH_2$, $—SO_2NHR^{22}$, $—SO_2N(R^{22})_2$, $—NHSO_2R^{22}$, $—SO_2R^{22}$, $—CH_2SO_2R^{22}$, $—CH_2NH_2$, $—CH_2NHR^{22}$, $—CH_2N(R^{22})_2$, $—C(O)R^{22}$,

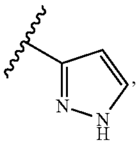,
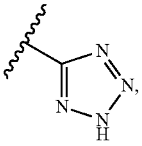, $—CH(OH)R^{22}$, $—C(OH)(R^{22})_2$, $—CH(NH_2)(R^{22})$, $—CH(NHR^{22})(R^{22})$, $—CH(N(R^{22})_2)(R^{22})$, pyrazol-3-yl, pyrazol-4-yl, and $—OR^{22}$, provided that at least one $R^{17}$ is $—R^{22}$, $—NH_2$, $—NHR^{22}$, $—N(R^{22})_2$, halogen, $—CO_2H$, $—CO_2R^{22}$, $—CONH_2$, $—CONHR^{22}$, $—CON(R^{22})_2$, $—C(NH_2)═N(OH)$, $—C(NHR^{22})═N(OH)$, $—C(N(R^{22})_2)═N(OH)$, $—C(NH_2)═NH$, $—C(NHR^{22})═NH$, $—C(NHR^{22})═NR^{22}$, $—C(N(R^{22})_2)═NH$, $—C(N(R^{22})_2)═NR^{22}$, —CN, $—CH_2CH_2OH$, $—CH_2OH$, $—CH_2SO_2NH_2$, $—CH_2SO_2NHR^{22}$, $—CH_2SO_2N(R^{22})_2$, $—SO_2NH_2$, $—SO_2NHR^{22}$, $—SO_2N(R^{22})_2$, $—NHSO_2R^{22}$, $—SO_2R^{22}$, $—CH_2SO_2R^{22}$, $—CH_2NH_2$, $—CH_2NHR^{22}$, $—CH_2N(R^{22})_2$, $—C(O)R^{22}$

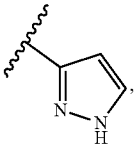,
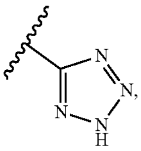, $—CH(OH)R^{22}—C(OH)(R^{22})_2$, $—CH(NH_2)(R^{22})$, $—CH(NHR^{22})(R^{22})$, $—CH(N(R^{22})_2)(R^{22})$, pyrazol-3-yl, pyrazol-4-yl, or $—OR^{22}$;

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide, preferably from H and substituted or unsubstituted alkyl, aralkyl, cycloalkyl, heterocyclyl, aryl, heteroaryl, heteroaralkyl, cycloalkylalkyl, heterocyclylalkyl, more preferably from H and substituted or unsubstituted alkyl, and most preferably from H and lower alkyl, such as methyl or ethyl; and $R^{22}$, independently for each occurrence, is selected from lower alkyl (e.g., $CH_3$ or $CF_3$) and cycloalkyl (preferably cyclopropyl or cyclobutyl).

In some embodiments of any of the foregoing aspects, the small molecule ALK2 inhibitor or a pharmaceutically acceptable salt thereof is a compound of Formula II, wherein X and Y are each N;

Z is $CR^{3'}$;

Ar is a substituted or unsubstituted aryl ring or a substituted or unsubstituted heteroaryl ring;

$L_1$ is absent or selected from substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclylheteroalkyl, and

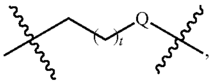

wherein Q is selected from $CR^{10'}R^{11}$, $NR^{12}$, O, S, S(O), and $SO_2$; $R^{10'}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and t is an integer selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and J and K are both absent or, independently for each occurrence, are each $CR^{16}$;

A is $CR^{16}$;

B and E are each independently $CR^{17}$;

if J and K are absent, then G is $R^{16}$ and M is $R^{17}$; if J and K are not absent, then G is $CR^{16}$ and M is $CR^{17}$;

$R^{3'}$ is H;

$R^7$ is selected from

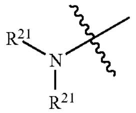

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and $—R^{22}$, $—NH_2$, $—NHR^{22}$, $—N(R^{22})_2$, $—CO_2H$, $—CO_2R^{22}$, $—CONH_2$, $—CONHR^{22}$, $—CON(R^{22})_2$, $—C(NH_2)═N(OH)$, $—C(NHR^{22})═N(OH)$, $—C(N(R^{22})_2)═N(OH)$, $—C(NH_2)═NH$, $—C(NHR^{22})═NH$, $—C(NHR^{22})═NR^{22}$, $—C(N(R^{22})_2)═NH$, $—C(N(R^{22})_2)═NR^{22}$, —CN, $—CH_2CH_2OH$, $—CH_2OH$, $—CH_2SO_2NH_2$, $—CH_2SO_2NHR^{22}$, $—CH_2SO_2N(R^{22})_2$, $—SO_2NH_2$, $—SO_2NHR^{22}$, $—SO_2N(R^{22})_2$, $—NHSO_2R^{22}$, $—SO_2R^{22}$, $—CH_2SO_2R^{22}$, $—CH_2NH_2$, $—CH_2NHR^{22}$, $—CH_2N(R^{22})_2$, $—C(O)R^{22}$,

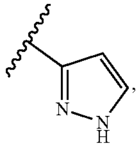, 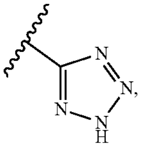

$—CH(OH)R^{22}$, $—C(OH)(R^{22})_2$, $—CH(NH_2)(R^{22})$, $—CH(NHR^{22})(R^{22})$, $—CH(N(R^{22})_2)(R^{22})$, pyrazol-3-yl, pyrazol-4-yl, and $—OR^{22}$, provided that at least one $R^{17}$ is $—R^{22}$, $—NH_2$, $—NHR^{22}$, $—N(R^{22})_2$, $—CO_2H$, $—CO_2R^{22}$, $—CONH_2$, $—CONHR^{22}$, $—CON(R^{22})_2$, $—C(NH_2)═N(OH)$, $—C(NHR^{22})═N(OH)$, $—C(N(R^{22})_2)═N(OH)$, $—C(NH_2)═NH$, $—C(NHR^{22})═NH$, $—C(NHR^{22})═NR^{22}$, $—C(N(R^{22})_2)═NH$, $—C(N(R^{22})_2)═NR^{22}$, —CN, $—CH_2CH_2OH$, $—CH_2OH$, $—CH_2SO_2NH_2$, $—CH_2SO_2NHR^{22}$, $—CH_2SO_2N(R^{22})_2$, $—SO_2NH_2$, $—SO_2NHR^{22}$, $—SO_2N(R^{22})_2$, $—NHSO_2R^{22}$, $—SO_2R^{22}$, $—CH_2SO_2R^{22}$, $—CH_2NH_2$, $—CH_2NHR^{22}$, $—CH_2N(R^{22})_2$, $—C(O)R^{22}$,

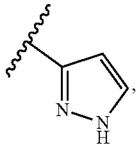, 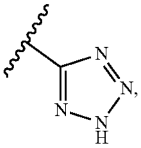

$—CH(OH)R^{22}$, $—C(OH)(R^{22})_2$, $—CH(NH_2)(R^{22})$, $—CH(NHR^{22})(R^{22})$, $—CH(N(R^{22})_2)(R^{22})$, pyrazol-3-yl, or pyrazol-4-yl, where at least one $R^{17}$ represents a moiety selected from $—CO_2H$, $—CONH_2$, $—CH_2OH$, —CN, $—C(O)CH_3$, $—CH(OH)CH_3$, $—C(OH)(CH_3)_2$, $—C(O)CF_3$, $—CH(NH_2)CF_3$, $—SO_2CH_3$, $—SO_2NH_2$ and

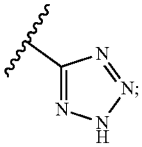 [SMILES: *c1nn[nH]n1];

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide; and $R^{22}$, independently for each occurrence, is selected from lower alkyl and cycloalkyl; wherein at least one $R^{16}$ or one $R^{17}$ is not H.

In some embodiments of any of the foregoing aspects, the small molecule ALK2 inhibitor or a pharmaceutically acceptable salt thereof is a compound of Formula II, wherein X and Y are each N;

Z is $CR^{3'}$;

Ar is a substituted or unsubstituted aryl ring or a substituted or unsubstituted heteroaryl ring;

$L_1$ is absent or

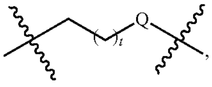, wherein Q is selected from $CR^{10'}R^{11}$, $NR^{12}$, O, S, S(O), and $SO_2$; $R^{10'}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and t is selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and J and K are both absent or, independently for each occurrence, are each $CR^{16}$;

A and B, independently for each occurrence, are $CR^{16}$;

E is $CR^{17}$;

if J and K are absent, then G and M are each independently $R^{16}$; if J and K are not absent, then G and M are each independently $CR^{17}$;

$R^{3'}$ is H;

$R^7$ is

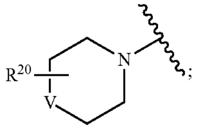

V is $NR^{30}$;

$R^{20}$ is absent or represents from 1-6 substituents on the ring to which it is attached, independently selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, sulfonamide, tetrazolyl, or trifluoromethylacyl;

$R^{17}$, independently for each occurrence, is selected from $R^{16}$ and H, $—CO_2H$, $—CONH_2$, $—CONHCH_3$, $—CON(CH_3)_2$, $—C(NH_2)═N(OH)$, $—C(NH_2)═NH$, $—CN$, $—CH_2OH$, $—SO_2NH_2$, $—CH_2NH_2$, $—C(O)CH_3$,

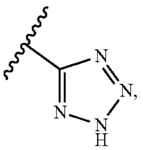 [SMILES: *c1nn[nH]n1]

$—CH(OH)CH_3$, $—C(O)CF_3$, and $—OCH_3$, provided that at least one $R^{17}$ is H, $—CO_2H$, $—CONH_2$, $—CONHCH_3$, $—CON(CH_3)_2$, $—C(NH_2)═N(OH)$, $—C(NH_2)═NH$, $—CN$, $—CH_2OH$, $—SO_2NH_2$, $—CH_2NH_2$, $—C(O)CH_3$,

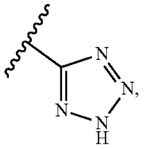 [SMILES: *c1nn[nH]n1]

$—CH(OH)CH_3$, or $—C(O)CF_3$; and $R^{30}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide;

wherein at least one $R^{16}$ or one $R^{17}$ is not H.

In some embodiments of any of the foregoing aspects, the small molecule ALK2 inhibitor or a pharmaceutically acceptable salt thereof is a compound of Formula II or a pharmaceutically acceptable salt thereof, wherein X and Y are independently selected from $CR^{15}$ and N, preferably both N;

Z is selected from $CR^{3'}$ and N, preferably $CR^{3'}$, most preferably CH;

Ar is a substituted or unsubstituted aryl ring (e.g., a substituted or unsubstituted phenyl ring) or a substituted or unsubstituted heteroaryl ring (e.g., a pyridyl or pyrimidyl ring);

$L_1$ is absent or selected from substituted or unsubstituted alkyl and heteroalkyl; and J and K are both absent or, independently for each occurrence, are each $CR^{16}$;

A and B, independently for each occurrence, are $CR^{16}$;

E is $CR^{17}$;

if J and K are absent, then G and M are each independently $R^{16}$; if J and K are not absent, then G and M are each independently $CR^{17}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from

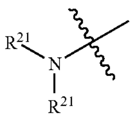

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, D, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, sulfonamide, tetrazolyl, or trifluoromethylacyl;

$R^{17}$, independently for each occurrence, is selected from $R^{16}$ and H, D, —$CO_2H$, —$CONH_2$, —$CONHCH_3$, —$CON(CH_3)_2$, —$C(NH_2)$=N(OH), —$C(NH_2)$=NH, —CN, —$CH_2OH$, —$SO_2NH_2$, —$CH_2NH_2$, —C(O)$CH_3$,

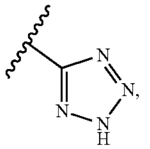 [SMILES: *c1nn[nH]n1]

—CH(OH)$CH_3$, —C(O)$CF_3$, and —$OCH_3$, provided that at least one $R^{17}$ is H, —$CO_2H$, —$CONH_2$, —$CONHCH_3$, —$CON(CH_3)_2$, —$C(NH_2)$=N(OH), —$C(NH_2)$=NH, —CN, —$CH_2OH$, —$SO_2NH_2$, —$CH_2NH_2$, —C(O)$CH_3$,

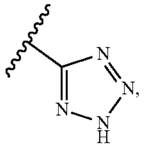 [SMILES: *c1nn[nH]n1]

—CH(OH)$CH_3$, —C(O)$CF_3$, or —$OCH_3$;

and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide.

In some embodiments of any of the foregoing aspects, the small molecule ALK2 inhibitor or a pharmaceutically acceptable salt thereof is a compound of Formula II or a pharmaceutically acceptable salt thereof, wherein X and Y are independently selected from $CR^{15}$ and N, preferably both N;

Z is selected from $CR^{3'}$ and N, preferably $CR^{3'}$, most preferably CH;

Ar is a phenyl ring substituted with at least one non-protium ($^1H$) substituent or a substituted or unsubstituted heteroaryl ring;

$L_1$ is absent or selected from substituted or unsubstituted alkyl and heteroalkyl; and G, J, K, and M are all absent or, independently for each occurrence, are selected from $CR^{16}$ and N;

A, B, and E, independently for each occurrence, are selected from $CR^{16}$ and N; provided that no more than three (and preferably no more than two) of A, B, E, G, J, K, and M are N, and at least one of E and M is N, and that if G, J, K, and M are absent then the carbon atom adjacent to E and M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and $R^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, or sulfonamide.

In some embodiments, the ALK2 inhibitor is a compound of Formula II or a pharmaceutically acceptable salt thereof, wherein X and Y are independently selected from $CR^{15}$ and N, preferably both N;

Z is selected from $CR^{3'}$ and N, preferably $CR^{3'}$, most preferably CH;

Ar is selected from substituted or unsubstituted aryl and heteroaryl;

$L_1$ is absent or selected from substituted or unsubstituted alkyl and heteroalkyl; and G, J, K, and M are all absent or, independently for each occurrence, are selected from $CR^{16}$ and N;

A, B, and E, independently for each occurrence, are selected from $CR^{16}$ and N;

provided that no more than three (and preferably no more than two) of A, B, E, G, J, K, and M are N, and at least one of E and M is N, and that if G, J, K, and M are absent then the carbon atom adjacent to E and M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and $R^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide;

wherein B is C—$R^{25}$ when E is N or K is C—$R^{25}$ when M is N or both such that at least one of B and K is C—$R^{25}$, where $R^{25}$ is selected from deuterium, halogen (preferably fluorine or chlorine), hydroxyl, lower alkyl (preferably methyl), and lower alkoxy (preferably methoxy), such as deuterium, fluorine, chlorine, methyl, ethyl, hydroxy, or methoxy.

In some embodiments of the compound of Formula II,

X and Y are independently selected from $CR^{15}$ and N;

Z is selected from $CR^{3'}$ and N;

Ar is selected from substituted or unsubstituted aryl and heteroaryl;

$L_1$ is absent or selected from substituted or unsubstituted alkyl and heteroalkyl;

G, J, K, and M are all absent or, independently for each occurrence, are selected from $CR^{16}$ and N;

A, B, and E, independently for each occurrence, are selected from $CR^{16}$ and N;

provided that:

no more than three of A, B, E, G, J, K, and M are N, at least one of E and M is N, and that if G, J, K, and M are absent, then the carbon atom drawn as connected to variable M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, and sulfonamido;

$R^7$ is selected from hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, and sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, and sulfonamido; and $R^{16}$, independently for each occurrence, is absent or is selected from H, OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide; provided that:

i) if Ar is a phenyl ring, it is substituted with at least one non-protium ($^1H$) substituent;

ii) B is C—$R^{25}$ when E is N, or K is C—$R^{25}$ when M is N, or both, such that at least one of B and K is C—$R^{25}$, wherein $R^{25}$ is selected from deuterium, halogen, hydroxyl, lower alkyl, and lower alkoxy; and/or iii) $R^7$ is

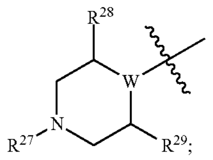

W is N, CH, or $CCH_3$;

$R^{27}$ is selected from H and substituted or unsubstituted alkyl, acyl, and ester; and $R^{28}$ and $R^{29}$ are each independently H or alkyl, or $R^{28}$ forms a one- or two-carbon bridge to the carbon atom adjacent to $R^{29}$ and $NR^{27}$; wherein either W is CH or $CCH_3$, or $R^{28}$ and $R^{29}$ are not both H.

In some embodiments, the compound of Formula II has a structure of any one of Formulas II-1 to II-275 or is a pharmaceutically acceptable salt thereof. In some embodiments, the compound of Formula II has the structure of Formula II-1. In some embodiments, the compound of Formula II has the structure of Formula II-2. In some embodiments, the compound of Formula II has the structure of Formula II-3. In some embodiments, the compound of Formula II has the structure of Formula II-4. In some embodiments, the compound of Formula II has the structure of Formula II-5. In some embodiments, the compound of Formula II has the structure of Formula II-6. In some embodiments, the compound of Formula II has the structure of Formula II-7. In some embodiments, the compound of Formula II has the structure of Formula II-8. In some embodiments, the compound of Formula II has the structure of Formula II-9. In some embodiments, the compound of Formula II has the structure of Formula II-10. In some embodiments, the compound of Formula II has the structure of Formula II-11. In some embodiments, the compound of Formula II has the structure of Formula II-12. In some embodiments, the compound of Formula II has the structure of Formula II-13. In some embodiments, the compound of Formula II has the structure of Formula II-14. In some embodiments, the compound of Formula II has the structure of Formula II-15. In some embodiments, the compound of Formula II has the structure of Formula II-16. In some embodiments, the compound of Formula II has the structure of Formula II-17. In some embodiments, the compound of Formula II has the structure of Formula II-18. In some embodiments, the compound of Formula II has the structure of Formula II-19. In some embodiments, the compound of Formula II has the structure of Formula II-20. In some embodiments, the compound of Formula II has the structure of Formula II-21. In some embodiments, the compound of Formula II has the structure of Formula II-22. In some embodiments, the compound of Formula II has the structure of Formula II-23. In some embodiments, the compound of Formula II has the structure of Formula II-24. In some embodiments, the compound of Formula II has the structure of Formula II-25. In some embodiments, the compound of Formula II has the structure of Formula II-26. In some embodiments, the compound of Formula II has the structure of Formula II-27. In some embodiments, the compound of Formula II has the structure of Formula II-28. In some embodiments, the compound of Formula II has the structure of Formula II-29. In some embodiments, the compound of Formula II has the structure of Formula II-30. In some embodiments, the compound of Formula II has the structure of Formula II-31. In some embodiments, the compound of Formula II has the structure of Formula II-32. In some embodiments, the compound of Formula II has the structure of Formula II-33. In some embodiments, the compound of Formula II has the structure of Formula II-34. In some embodiments, the compound of Formula II has the structure of Formula II-35. In some embodiments, the compound of Formula II has the structure of Formula II-36. In some embodiments, the compound of Formula II has the structure of Formula II-37. In some embodiments, the compound of Formula II has the structure of Formula II-38. In some embodiments, the compound of Formula II has the structure of Formula II-39. In some embodiments, the compound of Formula II has the structure of Formula II-40. In some embodiments, the compound of Formula II has the structure of Formula II-41. In some embodiments, the compound of Formula II has the structure of Formula II-42. In some embodiments, the compound of Formula II has the structure of Formula II-43. In some embodiments, the compound of Formula II has the structure of Formula II-44. In some embodiments, the compound of Formula II has the structure of Formula II-45. In some embodiments, the compound of Formula II has the structure of Formula II-46. In some embodiments, the compound of Formula II has the structure of Formula II-47. In some embodiments, the compound of Formula II has the structure of Formula II-48. In some embodiments, the compound of Formula II has the structure of Formula II-49. In some embodiments, the compound of Formula II has the structure of Formula II-50. In some embodiments, the compound of Formula II has the structure of Formula II-51a. In some embodiments, the compound of Formula II has the structure of Formula II-51b.

In some embodiments, the compound of Formula II has the structure of Formula II-52. In some embodiments, the compound of Formula II has the structure of Formula II-53. In some embodiments, the compound of Formula II has the structure of Formula II-54. In some embodiments, the compound of Formula II has the structure of Formula II-55. In some embodiments, the compound of Formula II has the structure of Formula II-56. In some embodiments, the compound of Formula II has the structure of Formula II-57. In some embodiments, the compound of Formula II has the structure of Formula II-58. In some embodiments, the compound of Formula II has the structure of Formula II-59. In some embodiments, the compound of Formula II has the structure of Formula II-60. In some embodiments, the compound of Formula II has the structure of Formula II-61. In some embodiments, the compound of Formula II has the structure of Formula II-62. In some embodiments, the compound of Formula II has the structure of Formula II-63. In some embodiments, the compound of Formula II has the structure of Formula II-64. In some embodiments, the compound of Formula II has the structure of Formula II-65. In some embodiments, the compound of Formula II has the structure of Formula II-66. In some embodiments, the compound of Formula II has the structure of Formula II-67. In some embodiments, the compound of Formula II has the structure of Formula II-68. In some embodiments, the compound of Formula II has the structure of Formula II-69. In some embodiments, the compound of Formula II has the structure of Formula II-70. In some embodiments, the compound of Formula II has the structure of Formula II-71. In some embodiments, the compound of Formula II has the structure of Formula II-72. In some embodiments, the compound of Formula II has the structure of Formula II-73. In some embodiments, the compound of Formula II has the structure of Formula II-74. In some embodiments, the compound of Formula II has the structure of Formula II-75. In some embodiments, the compound of Formula II has the structure of Formula II-76. In some embodiments, the compound of Formula II has the structure of Formula II-77. In some embodiments, the compound of Formula II has the structure of Formula II-78. In some embodiments, the compound of Formula II has the structure of Formula II-79. In some embodiments, the compound of Formula II has the structure of Formula II-80. In some embodiments, the compound of Formula II has the structure of Formula II-81. In some embodiments, the compound of Formula II has the structure of Formula II-82. In some embodiments, the compound of Formula II has the structure of Formula II-83. In some embodiments, the compound of Formula II has the structure of Formula II-84. In some embodiments, the compound of Formula II has the structure of Formula II-85. In some embodiments, the compound of Formula II has the structure of Formula II-86. In some embodiments, the compound of Formula II has the structure of Formula II-87. In some embodiments, the compound of Formula II has the structure of Formula II-88. In some embodiments, the compound of Formula II has the structure of Formula II-89. In some embodiments, the compound of Formula II has the structure of Formula II-90. In some embodiments, the compound of Formula II has the structure of Formula II-91. In some embodiments, the compound of Formula II has the structure of Formula II-92. In some embodiments, the compound of Formula II has the structure of Formula II-93. In some embodiments, the compound of Formula II has the structure of Formula II-94. In some embodiments, the compound of Formula II has the structure of Formula II-95. In some embodiments, the compound of Formula II has the structure of Formula II-96. In some embodiments, the compound of Formula II has the structure of Formula II-97. In some embodiments, the compound of Formula II has the structure of Formula II-98. In some embodiments, the compound of Formula II has the structure of Formula II-99. In some embodiments, the compound of Formula II has the structure of Formula II-100. In some embodiments, the compound of Formula II has the structure of Formula II-101. In some embodiments, the compound of Formula II has the structure of Formula II-102. In some embodiments, the compound of Formula II has the structure of Formula II-103. In some embodiments, the compound of Formula II has the structure of Formula II-104. In some embodiments, the compound of Formula II has the structure of Formula II-105. In some embodiments, the compound of Formula II has the structure of Formula II-106. In some embodiments, the compound of Formula II has the structure of Formula II-107. In some embodiments, the compound of Formula II has the structure of Formula II-108. In some embodiments, the compound of Formula II has the structure of Formula II-109. In some embodiments, the compound of Formula II has the structure of Formula II-110. In some embodiments, the compound of Formula II has the structure of Formula I-111. In some embodiments, the compound of Formula II has the structure of Formula II-112. In some embodiments, the compound of Formula II has the structure of Formula II-113. In some embodiments, the compound of Formula II has the structure of Formula II-114. In some embodiments, the compound of Formula II has the structure of Formula II-115. In some embodiments, the compound of Formula II has the structure of Formula II-116. In some embodiments, the compound of Formula II has the structure of Formula II-117. In some embodiments, the compound of Formula II has the structure of Formula II-118. In some embodiments, the compound of Formula II has the structure of Formula II-119. In some embodiments, the compound of Formula II has the structure of Formula II-120. In some embodiments, the compound of Formula II has the structure of Formula II-121. In some embodiments, the compound of Formula II has the structure of Formula II-122. In some embodiments, the compound of Formula II has the structure of Formula II-123. In some embodiments, the compound of Formula II has the structure of Formula II-124. In some embodiments, the compound of Formula II has the structure of Formula II-125. In some embodiments, the compound of Formula II has the structure of Formula II-126. In some embodiments, the compound of Formula II has the structure of Formula II-127. In some embodiments, the compound of Formula II has the structure of Formula II-128. In some embodiments, the compound of Formula II has the structure of Formula II-129. In some embodiments, the compound of Formula II has the structure of Formula II-130. In some embodiments, the compound of Formula II has the structure of Formula II-131. In some embodiments, the compound of Formula II has the structure of Formula II-132. In some embodiments, the compound of Formula II has the structure of Formula II-133. In some embodiments, the compound of Formula II has the structure of Formula II-134. In some embodiments, the compound of Formula II has the structure of Formula II-135. In some embodiments, the compound of Formula II has the structure of Formula II-136. In some embodiments, the compound of Formula II has the structure of Formula II-137. In some embodiments, the compound of Formula II has the structure of Formula II-138. In some embodiments, the compound of Formula II has the structure of Formula II-139. In some embodiments, the compound of Formula II has the structure of Formula II-140. In some embodiments, the compound of Formula II has the structure of Formula II-141. In some embodiments, the compound of Formula II has the structure of Formula II-142. In some embodiments, the compound of Formula II has the structure of Formula II-143. In some embodiments, the compound of Formula II has the structure of Formula II-144. In some embodiments, the compound of Formula II has the structure of Formula II-145. In some embodiments, the compound of Formula II has the structure of Formula II-146. In some embodiments, the compound of Formula II has the structure of Formula II-147. In some embodiments, the compound of Formula II has the structure of Formula II-148. In some embodiments, the compound of Formula II has the structure of Formula II-149. In some embodiments, the compound of Formula II has the structure of Formula II-150. In some embodiments, the compound of Formula II has the structure of Formula II-151. In some embodiments, the compound of Formula II has the structure of Formula II-152. In some embodiments, the compound of Formula II has the structure of Formula II-153. In some embodiments, the compound of Formula II has the structure of Formula II-154. In some embodiments, the compound of Formula II has the structure of Formula II-155. In some embodiments, the compound of Formula II has the structure of Formula II-156. In some embodiments, the compound of Formula II has the structure of Formula II-157. In some embodiments, the compound of Formula II has the structure of Formula II-158. In some embodiments, the compound of Formula II has the structure of Formula II-159. In some embodiments, the compound of Formula II has the structure of Formula II-160. In some embodiments, the compound of Formula II has the structure of Formula II-161. In some embodiments, the compound of Formula II has the structure of Formula II-162. In some embodiments, the compound of Formula II has the structure of Formula II-163. In some embodiments, the compound of Formula II has the structure of Formula II-164. In some embodiments, the compound of Formula II has the structure of Formula II-165. In some embodiments, the compound of Formula II has the structure of Formula II-166. In some embodiments, the compound of Formula II has the structure of Formula II-167. In some embodiments, the compound of Formula II has the structure of Formula II-168. In some embodiments, the compound of Formula II has the structure of Formula II-169. In some embodiments, the compound of Formula II has the structure of Formula II-170. In some embodiments, the compound of Formula II has the structure of Formula II-171. In some embodiments, the compound of Formula II has the structure of Formula II-172. In some embodiments, the compound of Formula II has the structure of Formula II-173. In some embodiments, the compound of Formula II has the structure of Formula II-174. In some embodiments, the compound of Formula II has the structure of Formula II-175. In some embodiments, the compound of Formula II has the structure of Formula II-176. In some embodiments, the compound of Formula II has the structure of Formula II-177. In some embodiments, the compound of Formula II has the structure of Formula II-178. In some embodiments, the compound of Formula II has the structure of Formula II-179. In some embodiments, the compound of Formula II has the structure of Formula II-180. In some embodiments, the compound of Formula II has the structure of Formula II-181. In some embodiments, the compound of Formula II has the structure of Formula II-182. In some embodiments, the compound of Formula II has the structure of Formula II-183. In some embodiments, the compound of Formula II has the structure of Formula II-184. In some embodiments, the compound of Formula II has the structure of Formula II-185. In some embodiments, the compound of Formula II has the structure of Formula II-186. In some embodiments, the compound of Formula II has the structure of Formula II-187. In some embodiments, the compound of Formula II has the structure of Formula II-188. In some embodiments, the compound of Formula II has the structure of Formula II-189. In some embodiments, the compound of Formula II has the structure of Formula II-190. In some embodiments, the compound of Formula II has the structure of Formula II-191. In some embodiments, the compound of Formula II has the structure of Formula II-192. In some embodiments, the compound of Formula II has the structure of Formula II-193. In some embodiments, the compound of Formula II has the structure of Formula II-194. In some embodiments, the compound of Formula II has the structure of Formula II-195. In some embodiments, the compound of Formula II has the structure of Formula II-196. In some embodiments, the compound of Formula II has the structure of Formula II-197. In some embodiments, the compound of Formula II has the structure of Formula II-198. In some embodiments, the compound of Formula II has the structure of Formula II-199. In some embodiments, the compound of Formula II has the structure of Formula II-200. In some embodiments, the compound of Formula II has the structure of Formula II-201. In some embodiments, the compound of Formula II has the structure of Formula II-202. In some embodiments, the compound of Formula II has the structure of Formula II-203. In some embodiments, the compound of Formula II has the structure of Formula II-204. In some embodiments, the compound of Formula II has the structure of Formula II-205. In some embodiments, the compound of Formula II has the structure of Formula II-206. In some embodiments, the compound of Formula II has the structure of Formula II-207. In some embodiments, the compound of Formula II has the structure of Formula II-208. In some embodiments, the compound of Formula II has the structure of Formula II-209. In some embodiments, the compound of Formula II has the structure of Formula II-210. In some embodiments, the compound of Formula II has the structure of Formula II-211. In some embodiments, the compound of Formula II has the structure of Formula II-212. In some embodiments, the compound of Formula II has the structure of Formula II-213. In some embodiments, the compound of Formula II has the structure of Formula II-214. In some embodiments, the compound of Formula II has the structure of Formula II-215. In some embodiments, the compound of Formula II has the structure of Formula II-216. In some embodiments, the compound of Formula II has the structure of Formula II-217. In some embodiments, the compound of Formula II has the structure of Formula II-218. In some embodiments, the compound of Formula II has the structure of Formula II-219. In some embodiments, the compound of Formula II has the structure of Formula II-220. In some embodiments, the compound of Formula II has the structure of Formula II-221. In some embodiments, the compound of Formula II has the structure of Formula II-222. In some embodiments, the compound of Formula II has the structure of Formula II-223. In some embodiments, the compound of Formula II has the structure of Formula II-224. In some embodiments, the compound of Formula II has the structure of Formula II-225. In some embodiments, the compound of Formula II has the structure of Formula II-226. In some embodiments, the compound of Formula II has the structure of Formula II-227.

In some embodiments, the compound of Formula II has the structure of Formula II-228. In some embodiments, the compound of Formula II has the structure of Formula II-229. In some embodiments, the compound of Formula II has the structure of Formula II-230. In some embodiments, the compound of Formula II has the structure of Formula II-231. In some embodiments, the compound of Formula II has the structure of Formula II-232. In some embodiments, the compound of Formula II has the structure of Formula II-233. In some embodiments, the compound of Formula II has the structure of Formula II-234. In some embodiments, the compound of Formula II has the structure of Formula II-235. In some embodiments, the compound of Formula II has the structure of Formula II-236. In some embodiments, the compound of Formula II has the structure of Formula II-237. In some embodiments, the compound of Formula II has the structure of Formula II-238. In some embodiments, the compound of Formula II has the structure of Formula II-239. In some embodiments, the compound of Formula II has the structure of Formula II-240. In some embodiments, the compound of Formula II has the structure of Formula II-241. In some embodiments, the compound of Formula II has the structure of Formula II-242. In some embodiments, the compound of Formula II has the structure of Formula II-243. In some embodiments, the compound of Formula II has the structure of Formula II-244. In some embodiments, the compound of Formula II has the structure of Formula II-245. In some embodiments, the compound of Formula II has the structure of Formula II-246. In some embodiments, the compound of Formula II has the structure of Formula II-247. In some embodiments, the compound of Formula II has the structure of Formula II-248. In some embodiments, the compound of Formula II has the structure of Formula II-249. In some embodiments, the compound of Formula II has the structure of Formula II-250. In some embodiments, the compound of Formula II has the structure of Formula II-251. In some embodiments, the compound of Formula II has the structure of Formula II-252. In some embodiments, the compound of Formula II has the structure of Formula II-253. In some embodiments, the compound of Formula II has the structure of Formula II-254. In some embodiments, the compound of Formula II has the structure of Formula II-255. In some embodiments, the compound of Formula II has the structure of Formula II-256. In some embodiments, the compound of Formula II has the structure of Formula II-257. In some embodiments, the compound of Formula II has the structure of Formula II-258. In some embodiments, the compound of Formula II has the structure of Formula II-259. In some embodiments, the compound of Formula II has the structure of Formula II-260. In some embodiments, the compound of Formula II has the structure of Formula II-261. In some embodiments, the compound of Formula II has the structure of Formula II-262. In some embodiments, the compound of Formula II has the structure of Formula II-263. In some embodiments, the compound of Formula II has the structure of Formula II-264. In some embodiments, the compound of Formula II has the structure of Formula II-265. In some embodiments, the compound of Formula II has the structure of Formula II-266. In some embodiments, the compound of Formula II has the structure of Formula II-267. In some embodiments, the compound of Formula II has the structure of Formula II-268. In some embodiments, the compound of Formula II has the structure of Formula II-269. In some embodiments, the compound of Formula II has the structure of Formula II-270. In some embodiments, the compound of Formula II has the structure of Formula II-271. In some embodiments, the compound of Formula II has the structure of Formula II-272. In some embodiments, the compound of Formula II has the structure of Formula II-273. In some embodiments, the compound of Formula II has the structure of Formula II-274. In some embodiments, the compound of Formula II has the structure of Formula II-275.

In some embodiments of any of the foregoing aspects, the small molecule ALK2 inhibitor or a pharmaceutically acceptable salt thereof is a compound of Formula III:

Formula III

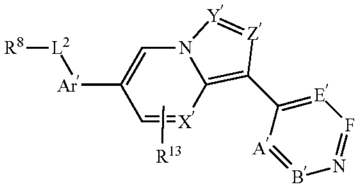

or a pharmaceutically acceptable salt thereof, wherein

X is selected from $CR^{15'}$ and N;

Y' is selected from $CR^{15'}$ and N;

Z' is selected from $CR^{26}$ and N;

Ar' is selected from substituted or unsubstituted aryl and heteroaryl, e.g., a six-membered ring, such as phenyl;

$L_2$ is absent or selected from substituted or unsubstituted alkyl and heteroalkyl;

A and B, independently for each occurrence, are selected from $CR^{16'}$ and N, preferably $CR^{16'}$, e.g., CH;

E and F, independently for each occurrence, are selected from $CR^{5'}$ and N, preferably $CR^{5'}$; preferably chosen such that no more than two of A, B, E, and F are N;

$R^{26}$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;

$R^8$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;

$R^{5'}$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^{5'}$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;

$R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano;

$R^{15}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;

$R^{16'}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In some embodiments, the compound of Formula III has a structure of Formula III-a:

Formula III-a

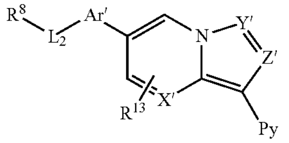

or a pharmaceutically acceptable salt thereof, wherein

X is selected from $CR^{15'}$ and N;

Y' is selected from $CR^{15'}$ and N;

Z' is selected from $CR^{26}$ and N;

Ar' is selected from substituted or unsubstituted aryl and heteroaryl, e.g., a six-membered ring, such as phenyl;

$L_2$ is absent or selected from substituted or unsubstituted alkyl and heteroalkyl;

Py is substituted or unsubstituted 4-pyridinyl or 4-quinolinyl, e.g., optionally substituted with substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, amino, acylamino, carbamate, amido, amidino, cyano, sulfonyl, sulfoxido, sulfamoyl, or sulfonamido; and $R^{26}$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;

$R^8$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;

$R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^{26}$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;

$R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano;

$R^{15'}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;

$R^{16'}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In some embodiments, the compound of Formula III has a structure of Formula III-b:

Formula III-b

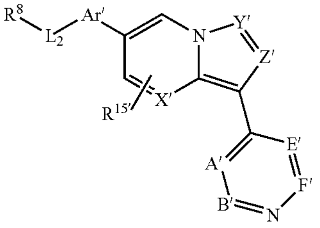

or a pharmaceutically acceptable salt thereof, wherein

X' and Y' are each N;

Z' is $CR^{26}$;

Ar' is substituted or unsubstituted phenyl;

$L_2$ is absent or selected from substituted or unsubstituted alkyl and heteroalkyl;

A' and B' are both $CR^{16'}$;

E' and F' are both $CR^{5'}$ and both occurrences of $R^{5'}$ taken together with E' and F' form a substituted or unsubstituted 5- or 6-membered cycloalkyl, heterocycloalkyl, aryl, or heteroaryl ring;

$R^{26}$ is selected from H and substituted or unsubstituted alkyl;

$R^8$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;

$R^{15'}$, independently for each occurrence, is selected from H and substituted or unsubstituted alkyl, cycloalkyl, heterocyclyl, cycloalkylalkyl, heterocyclylalkyl, halogen, acylamino, carbamate, cyano, sulfonyl, sulfoxido, sulfamoyl, or sulfonamido; and $R^{16'}$, independently for each occurrence, is absent or is selected from H and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In some embodiments, the compound of Formula III has a structure of Formula III-b, or a pharmaceutically acceptable salt thereof, wherein X' and Y' are each N;

Z' is $CR^{26}$;

Ar' is selected from substituted or unsubstituted aryl and heteroaryl;

$L_2$ is absent or selected from substituted or unsubstituted alkyl and heteroalkyl;

A' and B' are both $CR^{16}$;

E' and F' are both $CR^{5'}$ and both occurrences of $R^{5'}$ taken together with E' and F' form a substituted or unsubstituted 5- or 6-membered cycloalkyl, heterocycloalkyl, aryl, or heteroaryl ring;

$R^{26}$ is selected from H and substituted or unsubstituted alkyl;

$R^8$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H and substituted or unsubstituted alkyl, cycloalkyl, heterocyclyl, cycloalkylalkyl, heterocyclylalkyl, halogen, acylamino, carbamate, cyano, sulfonyl, sulfoxido, sulfamoyl, or sulfonamido;

$R^{16'}$, independently for each occurrence, is absent or is selected from H and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In some embodiments, the compound of Formula III has a structure of any one of Formulas III-1 to III-35 or is a pharmaceutically acceptable salt thereof. In some embodiments, the compound of Formula III has the structure of Formula III-1. In some embodiments, the compound of Formula III has the structure of Formula III-2. In some embodiments, the compound of Formula III has the structure of Formula III-3. In some embodiments, the compound of Formula III has the structure of Formula III-4. In some embodiments, the compound of Formula III has the structure of Formula III-5. In some embodiments, the compound of Formula III has the structure of Formula III-6. In some embodiments, the compound of Formula III has the structure of Formula III-7. In some embodiments, the compound of Formula III has the structure of Formula III-8. In some embodiments, the compound of Formula III has the structure of Formula III-9. In some embodiments, the compound of Formula III has the structure of Formula III-10. In some embodiments, the compound of Formula III has the structure of Formula III-11.

In some embodiments, the compound of Formula III has the structure of Formula III-12. In some embodiments, the compound of Formula III has the structure of Formula III-13. In some embodiments, the compound of Formula III has the structure of Formula III-14. In some embodiments, the compound of Formula III has the structure of Formula III-15. In some embodiments, the compound of Formula III has the structure of Formula III-16. In some embodiments, the compound of Formula III has the structure of Formula III-17. In some embodiments, the compound of Formula III has the structure of Formula III-18. In some embodiments, the compound of Formula III has the structure of Formula III-19. In some embodiments, the compound of Formula III has the structure of Formula III-20. In some embodiments, the compound of Formula III has the structure of Formula III-21. In some embodiments, the compound of Formula III has the structure of Formula III-22. In some embodiments, the compound of Formula III has the structure of Formula III-23. In some embodiments, the compound of Formula III has the structure of Formula III-24. In some embodiments, the compound of Formula III has the structure of Formula III-25. In some embodiments, the compound of Formula III has the structure of Formula III-26. In some embodiments, the compound of Formula III has the structure of Formula III-27. In some embodiments, the compound of Formula III has the structure of Formula III-28. In some embodiments, the compound of Formula III has the structure of Formula III-29. In some embodiments, the compound of Formula III has the structure of Formula III-30. In some embodiments, the compound of Formula III has the structure of Formula III-31. In some embodiments, the compound of Formula III has the structure of Formula III-32. In some embodiments, the compound of Formula III has the structure of Formula III-33. In some embodiments, the compound of Formula III has the structure of Formula III-34. In some embodiments, the compound of Formula III has the structure of Formula III-35.

In some embodiments of any of the foregoing aspects, the small molecule ALK2 inhibitor or a pharmaceutically acceptable salt thereof is Compound 1:

(Compound 1)

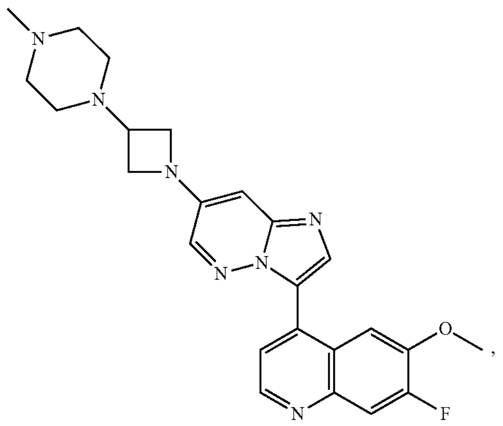

or a pharmaceutically acceptable salt thereof.

In some embodiments of any of the foregoing aspects, the small molecule ALK2 inhibitor or a pharmaceutically acceptable salt thereof is Compound 2:

(Compound 2)

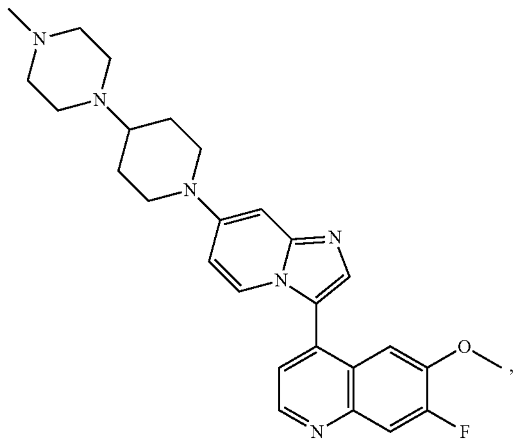

or a pharmaceutically acceptable salt thereof.

In some embodiments of any of the foregoing aspects, the small molecule ALK2 inhibitor or a pharmaceutically acceptable salt thereof is Compound 3:

(Compound 3)

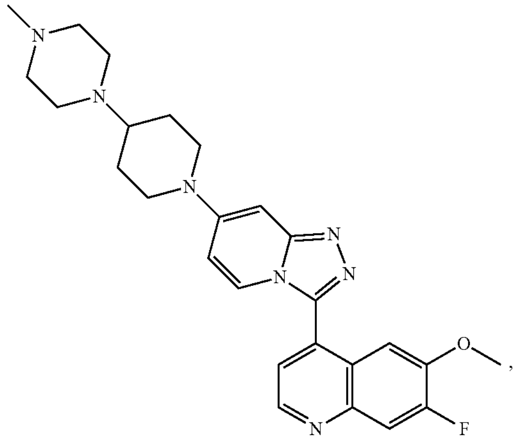

or a pharmaceutically acceptable salt thereof.

In some embodiments of any of the foregoing aspects, the small molecule ALK2 inhibitor or a pharmaceutically acceptable salt thereof is Compound 4:

(Compound 4)

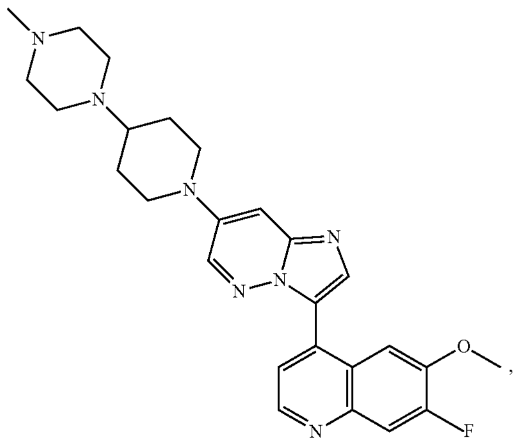

or a pharmaceutically acceptable salt thereof.

In some embodiments of any of the foregoing aspects, the small molecule ALK2 inhibitor or a pharmaceutically acceptable salt thereof is Compound 5:

(Compound 5)

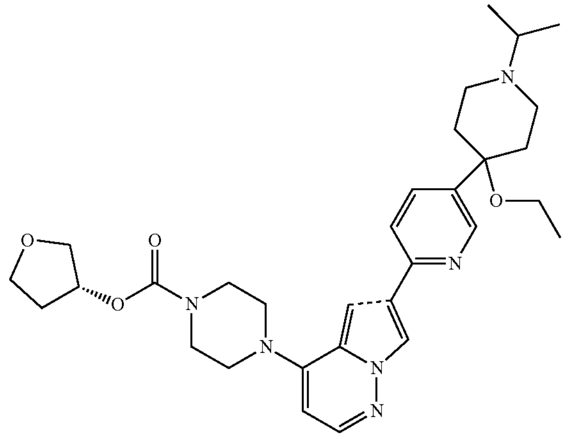

or a pharmaceutically acceptable salt thereof.

In some embodiments of any of the foregoing aspects, the small molecule ALK2 inhibitor or a pharmaceutically acceptable salt thereof is Compound 6:

(Compound 6)

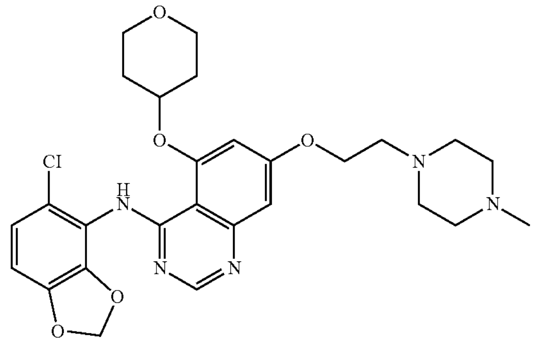

or a pharmaceutically acceptable salt thereof.

In some embodiments of any of the foregoing aspects, the small molecule ALK2 inhibitor or a pharmaceutically acceptable salt thereof is Compound 7:

(Compound 7)

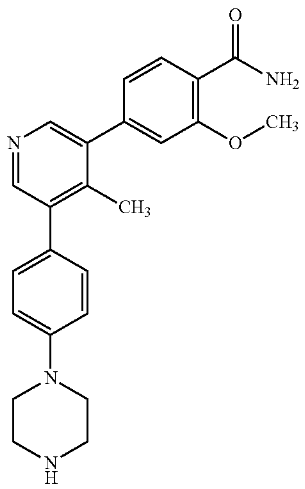

or a pharmaceutically acceptable salt thereof.

In some embodiments of any of the foregoing aspects, the small molecule ALK2 inhibitor or a pharmaceutically acceptable salt thereof is BCX9250 or a pharmaceutically acceptable salt thereof.

In some embodiments of any of the foregoing aspects, the small molecule ALK2 inhibitor or a pharmaceutically acceptable salt thereof is INCB00928 or a pharmaceutically acceptable salt thereof.

In some embodiments of any of the foregoing aspects, the compound of Formula I-11 is a crystalline compound having the structure of Formula I-11 or a salt thereof. In some embodiments, the crystalline compound has the structure of Formula I-11

(I-11)

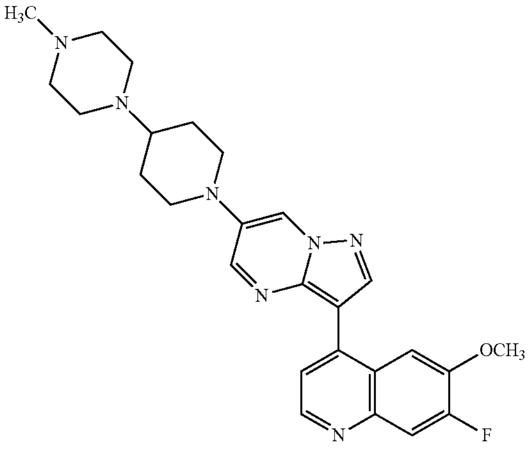

mono-succinate salt. In some embodiments, the compound is anhydrous. In some embodiments, the compound has 2θ values of about 7.05±0.2, 15.16±0.2, 21.05±0.2, 21.26±0.2, and 24.47±0.2. In some embodiments, the compound has 2θ values of about 3.58±0.2, 7.05±0.2, 13.8±0.2, 14.16±0.2, 15.16±0.2, 16.18±0.2, 16.80±0.2, 17.15±0.2, 17.69±0.2, 18.29±0.2, 18.84±0.2, 20.29±0.2, 21.05±0.2, 21.26±0.2, 22.68±0.2, 23.84±0.2, 24.47±0.2, 24.84±0.2, and 28.47±0.2. In some embodiments, the compound has 2θ values of about 3.58±0.2, 7.05±0.2, 10.59±0.2, 10.75±0.2, 13.80±0.2, 14.16±0.2, 15.16±0.2, 15.68±0.2, 16.18±0.2, 16.80±0.2, 17.15±0.2, 17.69±0.2, 17.97±0.2, 18.29±0.2, 18.59±0.2, 18.84±0.2, 19.27±0.2, 20.29±0.2, 21.05±0.2, 21.26±0.2, 21.56±0.22178±0.2, 22.68±0.2, 23.84±0.2, 24.47±0.2, 24.84±0.2, 25.15±0.2, 26.10±0.2, 27.12±0.2, 27.78±0.2, 28.47±0.2, and 29.06±0.2.

In some embodiments, the compound has 2θ values of about 9.79±0.2, 13.05±0.2, 22.91±0.2, 23.60±0.2, and 26.25±0.2. In some embodiments, the compound has 2θ values of about 3.25±0.2, 9.79±0.2, 13.05±0.2, 16.75±0.2, 19.50±0.2, 22.91±0.2, 23.60±0.2, and 26.25±0.2. In some embodiments, the compound has 2θ values of about 3.25±0.2, 9.79±0.2, 13.05±0.2, 13.61±0.2, 14.39±0.2, 16.75±0.2, 18.50±0.2, 19.50±0.2, 22.91±0.2, 23.60±0.2, and 26.25±0.2.

In some embodiments of any of the foregoing aspects, the compound of Formula I-11 is a crystalline compound having the structure of Formula I-11

(I-11)

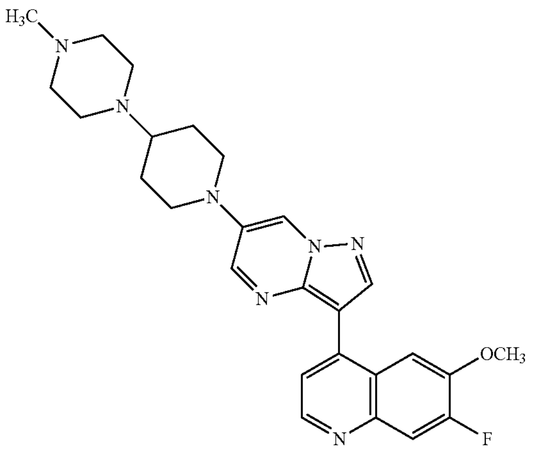

free base. In some embodiments, the compound has 2θ values of about 6.00±0.2, 12.00±0.2, 16.14±0.2, 17.72±0.2, 18.00±0.2, 18.64±0.2, and 23.50±0.2.

In some embodiments of any of the foregoing aspects, the compound of any one of Formulas I-III is administered in a pharmaceutical composition further including one or more pharmaceutically acceptable excipients.

BRIEF DESCRIPTION OF THE DRAWINGS

FIGS. 11A-11K are a series of graphs showing the effect of the compound of Formula I-42 on hemoglobin levels, hematocrit, red blood cell count, serum iron, and serum hepcidin in a mouse model of IRIDA. To establish a murine model of IRIDA, eight-week-old male C57BL/6 mice were dosed intravenously with lipid encapsulated siRNA targeted against either Luciferase (control) or TMPRSS6 (0.75 mg/kg). Following confirmation of disease at day 8 post initial siRNA administration, once-daily oral dosing with the compound of Formula I-42 (5 mg/kg) or vehicle commenced. A second siRNA administration was given on day 10. Studies were terminated 18 days post initial siRNA administration. TMPRSS6 expression was reduced by >80% within 24 hours of administration and knockdown was confirmed to persist through 10 days following injection (FIGS. 11A-11B). ** P<0.0001 via unpaired two-tail t-test. Eight days after siRNA administration, an 18.5% drop in serum iron, a 6.2% drop in both red blood cell counts and hemoglobin, and a 5.7% drop in hematocrit were observed in mice receiving TMPRSS6 siRNA compared to mice receiving control siRNA (FIGS. 11C-11F).  P<0.01 via unpaired two-tail t-test. At study termination, mice receiving TMPRSS6 siRNA in combination with the compound of Formula I-42 (ALK2 inhibitor) had an increase in hemoglobin levels, hematocrit, and red blood cell counts compared to vehicle-treated mice (FIGS. 11G-11I). Mice receiving TMPRSS6 siRNA in combination with the compound of Formula I-42 also exhibited decreased serum hepcidin and increased serum iron compared to vehicle-treated mice receiving TMPRSS6 siRNA (FIGS. 11J-11K). *P<0.05,  P<0.01, **P<0.0001 via two-way ANOVA. Data are shown as the mean±SEM.

DETAILED DESCRIPTION OF THE INVENTION

Figure 1:
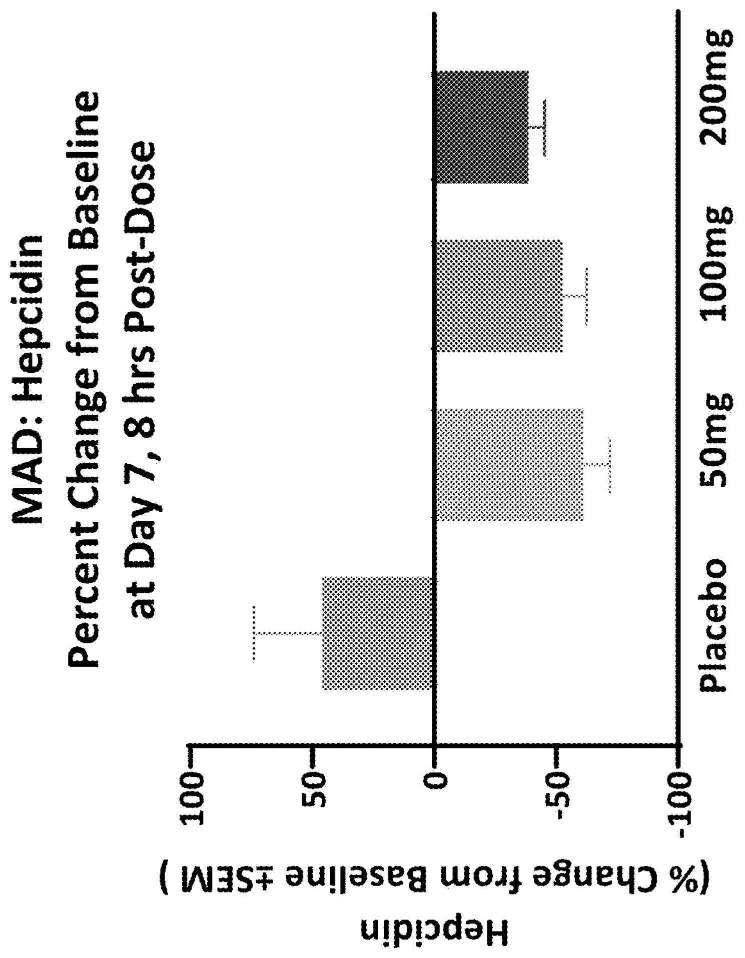
FIG. 1 is a graph showing the effect of the compound of Formula I-11 on serum hepcidin in healthy volunteers. Once-daily oral administration of the compound of Formula I-11 over 7 days resulted in robust decreases in baseline hepcidin when compared to placebo. The effect was similar at 50 mg, 100 mg, and 200 mg (hepcidin was not measured at 350 mg). The limited sampling scheme, variability of baseline serum hepcidin concentrations at Day 1, or limited dynamic range given normal hepcidin baseline levels may have precluded observation of dose- or exposure-related differences in hepcidin response.

The invention features methods of treating diseases or conditions in which BMP signaling is implicated using small molecule inhibitors. In some embodiments, the disease or condition is anemia resulting from iron imbalance. The ALK2 inhibitors described herein can treat anemia by increasing serum iron, increasing transferrin saturation, increasing iron bioavailability (e.g., by mobilizing iron from storage tissue), increasing reticulocyte hemoglobin, promoting the formation of hemoglobin-containing (e.g., hemoglobin-rich) red blood cells, reestablishing iron homeostasis, and/or reducing serum hepcidin. The ALK2 inhibitors described herein can also be used to treat multiple osteochondromas (MO).

ALK2 Inhibitors

In some embodiments, the ALK2 inhibitor for use in the methods and compositions described herein is a small molecule inhibitor of the BMP type I receptor ALK2, encoded by gene ACVR1.

In some embodiments, the ALK2 inhibitor is a compound of Formula I:

(Formula I)

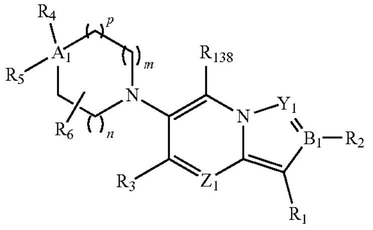

or a pharmaceutically acceptable salt thereof, wherein:

$R_1$ is hydrogen or an optionally substituted substituent;

$R_2$ is optionally absent, hydrogen, or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen or an optionally substituted substituent;

$R_6$ is independently one or more of hydrogen or an optionally substituted substituent; $B_1$, is C or N; $Y_1$ is N or $CR_{139}$, wherein $R_{139}$ is hydrogen or an optionally substituted substituent; $Z_1$ is N or $CR_{140}$, wherein $R_{140}$ is hydrogen or an optionally substituted substituent; $A_1$ is C, N, O, C(O), S, SO, or $SO_2$; m is 0, 1, 2, or 3; n is 0, 1, 2, or 3; and p is 0 or 1; wherein optionally any two or more of $R_4$, $R_5$, or $R_6$ may be joined together to form one or more rings.

Compounds of Formula I may be synthesized by methods known in the art, e.g., those described in US Patent Application Publication No. 2020/0179389, which is incorporated herein by reference.

In some embodiments, the compound of Formula I has a structure of Formula I-a:

(Formula I-a)

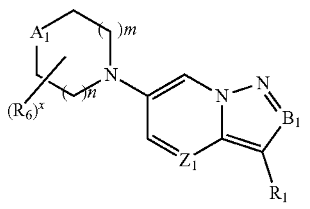

or a pharmaceutically acceptable salt thereof, wherein:

$A_1$ is $NR_{4a}$ or $CR_{4b}R_5$;

$B_1$ is N or $CR_2$;

$Z_1$ is N or $CR_3$;

$R_1$ is selected from cycloalkyl, aryl, heteroaryl, and heterocyclyl;

$R_2$ is H, CN, $NO_2$, alkyl, or amino;

$R_3$ is selected from H, CN, $NO_2$, alkyl, alkoxy, heterocyclyloxy, heteroaryloxy, aryloxy, cycloalkyloxy, carbonyl, amino, amido, sulfonyl, sulfonamido, cycloalkyl, aryl, heterocyclyl, and heteroaryl;

$R_{4a}$ is selected from alkyl, alkenyl, alkynyl, carbonyl, $O^-$, alkoxycarbonyl, cycloalkyl, aryl, heterocyclyl, and heteroaryl;

$R_{4b}$ is selected from halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl;

$R_5$ is selected from H, halo, hydroxy and alkyl, or $R_{4b}$ and $R_5$ together with $A_1$ form a ring selected from cycloalkyl and heterocyclyl;

each $R_6$ is independently selected from H, halo, CN, $NO_2$, hydroxy, alkyl, alkenyl, alkynyl, alkoxy, heterocyclyloxy, heteroaryloxy, aryloxy, cycloalkyloxy, amino, amido, carbonyl, alkoxycarbonyl, carboxy, sulfonyl, sulfonamido, thio, cycloalkyl, aryl, heterocyclyl, and heteroaryl and oxo;

n is 0 or 1;

m is 0 or 1; and x is 0, 1, 2, 3, or 4.

In some embodiments of the compound of Formula I-a, $A_1$ is $NR_{4a}$ or $CR_{4b}R_5$;

$B_1$ is N or $CR_2$;

$Z_1$ is N or $CR_3$;

$R_1$ is selected from aryl, heteroaryl, and heterocyclyl;

$R_2$ is H or amino;

$R_3$ is H or heterocyclyloxy;

$R_{4a}$ is selected from alkyl, $O^-$, aryl, heterocyclyl, and heteroaryl;

$R_{4b}$ is selected from alkyl, alkoxy, amino, aryl, heterocyclyl, and heteroaryl;

$R_5$ is selected from H and alkyl, or $R_{4b}$ and $R_5$ together with $A_1$ form a ring selected from cycloalkyl and heterocyclyl;

each $R_6$ is independently selected from H, halo, alkyl and oxo;

n is 0 or 1;

m is 0 or 1; and x is 0, 1, 2, 3, or 4.

In some embodiments of the compound of Formula I-a, $R_{4a}$ is selected from alkyl, $O^-$, heterocyclyl, and heteroaryl;

$R_{4b}$ is selected from alkyl, alkoxy, amino, amido, heterocyclyl, and heteroaryl;

$R_5$ is selected from H and alkyl, or $R_{4b}$ and $R_5$ together with $A_1$ form a heterocyclyl; and each $R_6$ is independently selected from H, halo, and alkyl; and x is 0 or 1.

In some embodiments of the compound of Formula I-a, $R_1$ is selected from H, aryl, 5-6 membered heteroaryl,

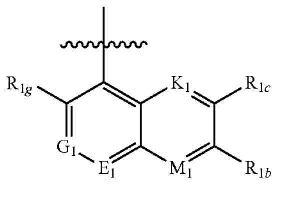

and

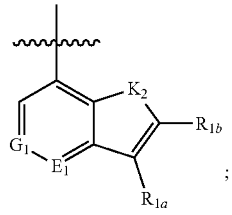

;

wherein:

each $E_1$ is independently selected from N and $CR_{1d}$;

each $G_1$ is independently selected from N and $CR_{1e}$;

$K_1$ is N or CH;

$K_2$ is NH or S;

$M_1$ is N or $CR_{1a}$;

$R_{1a}$ is selected from H, halo, alkyl, haloalkyl, and amido;

$R_{1b}$ is selected from H, halo, CN, alkyl, haloalkyl, hydroxy, alkoxy, and haloalkoxy;

$R_{1c}$ is selected from H, halo, CN, alkyl, haloalkyl, hydroxy, alkoxy, haloalkoxy, amino and amido, or $R_{1b}$ and $R_{1c}$ together with the carbon atoms to which they are attached form a heterocyclyl;

$R_{1d}$ is selected from H, CN, alkyl, haloalkyl, hydroxy, amido and sulfonamido;

$R_{1e}$ is selected from H, alkyl and amino; and $R_{1g}$ is H or halo.

In some embodiments of the compound of Formula I-a, $R_{4a}$ is selected from alkyl, $O^-$, heterocyclyl, and heteroaryl;

$R_{4b}$ is selected from alkyl, alkoxy, amino, amido, heterocyclyl, and heteroaryl;

$R_5$ is selected from H and alkyl, or $R_{4b}$ and $R_5$ together with $A_1$ form a heterocyclyl; and each $R_6$ is independently selected from H, halo, and alkyl; and x is 0 or 1.

In some embodiments, $R_1$ is selected from H, aryl, 5-6 membered heteroaryl,

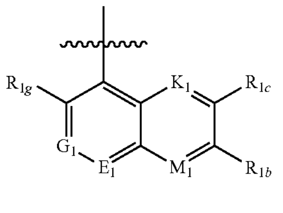

and

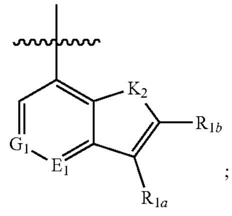

;

wherein:

each $E_1$ is independently selected from N and $CR_{1d}$;

each $G_1$ is independently selected from N and $CR_{1e}$;

$K_1$ is N or CH;

$K_2$ is NH or S;

$M_1$ is $CR_{1a}$;

$R_{1a}$ is selected from H and amido;

$R_{1b}$ is selected from H, halo, alkyl, and alkoxy;

$R_{1c}$ is selected from H, alkyl, and alkoxy, or $R_{1b}$ and $R_{1c}$ together with the carbon atoms to which they are attached form a heterocyclyl;

$R_{1d}$ is selected from H, alkyl, hydroxy, amido and sulfonamido;

$R_{1e}$ is selected from H, alkyl and amino;

$R_{1f}$ is H; and $R_{1g}$ is H.

In some embodiments, the compound of Formula I has a structure of Formula I-1:

(I-1)

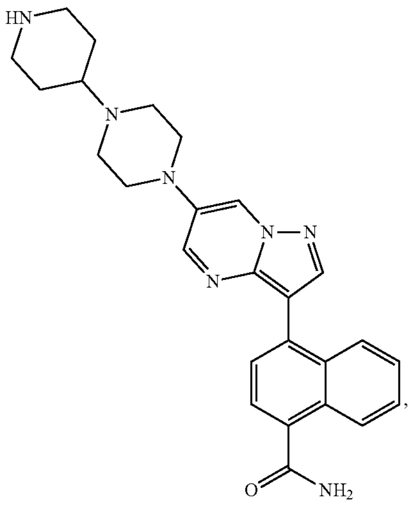

or a pharmaceutically acceptable salt thereof.

In some embodiments, the compound of Formula I has a structure of Formula I-2:

(I-2)

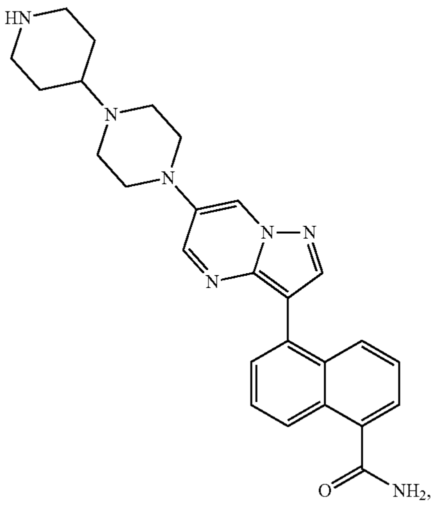

or a pharmaceutically acceptable salt thereof.

In some embodiments, the compound of Formula I has a structure of Formula I-3:

(I-3)

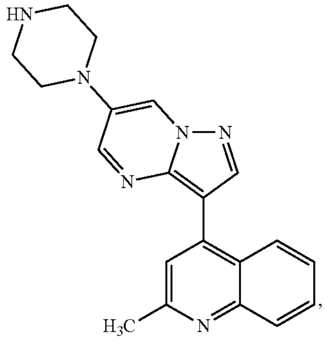

or a pharmaceutically acceptable salt thereof.

In some embodiments, the compound of Formula I has a structure of Formula I-4:

(I-4)

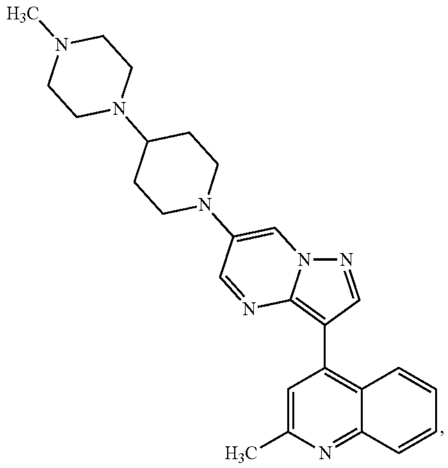

or a pharmaceutically acceptable salt thereof.

In some embodiments, the compound of Formula I has a structure of Formula I-5:

(I-5)

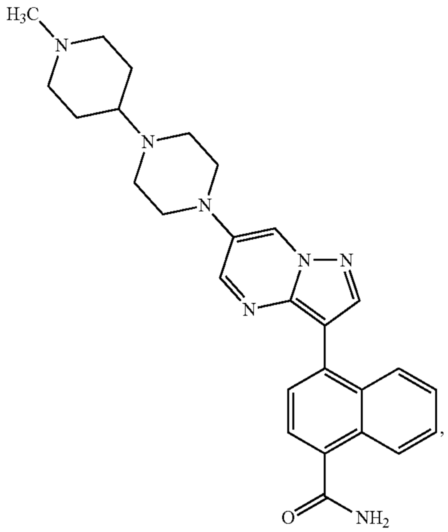

or a pharmaceutically acceptable salt thereof.

In some embodiments, the compound of Formula I has a structure of Formula I-6:

(I-6)

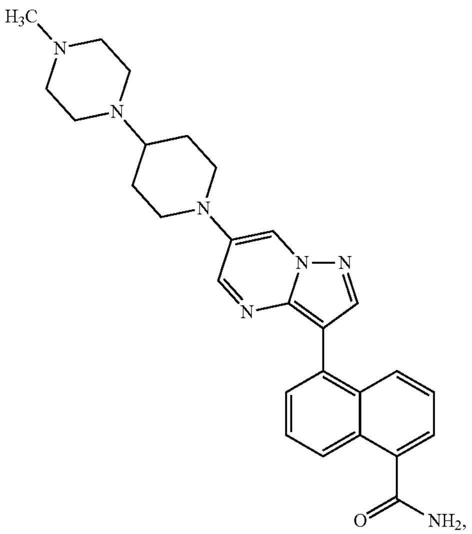

or a pharmaceutically acceptable salt thereof.

In some embodiments, the compound of Formula I has a structure of Formula I-7:

(I-7)

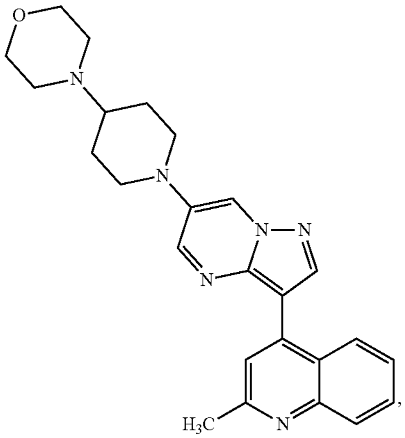

or a pharmaceutically acceptable salt thereof.

In some embodiments, the compound of Formula I has a structure of Formula I-8:

(I-8)

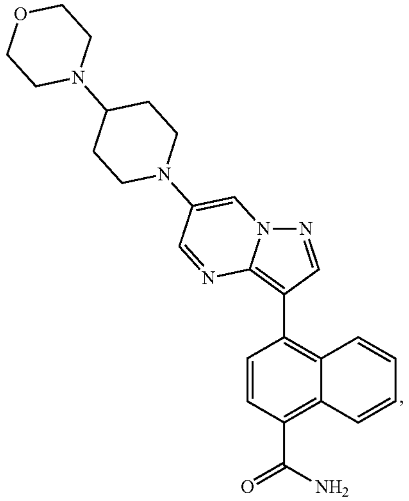

or a pharmaceutically acceptable salt thereof.

In some embodiments, the compound of Formula I has a structure of Formula I-9:

(I-9)

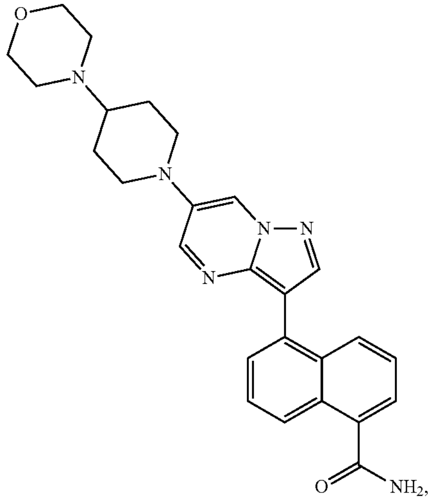

or a pharmaceutically acceptable salt thereof.

In some embodiments, the compound of Formula I has a structure of Formula I-10:

(I-10)

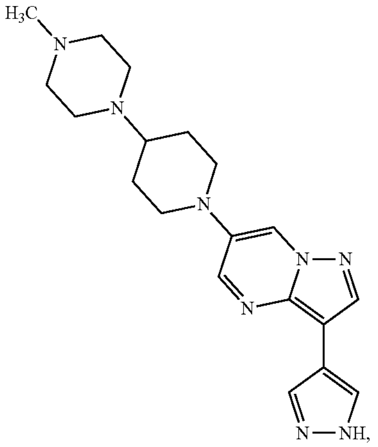

or a pharmaceutically acceptable salt thereof.

In some embodiments, the compound of Formula I has a structure of Formula I-11:

(I-11)

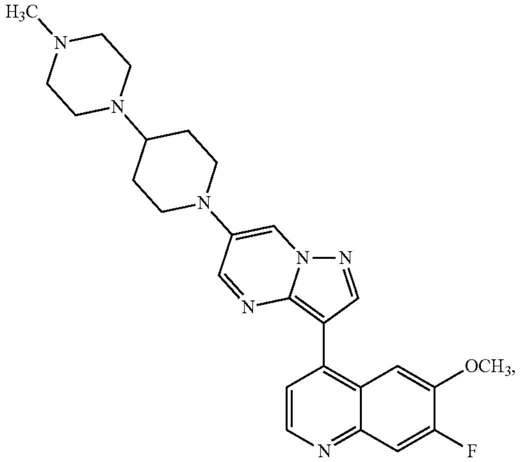

or a pharmaceutically acceptable salt thereof.

In some embodiments, the compound of Formula I has a structure of Formula I-12:

(I-12)

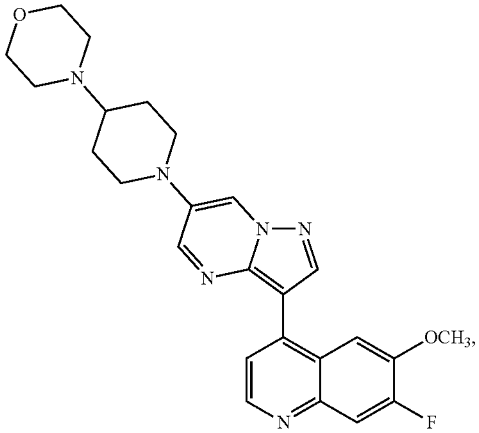

or a pharmaceutically acceptable salt thereof.

In some embodiments, the compound of Formula I has a structure of Formula I-13:

(I-13)

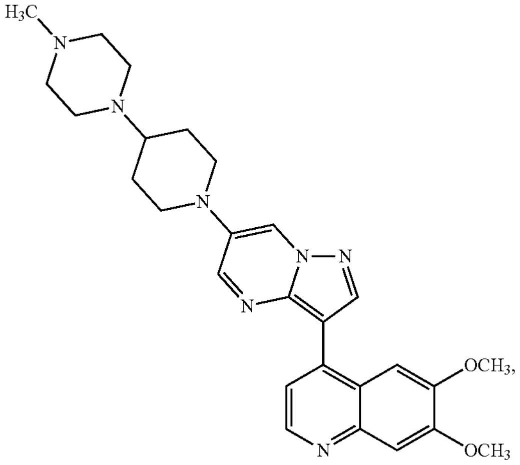

or a pharmaceutically acceptable salt thereof.

In some embodiments, the compound of Formula I has a structure of Formula I-14:

(I-14)

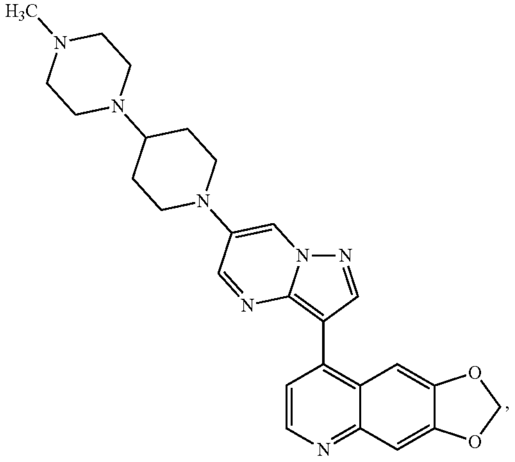

or a pharmaceutically acceptable salt thereof.

In some embodiments, the compound of Formula I has a structure of Formula I-15:

(I-15)

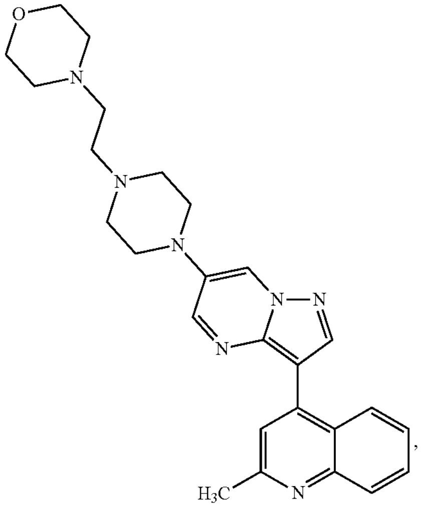

or a pharmaceutically acceptable salt thereof.

In some embodiments, the compound of Formula I has a structure of Formula I-16:

(I-16)

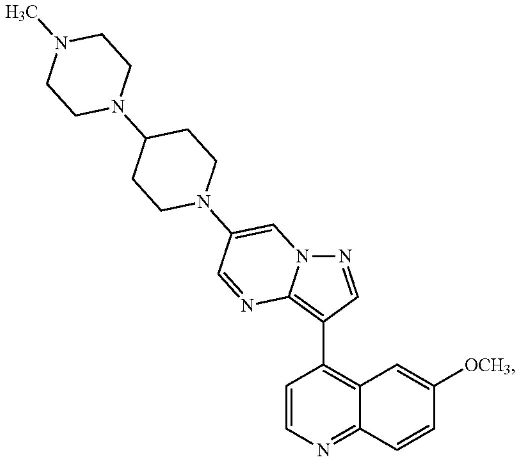

or a pharmaceutically acceptable salt thereof.

In some embodiments, the compound of Formula I has a structure of Formula I-17:

(I-17)

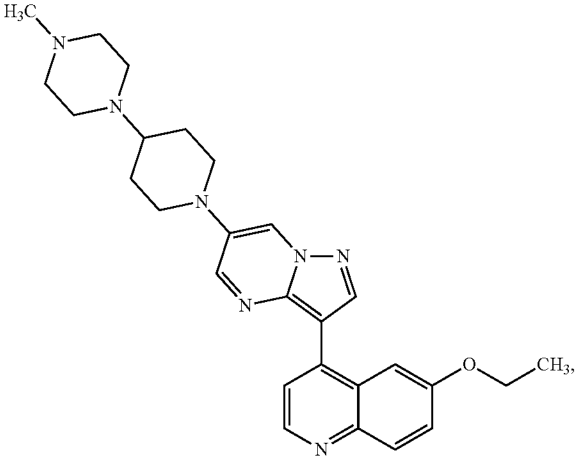

or a pharmaceutically acceptable salt thereof.

In some embodiments, the compound of Formula I has a structure of Formula I-18:

(I-18)

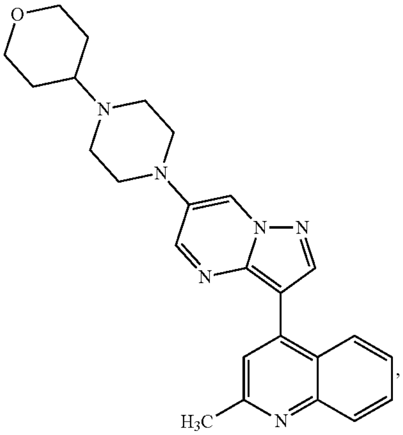

or a pharmaceutically acceptable salt thereof.

In some embodiments, the compound of Formula I has a structure of Formula I-19:

(I-19)

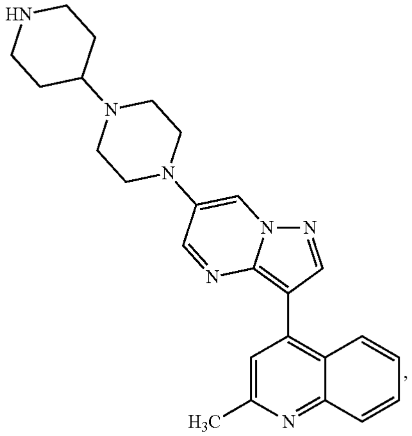

or a pharmaceutically acceptable salt thereof.

In some embodiments, the compound of Formula I has a structure of Formula I-20:

(I-20)

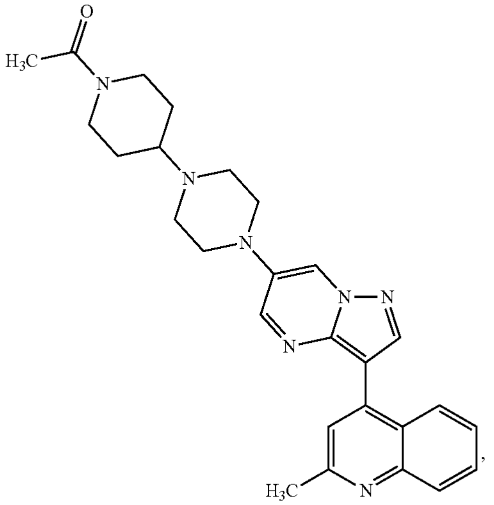

or a pharmaceutically acceptable salt thereof.

In some embodiments, the compound of Formula I has a structure of Formula I-21:

(I-21)

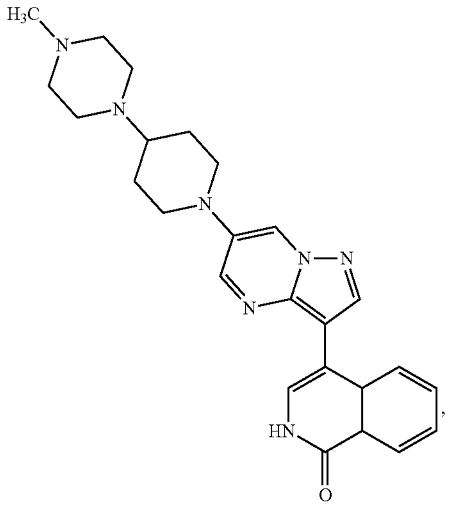

or a pharmaceutically acceptable salt thereof.

In some embodiments, the compound of Formula I has a structure of Formula I-22:

(I-22)

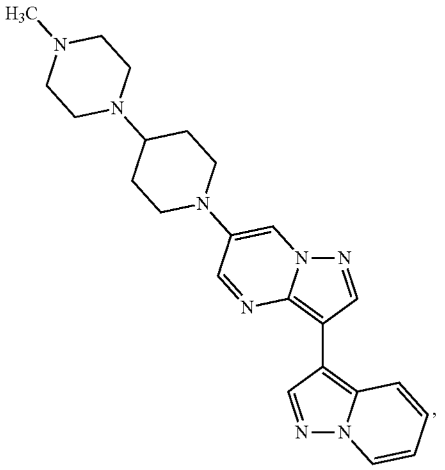

or a pharmaceutically acceptable salt thereof.

In some embodiments, the compound of Formula I has a structure of Formula I-23:

(I-23)

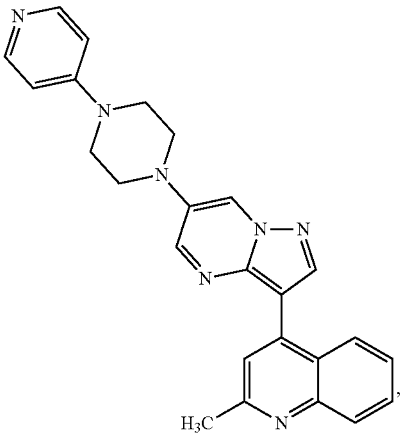

or a pharmaceutically acceptable salt thereof.

In some embodiments, the compound of Formula I has a structure of Formula I-24:

(I-24)

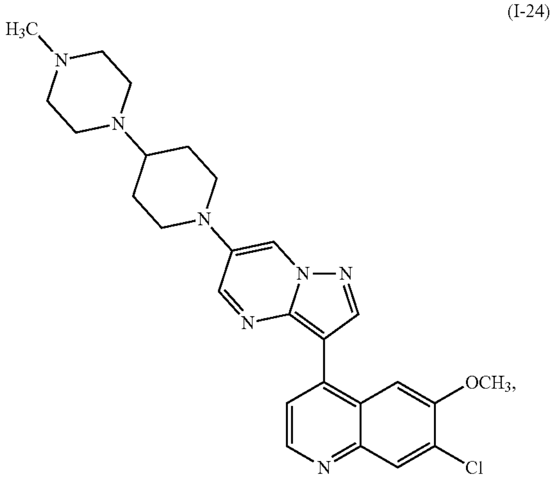 [SMILES: COc1cc2c(-c3cnn4cc(N5CCC(N6CCN(C)CC6)CC5)cnc34)ccnc2cc1Cl]

or a pharmaceutically acceptable salt thereof.

In some embodiments, the compound of Formula I has a structure of Formula I-25:

(I-25)

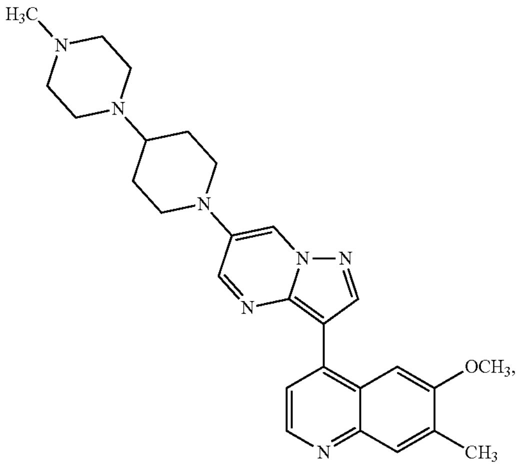

or a pharmaceutically acceptable salt thereof.

In some embodiments, the compound of Formula I has a structure of Formula I-26:

(I-26)

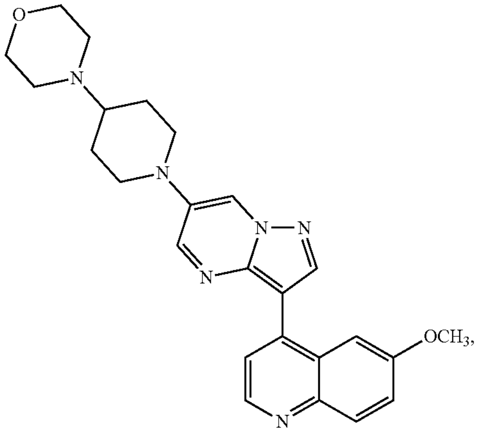

or a pharmaceutically acceptable salt thereof.

In some embodiments, the compound of Formula I has a structure of Formula I-27:

(I-27)

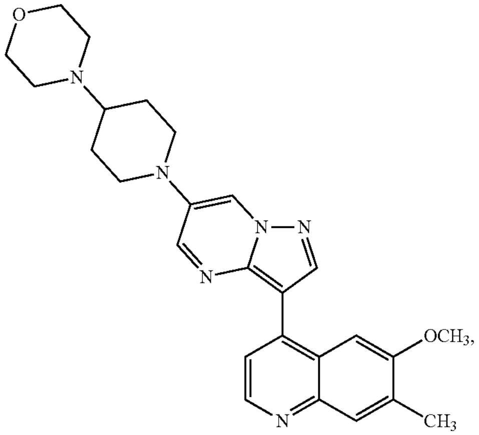

or a pharmaceutically acceptable salt thereof.

In some embodiments, the compound of Formula I has a structure of Formula I-28:

(I-28)

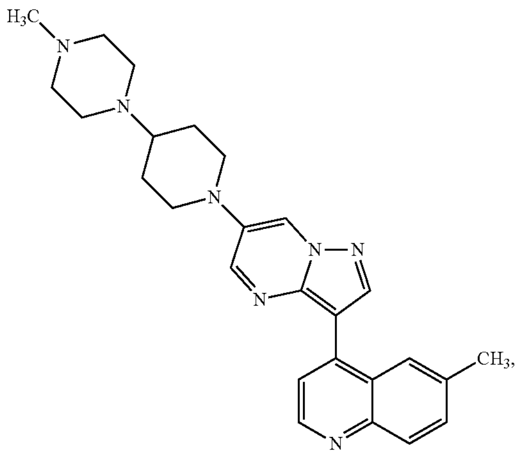

or a pharmaceutically acceptable salt thereof.

In some embodiments, the compound of Formula I has a structure of Formula I-29:

(I-29)

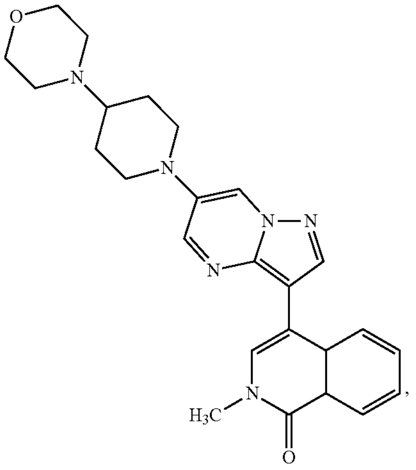

or a pharmaceutically acceptable salt thereof.

In some embodiments, the compound of Formula I has a structure of Formula I-30:

(I-30)

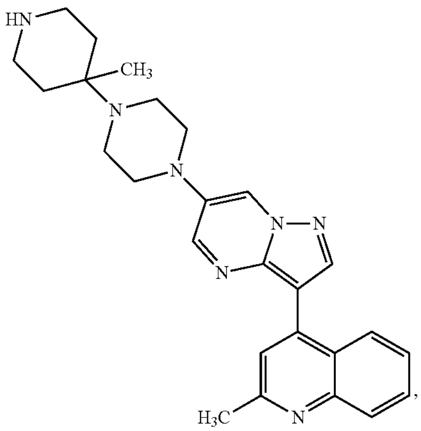

or a pharmaceutically acceptable salt thereof.

In some embodiments, the compound of Formula I has a structure of Formula I-31:

(I-31)

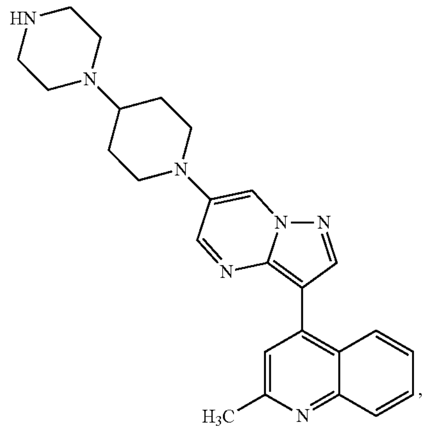

or a pharmaceutically acceptable salt thereof.

In some embodiments, the compound of Formula I has a structure of Formula I-32:

(I-32)

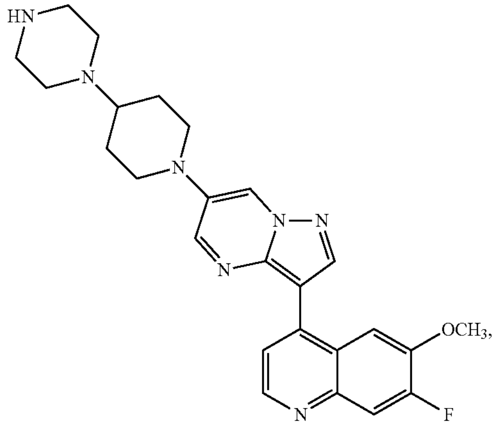

or a pharmaceutically acceptable salt thereof.

In some embodiments, the compound of Formula I has a structure of Formula I-33:

(I-33)

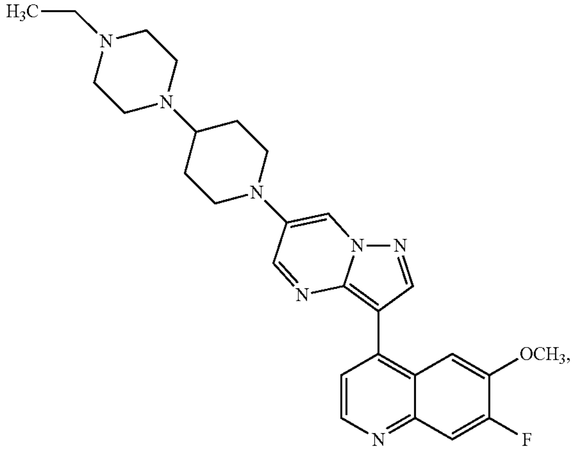

or a pharmaceutically acceptable salt thereof.

In some embodiments, the compound of Formula I has a structure of Formula I-34:

(I-34)

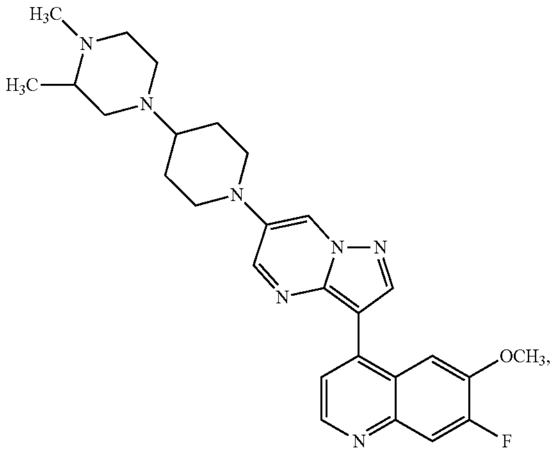

or a pharmaceutically acceptable salt thereof.

In some embodiments, the compound of Formula I has a structure of Formula I-35:

(I-35)

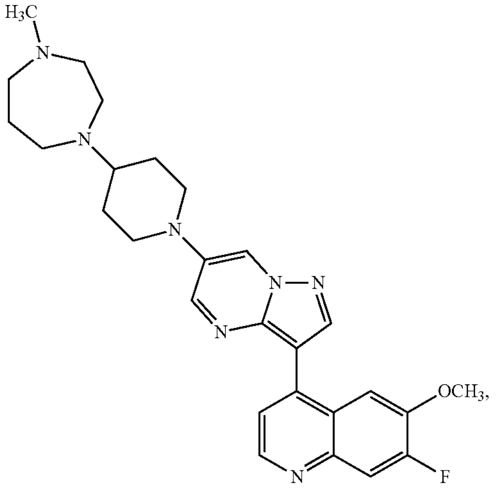

or a pharmaceutically acceptable salt thereof.

In some embodiments, the compound of Formula I has a structure of Formula I-36:

(I-36)

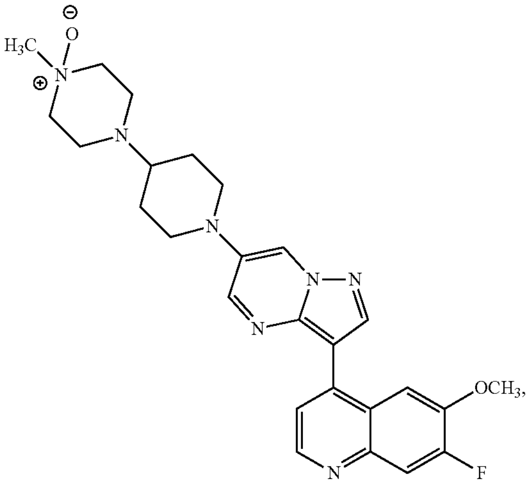

or a pharmaceutically acceptable salt thereof.

In some embodiments, the compound of Formula I has a structure of Formula I-37:

(I-37)

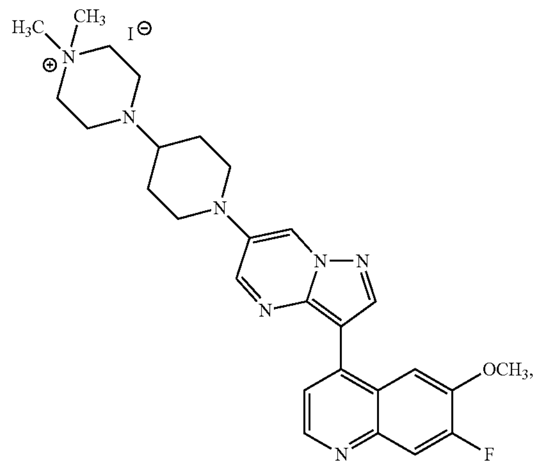

or a pharmaceutically acceptable salt thereof.

In some embodiments, the compound of Formula I has a structure of Formula I-38:

(I-38)

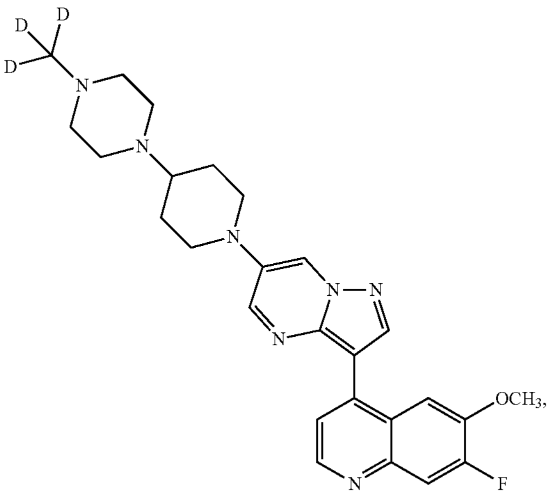

or a pharmaceutically acceptable salt thereof.

In some embodiments, the compound of Formula I has a structure of Formula I-39:

(I-39)

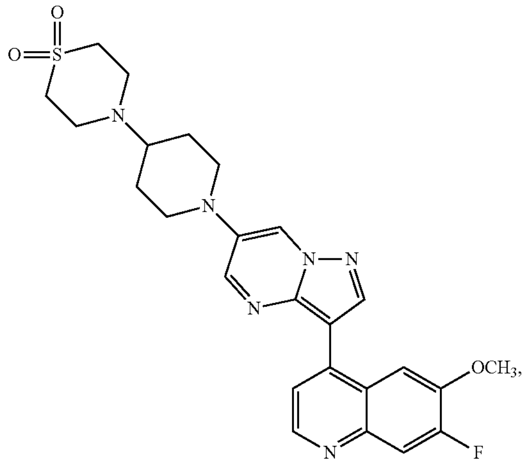

or a pharmaceutically acceptable salt thereof.

In some embodiments, the compound of Formula I has a structure of Formula I-40:

(I-40)

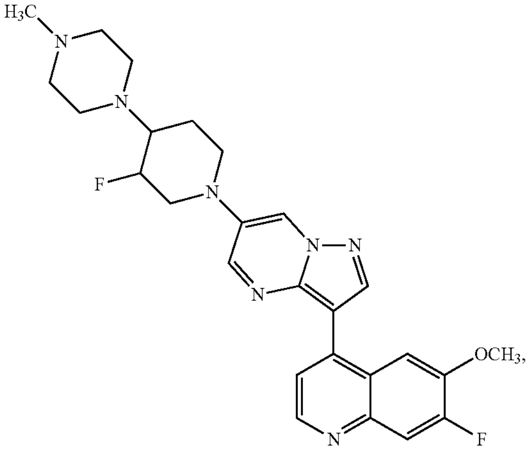

or a pharmaceutically acceptable salt thereof.

In some embodiments, the compound of Formula I has a structure of Formula I-41:

(I-41)

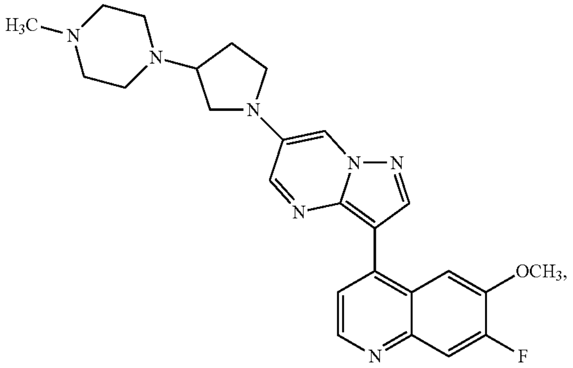

or a pharmaceutically acceptable salt thereof.

In some embodiments, the compound of Formula I has a structure of Formula I-42:

(I-42)

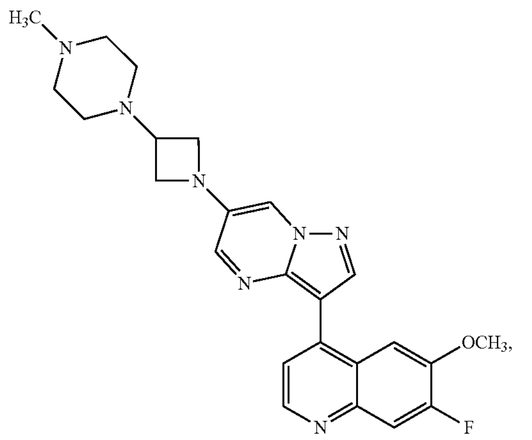

or a pharmaceutically acceptable salt thereof.

In some embodiments, the compound of Formula I has a structure of Formula I-43:

(I-43)

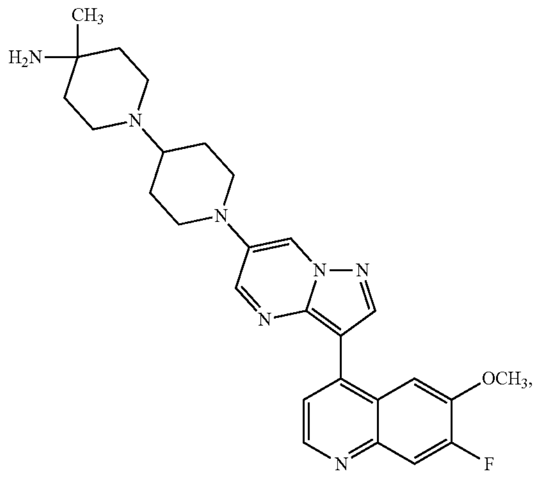

or a pharmaceutically acceptable salt thereof.

In some embodiments, the compound of Formula I has a structure of Formula I-44:

(I-44)

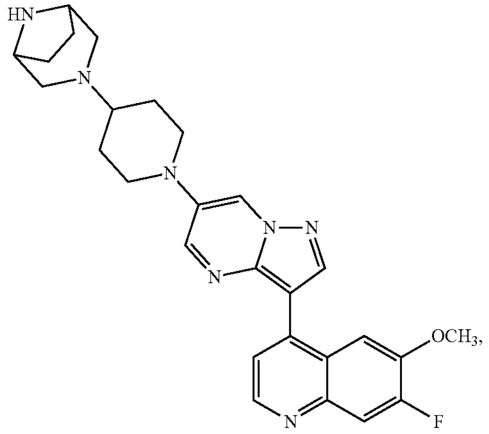

or a pharmaceutically acceptable salt thereof.

In some embodiments, the compound of Formula I has a structure of Formula I-45:

(I-45)

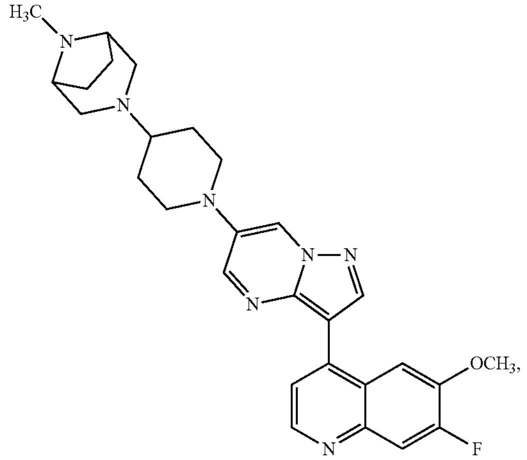

or a pharmaceutically acceptable salt thereof.

In some embodiments, the compound of Formula I has a structure of Formula I-46:

(I-46)

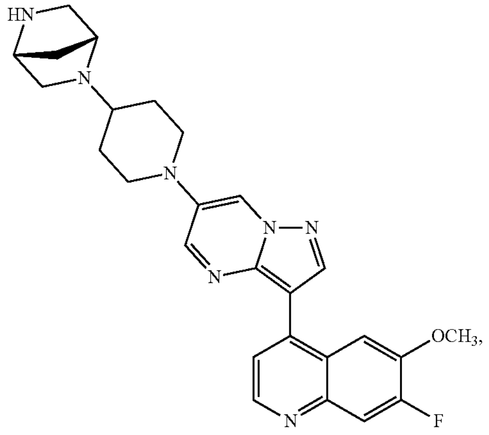

or a pharmaceutically acceptable salt thereof.

In some embodiments, the compound of Formula I has a structure of Formula I-47:

(I-47)

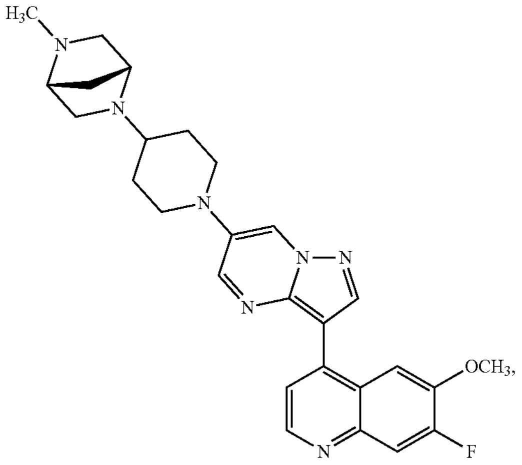

or a pharmaceutically acceptable salt thereof.

In some embodiments, the compound of Formula I has a structure of Formula I-48:

(I-48)

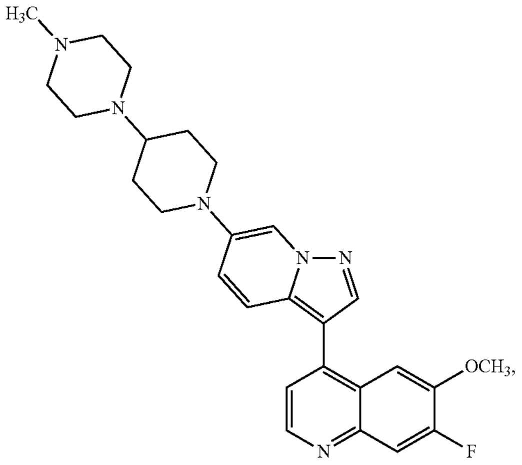

or a pharmaceutically acceptable salt thereof.

In some embodiments, the compound of Formula I has a structure of Formula I-49:

(I-49)

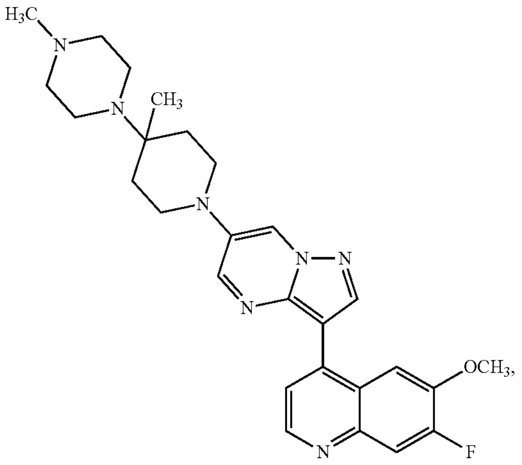

or a pharmaceutically acceptable salt thereof.

In some embodiments, the compound of Formula I has a structure of Formula I-50:

(I-50)

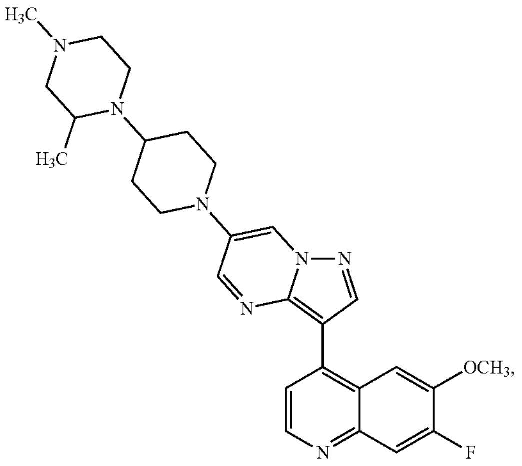

or a pharmaceutically acceptable salt thereof.

In some embodiments, the compound of Formula I has a structure of Formula I-51:

(I-51)

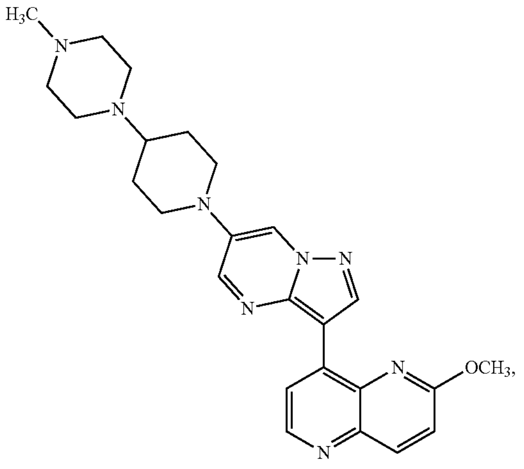

or a pharmaceutically acceptable salt thereof.

In some embodiments, the compound of Formula I has a structure of Formula I-52:

(I-52)

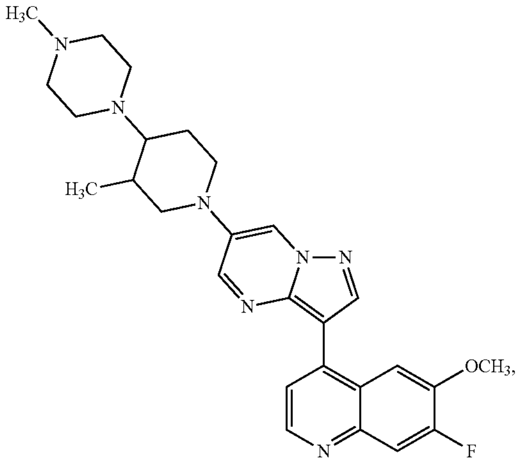

or a pharmaceutically acceptable salt thereof.

In some embodiments, the compound of Formula I has a structure of Formula I-53:

(I-53)

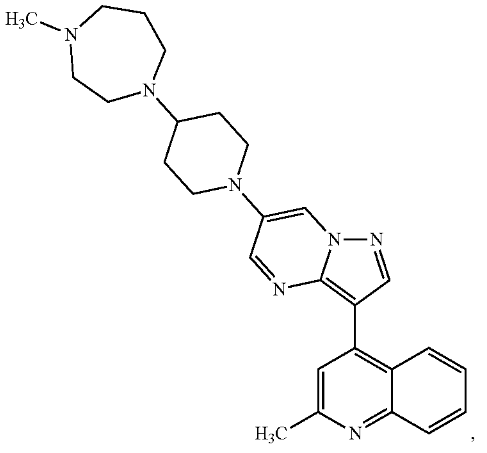

or a pharmaceutically acceptable salt thereof.

In some embodiments, the compound of Formula I has a structure of Formula I-54:

(I-54)

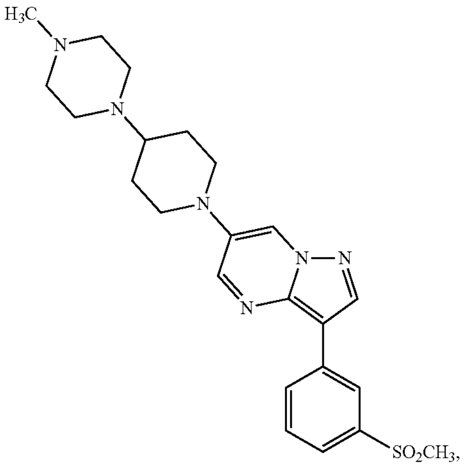

or a pharmaceutically acceptable salt thereof.

In some embodiments, the compound of Formula I has a structure of Formula I-55:

(I-55)

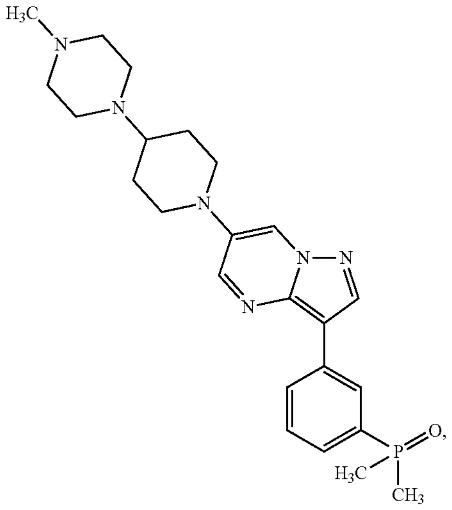

or a pharmaceutically acceptable salt thereof.

In some embodiments, the compound of Formula I has a structure of Formula I-56:

(I-56)

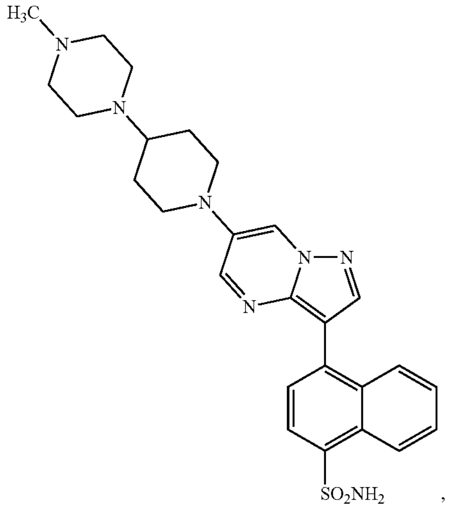

or a pharmaceutically acceptable salt thereof.

In some embodiments, the compound of Formula I has a structure of Formula I-57:

(I-57)

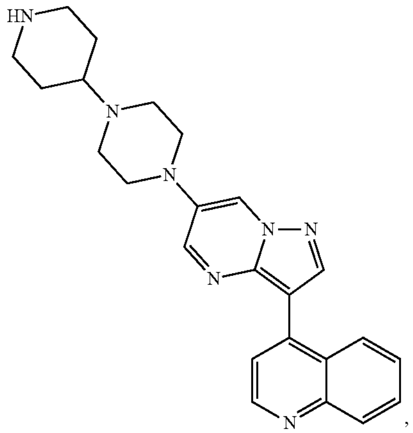

or a pharmaceutically acceptable salt thereof.

In some embodiments, the compound of Formula I has a structure of Formula I-58:

(I-58)

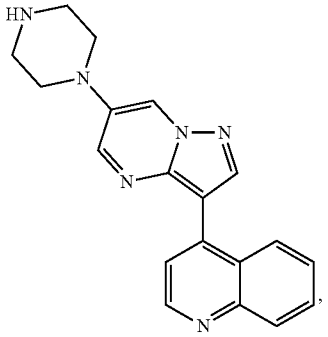

or a pharmaceutically acceptable salt thereof.

In some embodiments, the compound of Formula I has a structure of Formula I-59:

(I-59)

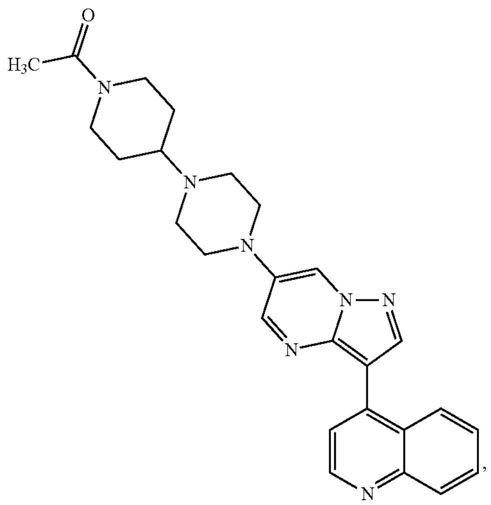

or a pharmaceutically acceptable salt thereof.

In some embodiments, the compound of Formula I has a structure of Formula I-60:

(I-60)

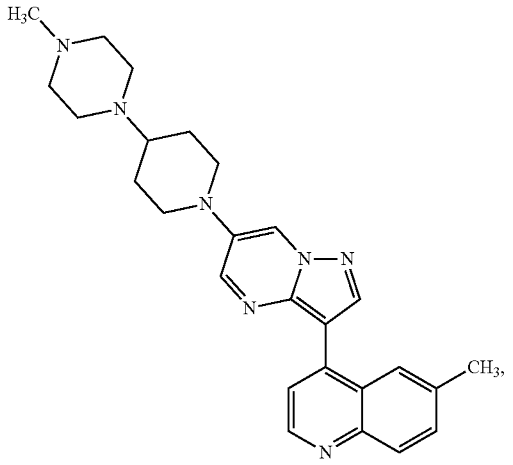

or a pharmaceutically acceptable salt thereof.

In some embodiments, the compound of Formula I has a structure of Formula I-61:

(I-61)

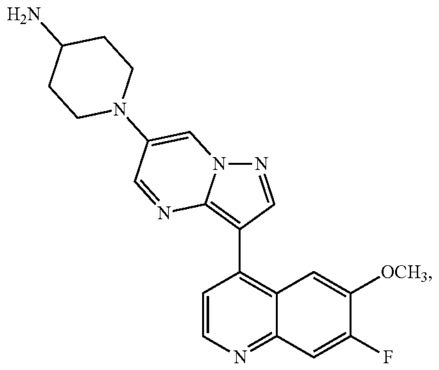

or a pharmaceutically acceptable salt thereof.

In some embodiments, the compound of Formula I has a structure of Formula I-62:

(I-62)

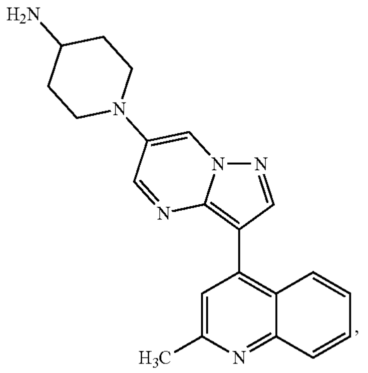

or a pharmaceutically acceptable salt thereof.

In some embodiments, the compound of Formula I has a structure of Formula I-63:

(I-63)

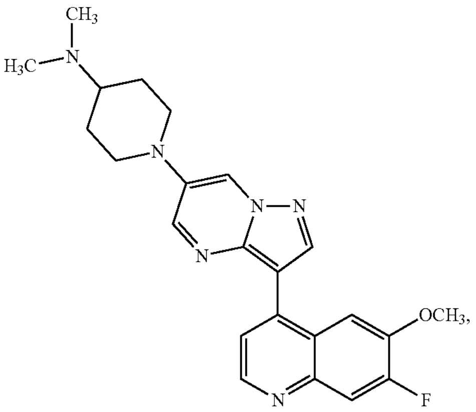

or a pharmaceutically acceptable salt thereof.

In some embodiments, the compound of Formula I has a structure of Formula I-64:

(I-64)

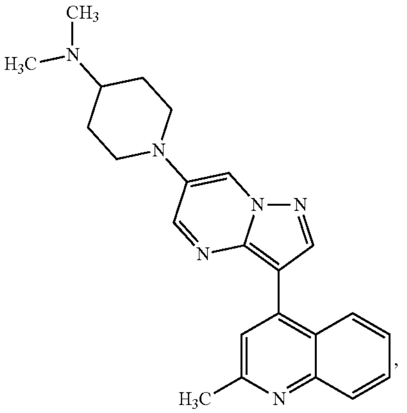

or a pharmaceutically acceptable salt thereof.

In some embodiments, the compound of Formula I has a structure of Formula I-65:

(I-65)

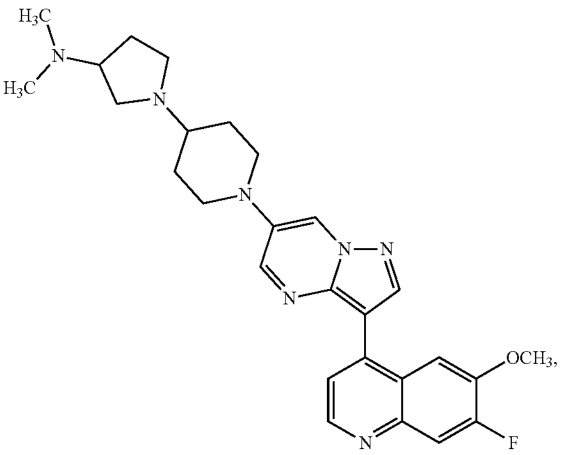

or a pharmaceutically acceptable salt thereof.

In some embodiments, the compound of Formula I has a structure of Formula I-66:

(I-66)

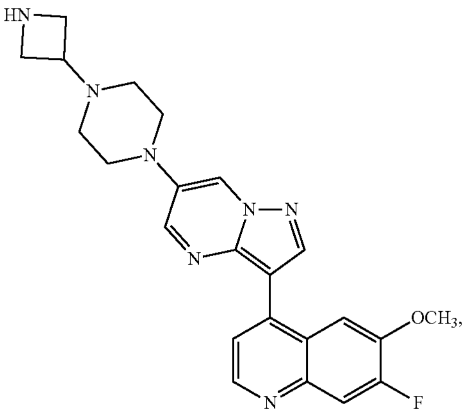

or a pharmaceutically acceptable salt thereof.

In some embodiments, the compound of Formula I has a structure of Formula I-67:

(I-67)

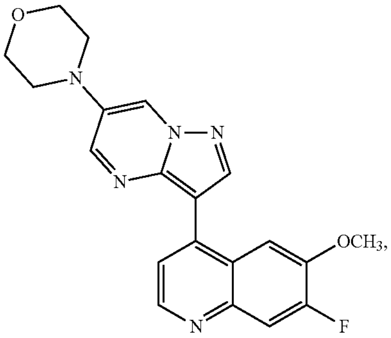

or a pharmaceutically acceptable salt thereof.

In some embodiments, the compound of Formula I has a structure of Formula I-68:

(I-68)

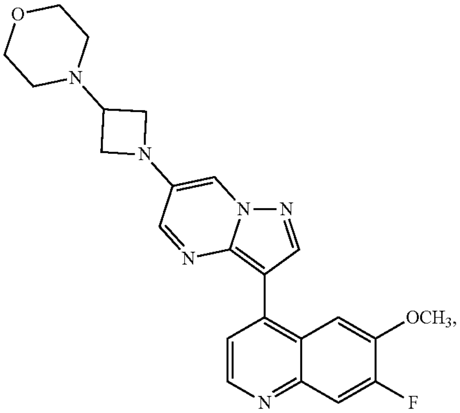

or a pharmaceutically acceptable salt thereof.

In some embodiments, the compound of Formula I has a structure of Formula I-69:

(I-69)

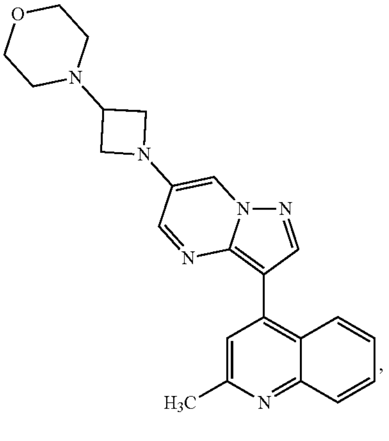

or a pharmaceutically acceptable salt thereof.

In some embodiments, the compound of Formula I has a structure of Formula I-70:

(I-70)

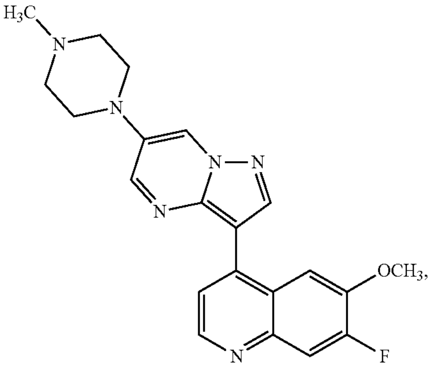

or a pharmaceutically acceptable salt thereof.

In some embodiments, the compound of Formula I has a structure of Formula I-71:

(I-71)

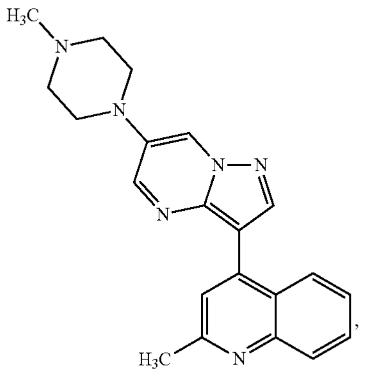

or a pharmaceutically acceptable salt thereof.

In some embodiments, the compound of Formula I has a structure of Formula I-72:

(I-72)

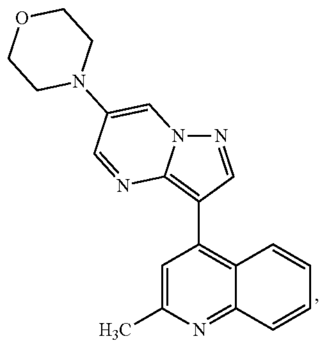

or a pharmaceutically acceptable salt thereof.

In some embodiments, the compound of Formula I has a structure of Formula I-73:

(I-73)

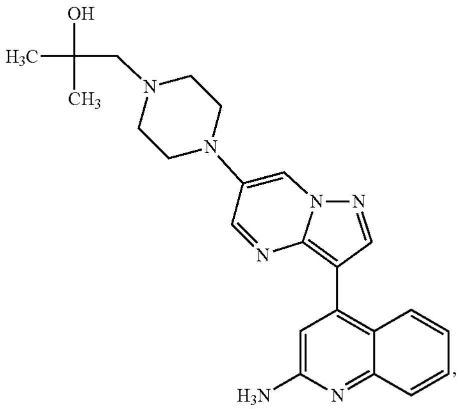

or a pharmaceutically acceptable salt thereof.

In some embodiments, the compound of Formula I has a structure of Formula I-74:

(I-74)

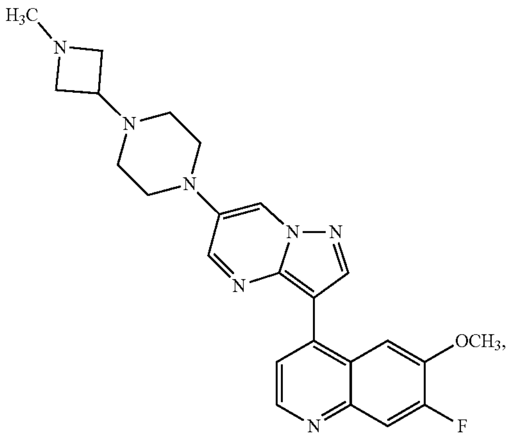

or a pharmaceutically acceptable salt thereof.

In some embodiments, the compound of Formula I has a structure of Formula I-75:

(I-75)

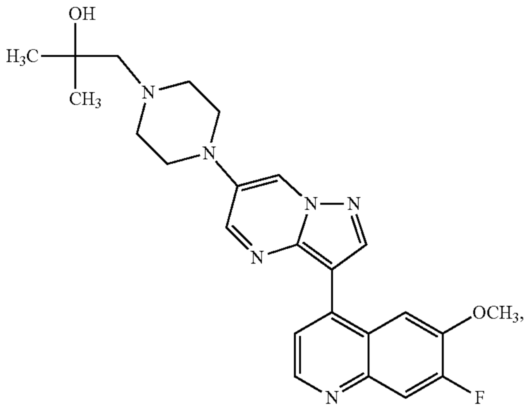

or a pharmaceutically acceptable salt thereof.

In some embodiments, the compound of Formula I has a structure of Formula I-76:

(I-76)

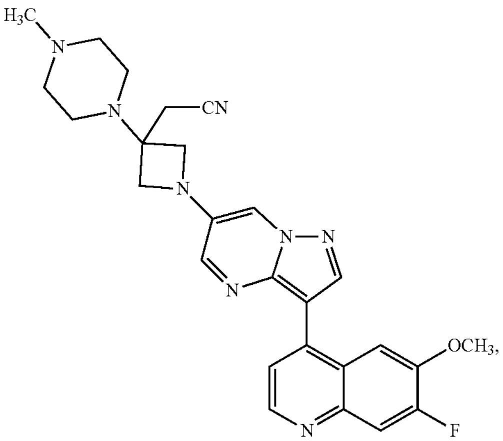

or a pharmaceutically acceptable salt thereof.

In some embodiments, the compound of Formula I has a structure of Formula I-77:

(I-77)

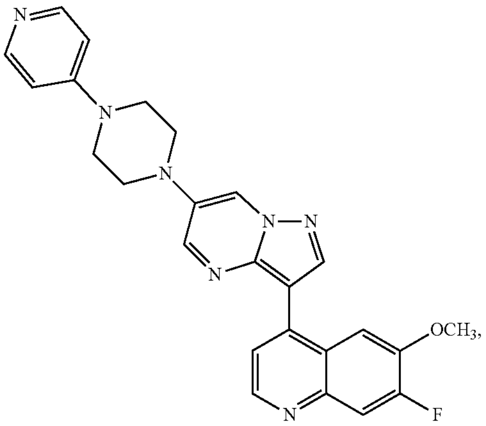

or a pharmaceutically acceptable salt thereof.

In some embodiments, the compound of Formula I has a structure of Formula I-78:

(I-78)

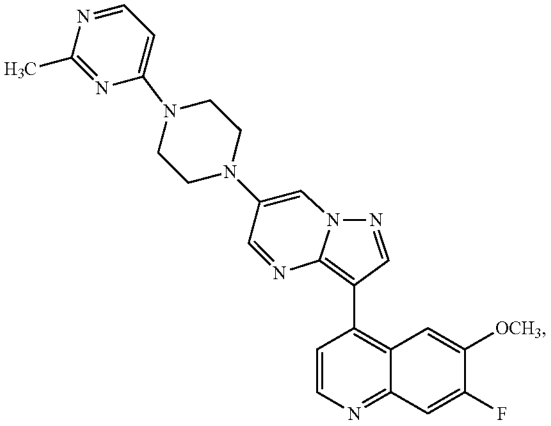

or a pharmaceutically acceptable salt thereof.

In some embodiments, the compound of Formula I has a structure of Formula I-79:

(I-79)

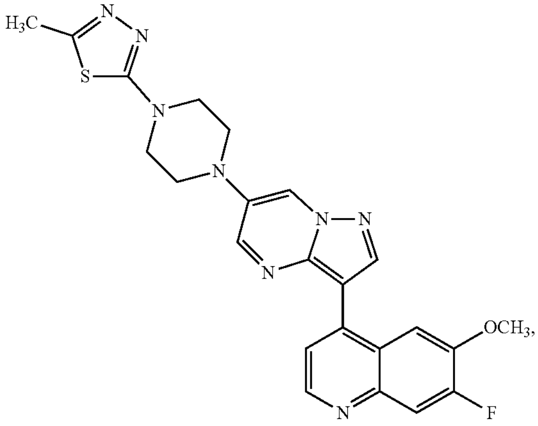

or a pharmaceutically acceptable salt thereof.

In some embodiments, the compound of Formula I has a structure of Formula I-80:

(I-80)

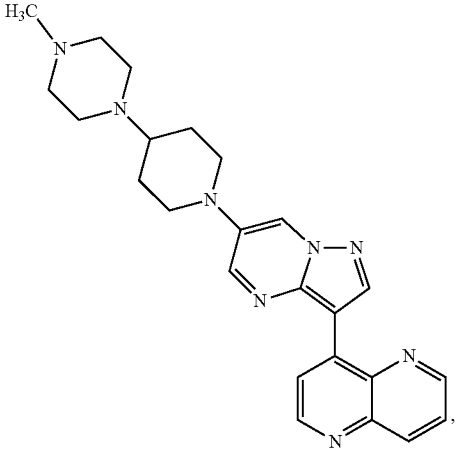

or a pharmaceutically acceptable salt thereof.

In some embodiments, the compound of Formula I has a structure of Formula I-81:

(I-81)

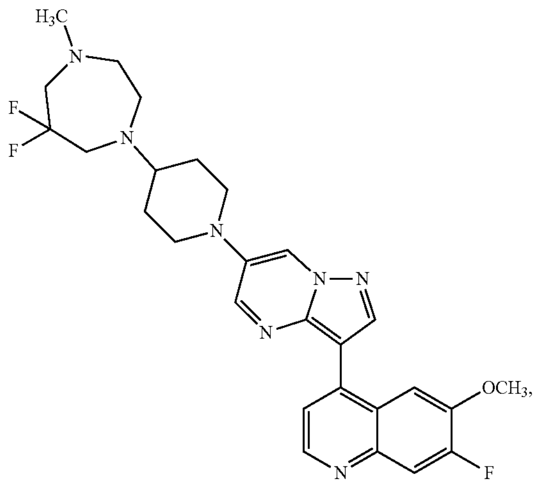

or a pharmaceutically acceptable salt thereof.

In some embodiments, the compound of Formula I has a structure of Formula I-82:

(I-82)

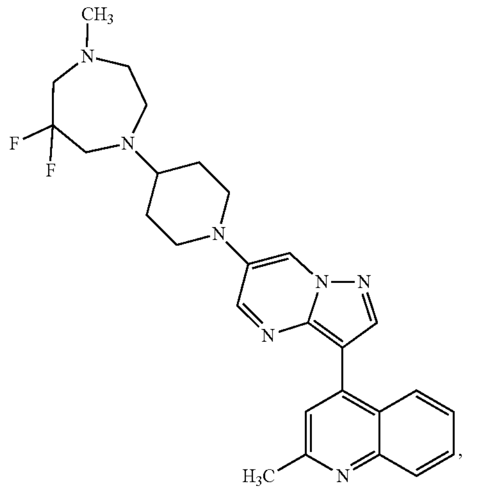

or a pharmaceutically acceptable salt thereof.

In some embodiments, the compound of Formula I has a structure of Formula I-83:

(I-83)

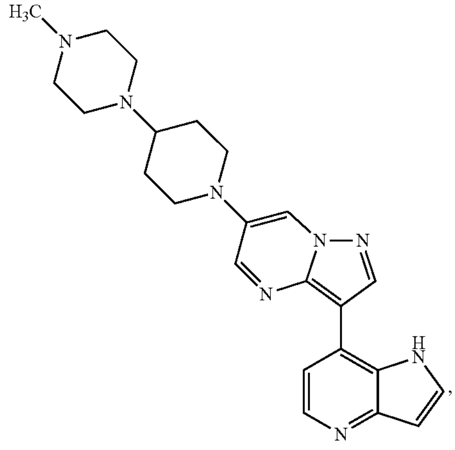

or a pharmaceutically acceptable salt thereof.

In some embodiments, the compound of Formula I has a structure of Formula I-84:

(I-84)

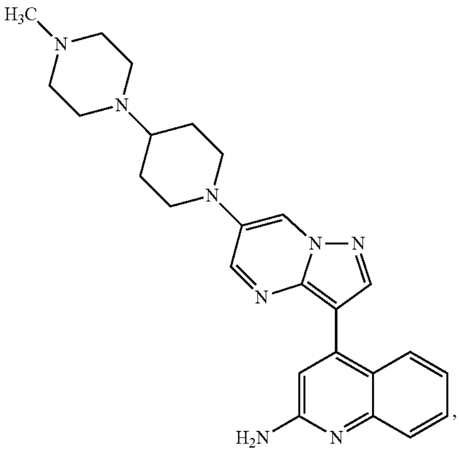

or a pharmaceutically acceptable salt thereof.

In some embodiments, the compound of Formula I has a structure of Formula I-85:

(I-85)

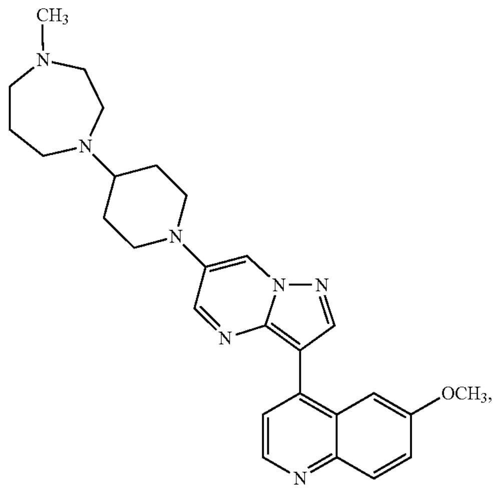

or a pharmaceutically acceptable salt thereof.

In some embodiments, the compound of Formula I has a structure of Formula I-86:

(I-86)

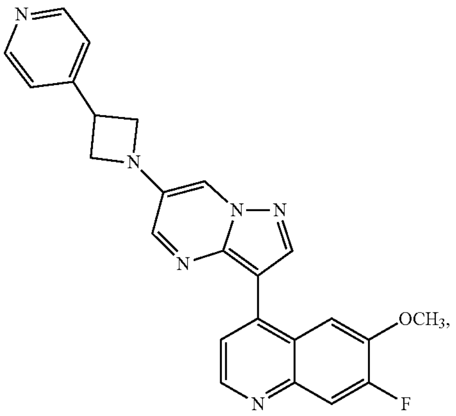

or a pharmaceutically acceptable salt thereof.

In some embodiments, the compound of Formula I has a structure of Formula I-87:

(I-87)

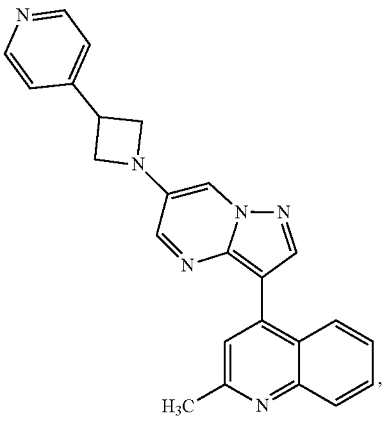

or a pharmaceutically acceptable salt thereof.

In some embodiments, the compound of Formula I has a structure of Formula I-88:

(I-88)

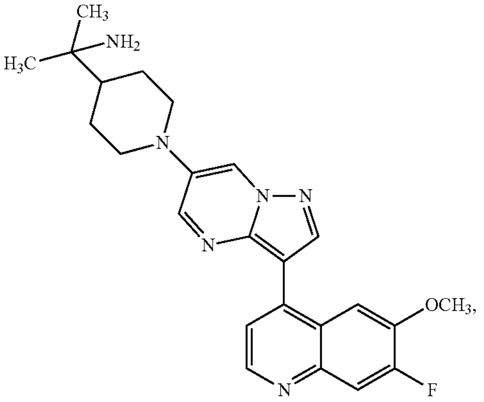

or a pharmaceutically acceptable salt thereof.

In some embodiments, the compound of Formula I has a structure of Formula I-89:

(I-89)

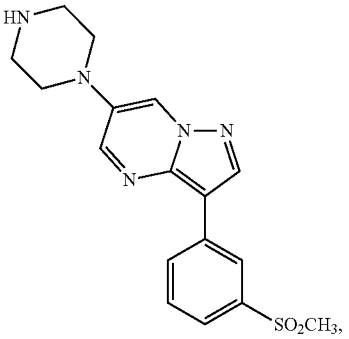

or a pharmaceutically acceptable salt thereof.

In some embodiments, the compound of Formula I has a structure of Formula I-90:

(I-90)

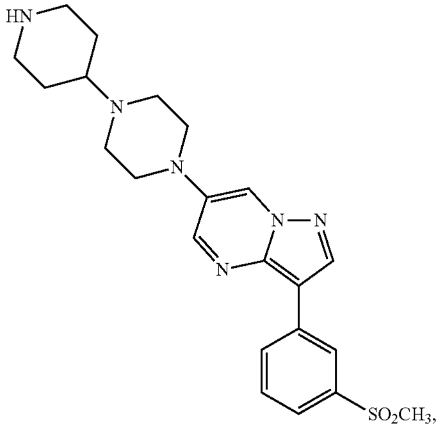

or a pharmaceutically acceptable salt thereof.

In some embodiments, the compound of Formula I has a structure of Formula I-91:

(I-91)

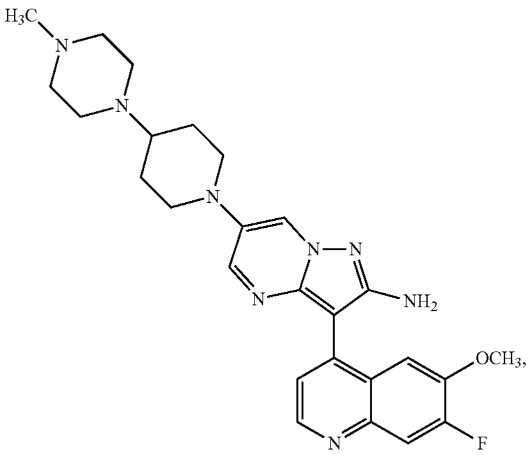

or a pharmaceutically acceptable salt thereof.

In some embodiments, the compound of Formula I has a structure of Formula I-92:

(I-92)

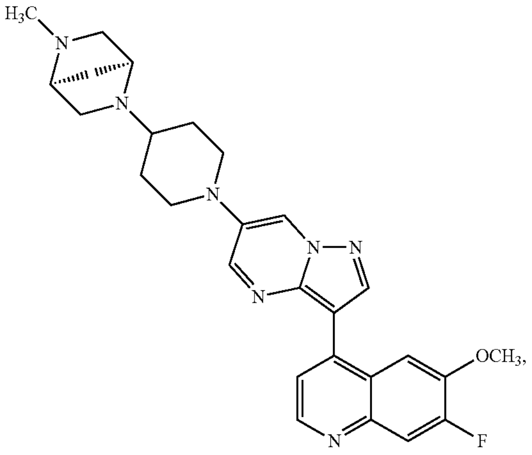

or a pharmaceutically acceptable salt thereof.

In some embodiments, the compound of Formula I has a structure of Formula I-93:

(I-93)

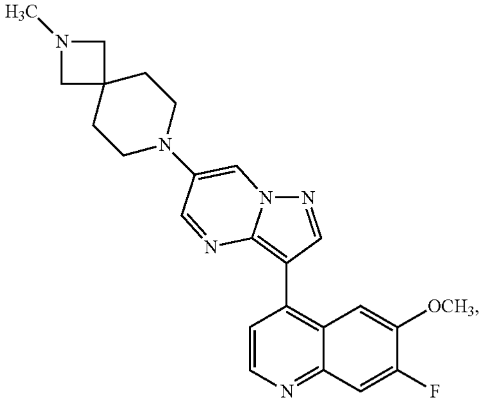

or a pharmaceutically acceptable salt thereof.

In some embodiments, the compound of Formula I has a structure of Formula I-94:

(I-94)

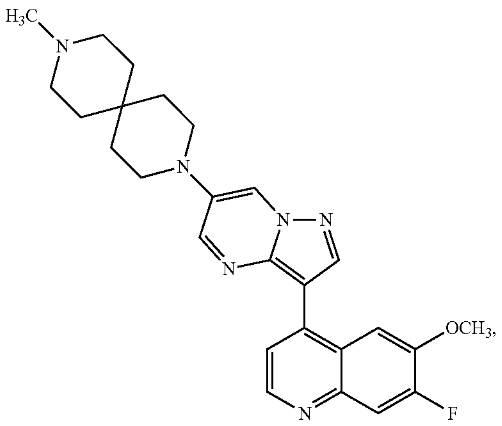

or a pharmaceutically acceptable salt thereof.

In some embodiments, the compound of Formula I has a structure of Formula I-95:

(I-95)

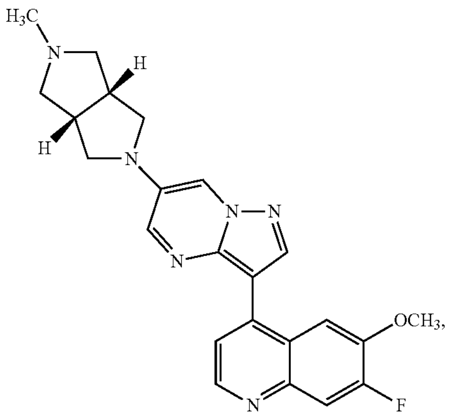

or a pharmaceutically acceptable salt thereof.

In some embodiments, the compound of Formula I has a structure of Formula I-96:

(I-96)

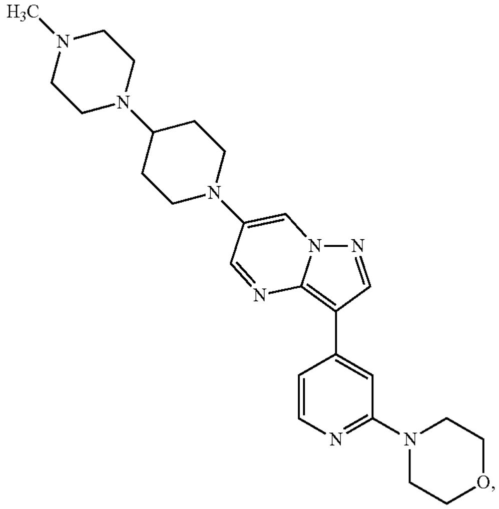

or a pharmaceutically acceptable salt thereof.

In some embodiments, the compound of Formula I has a structure of Formula I-97:

(I-97)

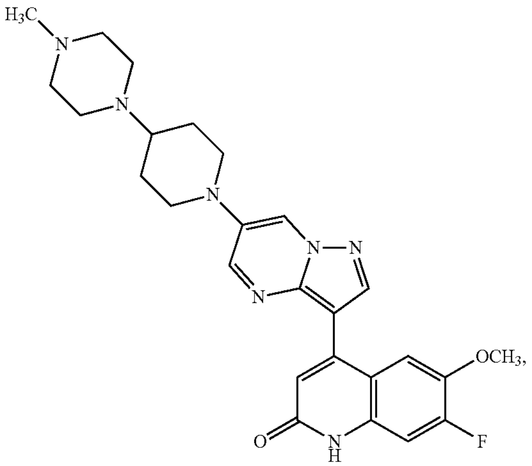

or a pharmaceutically acceptable salt thereof.

In some embodiments, the compound of Formula I has a structure of Formula I-98:

(I-98)

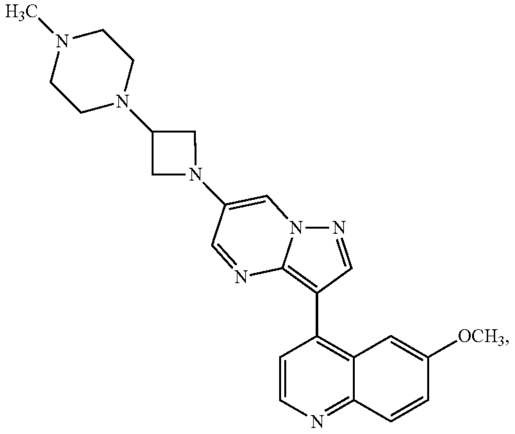

or a pharmaceutically acceptable salt thereof.

In some embodiments, the compound of Formula I has a structure of Formula I-99:

(I-99)

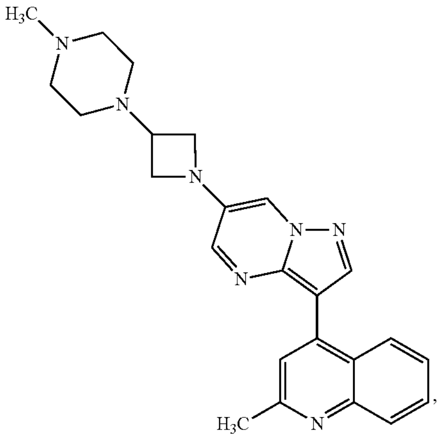

or a pharmaceutically acceptable salt thereof.

In some embodiments, the compound of Formula I has a structure of Formula I-100:

(I-100)

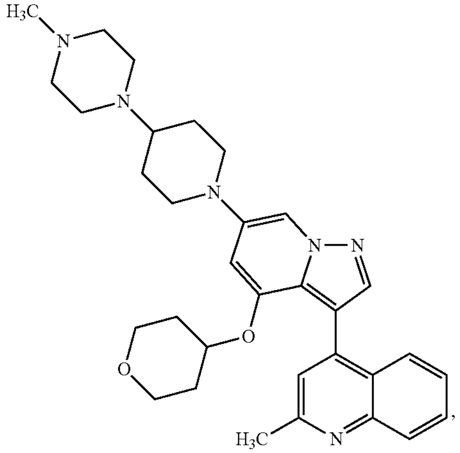

or a pharmaceutically acceptable salt thereof.

In some embodiments, the compound of Formula I has a structure of Formula I-101:

(I-101)

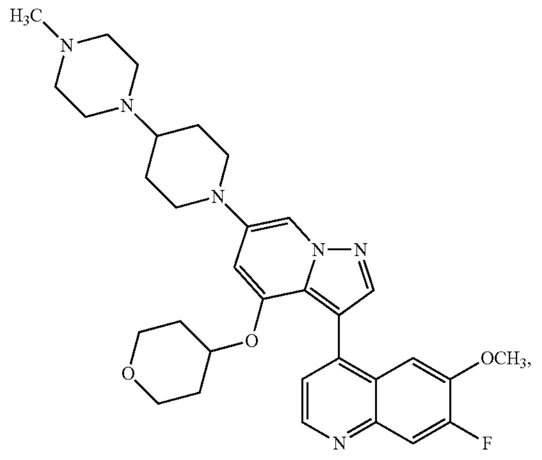

or a pharmaceutically acceptable salt thereof.

In some embodiments, the compound of Formula I has a structure of Formula I-102:

(I-102)

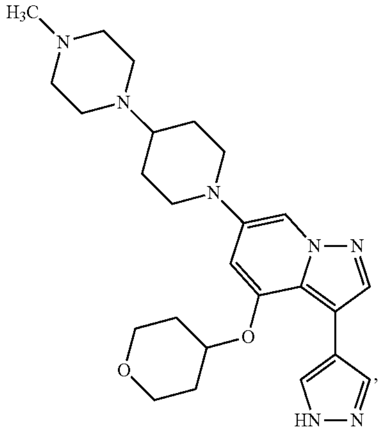

or a pharmaceutically acceptable salt thereof.

In some embodiments, the compound of Formula I has a structure of Formula I-103:

(I-103)

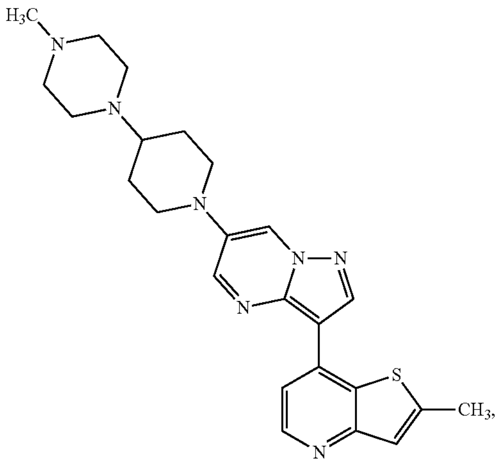

or a pharmaceutically acceptable salt thereof.

In some embodiments, the compound of Formula I has a structure of Formula I-104:

(I-104)

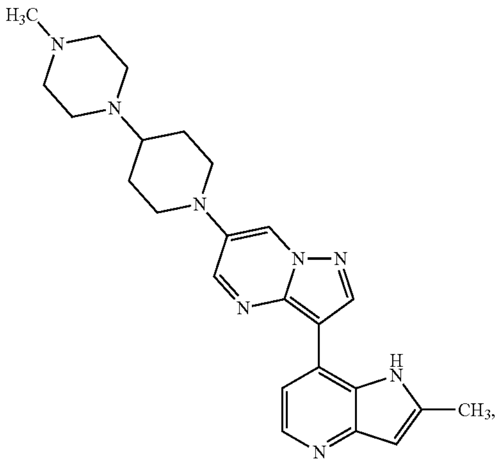

or a pharmaceutically acceptable salt thereof.

In some embodiments, the compound of Formula I has a structure of Formula I-105:

(I-105)

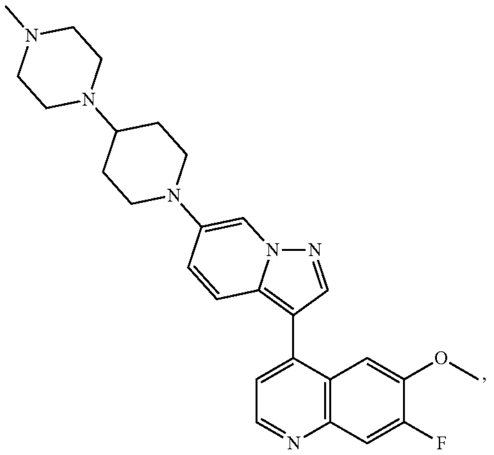

or a pharmaceutically acceptable salt thereof.

In some embodiments, the compound of Formula I has a structure of Formula I-106:

(I-106)

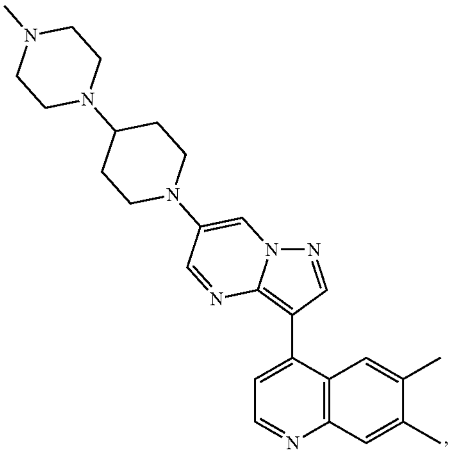

or a pharmaceutically acceptable salt thereof.

In some embodiments, the compound of Formula I has a structure of Formula I-107:

(I-107)

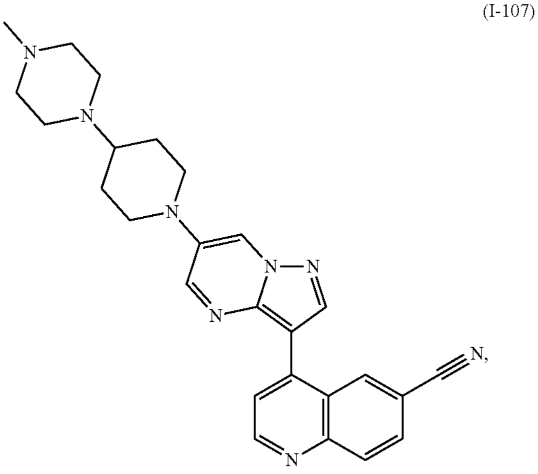 [SMILES: CN1CCN(C2CCN(c3cnc4c(-c5ccnc6ccc(C#N)cc56)cnn4c3)CC2)CC1]

or a pharmaceutically acceptable salt thereof.

In some embodiments, the compound of Formula I has a structure of Formula I-108:

(I-108)

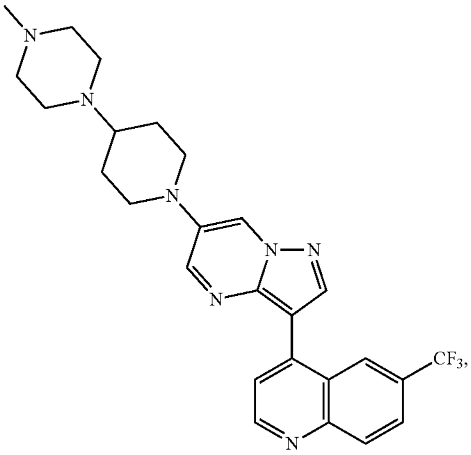

or a pharmaceutically acceptable salt thereof.

In some embodiments, the compound of Formula I has a structure of Formula I-109:

(I-109)

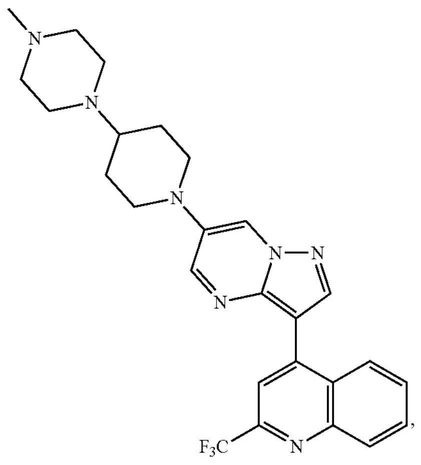

or a pharmaceutically acceptable salt thereof.

In some embodiments, the compound of Formula I has a structure of Formula I-110:

(I-110)

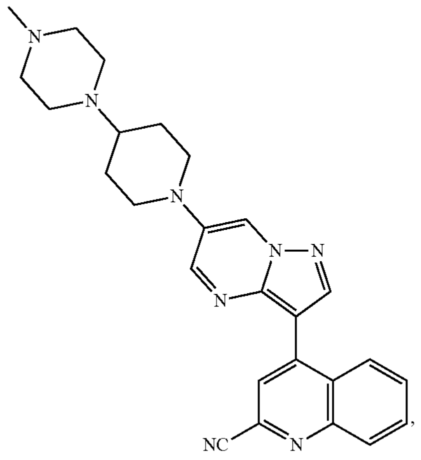

or a pharmaceutically acceptable salt thereof.

In some embodiments, the compound of Formula I has a structure of Formula I-111:

(I-111)

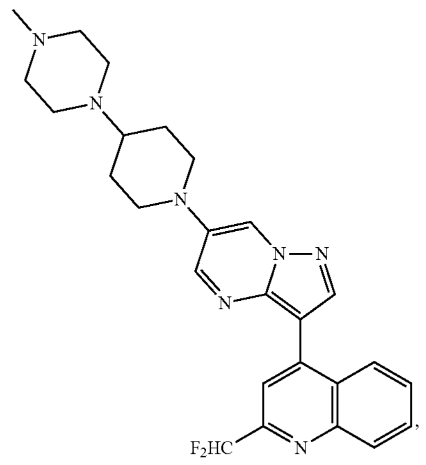

or a pharmaceutically acceptable salt thereof.

In some embodiments, the compound of Formula I has a structure of Formula I-112:

(I-112)

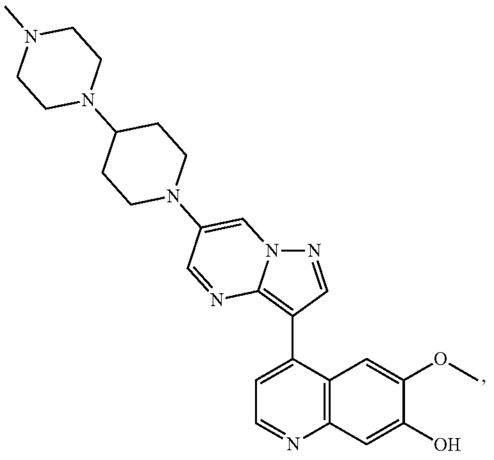

or a pharmaceutically acceptable salt thereof.

In some embodiments, the compound of Formula I has a structure of Formula I-113:

(I-113)

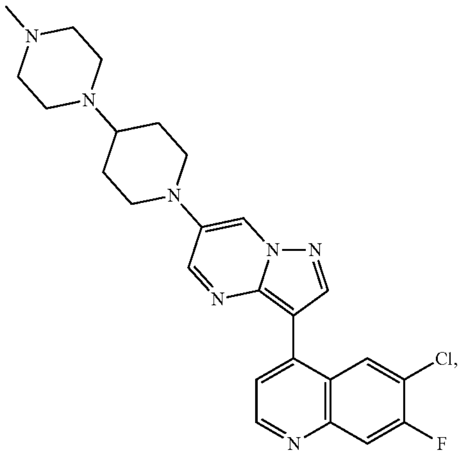

or a pharmaceutically acceptable salt thereof.

In some embodiments, the compound of Formula I has a structure of Formula I-114:

(I-114)

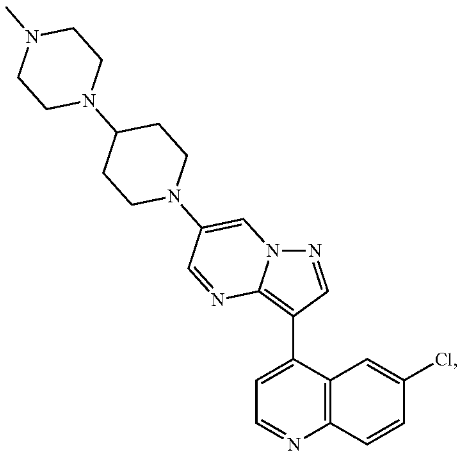

or a pharmaceutically acceptable salt thereof.

In some embodiments, the compound of Formula I has a structure of Formula I-115:

(I-115)

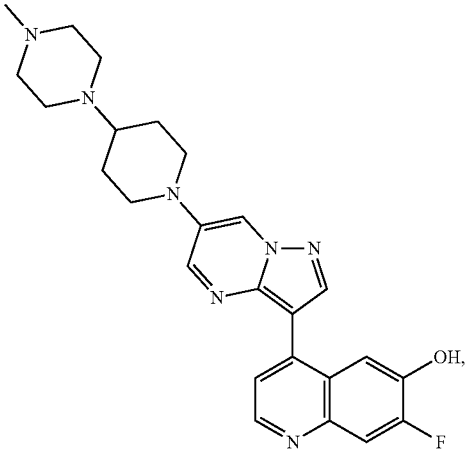

or a pharmaceutically acceptable salt thereof.

In some embodiments, the compound of Formula I has a structure of Formula I-116:

(I-116)

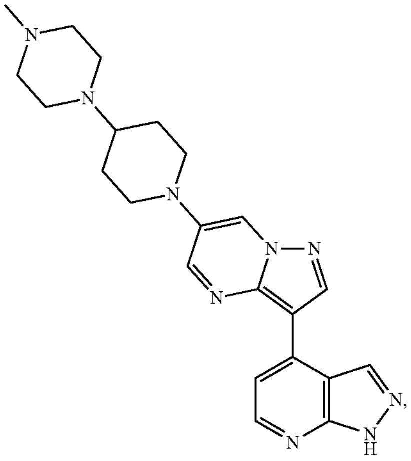

or a pharmaceutically acceptable salt thereof.

In some embodiments, the compound of Formula I has a structure of Formula I-117:

(I-117)

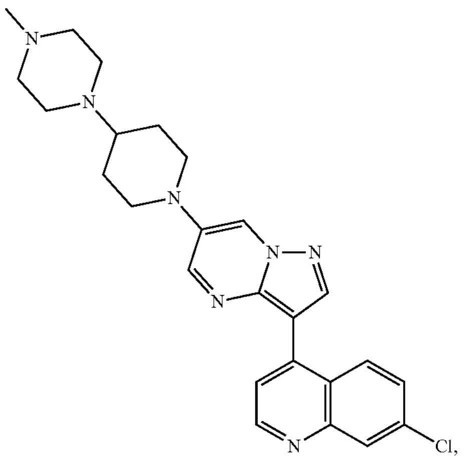

or a pharmaceutically acceptable salt thereof.

In some embodiments, the compound of Formula I has a structure of Formula I-118:

(I-118)

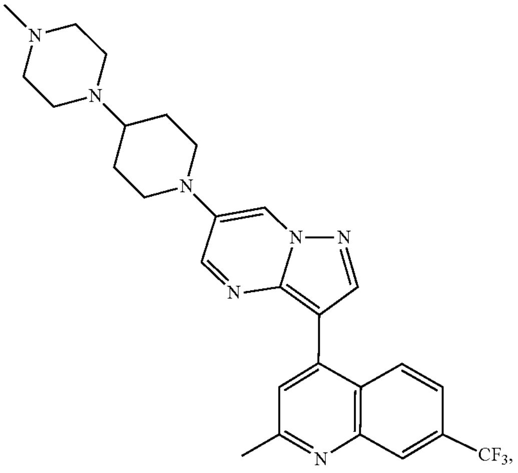

or a pharmaceutically acceptable salt thereof.

In some embodiments, the compound of Formula I has a structure of Formula I-119:

(I-121)

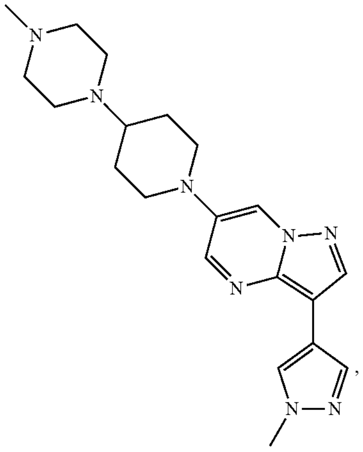

or a pharmaceutically acceptable salt thereof.

In some embodiments, the compound of Formula I has a structure of Formula I-120:

(I-120)

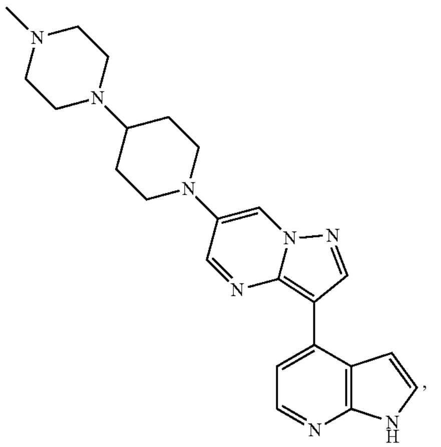

or a pharmaceutically acceptable salt thereof.

In some embodiments, the compound of Formula I has a structure of Formula I-121:

(I-121)

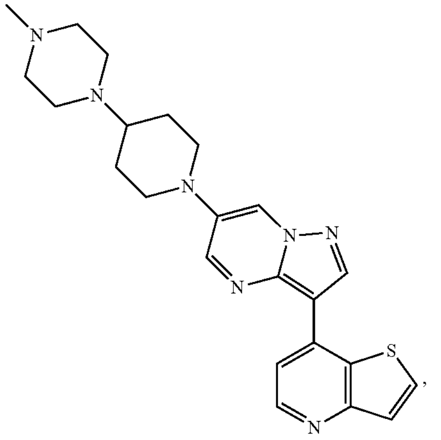

or a pharmaceutically acceptable salt thereof.

In some embodiments, the compound of Formula I has a structure of Formula I-122:

(I-122)

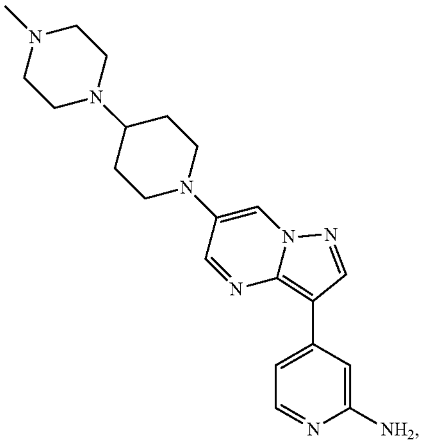

or a pharmaceutically acceptable salt thereof.

In some embodiments, the compound of Formula I has a structure of Formula I-123:

(I-123)

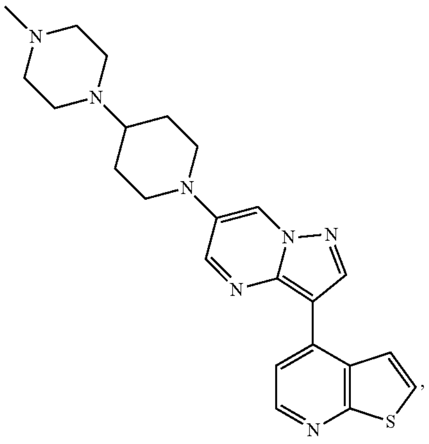

or a pharmaceutically acceptable salt thereof.

In some embodiments, the compound of Formula I has a structure of Formula I-124:

(I-124)

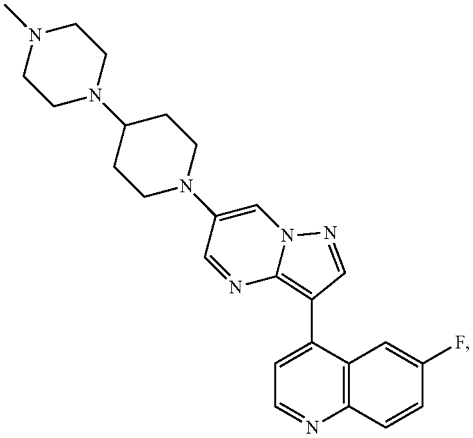

or a pharmaceutically acceptable salt thereof.

In some embodiments, the compound of Formula I has a structure of Formula I-125:

(I-125)

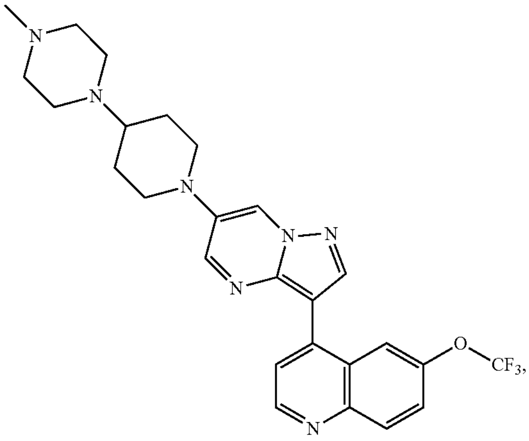

or a pharmaceutically acceptable salt thereof.

In some embodiments, the compound of Formula I has a structure of Formula I-126:

(I-126)

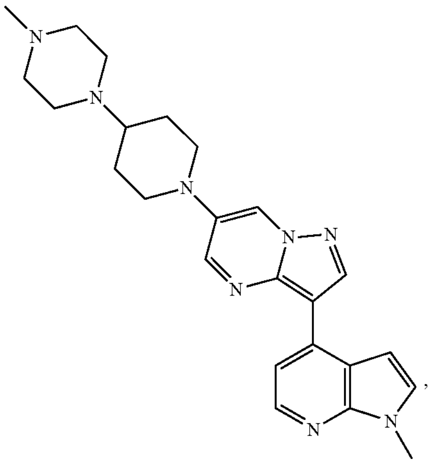

or a pharmaceutically acceptable salt thereof.

In some embodiments, the compound of Formula I has a structure of Formula I-127:

(I-127)

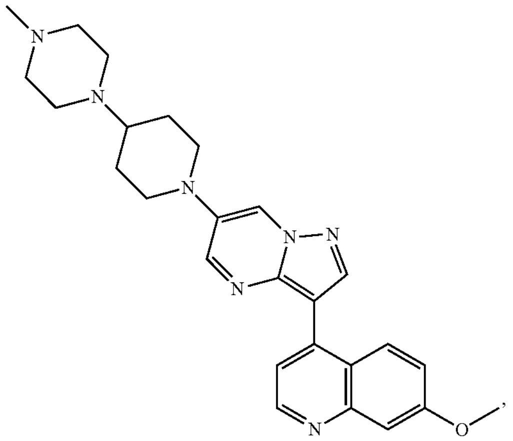

or a pharmaceutically acceptable salt thereof.

In some embodiments, the compound of Formula I has a structure of Formula I-128:

(I-128)

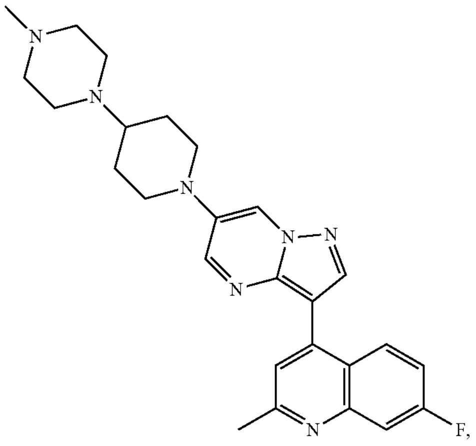

or a pharmaceutically acceptable salt thereof.

In some embodiments, the compound of Formula I has a structure of Formula I-129:

(I-129)

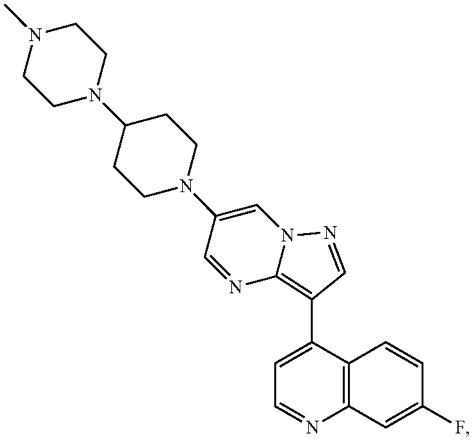

or a pharmaceutically acceptable salt thereof.

In some embodiments, the compound of Formula I has a structure of Formula I-130:

(I-130)

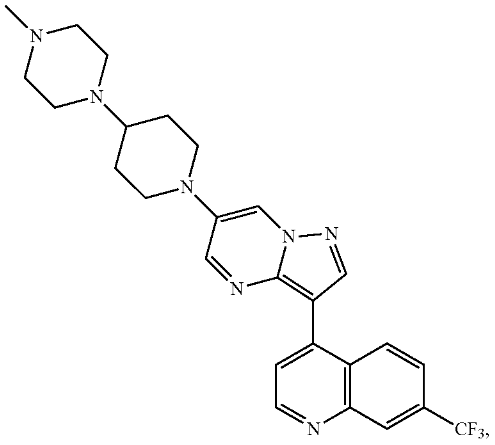

or a pharmaceutically acceptable salt thereof.

In some embodiments, the compound of Formula I has a structure of Formula I-131:

(I-131)

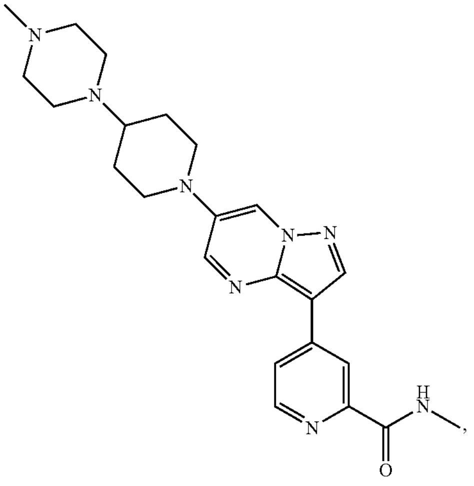

or a pharmaceutically acceptable salt thereof.

In some embodiments, the compound of Formula I has a structure of Formula I-132:

(I-132)

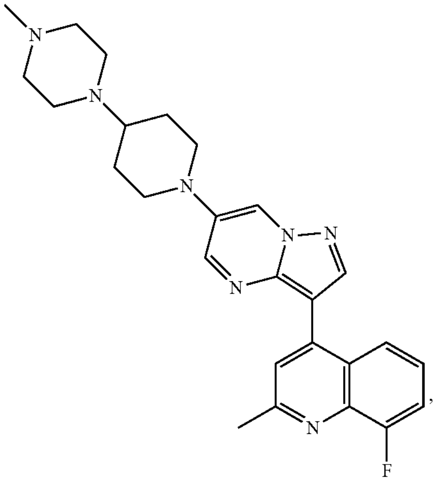

or a pharmaceutically acceptable salt thereof.

In some embodiments, the compound of Formula I has a structure of Formula I-133:

(I-133)

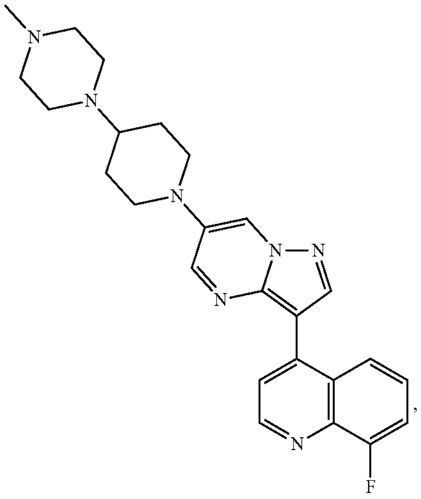

or a pharmaceutically acceptable salt thereof.

In some embodiments, the compound of Formula I has a structure of Formula I-134:

(I-134)

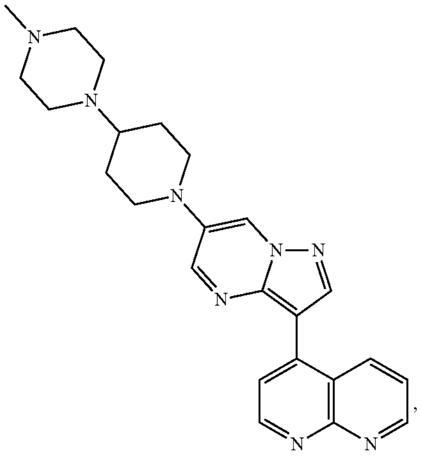

or a pharmaceutically acceptable salt thereof.

In some embodiments, the compound of Formula I has a structure of Formula I-135:

(I-135)

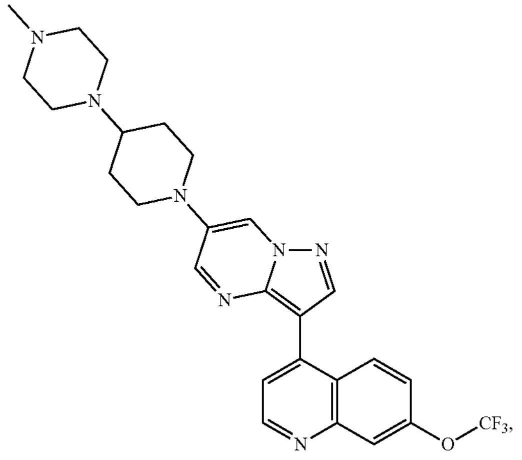

or a pharmaceutically acceptable salt thereof.

In some embodiments, the compound of Formula I has a structure of Formula I-136:

(I-136)

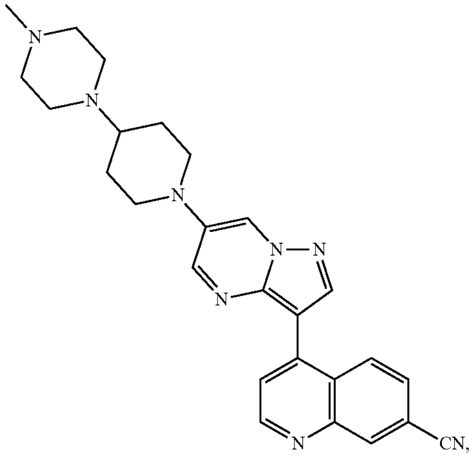

or a pharmaceutically acceptable salt thereof.

In some embodiments, the compound of Formula I has a structure of Formula I-137:

(I-137)

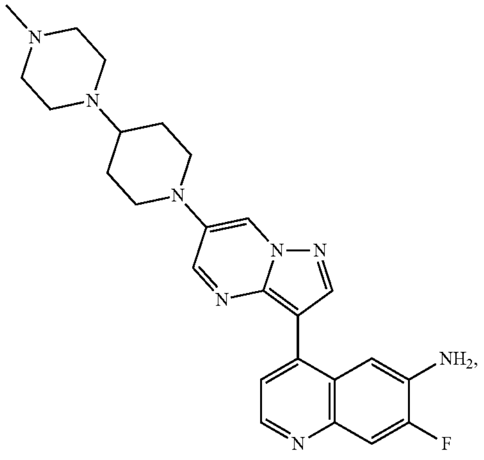

or a pharmaceutically acceptable salt thereof.

In some embodiments, the compound of Formula I has a structure of Formula I-138:

(I-138)

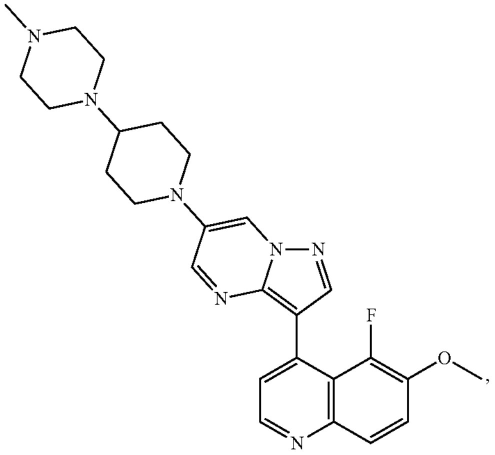

or a pharmaceutically acceptable salt thereof.

In some embodiments, the compound of Formula I has a structure of Formula I-139:

(I-139)

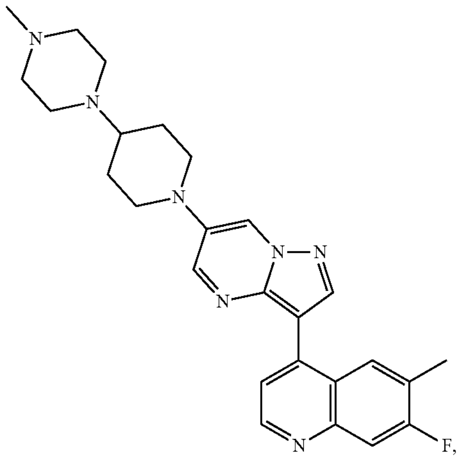

or a pharmaceutically acceptable salt thereof.

In some embodiments, the compound of Formula I has a structure of Formula I-140:

(I-140)

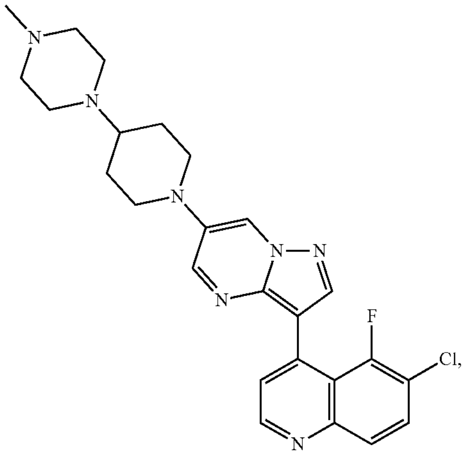

or a pharmaceutically acceptable salt thereof.

In some embodiments, the compound of Formula I has a structure of Formula I-141:

(I-141)

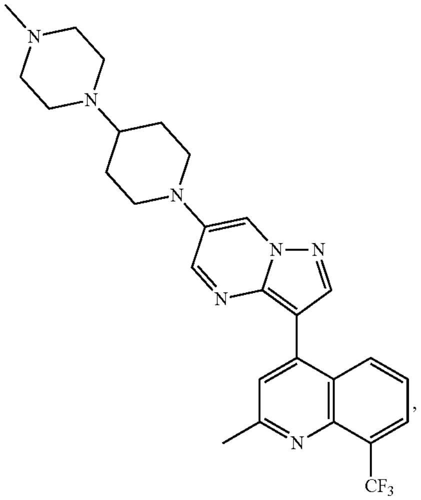

or a pharmaceutically acceptable salt thereof.

In some embodiments, the compound of Formula I has a structure of Formula I-142:

(I-142)

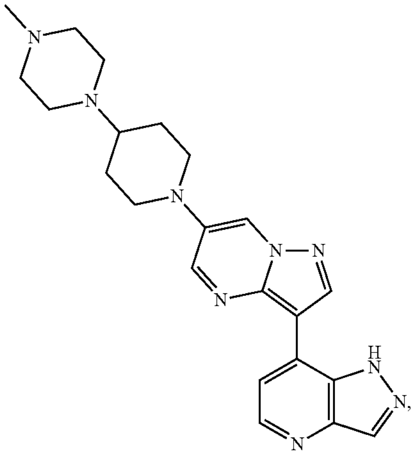

or a pharmaceutically acceptable salt thereof.

In some embodiments, the compound of Formula I has a structure of Formula I-143:

(I-143)

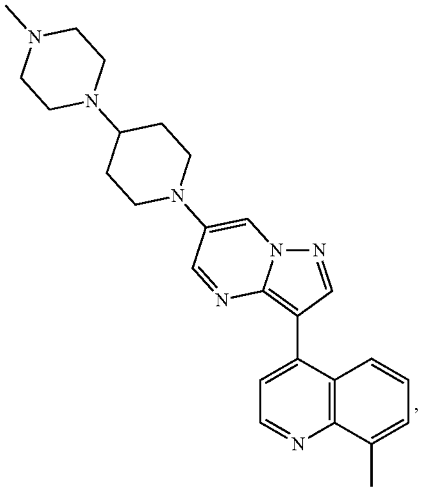

or a pharmaceutically acceptable salt thereof.

In some embodiments, the compound of Formula I has a structure of Formula I-144:

(I-144)

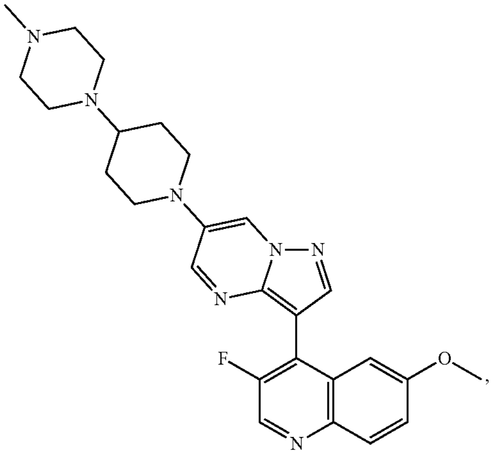

or a pharmaceutically acceptable salt thereof.

In some embodiments, the compound of Formula I has a structure of Formula I-145:

(I-145)

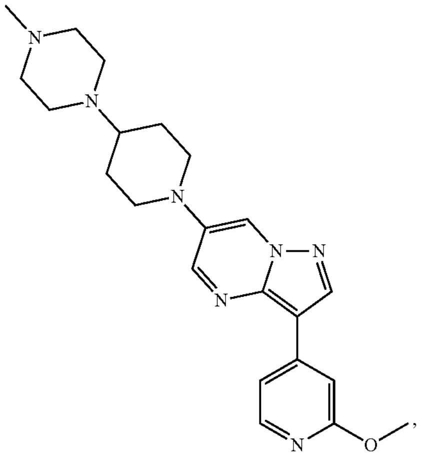

or a pharmaceutically acceptable salt thereof.

In some embodiments, the compound of Formula I has a structure of Formula I-146:

(I-146)

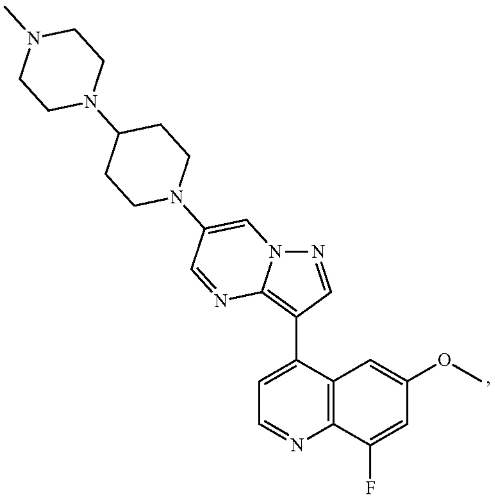

or a pharmaceutically acceptable salt thereof.

In some embodiments, the compound of Formula I has a structure of Formula I-147:

(I-147)

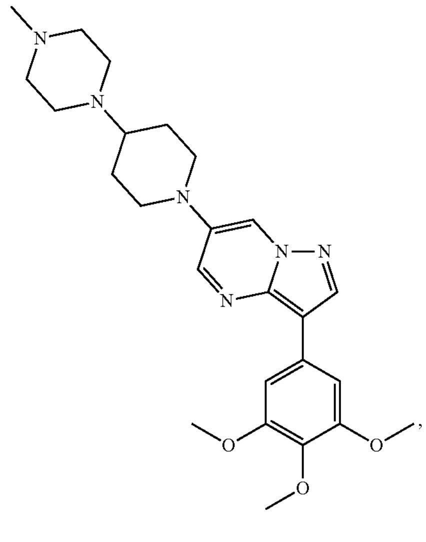

or a pharmaceutically acceptable salt thereof.

In some embodiments, the compound of Formula I has a structure of Formula I-148:

(I-148)

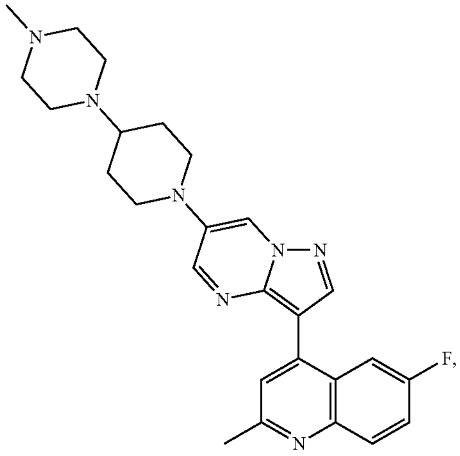

or a pharmaceutically acceptable salt thereof.

In some embodiments, the compound of Formula I has a structure of Formula I-149:

(I-149)

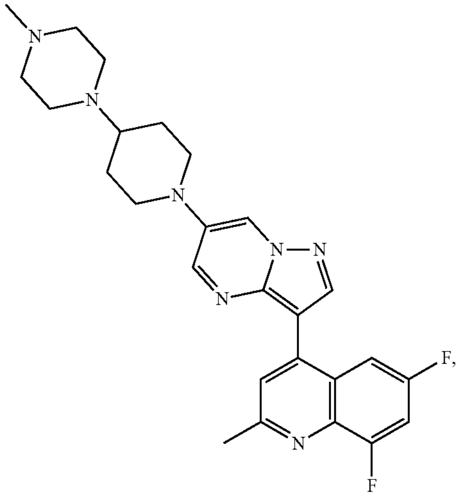

or a pharmaceutically acceptable salt thereof.

In some embodiments, the compound of Formula I has a structure of Formula I-150:

(I-150)

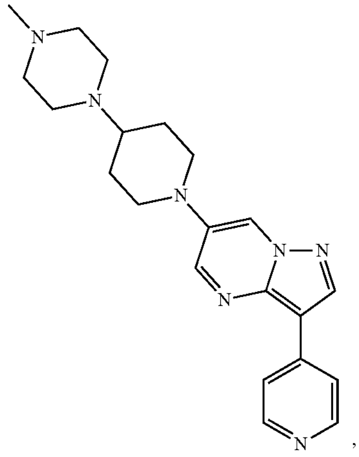

or a pharmaceutically acceptable salt thereof.

In some embodiments, the compound of Formula I has a structure of Formula I-151:

(I-151)

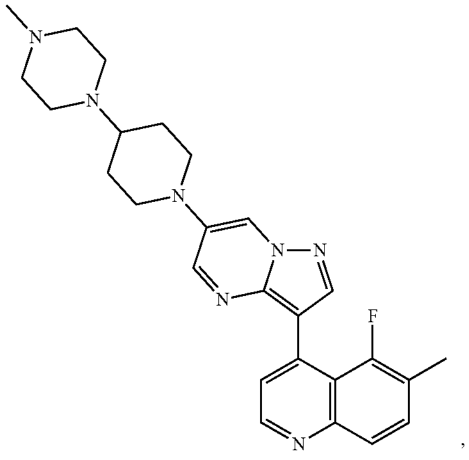

or a pharmaceutically acceptable salt thereof.

In some embodiments, the compound of Formula I has a structure of Formula I-152:

(I-152)

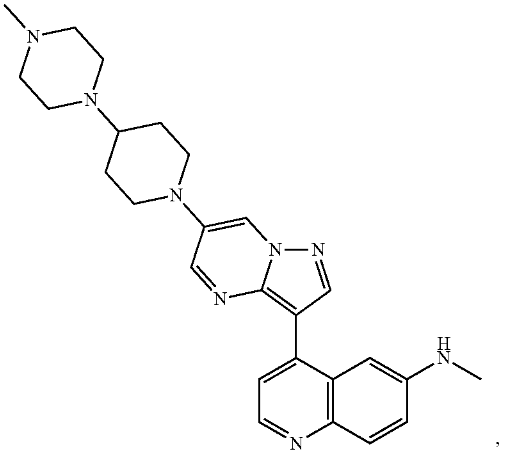

or a pharmaceutically acceptable salt thereof.

In some embodiments, the compound of Formula I has a structure of Formula I-153:

(I-153)

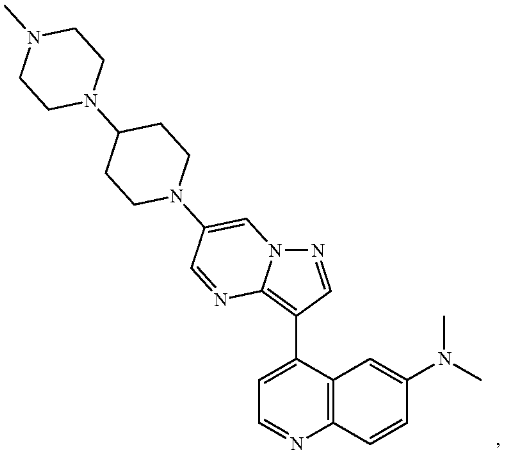

or a pharmaceutically acceptable salt thereof.

In some embodiments, the compound of Formula I has a structure of Formula I-154:

(I-154)

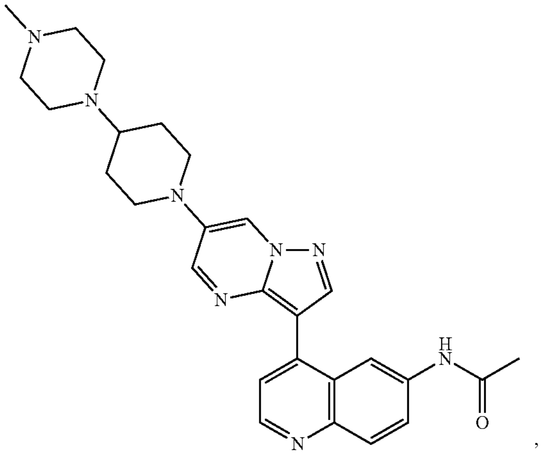

or a pharmaceutically acceptable salt thereof.

In some embodiments the compound of Formula I has a structure of Formula I-155:

(I-155)

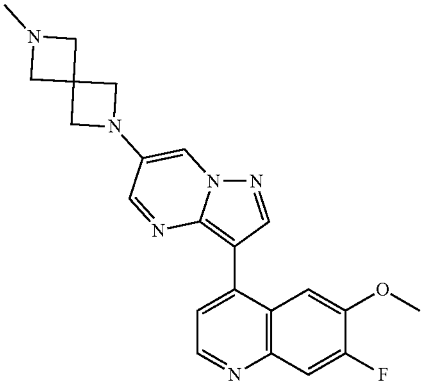
, or a pharmaceutically acceptable salt thereof.

In some embodiments, the compound of Formula I has a structure of Formula I-156:

(I-156)

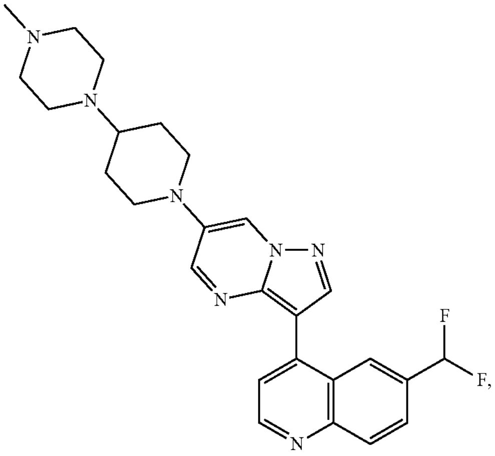

or a pharmaceutically acceptable salt thereof.

In some embodiments, the compound of Formula I has a structure of Formula I-157:

(I-157)

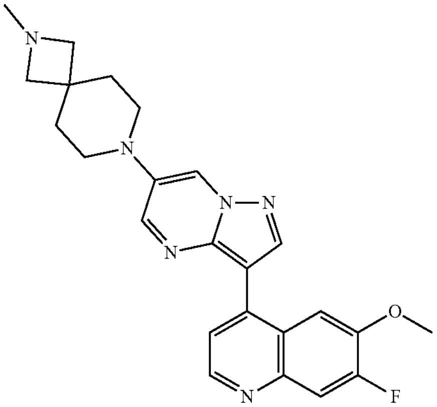
, or a pharmaceutically acceptable salt thereof.

In some embodiments, the compound of Formula I has a structure of Formula I-158:

(I-158)

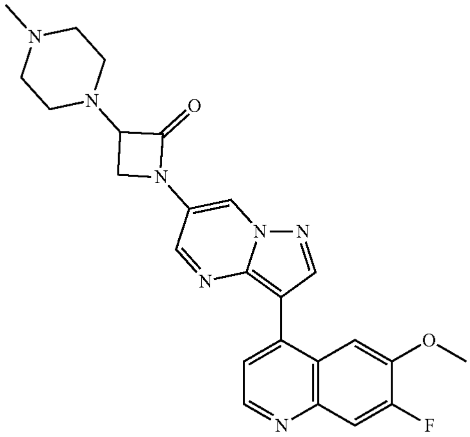
, or a pharmaceutically acceptable salt thereof.

In some embodiments, the compound of Formula I has a structure of Formula I-159:

(I-159)

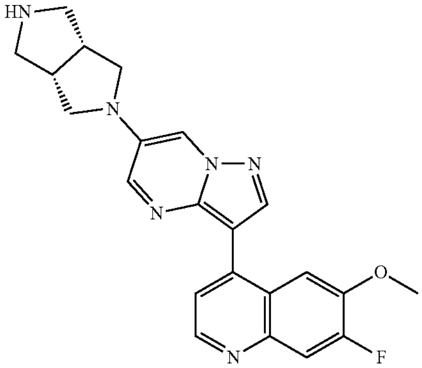
, or a pharmaceutically acceptable salt thereof.

In some embodiments, the compound of Formula I has a structure of Formula I-160:

(I-160)

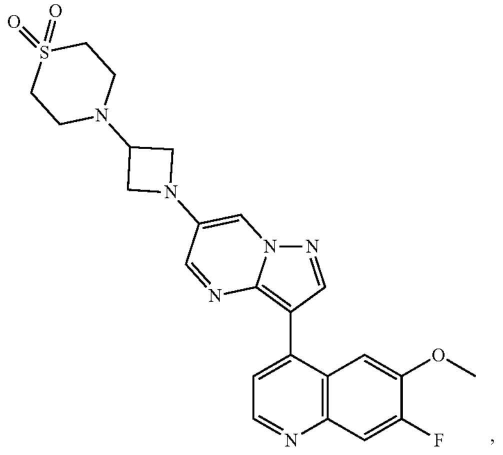

or a pharmaceutically acceptable salt thereof.

In some embodiments, the compound of Formula I has a structure of Formula I-161:

(I-161)

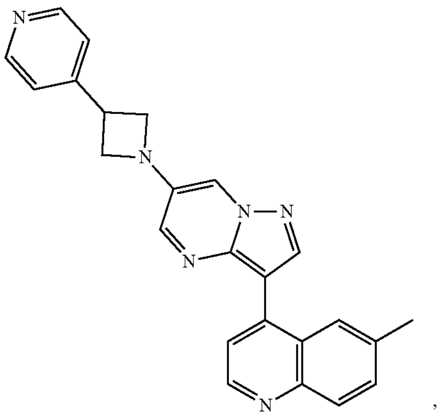

(1-161), or a pharmaceutically acceptable salt thereof.

In some embodiments, the compound of Formula I has a structure of Formula I-162:

(I-162)

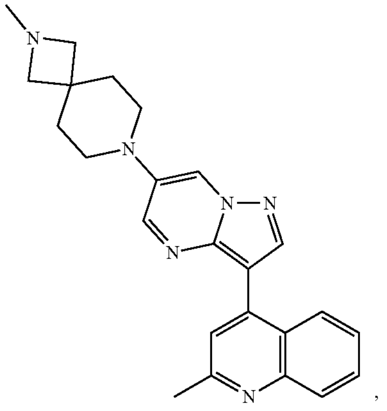

or a pharmaceutically acceptable salt thereof.

In some embodiments, the compound of Formula I has a structure of Formula I-163:

(I-163)

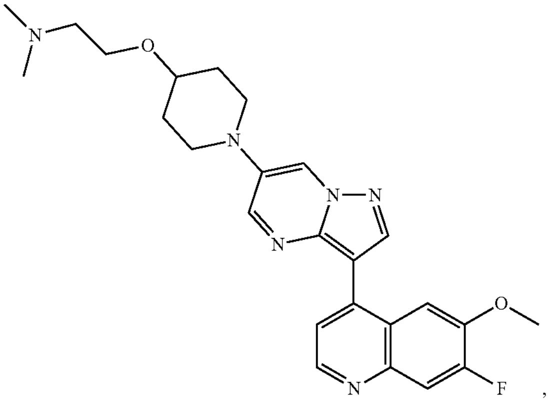

or a pharmaceutically acceptable salt thereof.

In some embodiments, the compound of Formula I has a structure of Formula I-164:

(I-164)

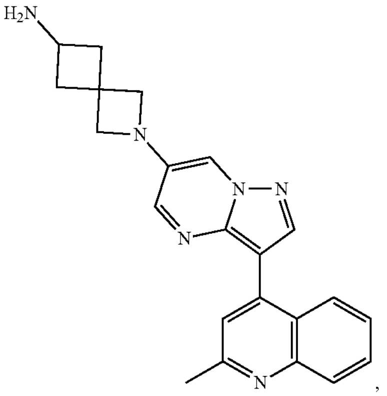

(1-164), or a pharmaceutically acceptable salt thereof.

In some embodiments, the compound of Formula I has a structure of Formula I-165:

(I-165)

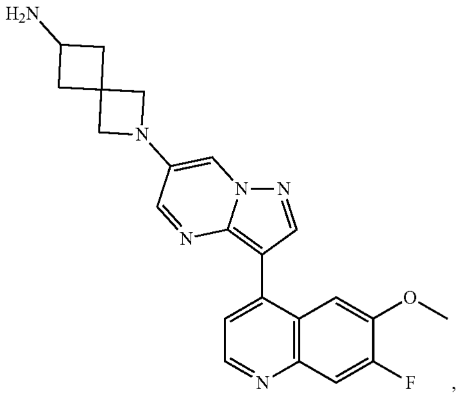

or a pharmaceutically acceptable salt thereof.

In some embodiments, the compound of Formula I has a structure of Formula I-166:

(I-166)

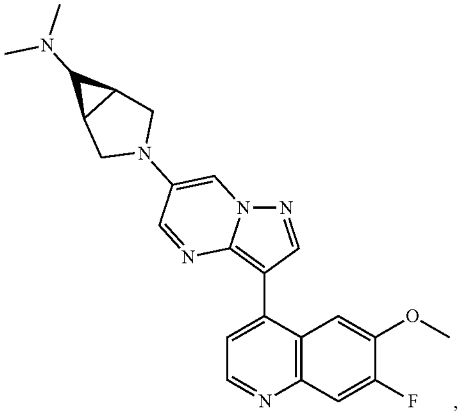

or a pharmaceutically acceptable salt thereof.

In some embodiments, the compound of Formula I has a structure of Formula I-167:

(I-167)

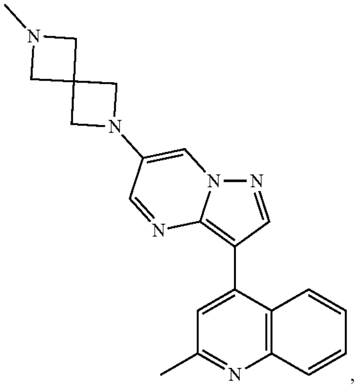

or a pharmaceutically acceptable salt thereof.

In some embodiments, the compound of Formula I has a structure of Formula I-168:

(I-168)

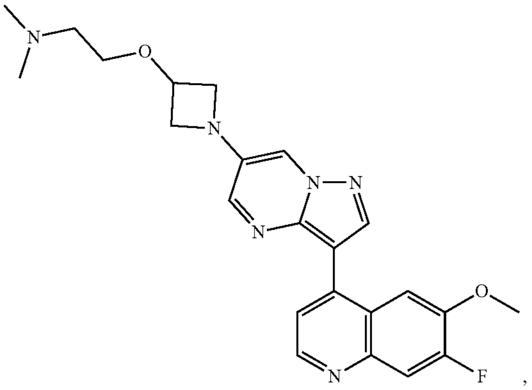

or a pharmaceutically acceptable salt thereof.

In some embodiments, the compound of Formula I has a structure of Formula I-169:

(I-169)

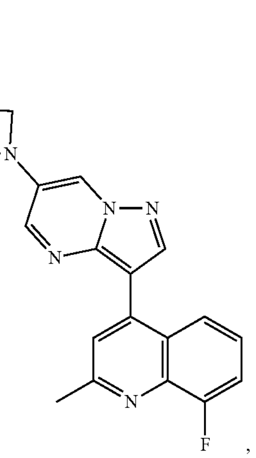

or a pharmaceutically acceptable salt thereof.

In some embodiments, the compound of Formula I has a structure of Formula I-170:

(I-170)

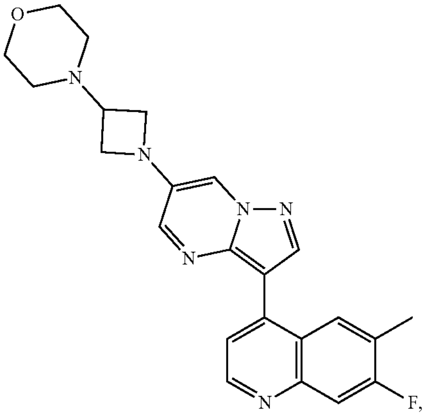

or a pharmaceutically acceptable salt thereof.

In some embodiments, the compound of Formula I has a structure of Formula I-171:

(I-171)

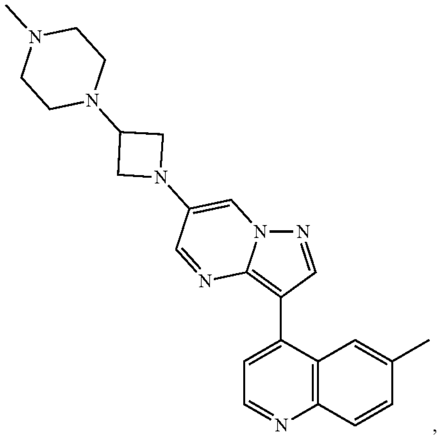

, or a pharmaceutically acceptable salt thereof.

In some embodiments, the compound of Formula I has a structure of Formula I-172:

(I-172)

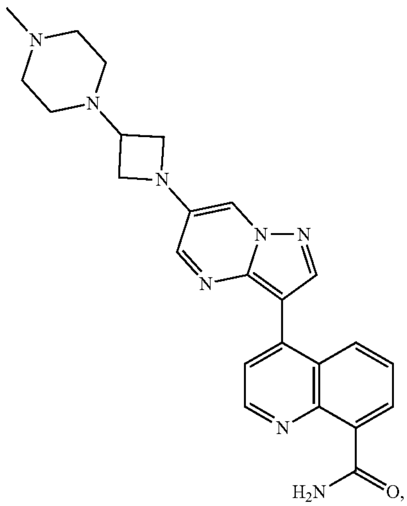

or a pharmaceutically acceptable salt thereof.

In some embodiments, the compound of Formula I has a structure of Formula I-173:

(I-173)

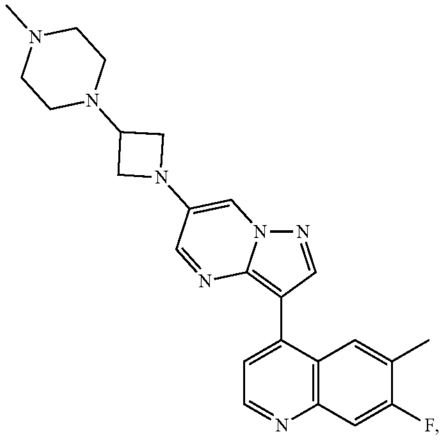

or a pharmaceutically acceptable salt thereof.

In some embodiments, the compound of Formula I has a structure of Formula I-174:

(I-174)

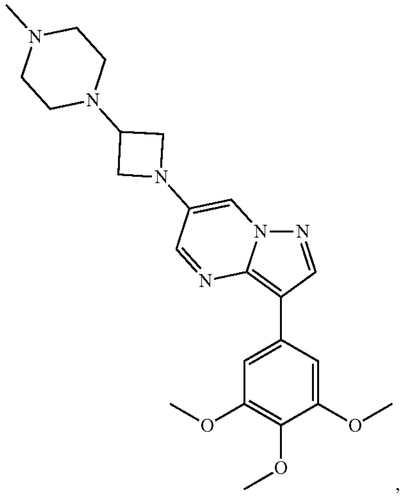

, or a pharmaceutically acceptable salt thereof.

In some embodiments, the compound of Formula I has a structure of Formula I-175:

(I-173)

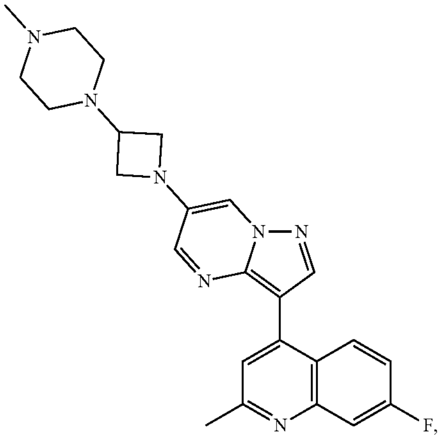

or a pharmaceutically acceptable salt thereof.

In some embodiments, the compound of Formula I has a structure of Formula I-176:

(I-176)

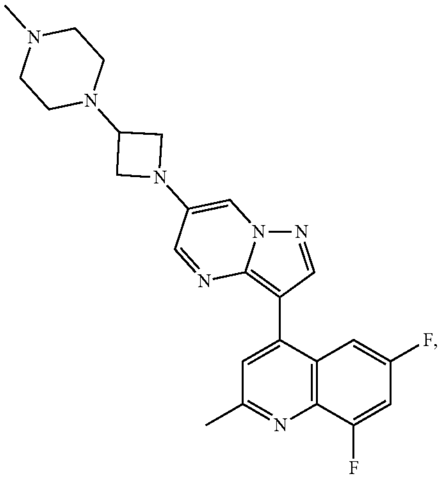

or a pharmaceutically acceptable salt thereof.

In some embodiments, the compound of Formula I has a structure of Formula I-177:

(I-176)

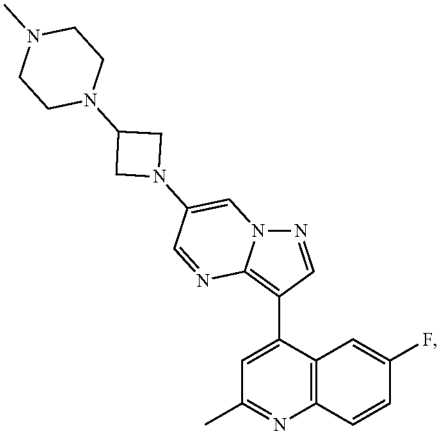

or a pharmaceutically acceptable salt thereof.

In some embodiments, the compound of Formula I has a structure of Formula I-178:

(I-178)

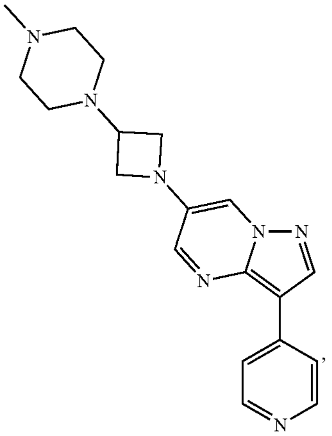

or a pharmaceutically acceptable salt thereof.

In some embodiments, the compound of Formula I has a structure of Formula I-179:

(I-179)

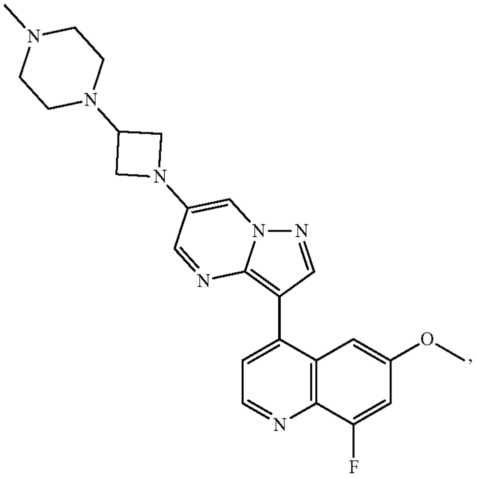

or a pharmaceutically acceptable salt thereof.

In some embodiments, the compound of Formula I has a structure of Formula I-180:

(I-180)

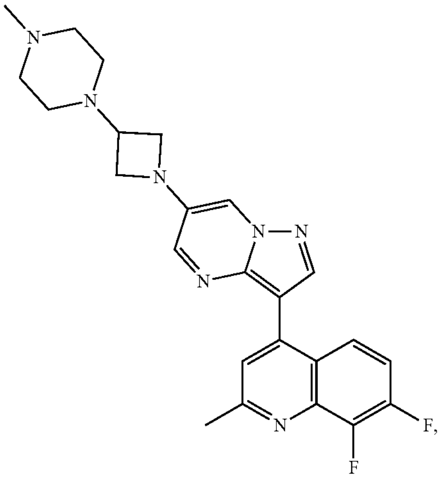

or a pharmaceutically acceptable salt thereof.

In some embodiments, the compound of Formula I has a structure of Formula I-181:

(I-181)

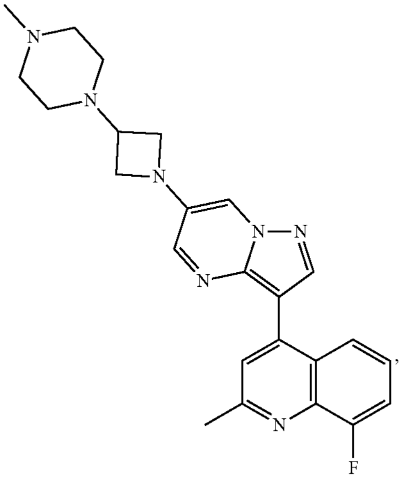

or a pharmaceutically acceptable salt thereof.

In some embodiments, the compound of Formula I has a structure of Formula I-182:

(I-182)

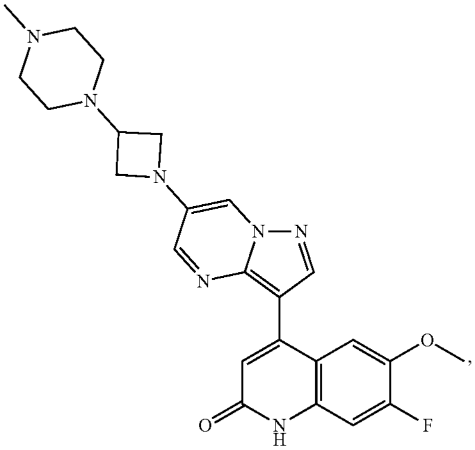

or a pharmaceutically acceptable salt thereof.

In some embodiments, the compound of Formula I has a structure of Formula I-183:

(I-183)

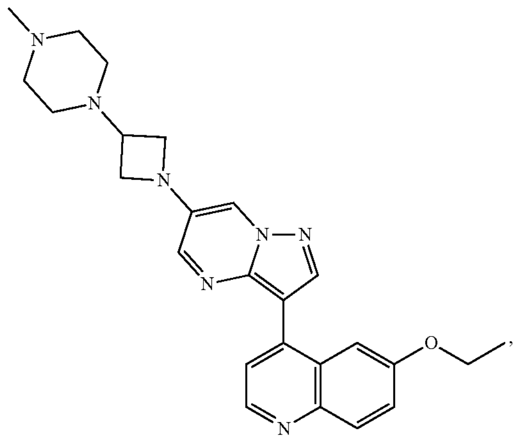

or a pharmaceutically acceptable salt thereof.

In some embodiments, the compound of Formula I has a structure of Formula I-184:

(I-184)

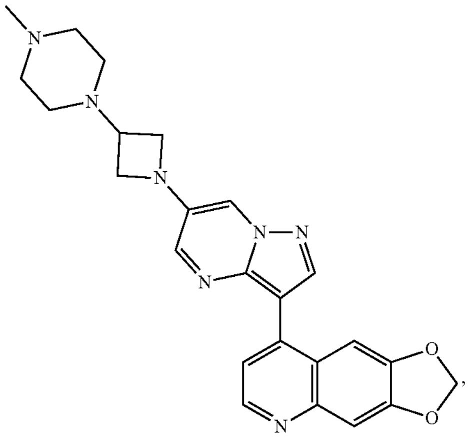

or a pharmaceutically acceptable salt thereof.

In some embodiments, the compound of Formula I has a structure of Formula I-185:

(I-185)

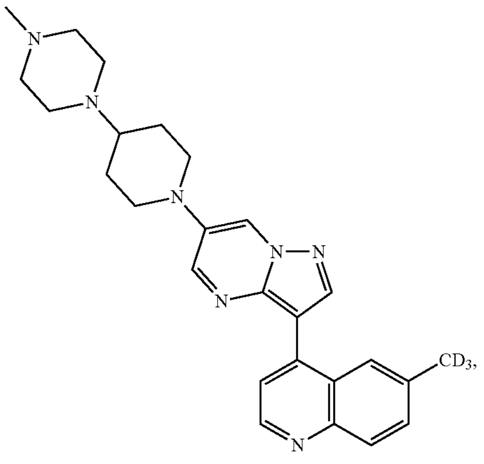

or a pharmaceutically acceptable salt thereof.

In some embodiments, the compound of Formula I has a structure of Formula I-186:

(I-186)

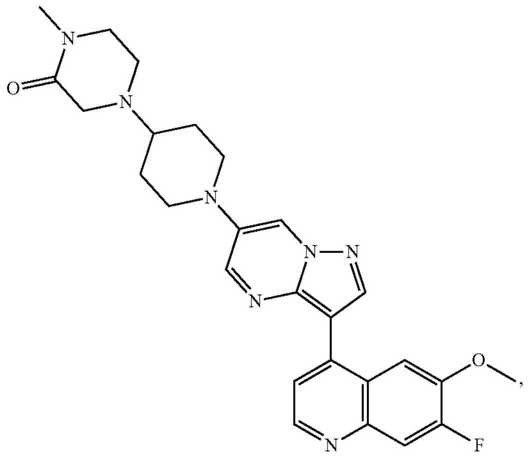

or a pharmaceutically acceptable salt thereof.

In some embodiments, the compound of Formula I has a structure of Formula I-187:

(I-187)

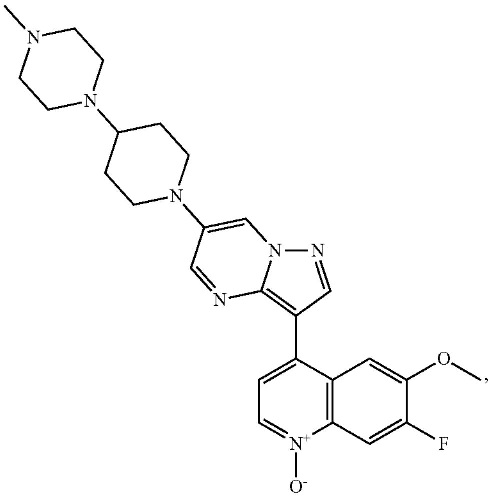

or a pharmaceutically acceptable salt thereof.

In some embodiments, the compound of Formula I has a structure of Formula I-188:

(I-188)

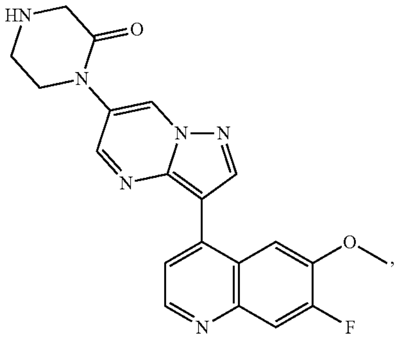

or a pharmaceutically acceptable salt thereof.

In some embodiments, the compound of Formula I has a structure of Formula I-189:

(I-189)

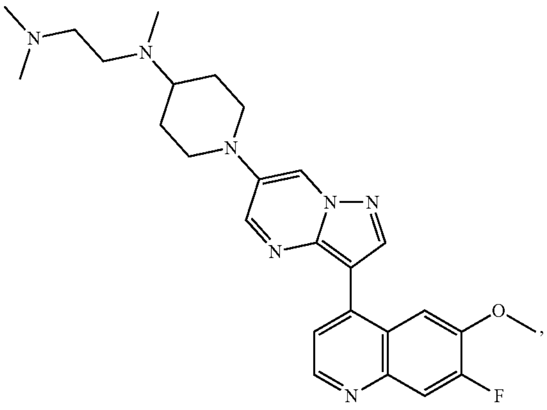

or a pharmaceutically acceptable salt thereof.

In some embodiments, the compound of Formula I has a structure of Formula I-190:

(I-190)

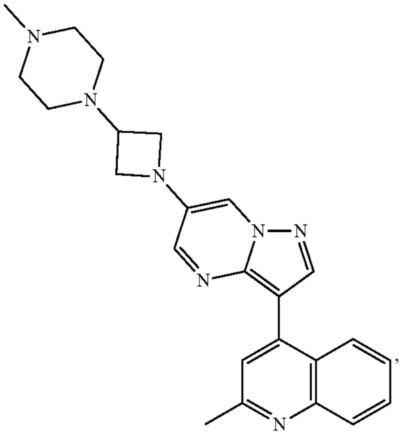

or a pharmaceutically acceptable salt thereof.

In some embodiments, the compound of Formula I has a structure of Formula I-191:

(I-191)

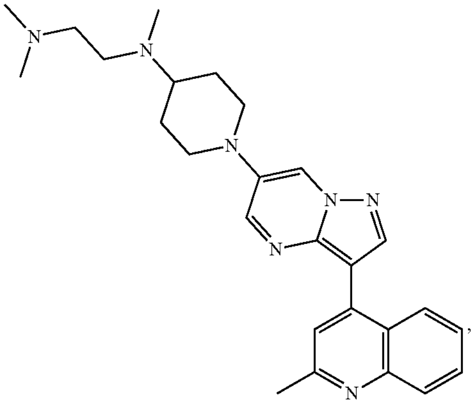

or a pharmaceutically acceptable salt thereof.

In some embodiments, the compound of Formula I has a structure of Formula I-192:

(I-192)

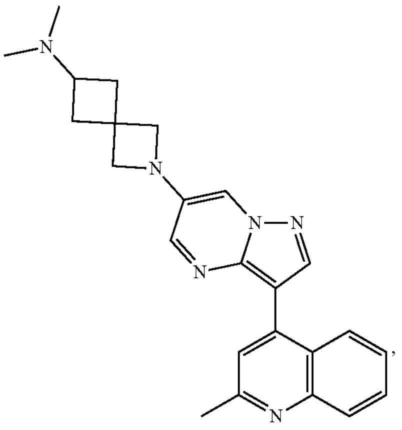

or a pharmaceutically acceptable salt thereof.

In some embodiments, the compound of Formula I has a structure of Formula I-193:

(I-193)

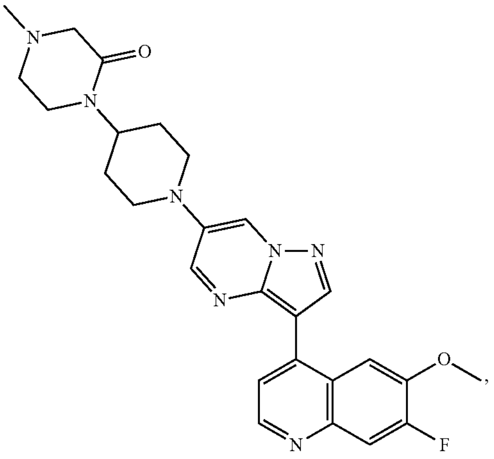

or a pharmaceutically acceptable salt thereof.

In some embodiments, the compound of Formula I has a structure of Formula I-194:

(I-194)

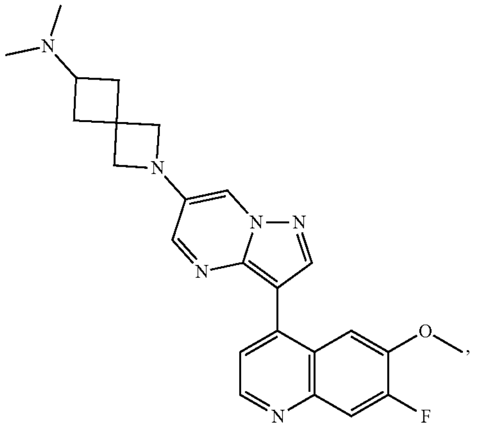

or a pharmaceutically acceptable salt thereof.

In some embodiments, the compound of Formula I has a structure of Formula I-195:

(I-195)

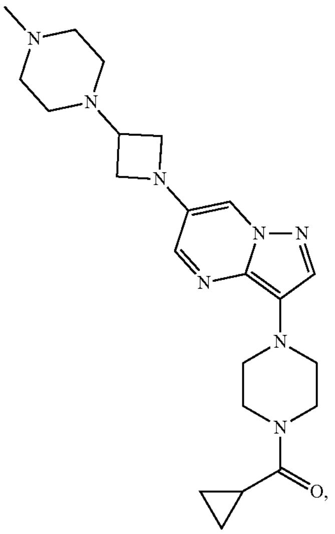

or a pharmaceutically acceptable salt thereof.

In some embodiments, the compound of Formula I has a structure of Formula I-196:

(I-196)

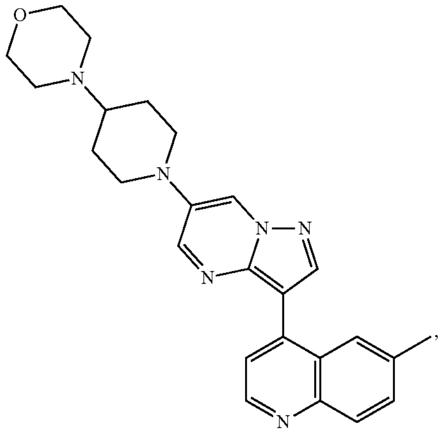

or a pharmaceutically acceptable salt thereof.

In some embodiments, the compound of Formula I has a structure of Formula I-197:

(I-197)

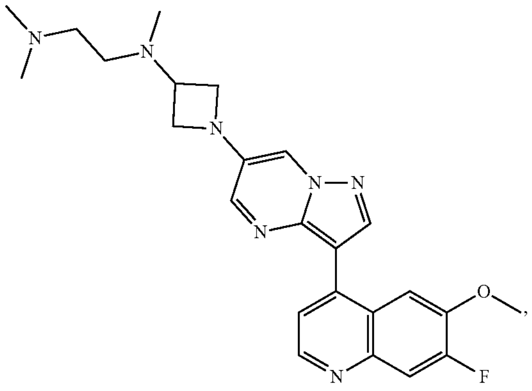

or a pharmaceutically acceptable salt thereof.

In some embodiments, the compound of Formula I has a structure of Formula I-198:

(I-198)

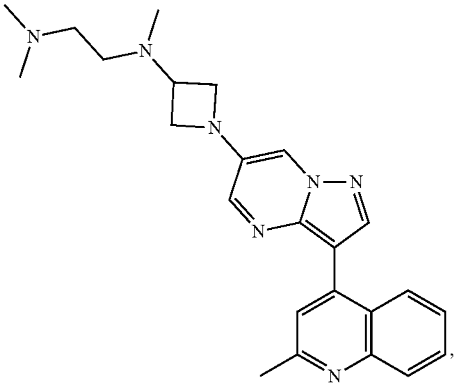

or a pharmaceutically acceptable salt thereof.

In some embodiments, the compound of Formula I has a structure of Formula I-199:

(I-199)

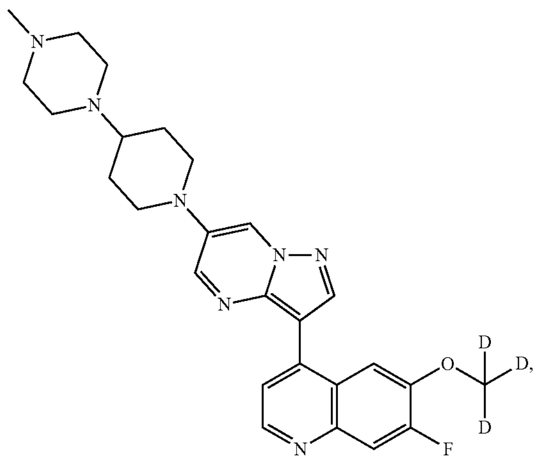

or a pharmaceutically acceptable salt thereof.

In some embodiments, the compound of Formula I has a structure of Formula I-200:

(I-200)

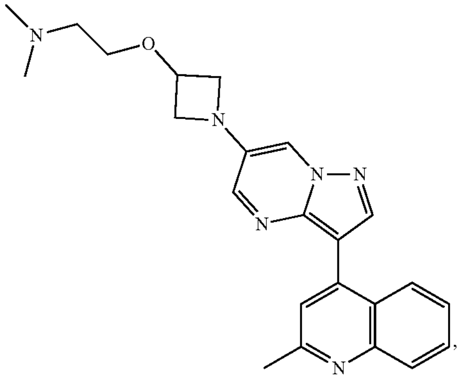

or a pharmaceutically acceptable salt thereof.

Additional compounds of Formula I are described US Patent Application Publication No. 2020/0179389, and are incorporated herein by reference.

In some embodiments, the ALK2 inhibitor is a compound of Formula II:

Formula II

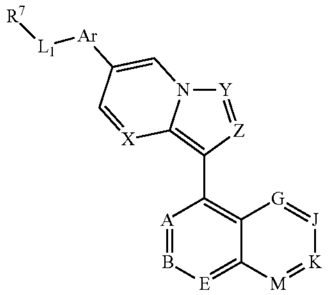

or a pharmaceutically acceptable salt thereof, wherein

X and Y are independently selected from $CR^{15}$ and N, preferably both N;

Z is selected from $CR^{3'}$ and N, preferably $CR^{3'}$, most preferably CH;

Ar is a substituted or unsubstituted aryl ring or a substituted or unsubstituted heteroaryl ring;

$L_1$ is absent or selected from substituted or unsubstituted alkyl, substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclylheteroalkyl, and substituted or unsubstituted heteroalkyl; and J and K are both absent or, independently for each occurrence, are each $CR^{16}$;

A is $CR^{16}$;

B and E are each independently $CR^{17}$;

if J and K are absent, then G is $R^{16}$ and M is $R^{17}$; if J and K are not absent, then G is $CR^{16}$ and M is $CR^{17}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from

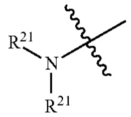

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido, preferably H;

$R^{16}$, independently for each occurrence, is selected from H, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and $-R^{22}$, $-NH_2$, $-NHR^{22}$, $-N(R^{22})_2$, halogen, $-CO_2H$, $-CO_2R^{22}$, $-CONH_2$, $-CONHR^{22}$, $-CON(R^{22})_2$, $-C(NH_2)=N(OH)$, $-C(NHR^{22})=N(OH)$, $-C(N(R^{22})_2)=N(OH)$, $-C(NH_2)=NH$, $-C(NHR^{22})=NH$, $-C(NHR^{22})=NR^{22}$, $-C(N(R^{22})_2)=NH$, $-C(N(R^{22})_2)=NR^{22}$, $-CN$, $-CH_2CH_2OH$, $-CH_2OH$, $-CH_2SO_2NH_2$, $-CH_2SO_2NHR^{22}$, $-CH_2SO_2N(R^{22})_2$, $-SO_2NH_2$, $-SO_2NHR^{22}$, $-SO_2N(R^{22})_2$, $-NHSO_2R^{22}$, $-SO_2R^{22}$, $-CH_2SO_2R^{22}$, $-CH_2NH_2$, $-CH_2NHR^{22}$, $-CH_2N(R^{22})_2$, $-C(O)R^{22}$,

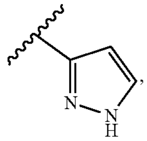, 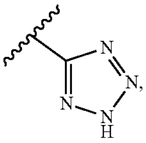, $-CH(OH)R^{22}$, $-C(OH)(R^{22})_2$, $-CH(NH_2)(R^{22})$, $-CH(NHR^{22})(R^{22})$, $-CH(N(R^{22})_2)(R^{22})$, pyrazol-3-yl, pyrazol-4-yl, and $-OR^{22}$, provided that at least one $R^{17}$ is $-R^{22}$, —$NH_2$, —$NHR^{22}$, —$N(R^{22})_2$, halogen, —$CO_2H$, —$CO_2R^{22}$, —$CONH_2$, —$CONHR^{22}$, —$CON(R^{22})_2$, —$C(NH_2)$═$N(OH)$, —$C(NHR^{22})$═$N(OH)$, —$C(N(R^{22})_2)$═$N(OH)$, —$C(NH_2)$═NH, —$C(NHR^{22})$═NH, —$C(NHR^{22})$═$NR^{22}$, —$C(N(R^{22})_2)$═NH, —$C(N(R^{22})_2)$═$NR^{22}$, —CN, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$

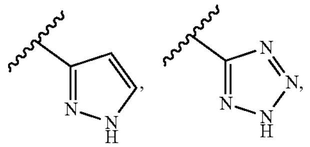 [SMILES: *c1cc[nH]n1 ; *c1nn[nH]n1]

—$CH(OH)R^{22}$—$C(OH)(R^{22})_2$, —$CH(NH_2)(R^{22})$, —$CH(NHR^{22})(R^{22})$, —$CH(N(R^{22})_2)(R^{22})$, pyrazol-3-yl, pyrazol-4-yl, or —$OR^{22}$;

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide, preferably from H and substituted or unsubstituted alkyl, aralkyl, cycloalkyl, heterocyclyl, aryl, heteroaryl, heteroaralkyl, cycloalkylalkyl, heterocyclylalkyl, more preferably from H and substituted or unsubstituted alkyl, and most preferably from H and lower alkyl, such as methyl or ethyl; and $R^{22}$, independently for each occurrence, is selected from lower alkyl (e.g., $CH_3$ or $CF_3$) and cycloalkyl (preferably cyclopropyl or cyclobutyl).

In some embodiments, the ALK2 inhibitor is a compound of Formula II or a pharmaceutically acceptable salt thereof, wherein X and Y are each N;

Z is $CR^{3'}$;

Ar is a substituted or unsubstituted aryl ring or a substituted or unsubstituted heteroaryl ring;

$L_1$ is absent or selected from substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclylheteroalkyl, and

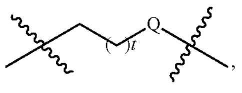

wherein Q is selected from $CR^{10'}R^{11}$, $NR^{12}$, O, S, S(O), and $SO_2$; $R^{10'}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and t is an integer selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and J and K are both absent or, independently for each occurrence, are each $CR^{16}$;

A is $CR^{16}$;

B and E are each independently $CR^{17}$;

if J and K are absent, then G is $R^{16}$ and M is $R^{17}$; if J and K are not absent, then G is $CR^{16}$ and M is $CR^{17}$;

$R^{3'}$ is H;

$R^7$ is selected from

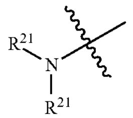

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and —$R^{22}$, —$NH_2$, —$NHR^{22}$, —$N(R^{22})_2$, —$CO_2H$, —$CO_2R^{22}$, —$CONH_2$, —$CONHR^{22}$, —$CON(R^{22})_2$, —$C(NH_2)$═$N(OH)$, —$C(NHR^{22})$═$N(OH)$, —$C(N(R^{22})_2)$═$N(OH)$, —$C(NH_2)$═NH, —$C(NHR^{22})$═NH, —$C(NHR^{22})$═$NR^{22}$, —$C(N(R^{22})_2)$═NH, —$C(N(R^{22})_2)$═$NR^{22}$, —CN, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$,

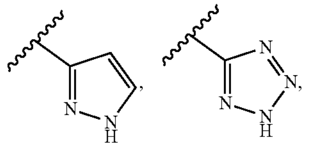 [SMILES: *c1cc[nH]n1 ; *c1nn[nH]n1]

—$CH(OH)R^{22}$, —$C(OH)(R^{22})_2$, —$CH(NH_2)(R^{22})$, —$CH(NHR^{22})(R^{22})$, —$CH(N(R^{22})_2)(R^{22})$, pyrazol-3-yl, pyrazol-4-yl, and —$OR^{22}$, provided that at least one $R^{17}$ is —$R^{22}$, —$NH_2$, —$NHR^{22}$, —$N(R^{22})_2$, —$CO_2H$, —$CO_2R^{22}$, —$CONH_2$, —$CONHR^{22}$, —$CON(R^{22})_2$, —$C(NH_2)$═$N(OH)$, —$C(NHR^{22})$═$N(OH)$, —$C(N(R^{22})_2)$═$N(OH)$, —$C(NH_2)$═NH, —$C(NHR^{22})$═NH, —$C(NHR^{22})$═$NR^{22}$, —$C(N(R^{22})_2)$═NH, —$C(N(R^{22})_2)$═$NR^{22}$, —CN, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$

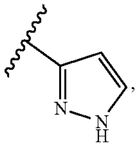, 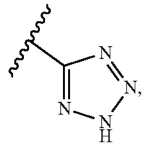

—CH(OH)$R^{22}$, —C(OH)$(R^{22})_2$, —CH$(NH_2)(R^{22})$, —CH$(NHR^{22})(R^{22})$, —CH$(N(R^{22})_2)(R^{22})$, pyrazol-3-yl, or pyrazol-4-yl, where at least one $R^{17}$ represents a moiety selected from —$CO_2H$, —$CONH_2$, —$CH_2OH$, —CN, —C(O)$CH_3$, —CH(OH)$CH_3$, —C(OH)$(CH_3)_2$, —C(O)$CF_3$, —CH$(NH_2)CF_3$, —$SO_2CH_3$, —$SO_2NH_2$ and

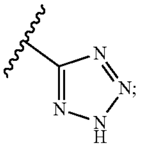 [SMILES: *c1nn[nH]n1];

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide; and $R^{22}$, independently for each occurrence, is selected from lower alkyl and cycloalkyl; wherein at least one $R^{16}$ or one $R^{17}$ is not H.

In some embodiments, the ALK2 inhibitor is a compound of Formula II or a pharmaceutically acceptable salt thereof, wherein X and Y are each N;

Z is $CR^{3'}$;

Ar is a substituted or unsubstituted aryl ring or a substituted or unsubstituted heteroaryl ring;

$L_1$ is absent or

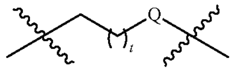

wherein Q is selected from $CR^{10}R^{11}$, $NR^{12}$, O, S, S(O), and $SO_2$; $R^{10'}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and t is selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and J and K are both absent or, independently for each occurrence, are each $CR^{16}$;

A and B, independently for each occurrence, are $CR^{16}$;

E is $CR^{17}$;

if J and K are absent, then G and M are each independently $R^{16}$; if J and K are not absent, then G and M are each independently $CR^{17}$;

$R^{3'}$ is H;

$R^7$ is

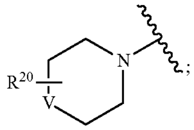;

V is $NR^{30}$;

$R^{20}$ is absent or represents from 1-6 substituents on the ring to which it is attached, independently selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, sulfonamide, tetrazolyl, or trifluoromethylacyl;

$R^{17}$, independently for each occurrence, is selected from $R^{16}$ and H, —$CO_2H$, —$CONH_2$, —$CONHCH_3$, —$CON(CH_3)_2$, —C$(NH_2)$=N(OH), —C$(NH_2)$=NH, —CN, —$CH_2OH$, —$SO_2NH_2$, —$CH_2NH_2$, —C(O)$CH_3$,

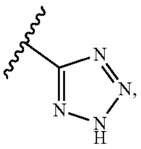 [SMILES: *c1nn[nH]n1],

—CH(OH)$CH_3$, —C(O)$CF_3$, and —$OCH_3$, provided that at least one $R^{17}$ is H, —$CO_2H$, —$CONH_2$, —$CONHCH_3$, —$CON(CH_3)_2$, —C$(NH_2)$=N(OH), —C$(NH_2)$=NH, —CN, —$CH_2OH$, —$SO_2NH_2$, —$CH_2NH_2$, —C(O)$CH_3$,

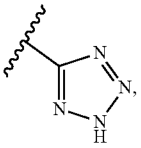 [SMILES: *c1nn[nH]n1],

—CH(OH)$CH_3$, or —C(O)$CF_3$; and $R^{30}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide;

wherein at least one $R^{16}$ or one $R^{17}$ is not H.

In other embodiments, the ALK2 inhibitor is a compound of Formula II or a pharmaceutically acceptable salt thereof, wherein X and Y are independently selected from $CR^{15}$ and N, preferably both N;

Z is selected from $CR^{3'}$ and N, preferably $CR^{3'}$, most preferably CH;

Ar is a substituted or unsubstituted aryl ring (e.g., a substituted or unsubstituted phenyl ring) or a substituted or unsubstituted heteroaryl ring (e.g., a pyridyl or pyrimidyl ring);

$L_1$ is absent or selected from substituted or unsubstituted alkyl and heteroalkyl; and J and K are both absent or, independently for each occurrence, are each $CR^{16}$;

A and B, independently for each occurrence, are $CR^{16}$;

E is $CR^{17}$;

if J and K are absent, then G and M are each independently $R^{16}$; if J and K are not absent, then G and M are each independently $CR^{17}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from

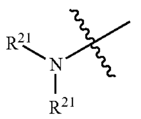

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, D, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, sulfonamide, tetrazolyl, or trifluoromethylacyl;

$R^{17}$, independently for each occurrence, is selected from $R^{16}$ and H, D, $-CO_2H$, $-CONH_2$, $-CONHCH_3$, $-CON(CH_3)_2$, $-C(NH_2)=N(OH)$, $-C(NH_2)=NH$, $-CN$, $-CH_2OH$, $-SO_2NH_2$, $-CH_2NH_2$, $-C(O)CH_3$,

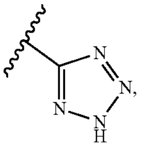

$-CH(OH)CH_3$, $-C(O)CF_3$, and $-OCH_3$, provided that at least one $R^{17}$ is H, $-CO_2H$, $-CONH_2$, $-CONHCH_3$, $-CON(CH_3)_2$, $-C(NH_2)=N(OH)$, $-C(NH_2)=NH$, $-CN$, $-CH_2OH$, $-SO_2NH_2$, $-CH_2NH_2$, $-C(O)CH_3$,

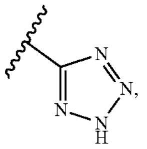 [SMILES: *c1nn[nH]n1]

$-CH(OH)CH_3$, $-C(O)CF_3$, or $-OCH_3$;

and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide.

Compounds of Formula II may be synthesized by methods known in the art, e.g., those described in U.S. Pat. No. 10,513,521, which is incorporated herein by reference.

In some embodiments the compound of Formula II has a structure of Formula II-1:

(II-1)

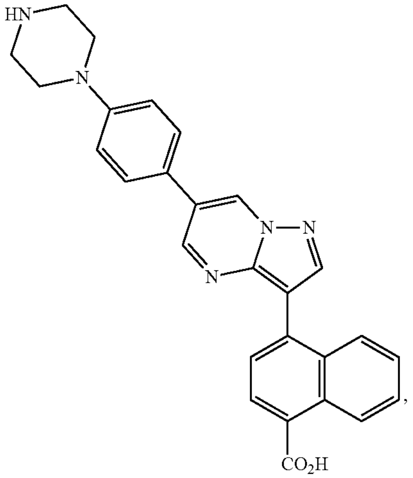

or a pharmaceutically acceptable salt thereof.

In some embodiments, the compound of Formula II has a structure of Formula II-2:

or a pharmaceutically acceptable salt thereof.

In some embodiments, the compound of Formula II has a structure of Formula II-3:

(II-2)

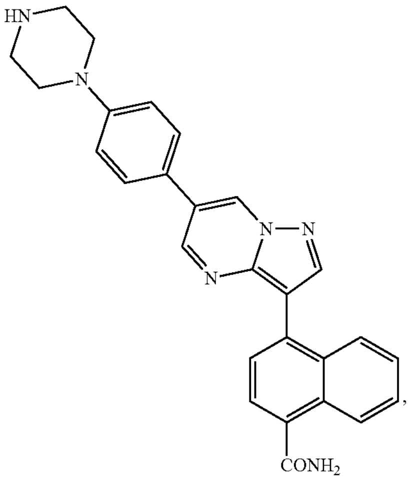

or a pharmaceutically acceptable salt thereof.

(II-3)

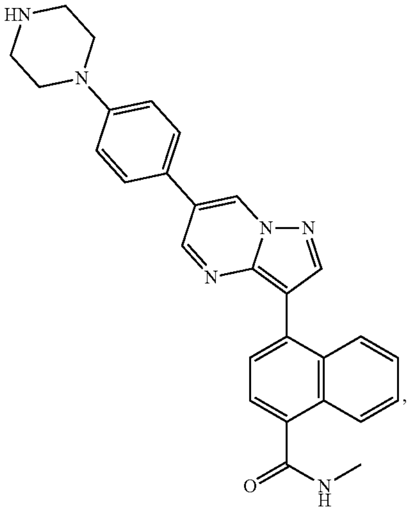

In some embodiments, the compound of Formula II has a structure of Formula II-4:

(II-4)

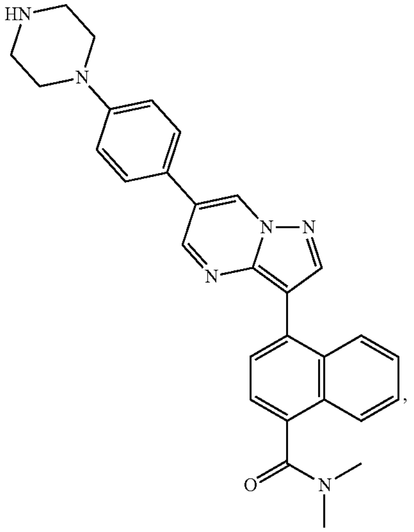

or a pharmaceutically acceptable salt thereof.

In some embodiments, the compound of Formula II has a structure of Formula II-5:

(II-5)

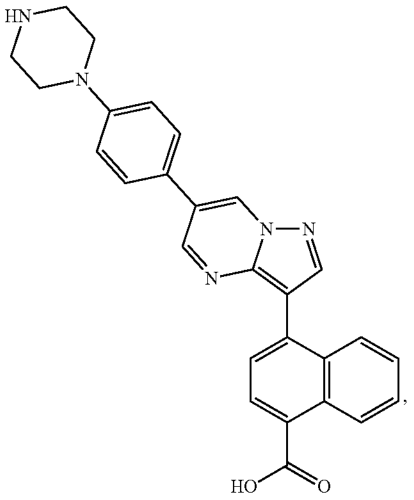

or a pharmaceutically acceptable salt thereof.

In some embodiments, the compound of Formula II has a structure of Formula II-6:

(II-6)

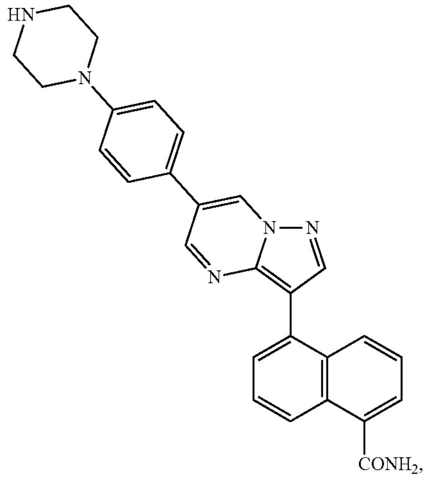

or a pharmaceutically acceptable salt thereof.

In some embodiments, the compound of Formula II has a structure of Formula II-7:

(II-7)

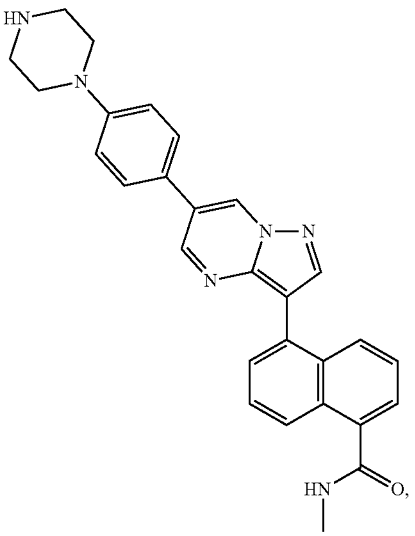

or a pharmaceutically acceptable salt thereof.

In some embodiments, the compound of Formula II has a structure of Formula II-8:

(II-8)

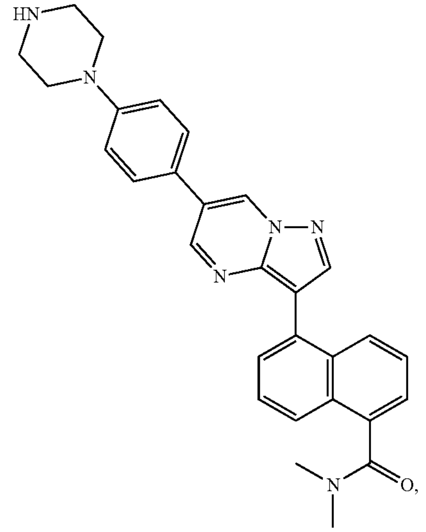

or a pharmaceutically acceptable salt thereof.

In some embodiments, the compound of Formula II has a structure of Formula II-9:

(II-9)

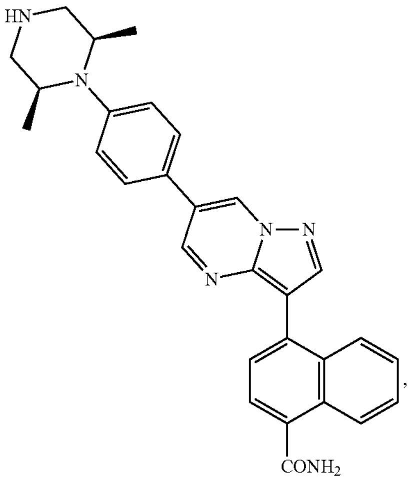

or a pharmaceutically acceptable salt thereof.

In some embodiments, the compound of Formula II has a structure of Formula II-10:

(II-10)

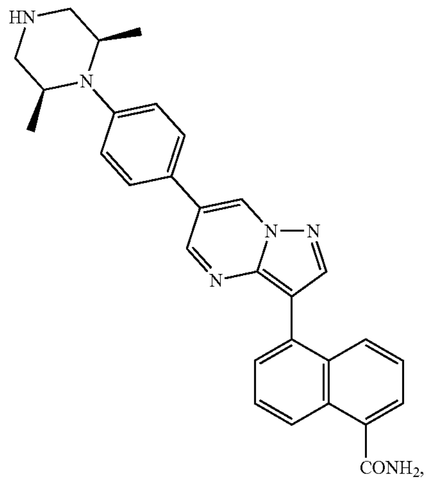

or a pharmaceutically acceptable salt thereof.

In some embodiments, the compound of Formula II has a structure of Formula II-11:

(II-11)

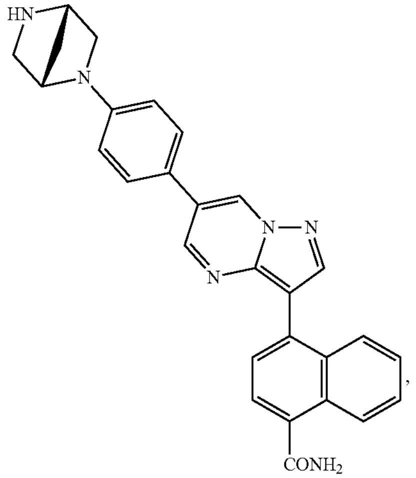

or a pharmaceutically acceptable salt thereof.

In some embodiments, the compound of Formula II has a structure of Formula II-12:

(II-12)

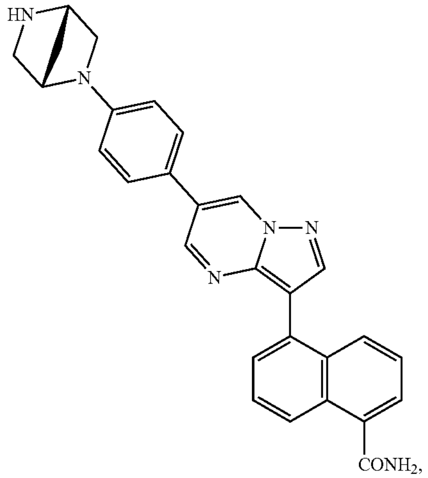

or a pharmaceutically acceptable salt thereof.

In some embodiments, the compound of Formula II has a structure of Formula II-13:

(II-13)

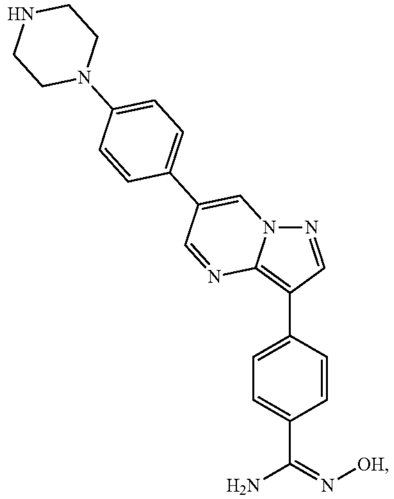

or a pharmaceutically acceptable salt thereof.

In some embodiments, the compound of Formula II has a structure of Formula II-14:

(II-14)

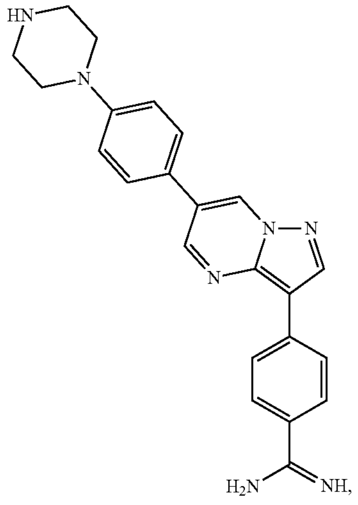

or a pharmaceutically acceptable salt thereof.

In some embodiments, the compound of Formula II has a structure of Formula II-15:

(II-15)

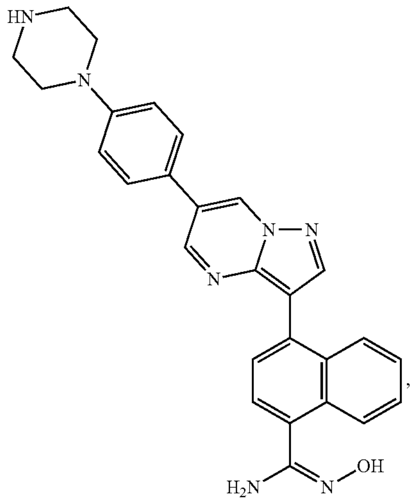

or a pharmaceutically acceptable salt thereof.

In some embodiments, the compound of Formula II has a structure of Formula II-16:

(II-16)

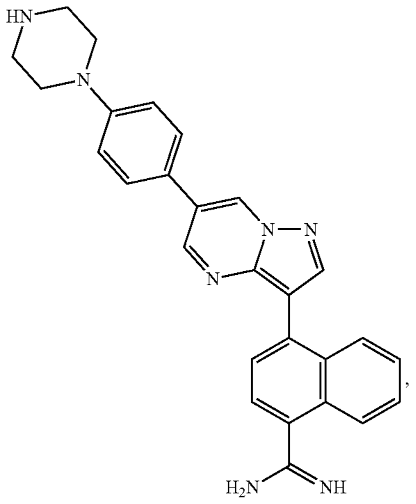

or a pharmaceutically acceptable salt thereof.

In some embodiments, the compound of Formula II has a structure of Formula II-17:

(II-17)

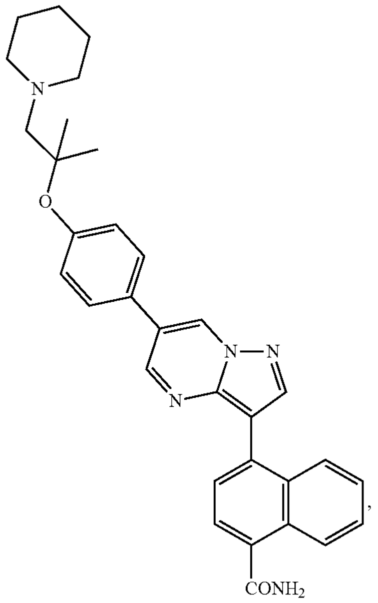

or a pharmaceutically acceptable salt thereof.

In some embodiments, the compound of Formula II has a structure of Formula II-18:

(II-18)

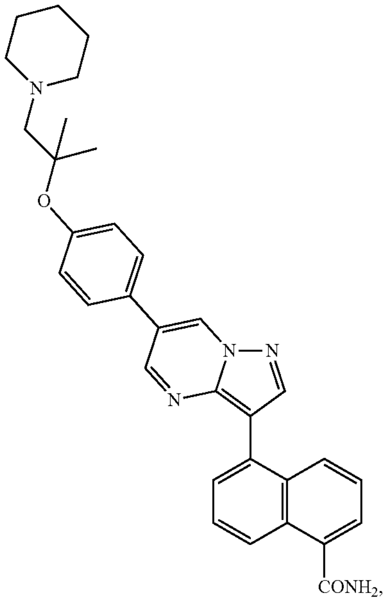

or a pharmaceutically acceptable salt thereof.

In some embodiments, the compound of Formula II has a structure of Formula II-19:

(II-19)

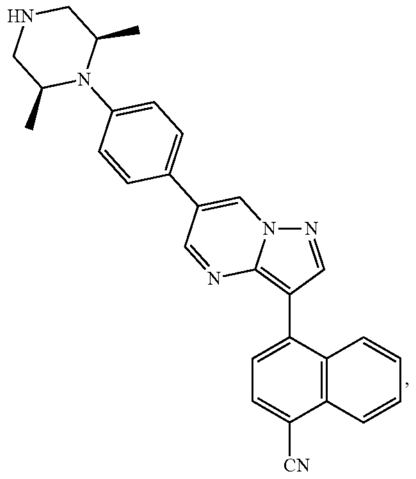

or a pharmaceutically acceptable salt thereof.

In some embodiments, the compound of Formula II has a structure of Formula II-20:

(II-20)

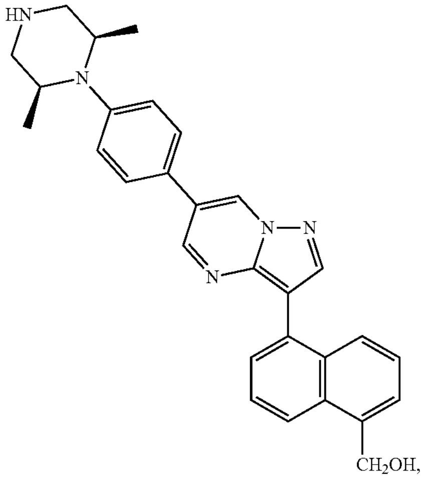

or a pharmaceutically acceptable salt thereof.

In some embodiments, the compound of Formula II has a structure of Formula II-21:

(II-21)

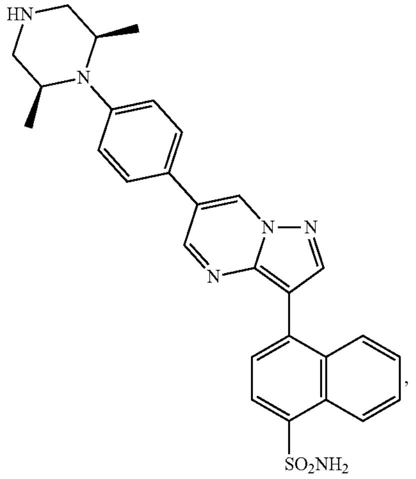

or a pharmaceutically acceptable salt thereof.

In some embodiments, the compound of Formula II has a structure of Formula II-22:

(II-22)

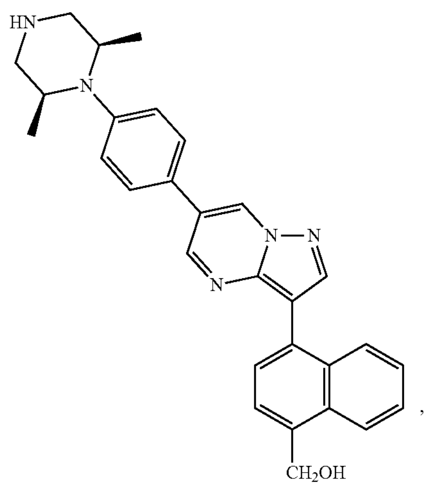

or a pharmaceutically acceptable salt thereof.

In some embodiments, the compound of Formula II has a structure of Formula II-23:

(II-23)

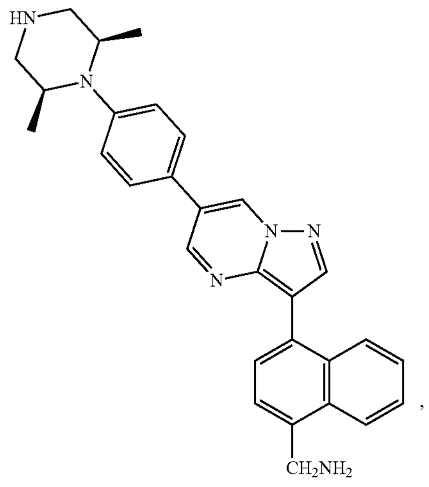

or a pharmaceutically acceptable salt thereof.

In some embodiments, the compound of Formula II has a structure of Formula II-24:

(II-24)

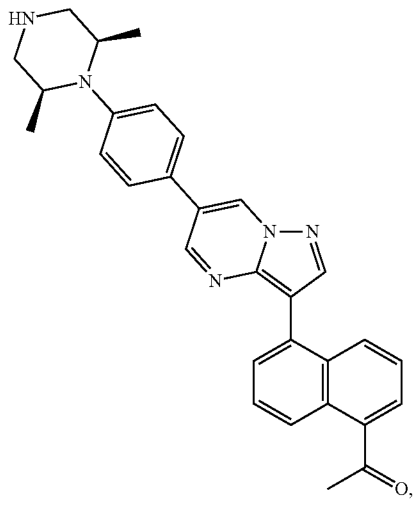

or a pharmaceutically acceptable salt thereof.

In some embodiments, the compound of Formula II has a structure of Formula II-25:

(II-25)

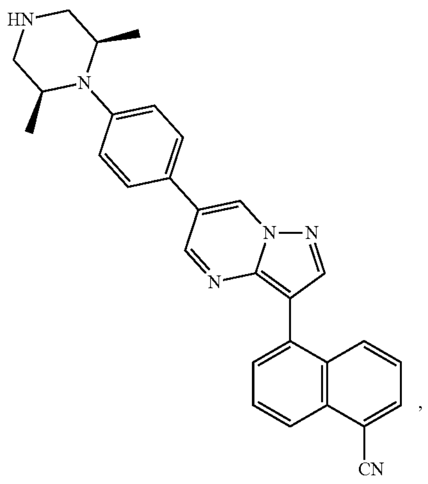

or a pharmaceutically acceptable salt thereof.

In some embodiments, the compound of Formula II has a structure of Formula II-26:

(II-26)

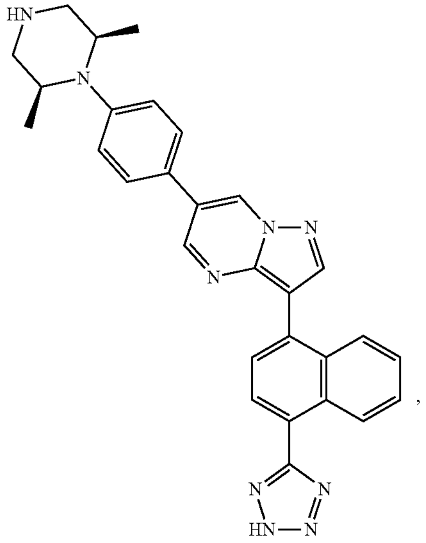

or a pharmaceutically acceptable salt thereof.

In some embodiments, the compound of Formula II has a structure of Formula II-27:

(II-27)

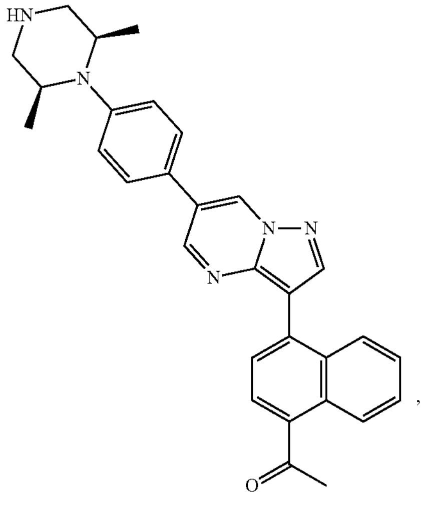

or a pharmaceutically acceptable salt thereof.

In some embodiments, the compound of Formula II has a structure of Formula II-28:

(II-28)

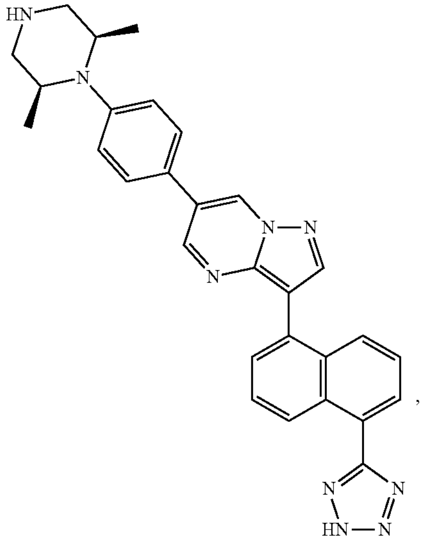

or a pharmaceutically acceptable salt thereof.

In some embodiments, the compound of Formula II has a structure of Formula II-29:

(II-29)

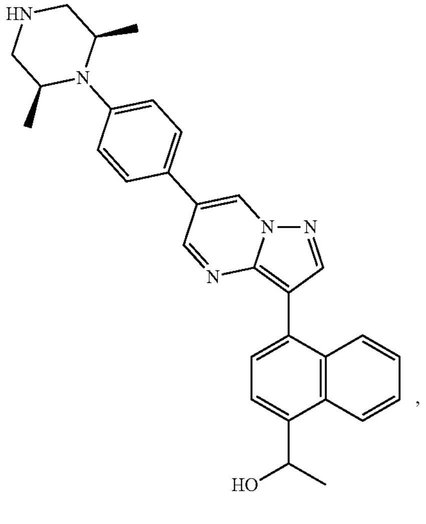

or a pharmaceutically acceptable salt thereof.

In some embodiments, the compound of Formula II has a structure of Formula II-30:

(II-30)

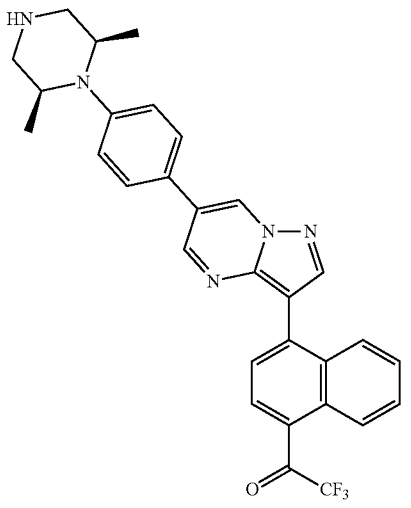

, or a pharmaceutically acceptable salt thereof.

In some embodiments, the compound of Formula II has a structure of Formula II-31:

(II-31)

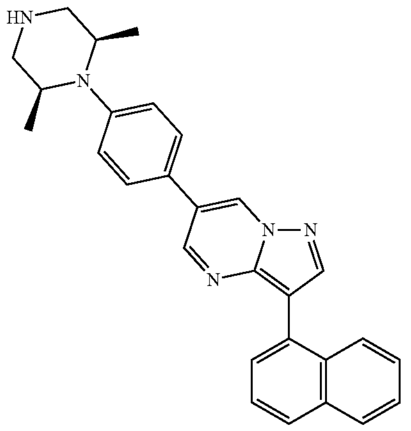

, or a pharmaceutically acceptable salt thereof.

In some embodiments, the compound of Formula II has a structure of Formula II-32:

(II-32)

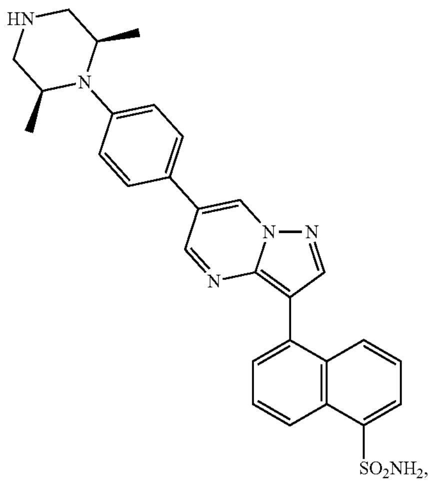

, or a pharmaceutically acceptable salt thereof.

In some embodiments, the compound of Formula II has a structure of Formula II-33:

(II-33)

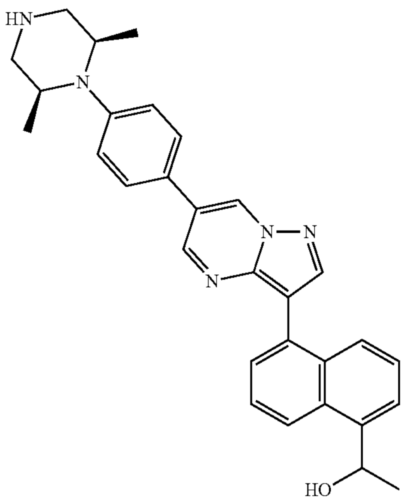

, or a pharmaceutically acceptable salt thereof.

In some embodiments, the compound of Formula II has a structure of Formula II-34:

(II-34)

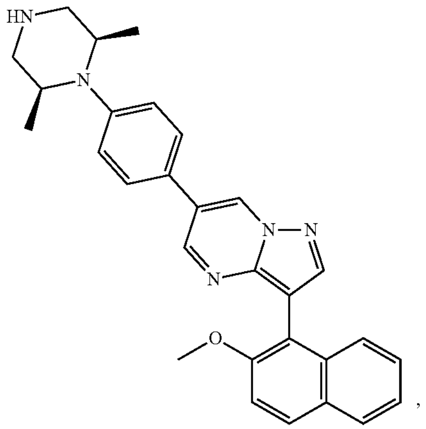

or a pharmaceutically acceptable salt thereof.

In some embodiments, the compound of Formula II has a structure of Formula II-35:

(II-35)

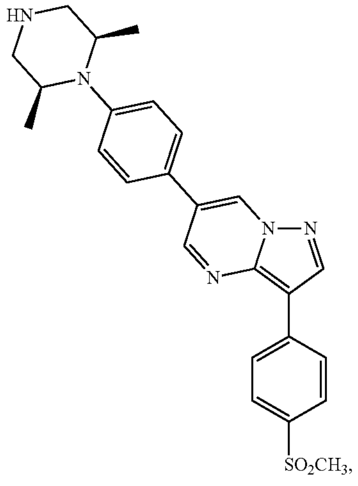

or a pharmaceutically acceptable salt thereof.

In some embodiments, the compound of Formula II has a structure of Formula II-36:

(II-36)

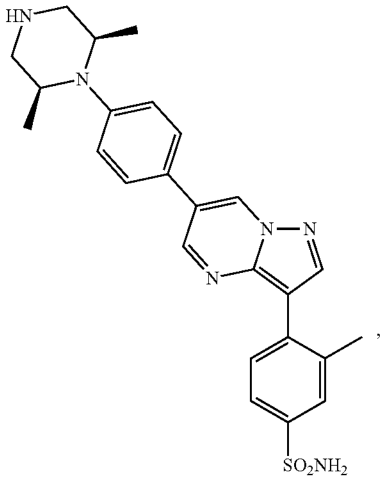

or a pharmaceutically acceptable salt thereof.

In some embodiments, the compound of Formula II has a structure of Formula II-37:

(II-37)

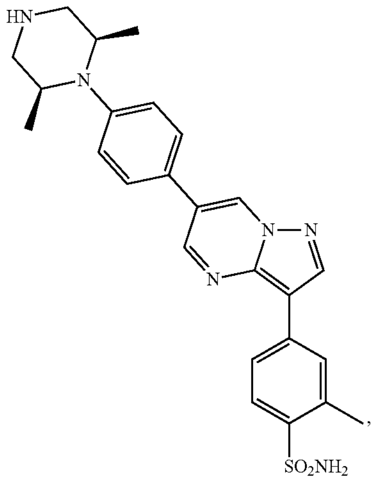

or a pharmaceutically acceptable salt thereof.

In some embodiments, the compound of Formula II has a structure of Formula II-38:

(II-38)

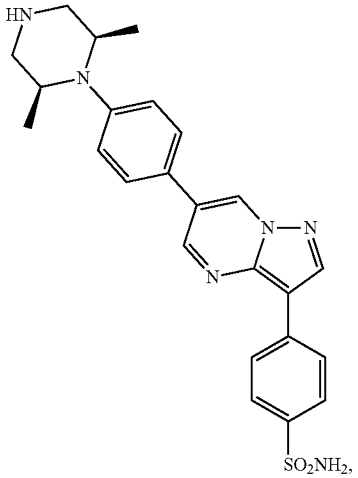

or a pharmaceutically acceptable salt thereof.

In some embodiments, the compound of Formula II has a structure of Formula II-39:

(II-39)

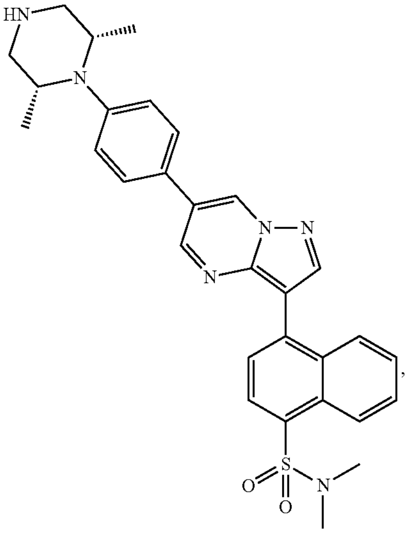

or a pharmaceutically acceptable salt thereof.

In some embodiments, the compound of Formula II has a structure of Formula II-40:

(II-40)

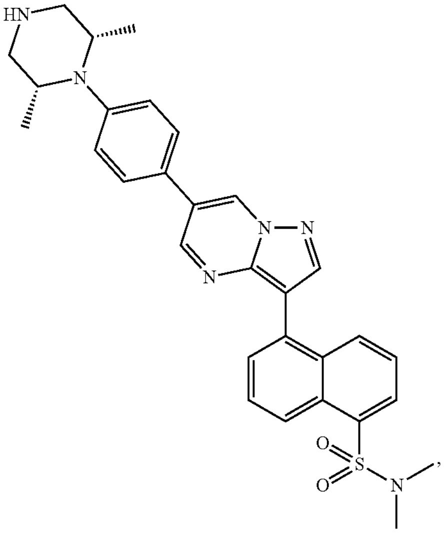

or a pharmaceutically acceptable salt thereof.

In some embodiments, the compound of Formula II has a structure of Formula II-41:

(II-41)

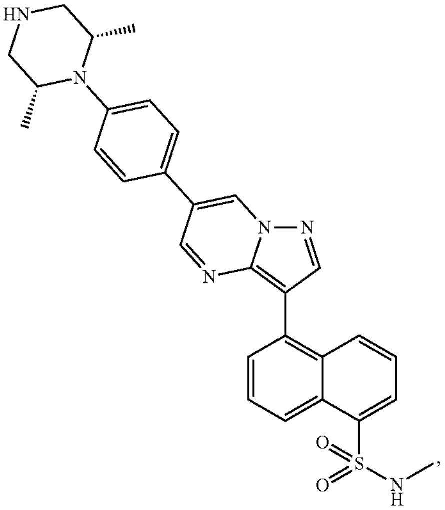

or a pharmaceutically acceptable salt thereof.

In some embodiments, the compound of Formula II has a structure of Formula II-42:

(II-42)

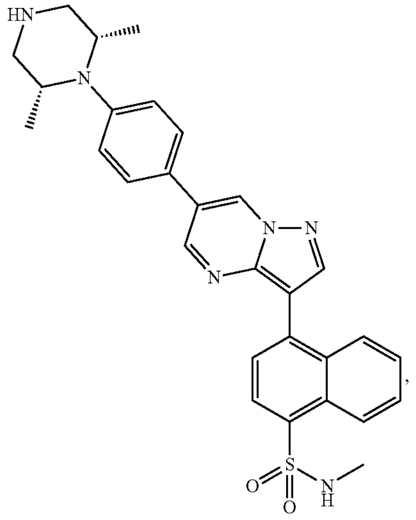

or a pharmaceutically acceptable salt thereof.

In some embodiments, the compound of Formula II has a structure of Formula II-43:

(II-43)

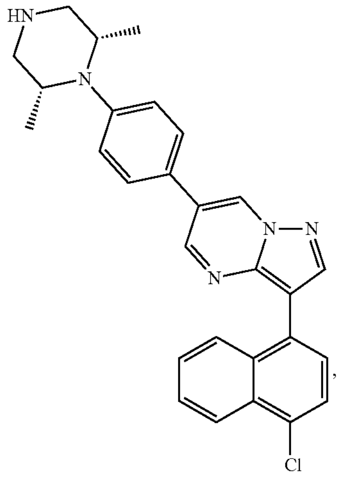

or a pharmaceutically acceptable salt thereof.

In some embodiments, the compound of Formula II has a structure of Formula II-44:

(II-44)

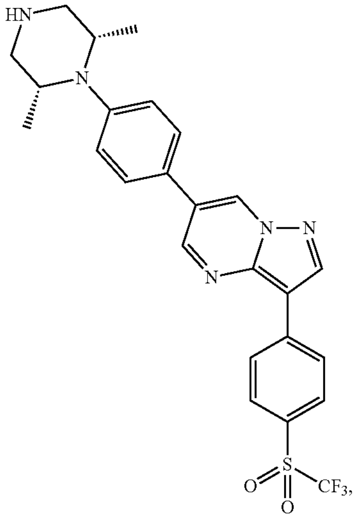

or a pharmaceutically acceptable salt thereof.

In some embodiments, the compound of Formula II has a structure of Formula II-45:

(II-45)

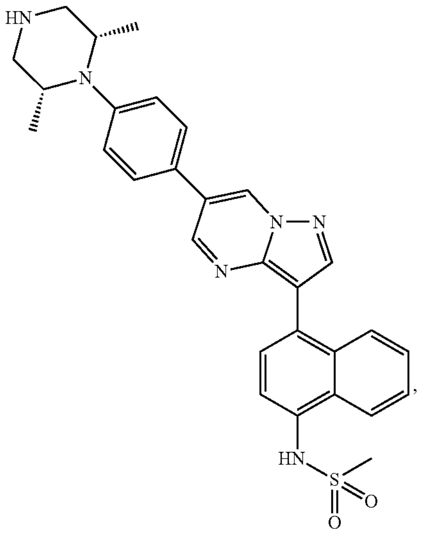

or a pharmaceutically acceptable salt thereof.

In some embodiments, the compound of Formula II has a structure of Formula II-46:

(II-46)

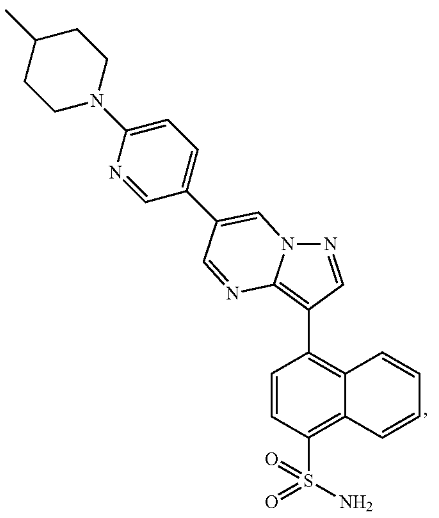

or a pharmaceutically acceptable salt thereof.

In some embodiments, the compound of Formula II has a structure of Formula II-47:

(II-47)

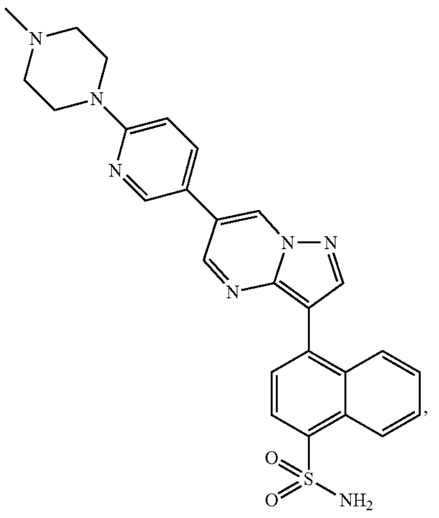

or a pharmaceutically acceptable salt thereof

In some embodiments, the compound of Formula II has a structure of Formula II-48:

(II-48)

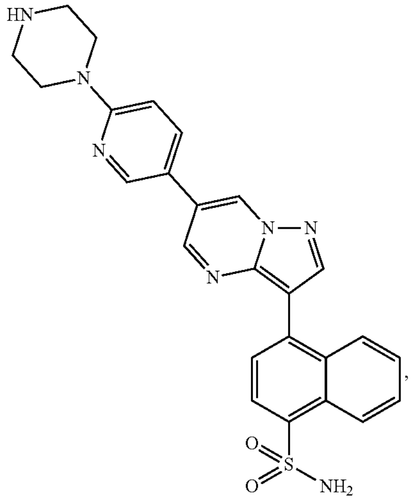

or a pharmaceutically acceptable salt thereof.

In some embodiments, the compound of Formula II has a structure of Formula II-49:

(II-49)

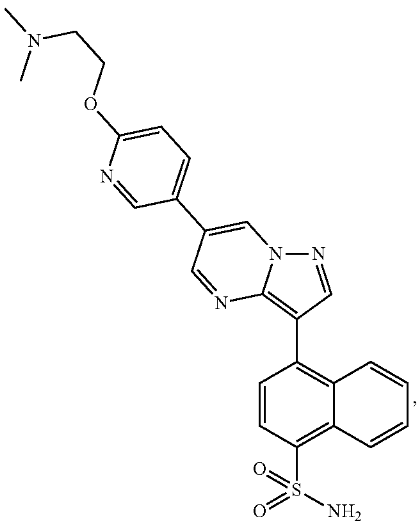

or a pharmaceutically acceptable salt thereof.

In some embodiments, the compound of Formula II has a structure of Formula II-50:

(II-50)

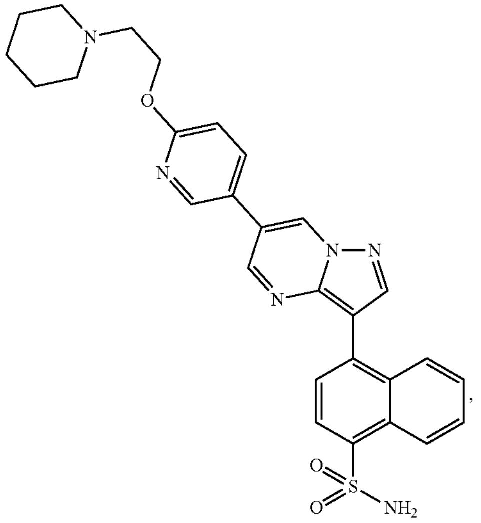

or a pharmaceutically acceptable salt thereof.

In some embodiments, the compound of Formula II has a structure of Formula II-51a:

(II-51a)

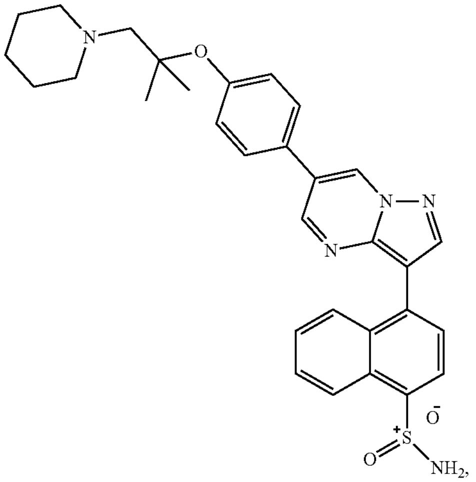

or a pharmaceutically acceptable salt thereof.

In some embodiments, the compound of Formula II has a structure of Formula II-51b:

(II-51b)

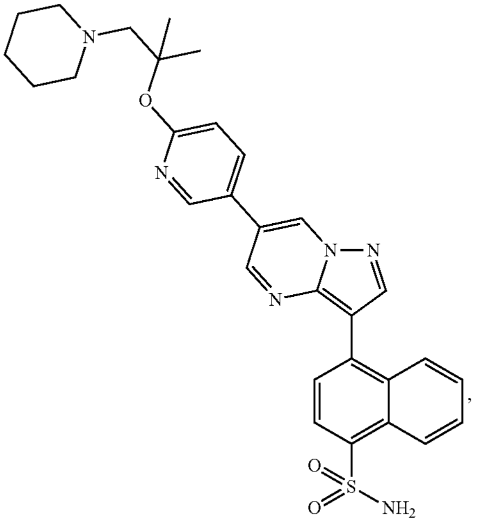

or a pharmaceutically acceptable salt thereof.

In some embodiments, the compound of Formula II has a structure of Formula II-52:

(II-52)

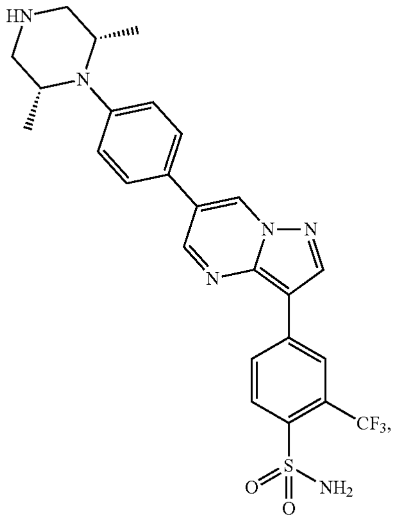

or a pharmaceutically acceptable salt thereof.

In some embodiments, the compound of Formula II has a structure of Formula II-53:

(II-53)

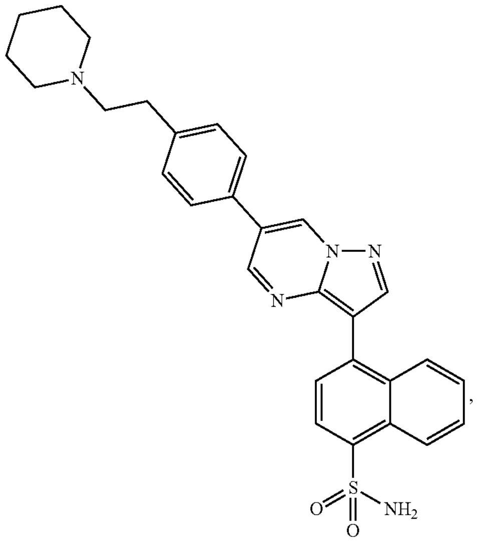

or a pharmaceutically acceptable salt thereof.

In some embodiments, the compound of Formula II has a structure of Formula II-54:

(II-54)

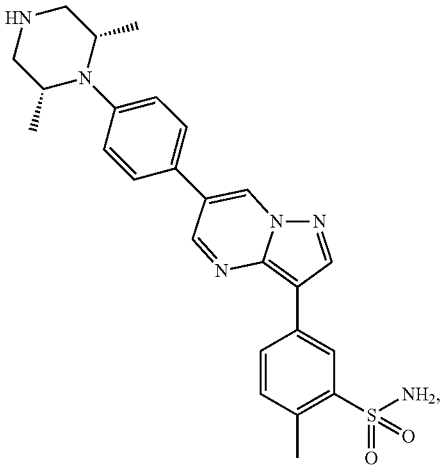

or a pharmaceutically acceptable salt thereof.

In some embodiments, the compound of Formula II has a structure of Formula II-55:

(II-55)

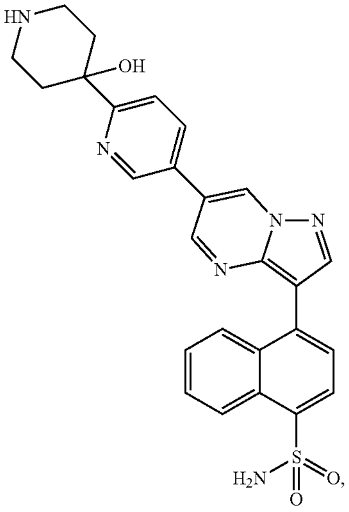

or a pharmaceutically acceptable salt thereof.

In some embodiments, the compound of Formula II has a structure of Formula II-56:

(II-56)

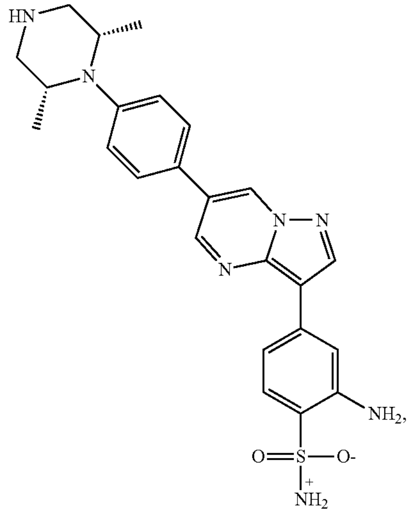

or a pharmaceutically acceptable salt thereof.

In some embodiments, the compound of Formula II has a structure of Formula II-57:

(II-57)

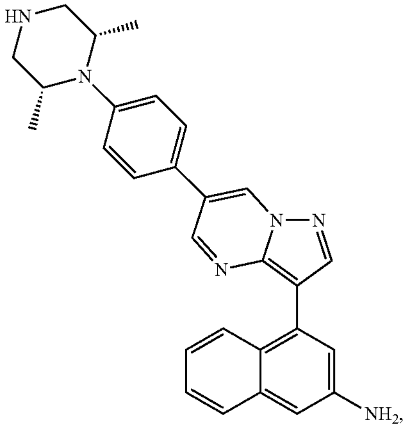

or a pharmaceutically acceptable salt thereof.

In some embodiments, the compound of Formula II has a structure of Formula II-58:

(II-58)

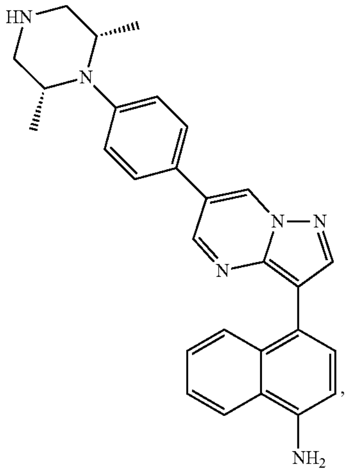

or a pharmaceutically acceptable salt thereof.

In some embodiments, the compound of Formula II has a structure of Formula II-59:

(II-59)

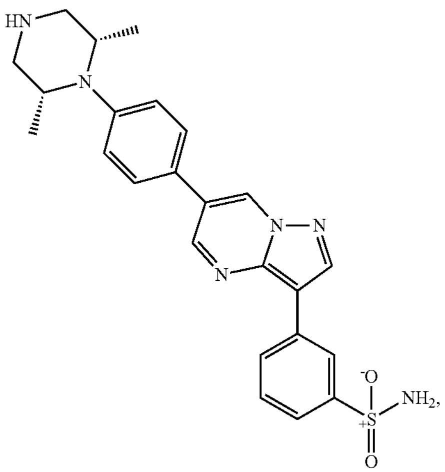

or a pharmaceutically acceptable salt thereof.

In some embodiments, the compound of Formula II has a structure of Formula II-60:

(II-60)

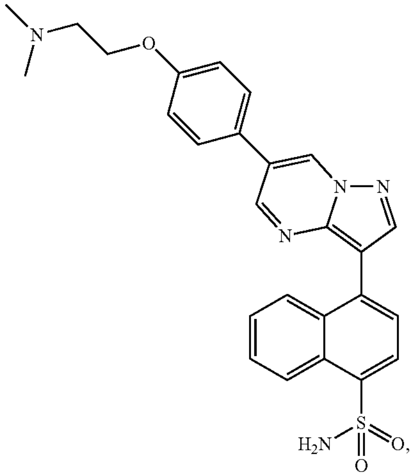

or a pharmaceutically acceptable salt thereof.

In some embodiments, the compound of Formula II has a structure of Formula II-61:

(II-61)

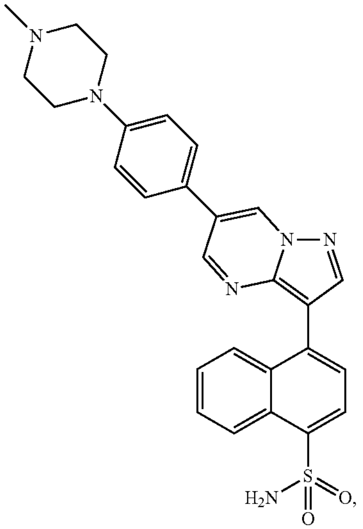

or a pharmaceutically acceptable salt thereof.

In some embodiments, the compound of Formula II has a structure of Formula II-62:

(II-62)

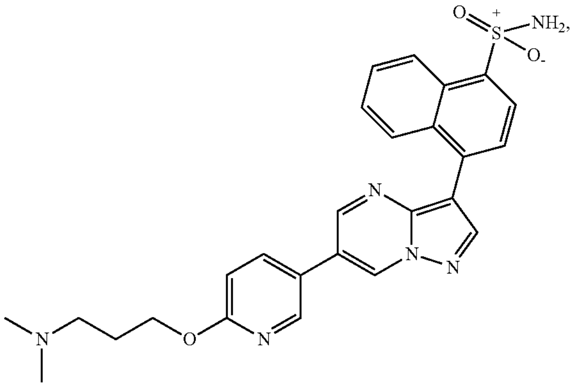

or a pharmaceutically acceptable salt thereof.

In some embodiments, the compound of Formula II has a structure of Formula II-63:

(II-63)

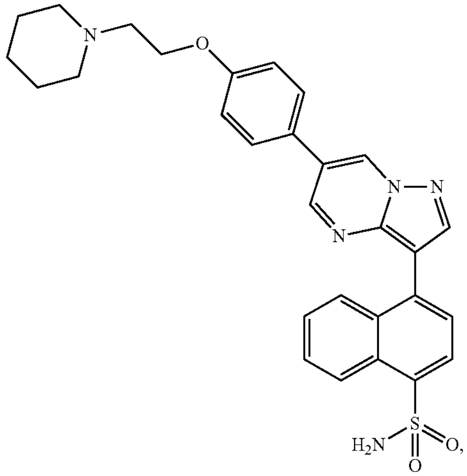

or a pharmaceutically acceptable salt thereof.

In some embodiments, the compound of Formula II has a structure of Formula II-64:

(II-64)

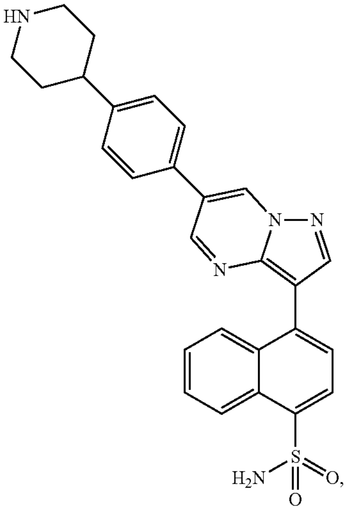

or a pharmaceutically acceptable salt thereof.

In some embodiments, the compound of Formula II has a structure of Formula II-65:

(II-65)

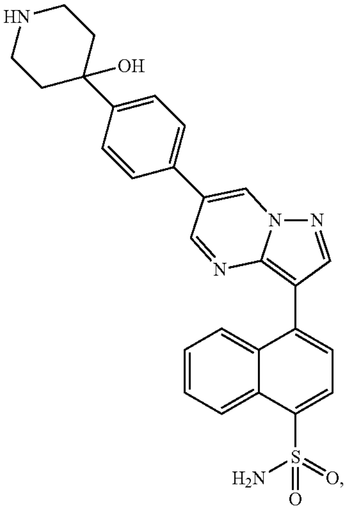

or a pharmaceutically acceptable salt thereof.

In some embodiments, the compound of Formula II has a structure of Formula II-66:

(II-66)

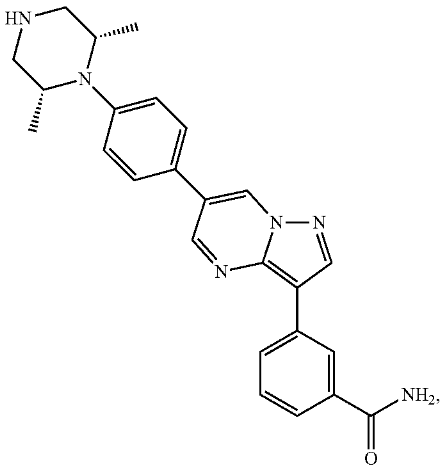

or a pharmaceutically acceptable salt thereof.

In some embodiments, the compound of Formula II has a structure of Formula II-67:

(II-67)

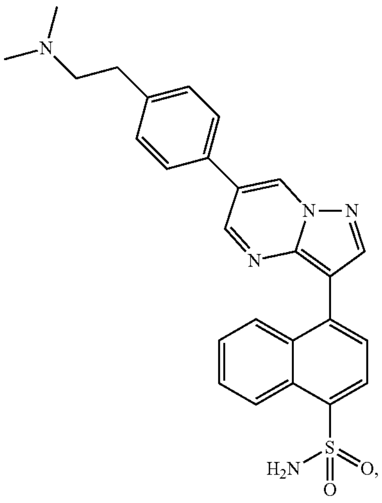

or a pharmaceutically acceptable salt thereof.

In some embodiments, the compound of Formula II has a structure of Formula II-68:

(II-68)

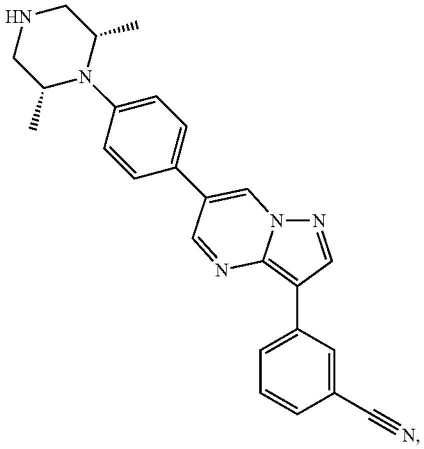

or a pharmaceutically acceptable salt thereof.

In some embodiments, the compound of Formula II has a structure of Formula II-69:

(II-69)

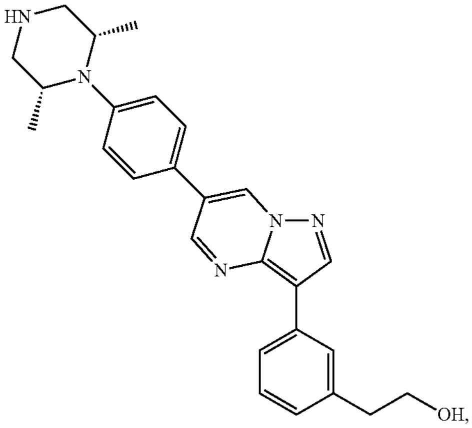

or a pharmaceutically acceptable salt thereof.

In some embodiments, the compound of Formula II has a structure of Formula II-70:

(II-70)

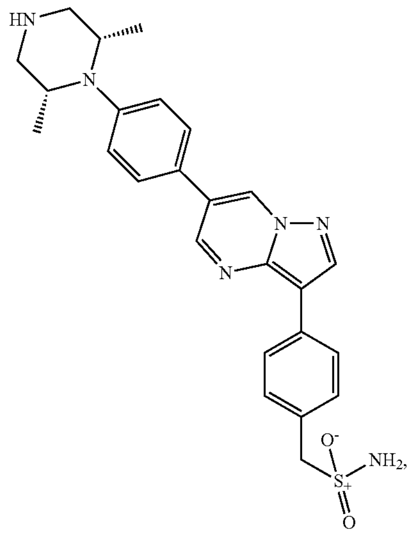

or a pharmaceutically acceptable salt thereof.

In some embodiments, the compound of Formula II has a structure of Formula II-71:

(II-71)

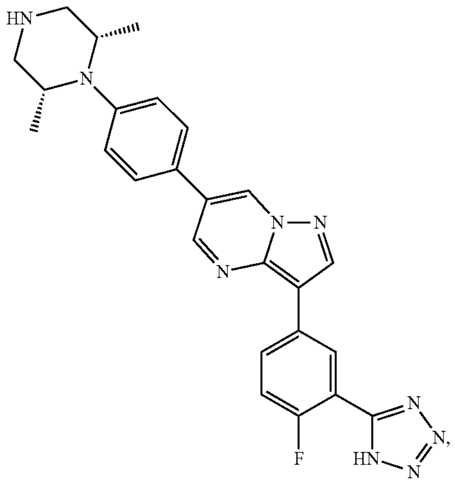

or a pharmaceutically acceptable salt thereof.

In some embodiments, the compound of Formula II has a structure of Formula II-72:

(II-72)

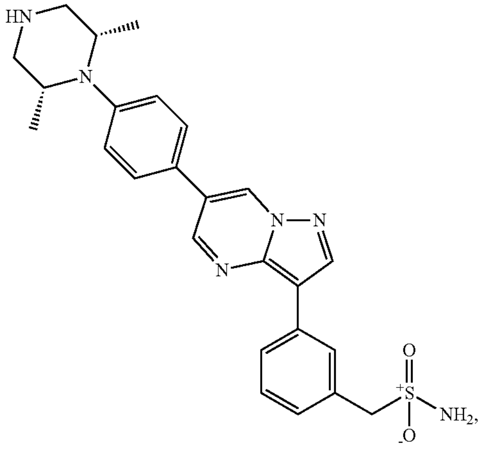

or a pharmaceutically acceptable salt thereof.

In some embodiments, the compound of Formula II has a structure of Formula II-73:

(II-73)

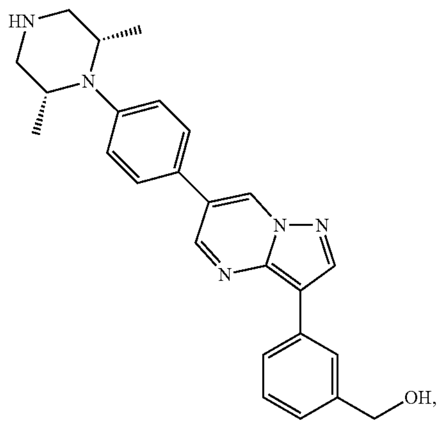

or a pharmaceutically acceptable salt thereof.

In some embodiments, the compound of Formula II has a structure of Formula II-74:

(II-74)

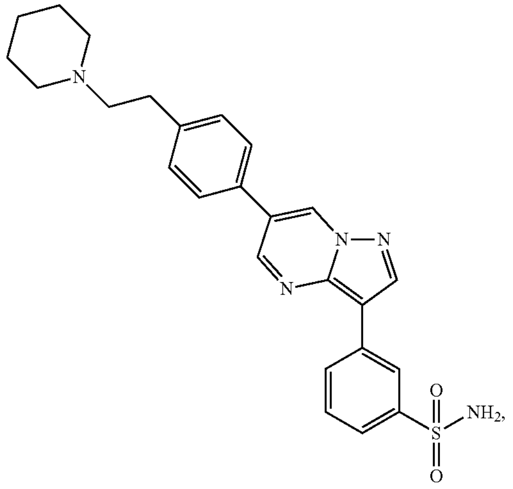

or a pharmaceutically acceptable salt thereof.

In some embodiments, the compound of Formula II has a structure of Formula II-75:

(II-75)

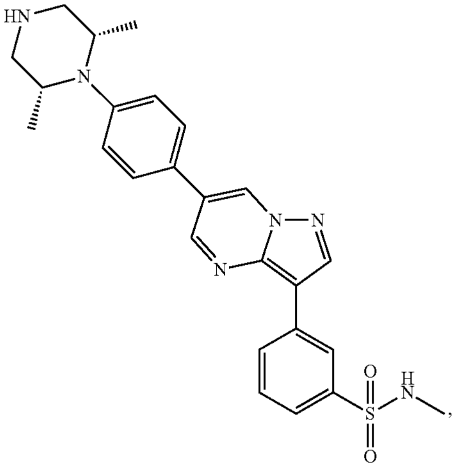

or a pharmaceutically acceptable salt thereof.

In some embodiments, the compound of Formula II has a structure of Formula II-76:

(II-76)

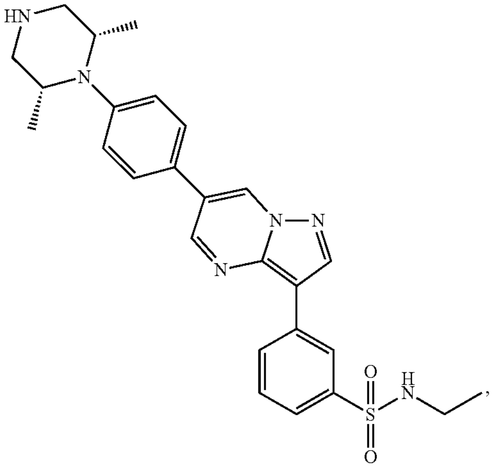

or a pharmaceutically acceptable salt thereof.

In some embodiments, the compound of Formula II has a structure of Formula II-77:

(II-77)

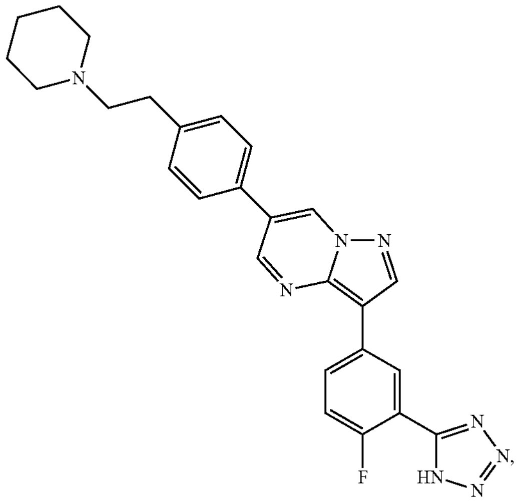

or a pharmaceutically acceptable salt thereof.

In some embodiments, the compound of Formula II has a structure of Formula II-78:

(II-78)

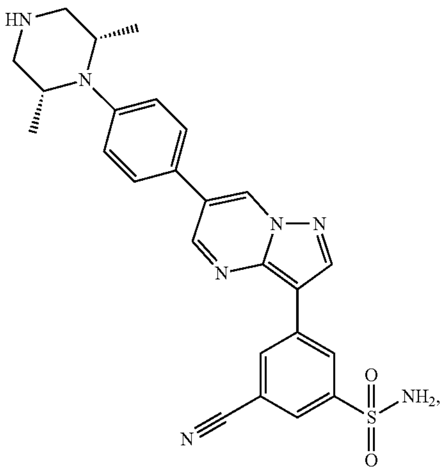

or a pharmaceutically acceptable salt thereof.

In some embodiments, the compound of Formula II has a structure of Formula II-79:

(II-79)

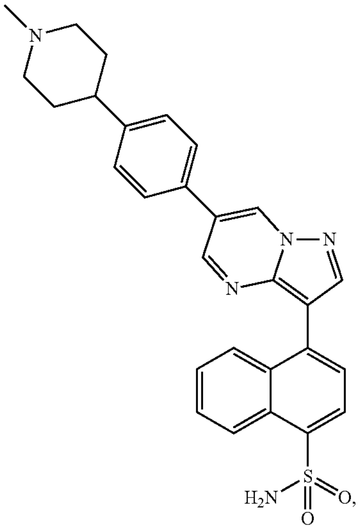

or a pharmaceutically acceptable salt thereof.

In some embodiments, the compound of Formula II has a structure of Formula II-80:

(II-80)

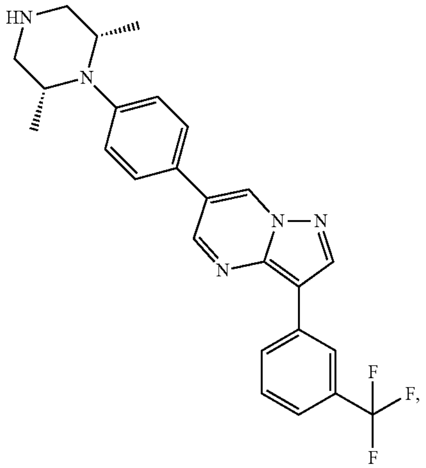

or a pharmaceutically acceptable salt thereof.

In some embodiments, the compound of Formula II has a structure of Formula II-81:

(II-81)

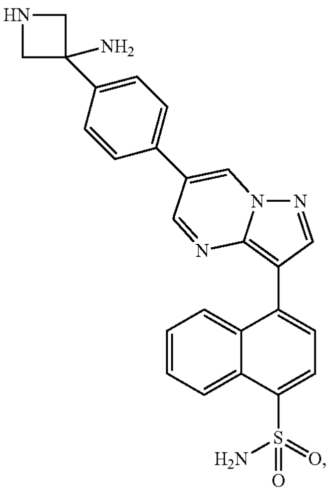

or a pharmaceutically acceptable salt thereof.

In some embodiments, the compound of Formula II has a structure of Formula II-82:

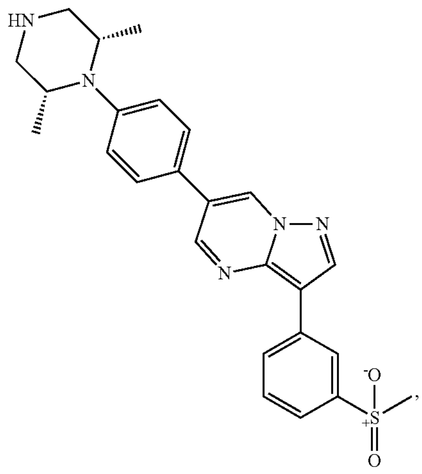

(II-82)

or a pharmaceutically acceptable salt thereof.

In some embodiments, the compound of Formula II has a structure of Formula II-83:

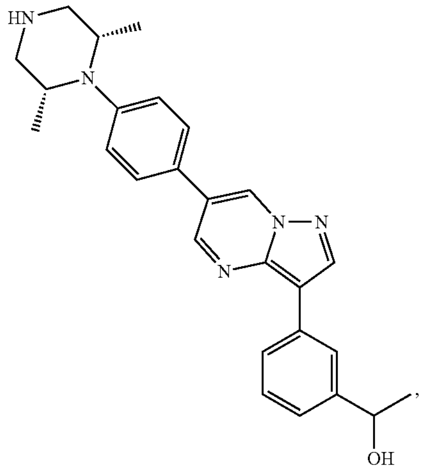

(II-83)

or a pharmaceutically acceptable salt thereof.

In some embodiments, the compound of Formula II has a structure of Formula II-84:

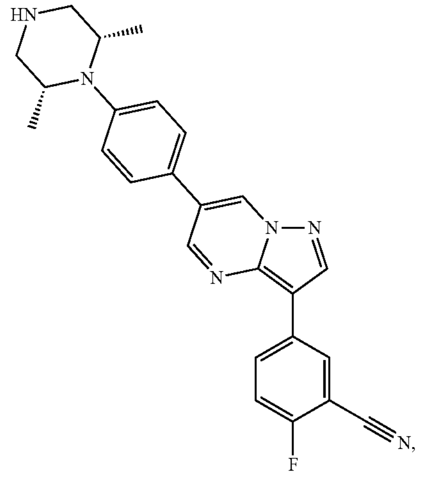

(II-84)

or a pharmaceutically acceptable salt thereof.

In some embodiments, the compound of Formula II has a structure of Formula II-85:

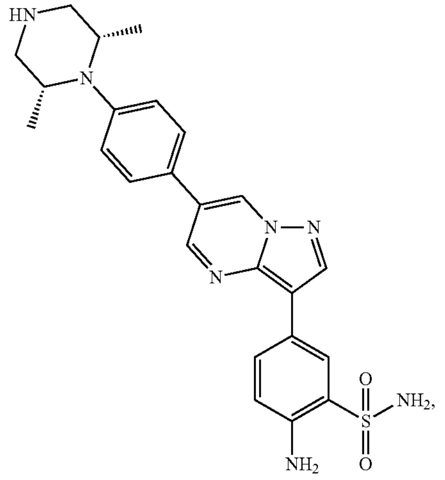

(II-85)

or a pharmaceutically acceptable salt thereof.

In some embodiments, the compound of Formula II has a structure of Formula II-86:

(II-86)

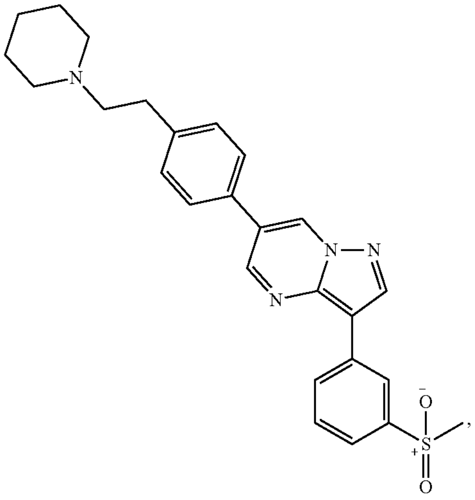

or a pharmaceutically acceptable salt thereof.

In some embodiments, the compound of Formula II has a structure of Formula II-87:

(II-87)

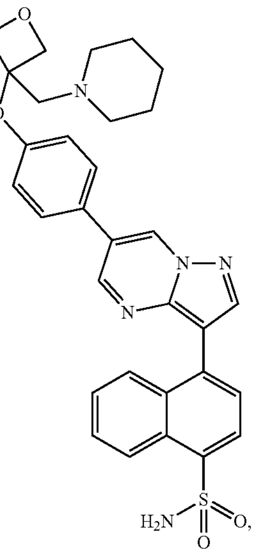

or a pharmaceutically acceptable salt thereof.

In some embodiments, the compound of Formula II has a structure of Formula II-88:

(II-88)

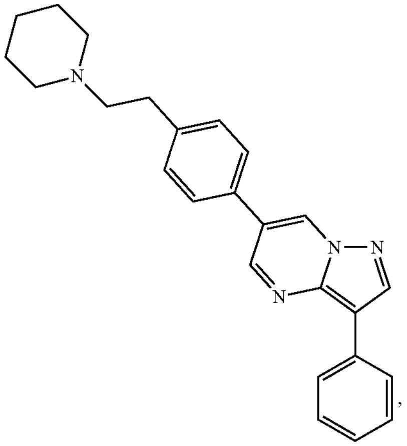

or a pharmaceutically acceptable salt thereof.

In some embodiments, the compound of Formula II has a structure of Formula II-89:

(II-89)

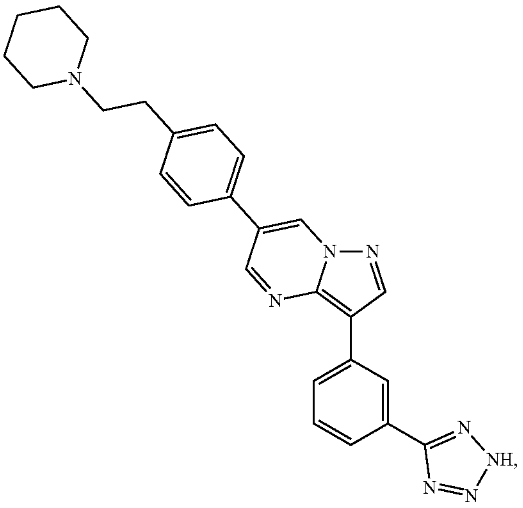

or a pharmaceutically acceptable salt thereof.

In some embodiments, the compound of Formula II has a structure of Formula II-90:

(II-90)

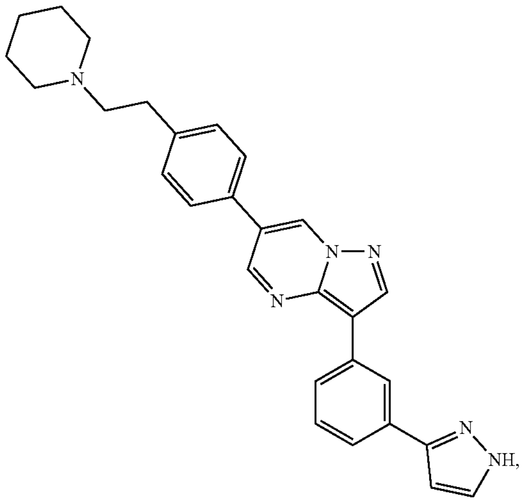

or a pharmaceutically acceptable salt thereof.

In some embodiments, the compound of Formula II has a structure of Formula II-91:

(II-91)

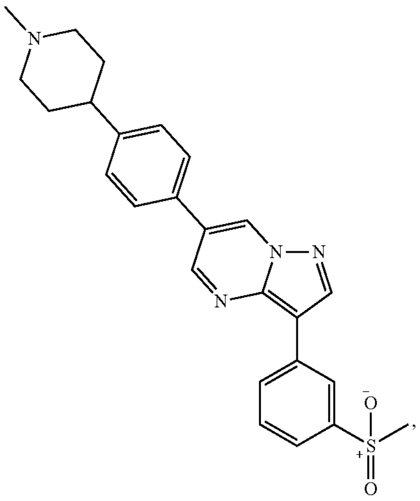

or a pharmaceutically acceptable salt thereof.

In some embodiments, the compound of Formula II has a structure of Formula II-92:

(II-92)

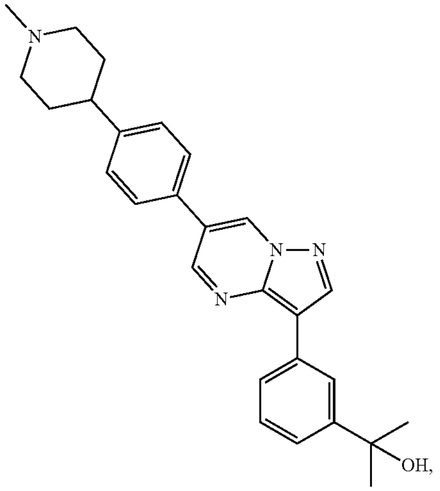

or a pharmaceutically acceptable salt thereof.

In some embodiments, the compound of Formula II has a structure of Formula II-93:

(II-93)

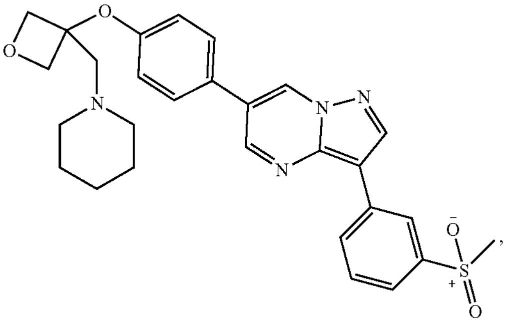

or a pharmaceutically acceptable salt thereof.

In some embodiments, the compound of Formula II has a structure of Formula II-94:

(II-94)

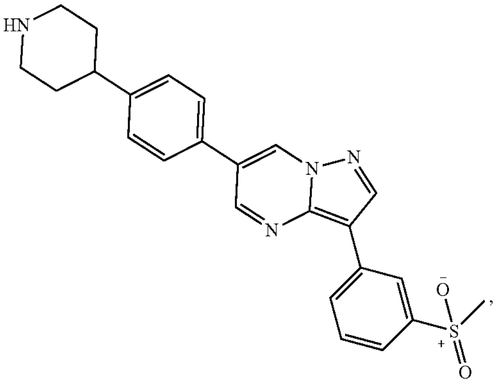

or a pharmaceutically acceptable salt thereof.

In some embodiments, the compound of Formula II has a structure of Formula II-95:

(II-95)

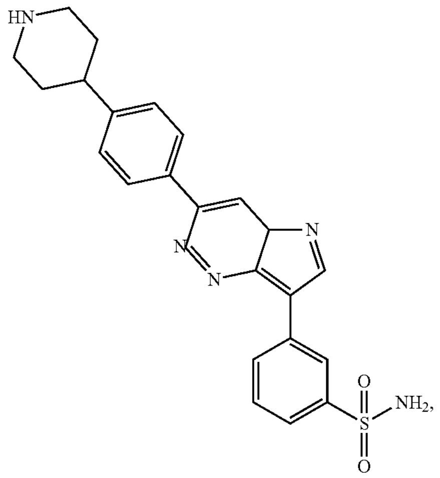

or a pharmaceutically acceptable salt thereof.

In some embodiments, the compound of Formula II has a structure of Formula II-96:

(II-96)

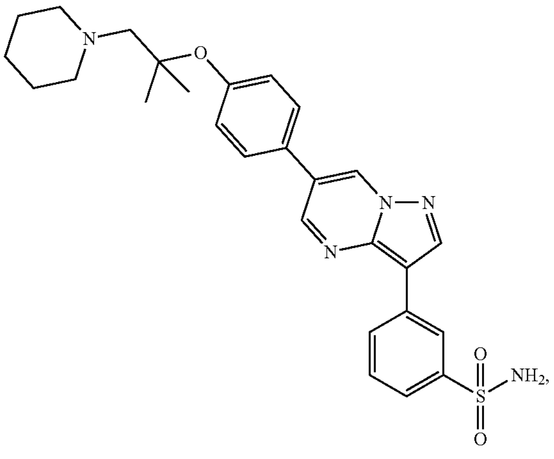

or a pharmaceutically acceptable salt thereof.

In some embodiments, the compound of Formula II has a structure of Formula II-97:

(II-97)

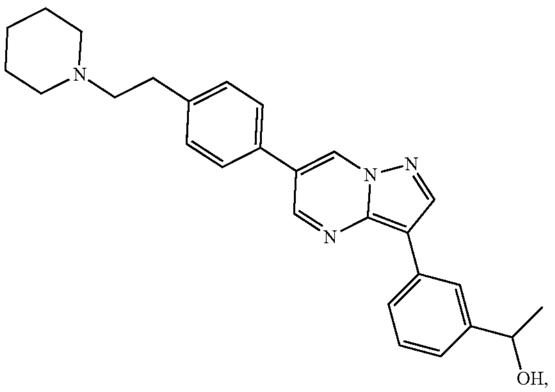

or a pharmaceutically acceptable salt thereof.

In some embodiments, the compound of Formula II has a structure of Formula II-98:

(II-98)

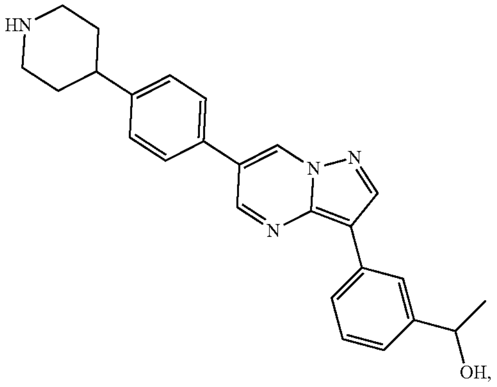

or a pharmaceutically acceptable salt thereof.

In some embodiments, the compound of Formula II has a structure of Formula II-99:

(II-99)

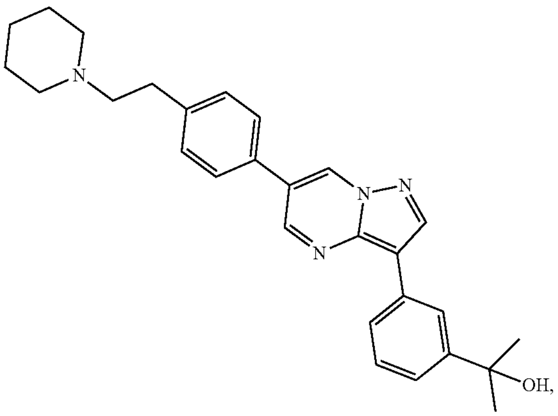

or a pharmaceutically acceptable salt thereof.

In some embodiments, the compound of Formula II has a structure of Formula II-100:

(II-100)

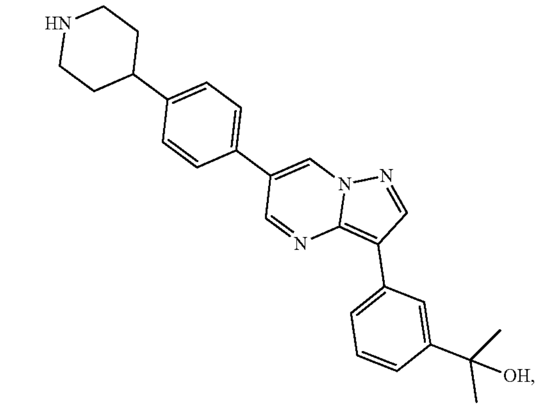

or a pharmaceutically acceptable salt thereof.

In some embodiments, the compound of Formula II has a structure of Formula II-101:

(II-101)

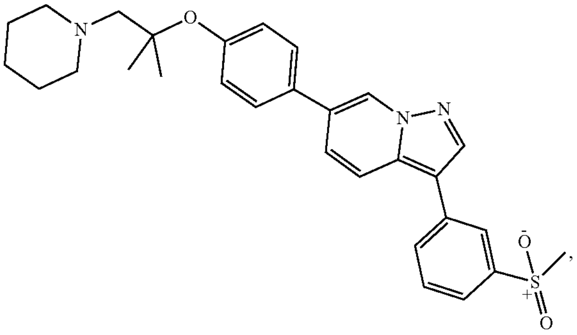

or a pharmaceutically acceptable salt thereof.

In some embodiments, the compound of Formula II has a structure of Formula II-102:

(II-102)

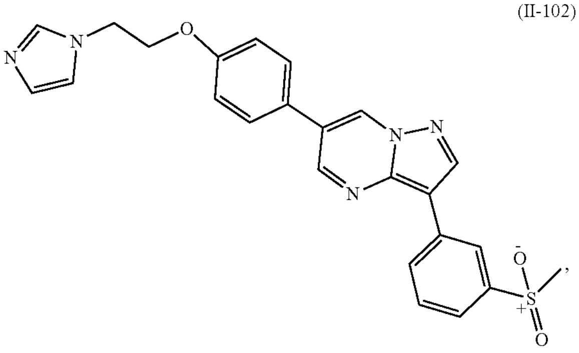

or a pharmaceutically acceptable salt thereof.

In some embodiments, the compound of Formula II has a structure of Formula II-103:

(II-103)

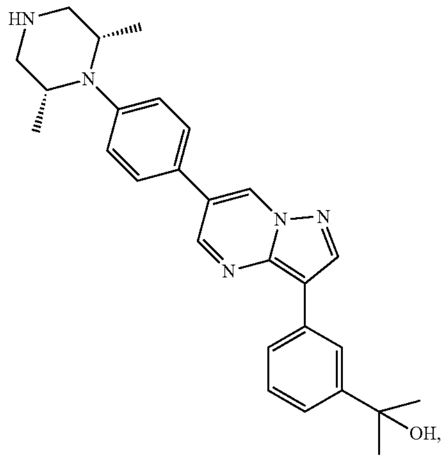

or a pharmaceutically acceptable salt thereof.

In some embodiments, the compound of Formula II has a structure of Formula II-104:

(II-104)

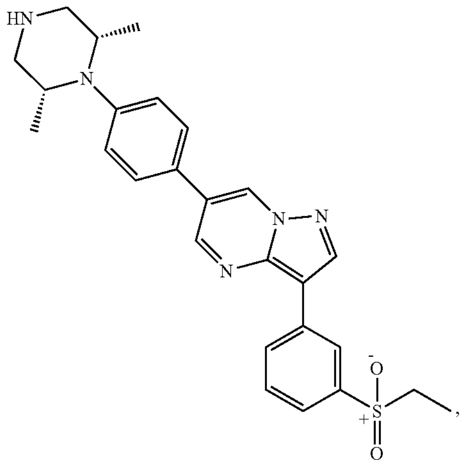

or a pharmaceutically acceptable salt thereof.

In some embodiments, the compound of Formula II has a structure of Formula II-105:

(II-105)

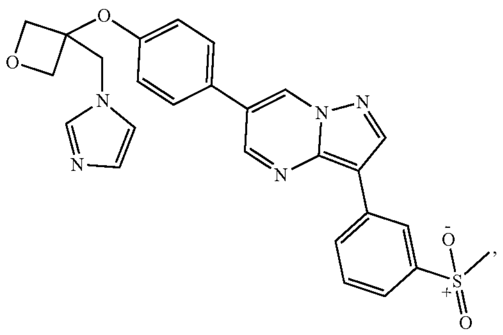

or a pharmaceutically acceptable salt thereof.

In some embodiments, the compound of Formula II has a structure of Formula II-106:

(II-106)

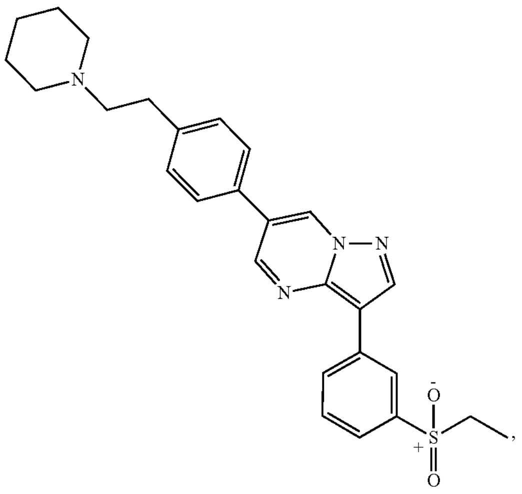

or a pharmaceutically acceptable salt thereof.

In some embodiments, the compound of Formula II has a structure of Formula II-107:

(II-107)

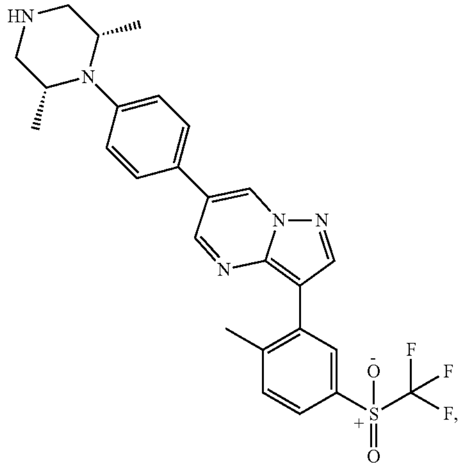

or a pharmaceutically acceptable salt thereof.

In some embodiments, the compound of Formula II has a structure of Formula II-108:

(II-108)

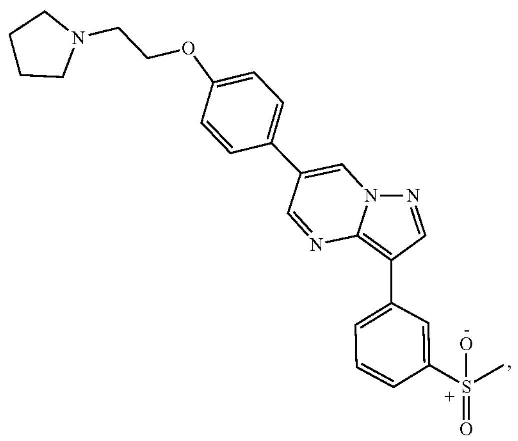

or a pharmaceutically acceptable salt thereof.

In some embodiments, the compound of Formula II has a structure of Formula II-109:

(II-109)

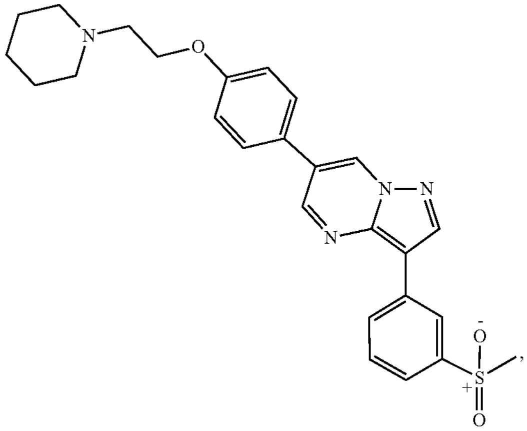

or a pharmaceutically acceptable salt thereof.

In some embodiments, the compound of Formula II has a structure of Formula II-110:

(II-110)

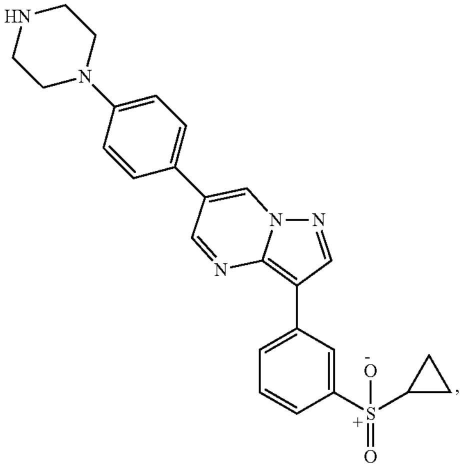

or a pharmaceutically acceptable salt thereof.

In some embodiments, the compound of Formula II has a structure of Formula II-111:

(II-111)

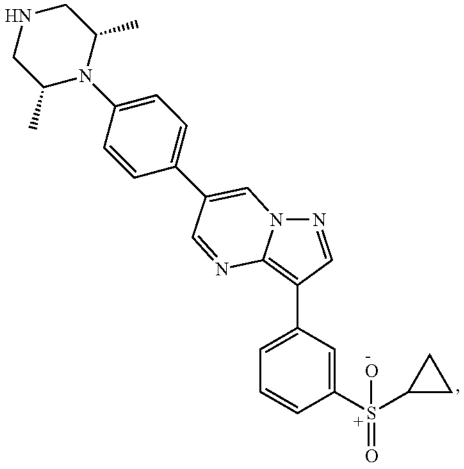

or a pharmaceutically acceptable salt thereof.

In some embodiments, the compound of Formula II has a structure of Formula II-112:

(II-112)

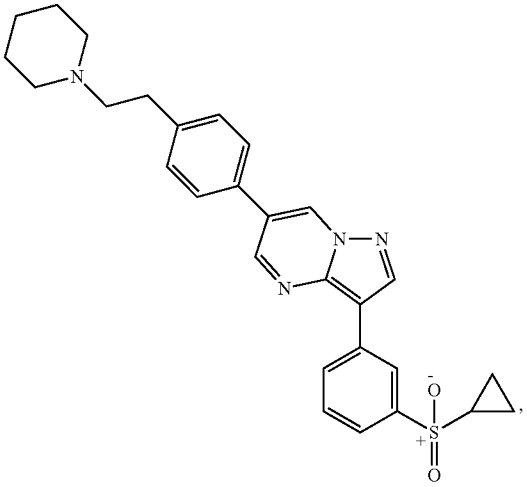

or a pharmaceutically acceptable salt thereof.

In some embodiments, the compound of Formula II has a structure of Formula II-113:

(II-113)

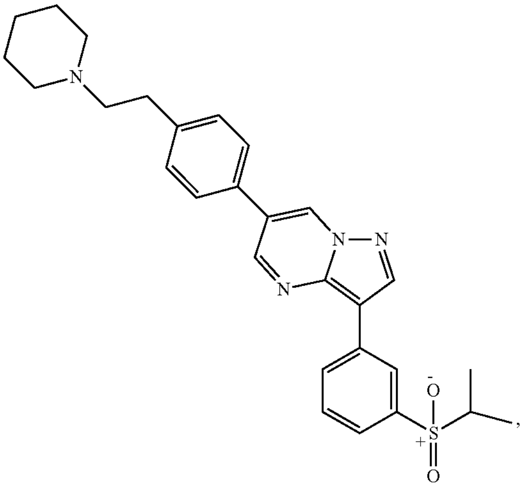

or a pharmaceutically acceptable salt thereof.

In some embodiments, the compound of Formula II has a structure of Formula II-114:

(II-114)

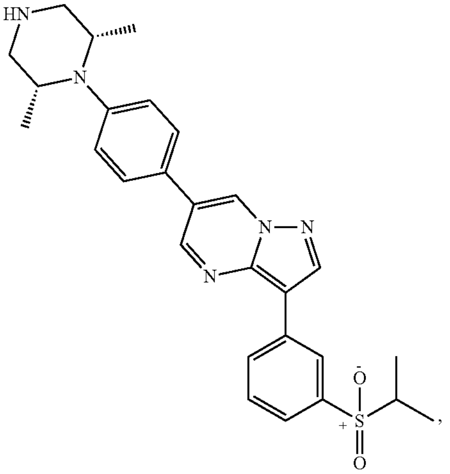

or a pharmaceutically acceptable salt thereof.

In some embodiments, the compound of Formula II has a structure of Formula II-115:

(II-115)

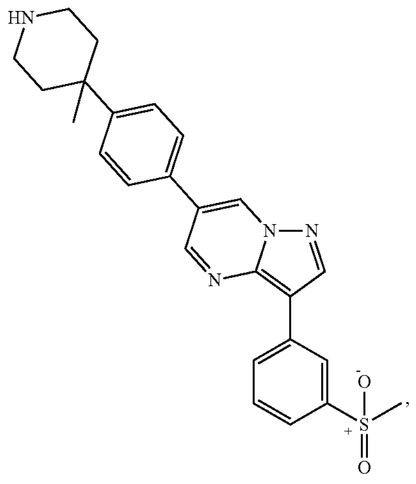

or a pharmaceutically acceptable salt thereof.

In some embodiments, the compound of Formula II has a structure of Formula II-116:

(II-116)

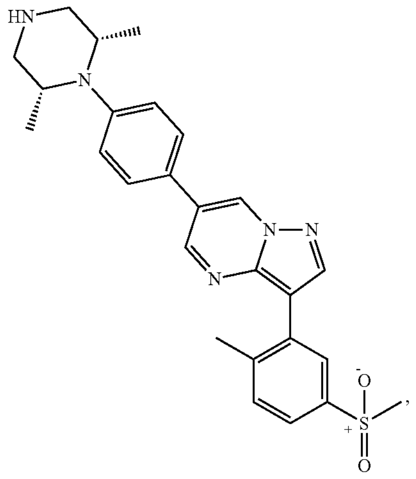

or a pharmaceutically acceptable salt thereof.

In some embodiments, the compound of Formula II has a structure of Formula II-117:

(II-117)

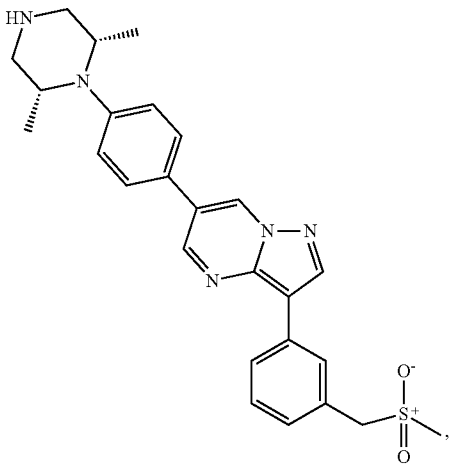

or a pharmaceutically acceptable salt thereof.

In some embodiments, the compound of Formula II has a structure of Formula II-118:

(II-118)

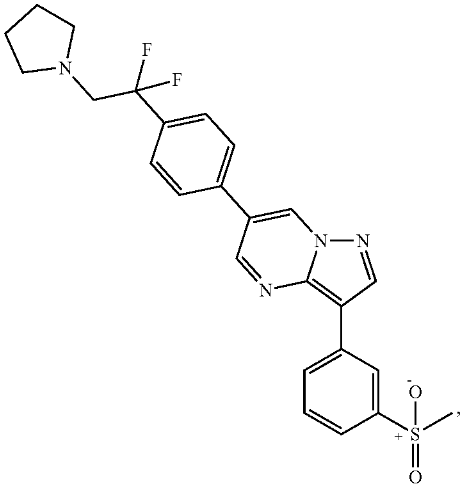

or a pharmaceutically acceptable salt thereof.

In some embodiments, the compound of Formula II has a structure of Formula II-119:

(II-119)

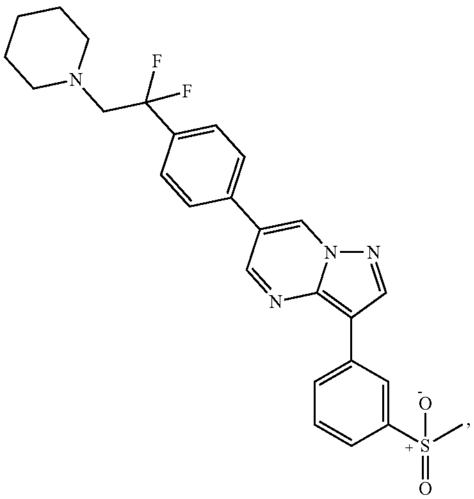

or a pharmaceutically acceptable salt thereof.

In some embodiments, the compound of Formula II has a structure of Formula II-120:

(II-120)

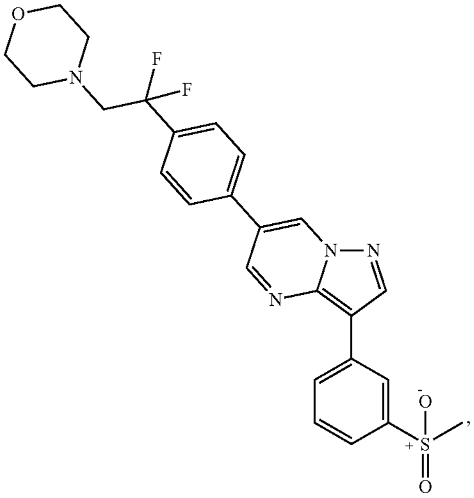

or a pharmaceutically acceptable salt thereof.

In some embodiments, the compound of Formula II has a structure of Formula II-121:

(II-121)

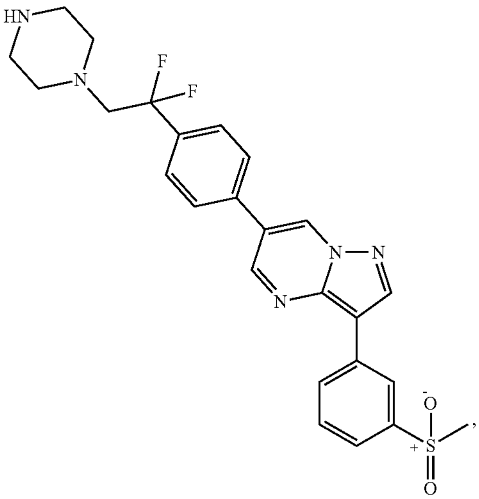

or a pharmaceutically acceptable salt thereof.

In some embodiments, the compound of Formula II has a structure of Formula II-122:

(II-122)

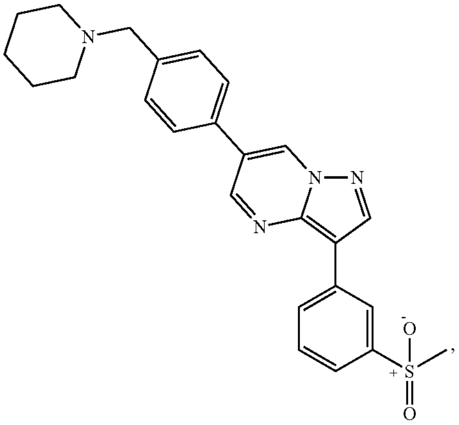

or a pharmaceutically acceptable salt thereof.

In some embodiments, the compound of Formula II has a structure of Formula II-123:

(II-123)

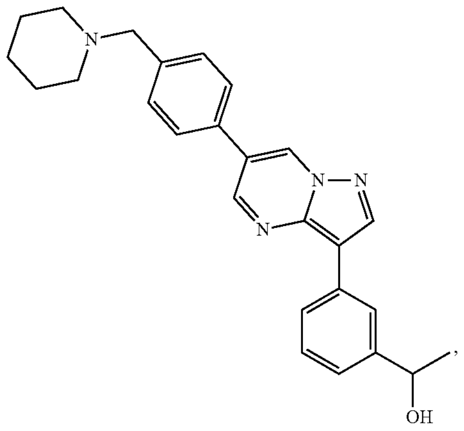

or a pharmaceutically acceptable salt thereof.

In some embodiments, the compound of Formula II has a structure of Formula II-124:

(II-124)

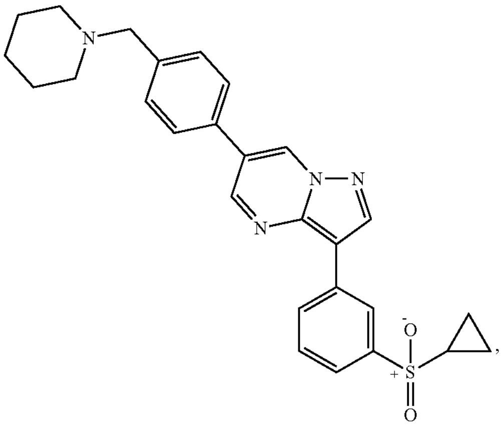

or a pharmaceutically acceptable salt thereof.

In some embodiments, the compound of Formula II has a structure of Formula II-125:

(II-125)

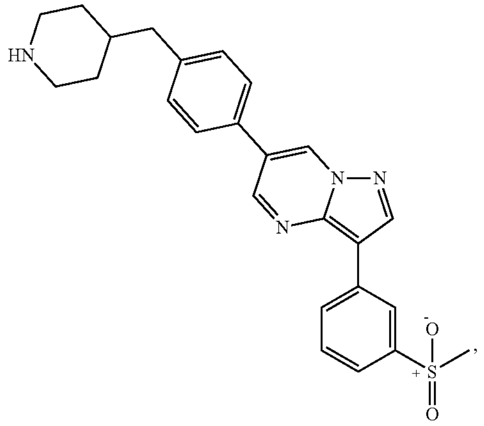

or a pharmaceutically acceptable salt thereof.

In some embodiments, the compound of Formula II has a structure of Formula II-126:

(II-126)

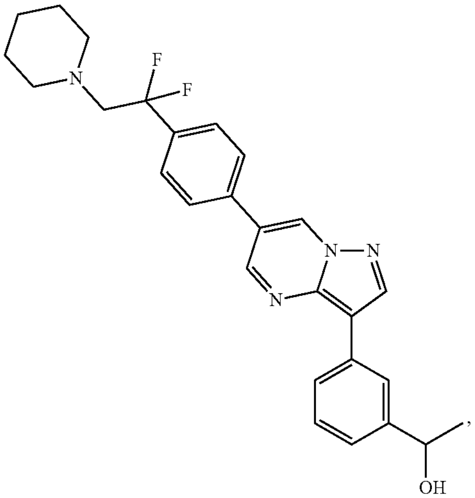

or a pharmaceutically acceptable salt thereof.

In some embodiments, the compound of Formula II has a structure of Formula II-127:

(II-127)

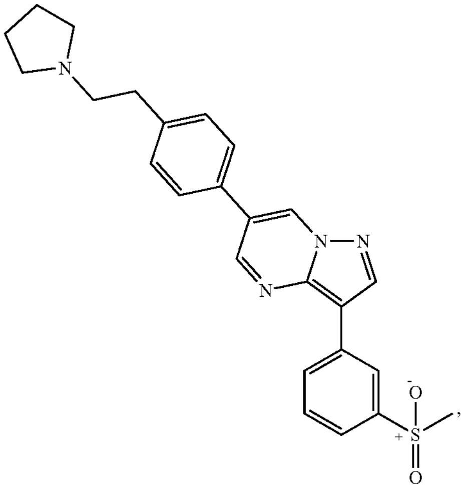

or a pharmaceutically acceptable salt thereof.

In some embodiments, the compound of Formula II has a structure of Formula II-128:

(II-128)

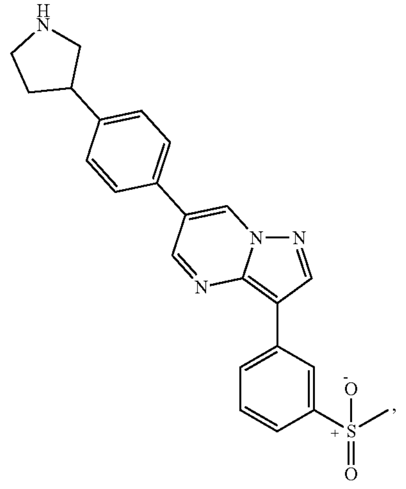

or a pharmaceutically acceptable salt thereof.

In some embodiments, the compound of Formula II has a structure of Formula II-129:

(II-129)

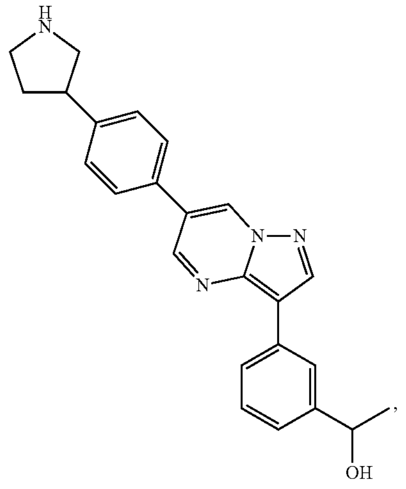

or a pharmaceutically acceptable salt thereof.

In some embodiments, the compound of Formula II has a structure of Formula II-130:

(II-130)

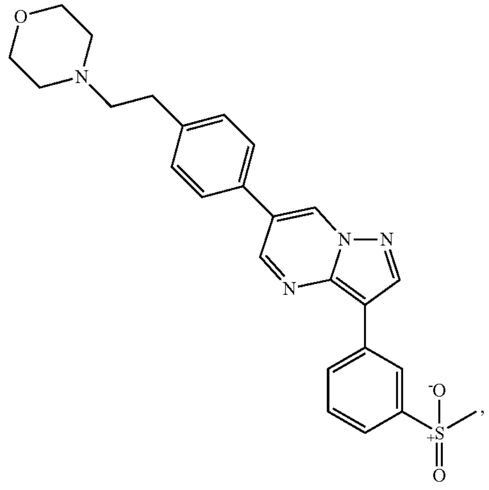

or a pharmaceutically acceptable salt thereof.

In some embodiments, the compound of Formula II has a structure of Formula II-131:

(II-131)

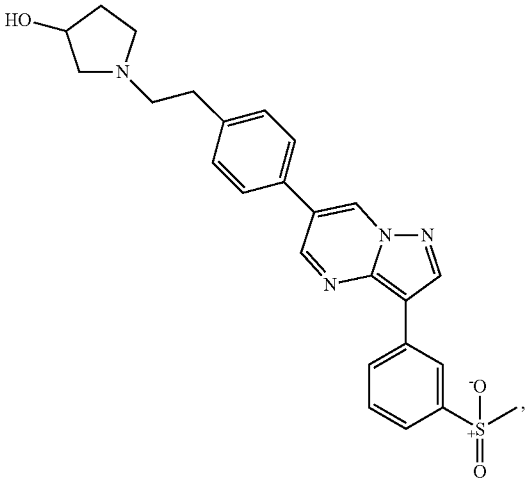

or a pharmaceutically acceptable salt thereof.

In some embodiments, the compound of Formula II has a structure of Formula II-132:

(II-132)

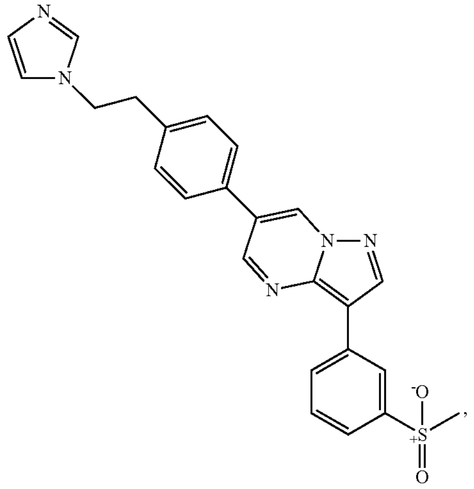

or a pharmaceutically acceptable salt thereof.

In some embodiments, the compound of Formula II has a structure of Formula II-133:

(II-133)

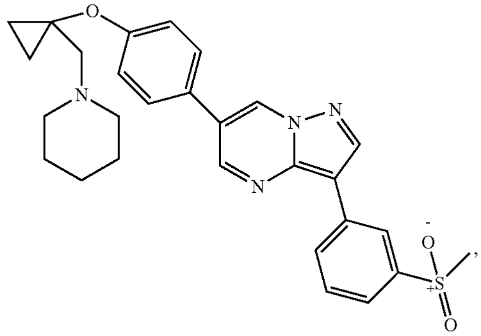

or a pharmaceutically acceptable salt thereof.

In some embodiments, the compound of Formula II has a structure of Formula II-134:

(II-134)

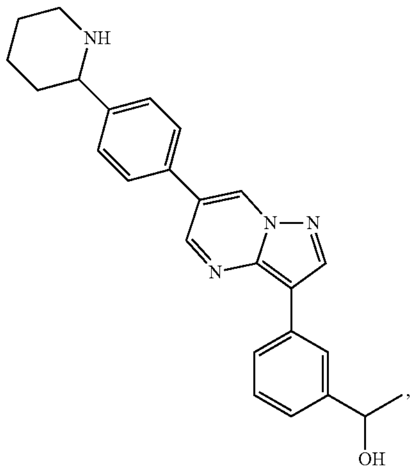

or a pharmaceutically acceptable salt thereof.

In some embodiments, the compound of Formula II has a structure of Formula II-135:

(II-135)

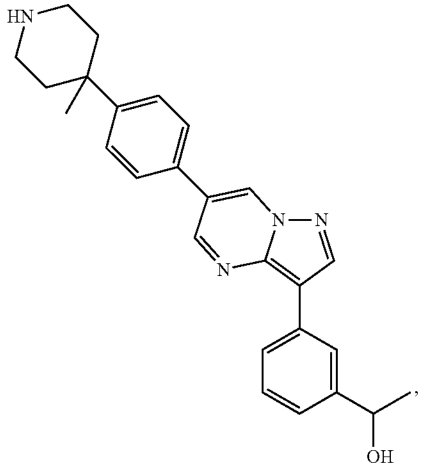

or a pharmaceutically acceptable salt thereof.

In some embodiments, the compound of Formula II has a structure of Formula II-136:

(II-136)

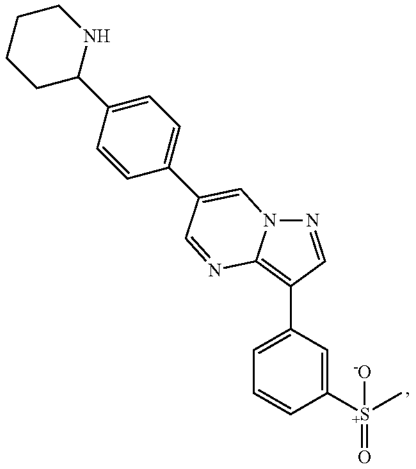

or a pharmaceutically acceptable salt thereof.

In some embodiments, the compound of Formula II has a structure of Formula II-137:

(II-137)

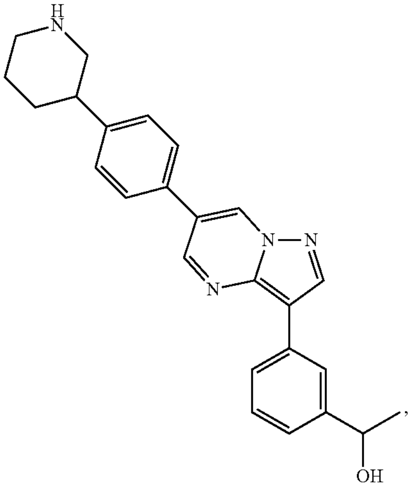

or a pharmaceutically acceptable salt thereof.

In some embodiments, the compound of Formula II has a structure of Formula II-138:

(II-138)

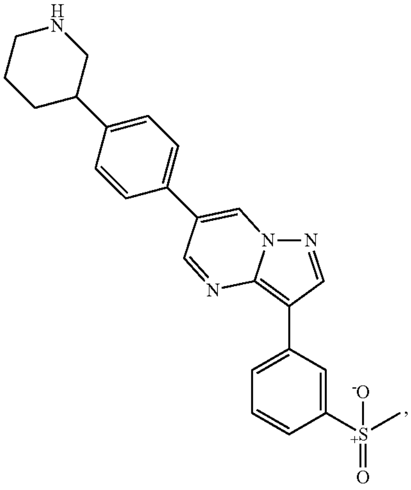

or a pharmaceutically acceptable salt thereof.

In some embodiments, the compound of Formula II has a structure of Formula II-139:

(II-139)

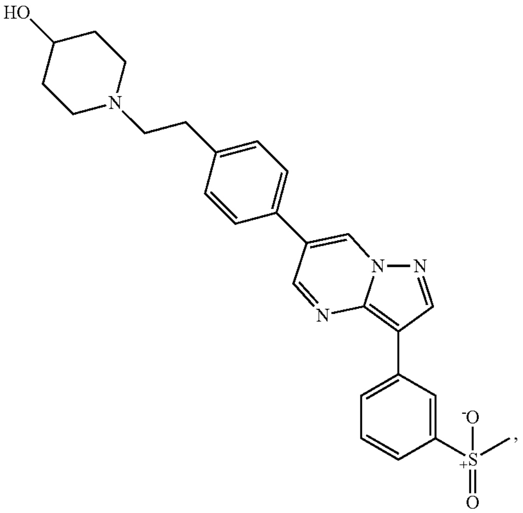

or a pharmaceutically acceptable salt thereof.

In some embodiments, the compound of Formula II has a structure of Formula II-140:

(II-140)

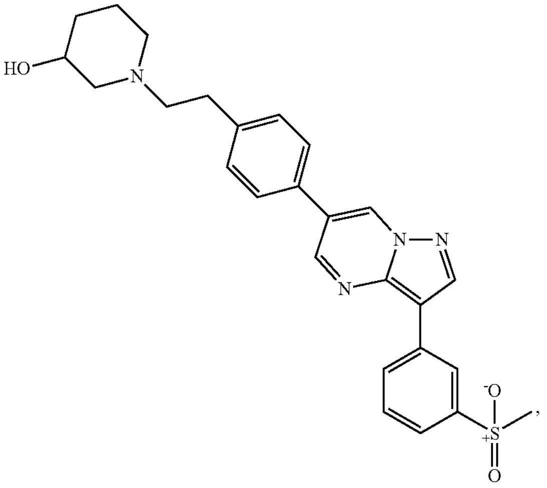

or a pharmaceutically acceptable salt thereof.

In some embodiments, the compound of Formula II has a structure of Formula II-141:

(II-141)

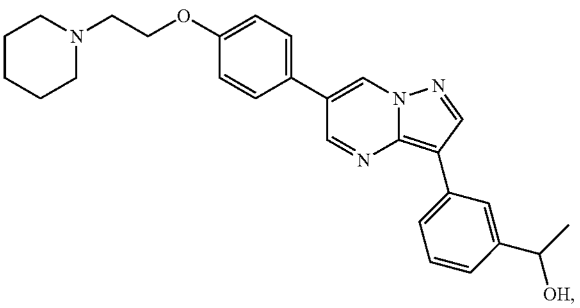

or a pharmaceutically acceptable salt thereof.

In some embodiments, the compound of Formula II has a structure of Formula II-142:

(II-142)

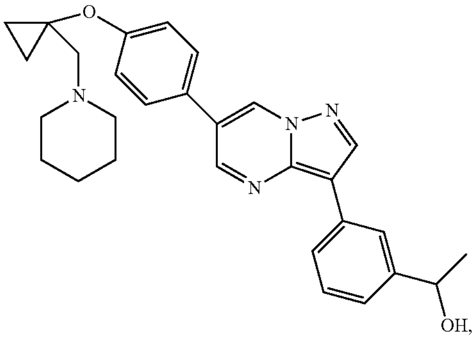

or a pharmaceutically acceptable salt thereof.

In some embodiments, the compound of Formula II has a structure of Formula II-143:

(II-143)

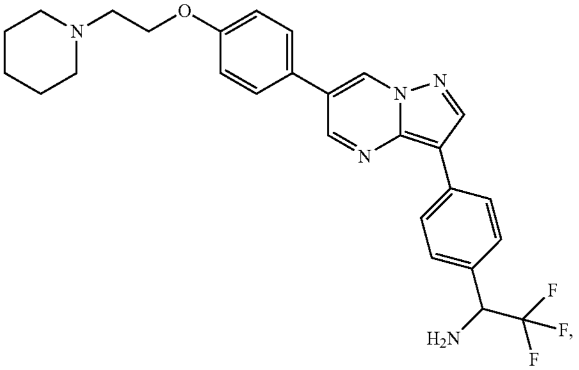

or a pharmaceutically acceptable salt thereof.

In some embodiments, the compound of Formula II has a structure of Formula II-144:

(II-144)

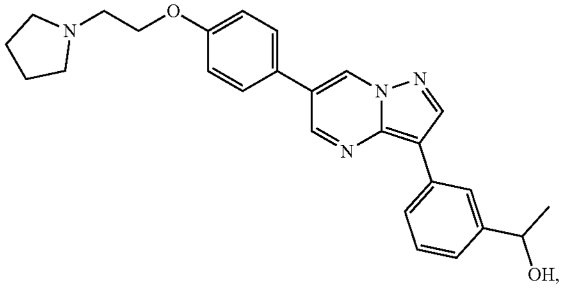

or a pharmaceutically acceptable salt thereof.

In some embodiments, the compound of Formula II has a structure of Formula II-145:

(II-145)

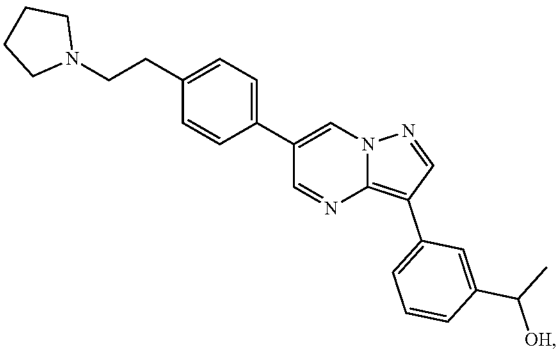

or a pharmaceutically acceptable salt thereof.

In some embodiments, the compound of Formula II has a structure of Formula II-146:

(II-146)

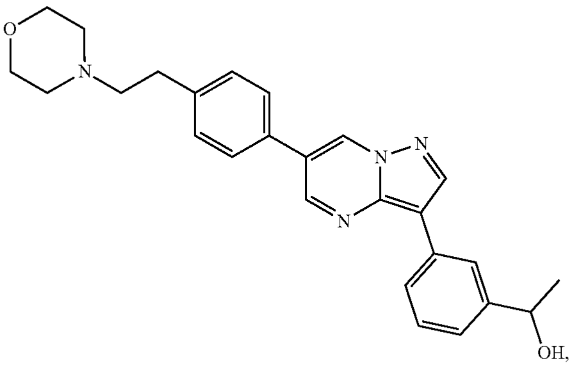

or a pharmaceutically acceptable salt thereof.

In some embodiments, the compound of Formula II has a structure of Formula II-147:

(II-147)

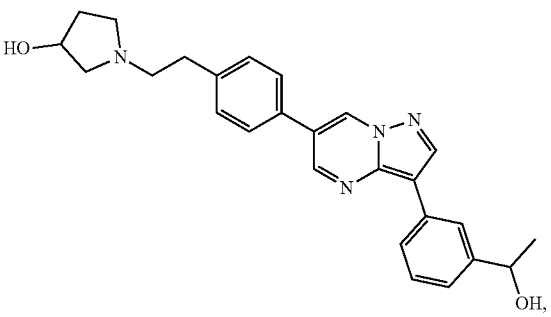

or a pharmaceutically acceptable salt thereof.

In some embodiments, the compound of Formula II has a structure of Formula II-148:

(II-148)

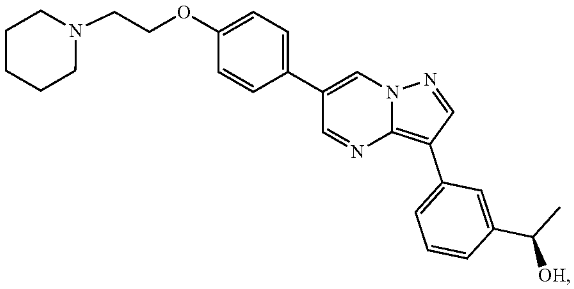

or a pharmaceutically acceptable salt thereof.

In some embodiments, the compound of Formula II has a structure of Formula II-149:

(II-149)

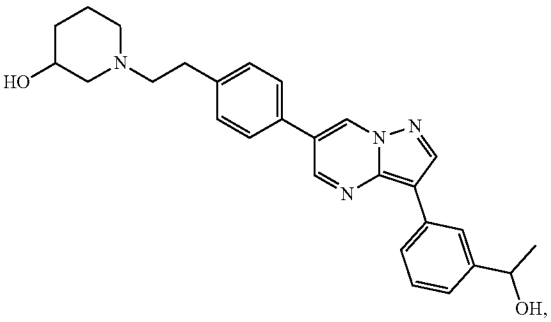

or a pharmaceutically acceptable salt thereof.

In some embodiments, the compound of Formula II has a structure of Formula II-150:

(II-150)

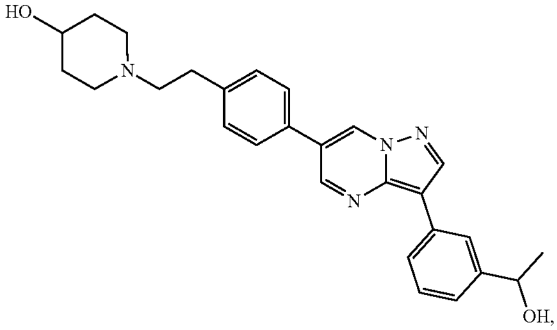

or a pharmaceutically acceptable salt thereof.

In some embodiments, the compound of Formula II has a structure of Formula II-151:

(II-151)

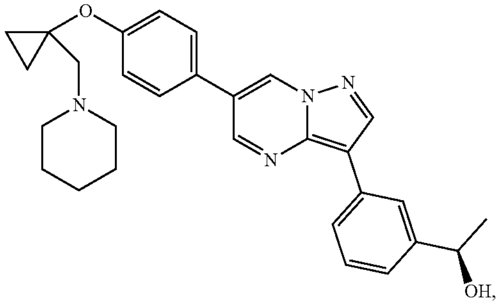

or a pharmaceutically acceptable salt thereof.

In some embodiments, the compound of Formula II has a structure of Formula II-152:

(II-152)

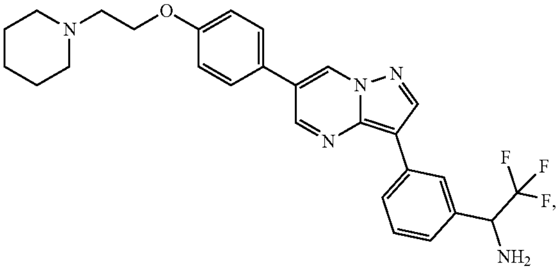

or a pharmaceutically acceptable salt thereof.

In some embodiments, the compound of Formula II has a structure of Formula II-153:

(II-153)

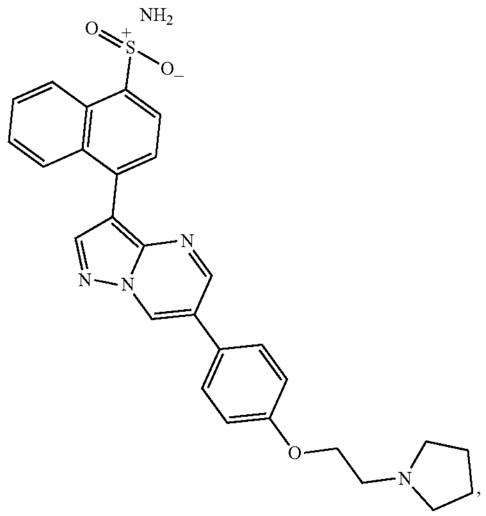

or a pharmaceutically acceptable salt thereof.

In some embodiments, the compound of Formula II has a structure of Formula II-154:

(II-154)

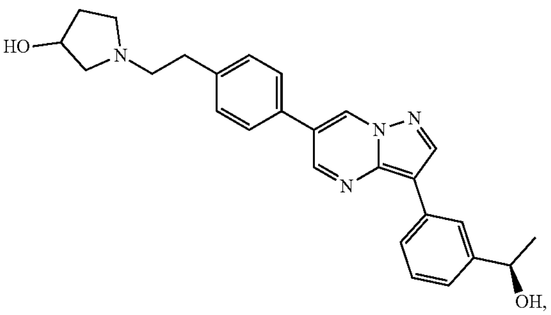

or a pharmaceutically acceptable salt thereof.

In some embodiments, the compound of Formula II has a structure of Formula II-155:

(II-155)

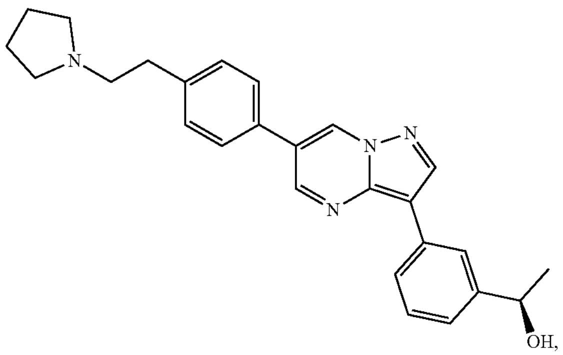

or a pharmaceutically acceptable salt thereof.

In some embodiments, the compound of Formula II has a structure of Formula II-156:

(II-156)

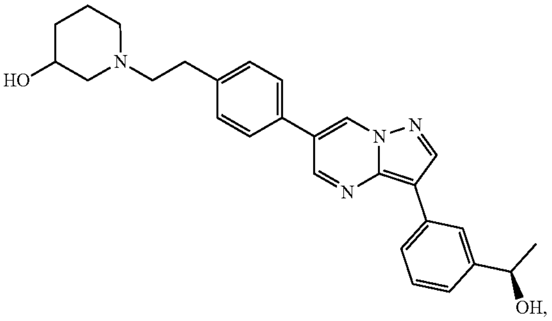

or a pharmaceutically acceptable salt thereof.

In some embodiments, the compound of Formula II has a structure of Formula II-157:

(II-157)

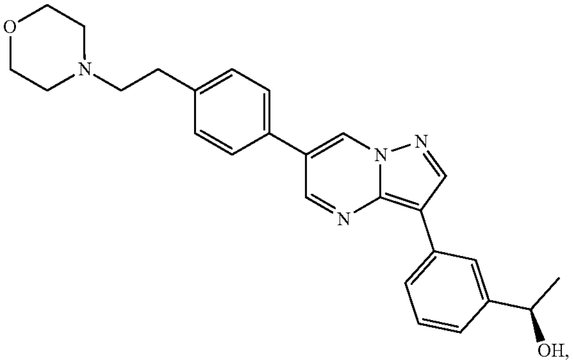

or a pharmaceutically acceptable salt thereof.

In some embodiments, the compound of Formula II has a structure of Formula II-158:

(II-158)

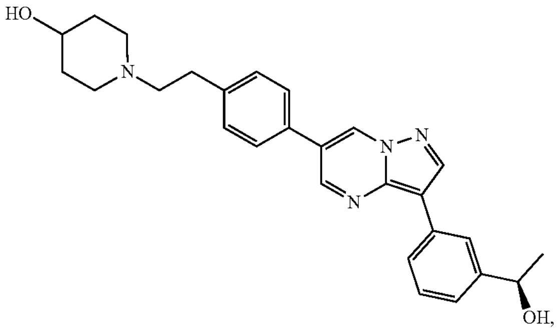

or a pharmaceutically acceptable salt thereof.

In some embodiments, the compound of Formula II has a structure of Formula II-159:

(II-159)

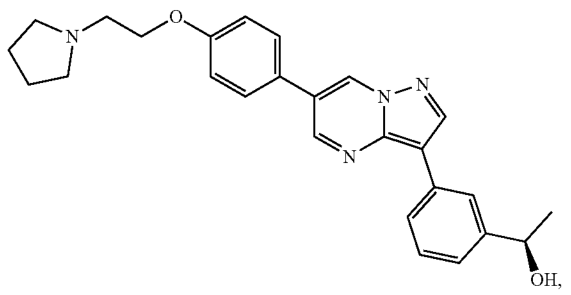

or a pharmaceutically acceptable salt thereof.

In some embodiments, the compound of Formula II has a structure of Formula II-160:

(II-160)

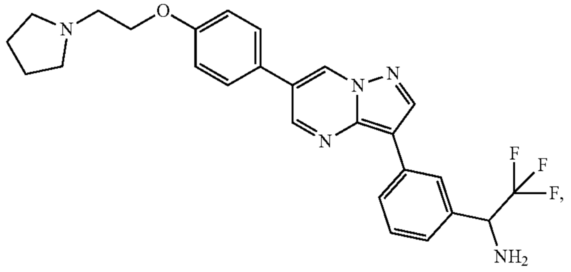

or a pharmaceutically acceptable salt thereof.

In some embodiments, the compound of Formula II has a structure of Formula II-161:

(II-161)

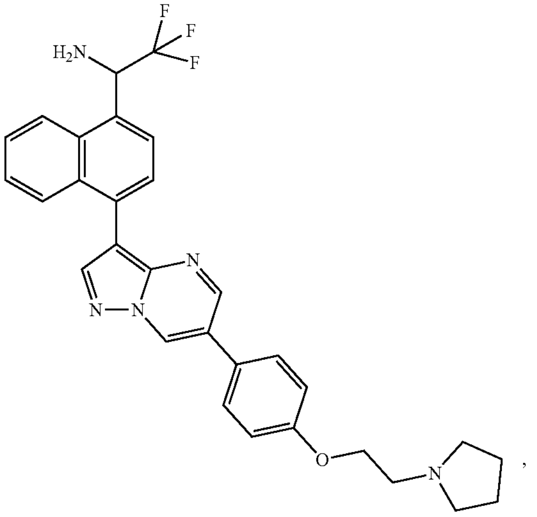

or a pharmaceutically acceptable salt thereof.

In some embodiments, the compound of Formula II has a structure of Formula II-162:

(II-162)

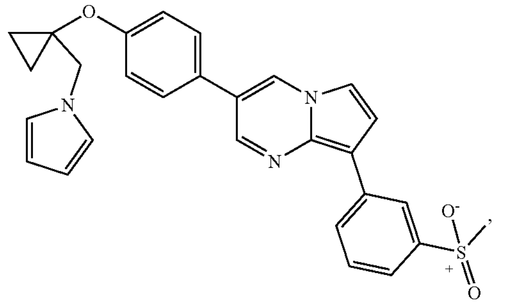

or a pharmaceutically acceptable salt thereof.

In some embodiments, the compound of Formula II has a structure of Formula II-163:

(II-163)

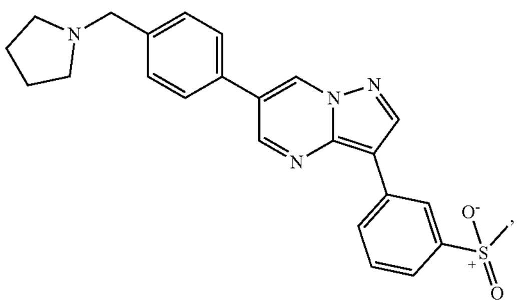

or a pharmaceutically acceptable salt thereof.

In some embodiments, the compound of Formula II has a structure of Formula II-164:

(II-164)

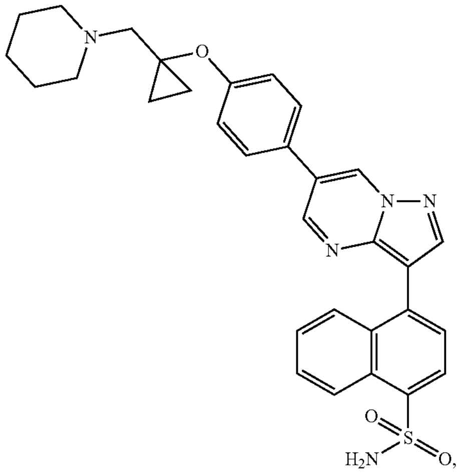

or a pharmaceutically acceptable salt thereof.

In some embodiments, the compound of Formula II has a structure of Formula II-165:

(II-165)

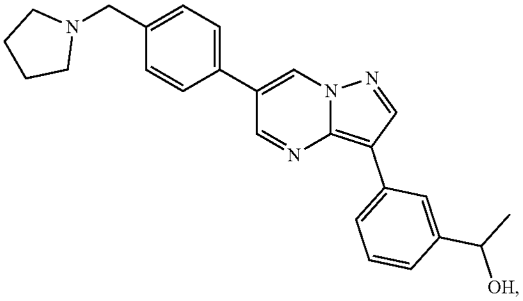

or a pharmaceutically acceptable salt thereof.

In some embodiments, the compound of Formula II has a structure of Formula II-166:

(II-166)

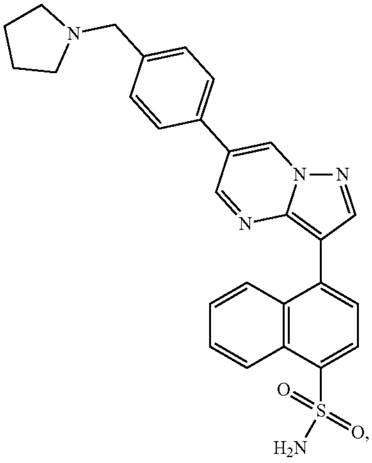

or a pharmaceutically acceptable salt thereof.

In some embodiments, the compound of Formula II has a structure of Formula II-167:

(II-167)

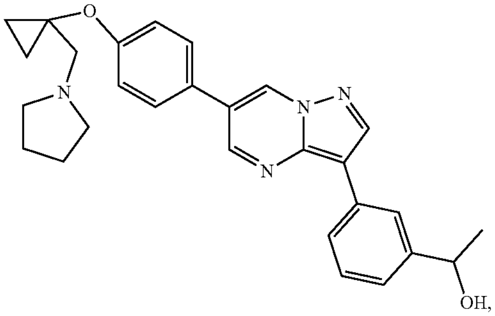

or a pharmaceutically acceptable salt thereof.

In some embodiments, the compound of Formula II has a structure of Formula II-168:

(II-168)

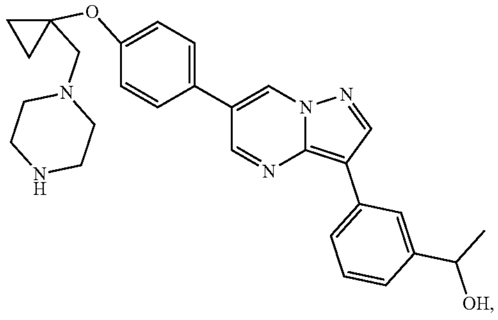

or a pharmaceutically acceptable salt thereof.

In some embodiments: the compound of Formula II has a structure of Formula II-169:

(II-169)

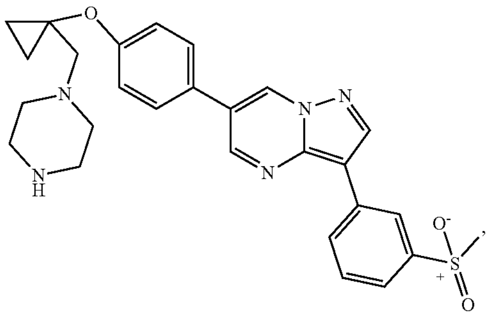

or a pharmaceutically acceptable salt thereof.

In some embodiments, the compound of Formula II has a structure of Formula II-170:

(II-170)

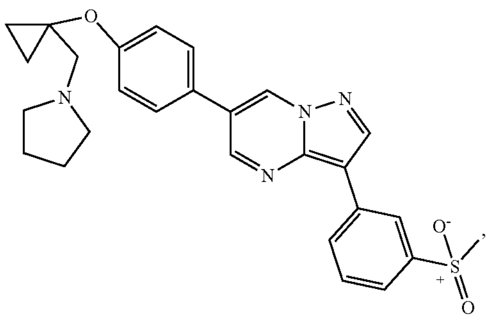

or a pharmaceutically acceptable salt thereof.

In some embodiments, the compound of Formula II has a structure of Formula II-171:

(II-171)

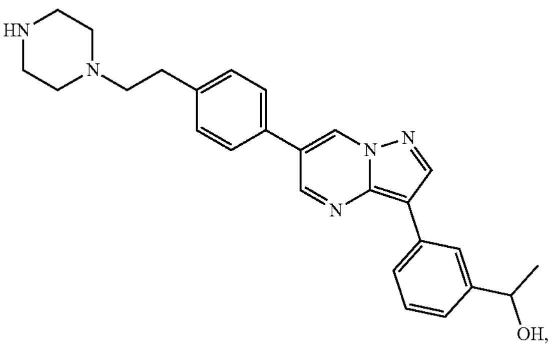

or a pharmaceutically acceptable salt thereof.

In some embodiments, the compound of Formula II has a structure of Formula II-172:

(II-172)

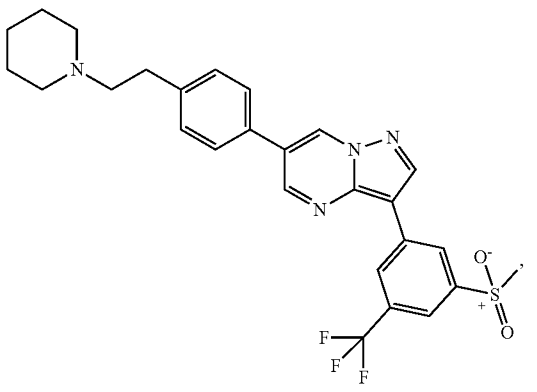

or a pharmaceutically acceptable salt thereof.

In some embodiments, the compound of Formula II has a structure of Formula II-173:

(II-173)

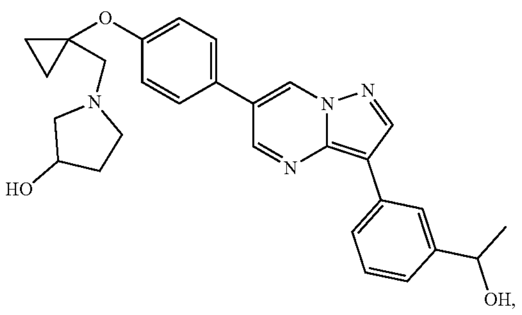

or a pharmaceutically acceptable salt thereof.

In some embodiments, the compound of Formula II has a structure of Formula II-174:

(II-174)

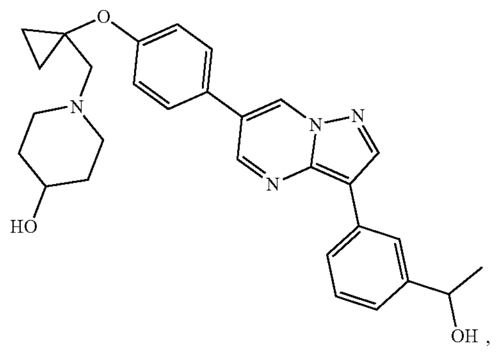

or a pharmaceutically acceptable salt thereof.

In some embodiments, the compound of Formula II has a structure of Formula II-175:

(II-175)

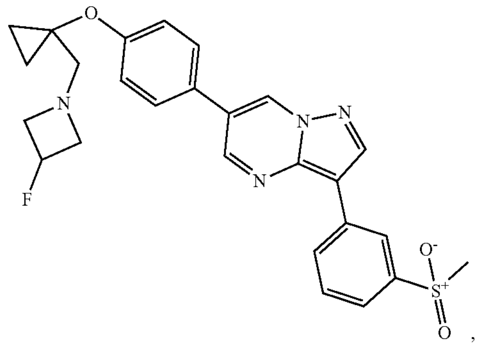

or a pharmaceutically acceptable salt thereof.

In some embodiments, the compound of Formula II has a structure of Formula II-176:

(II-176)

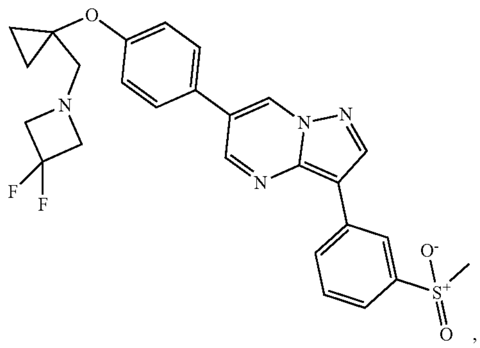

or a pharmaceutically acceptable salt thereof.

In some embodiments, the compound of Formula II has a structure of Formula II-177:

(II-177)

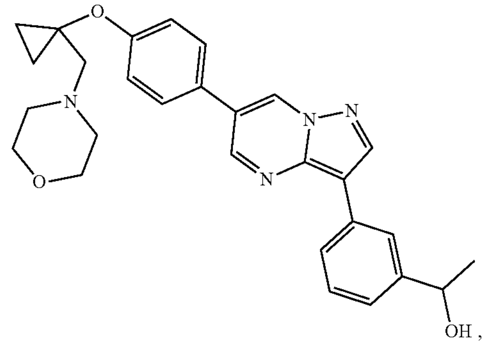

or a pharmaceutically acceptable salt thereof.

In some embodiments, the compound of Formula II has a structure of Formula II-178:

(II-178)

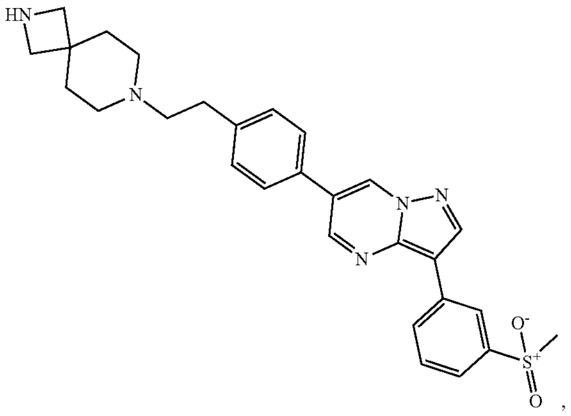

or a pharmaceutically acceptable salt thereof.

In some embodiments, the compound of Formula II has a structure of Formula II-179:

(II-179)

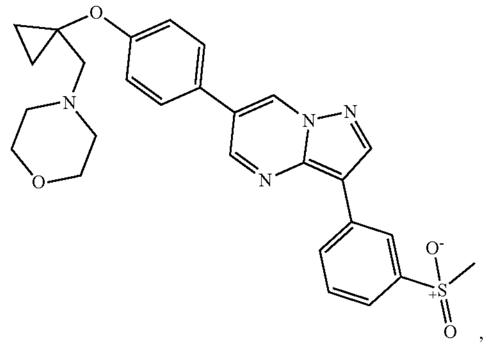

or a pharmaceutically acceptable salt thereof.

In some embodiments, the compound of Formula II has a structure of Formula II-180:

(II-180)

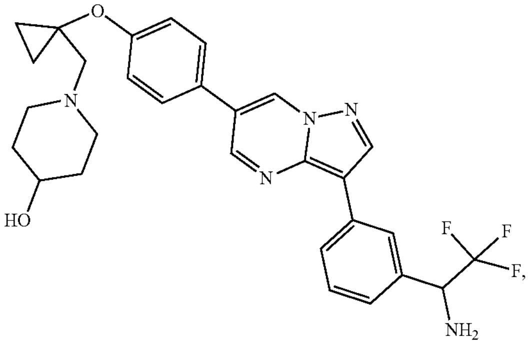

or a pharmaceutically acceptable salt thereof.

In some embodiments, the compound of Formula II has a structure of Formula II-181:

(II-181)

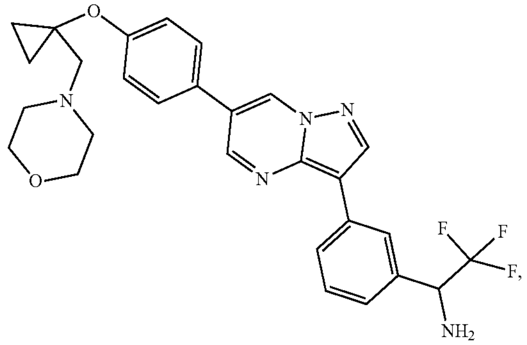

or a pharmaceutically acceptable salt thereof.

In some embodiments, the compound of Formula II has a structure of Formula II-182:

(II-182)

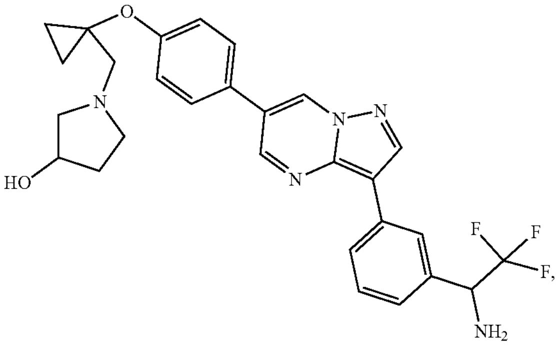

or a pharmaceutically acceptable salt thereof.

In some embodiments, the compound of Formula II has a structure of Formula II-183:

(II-183)

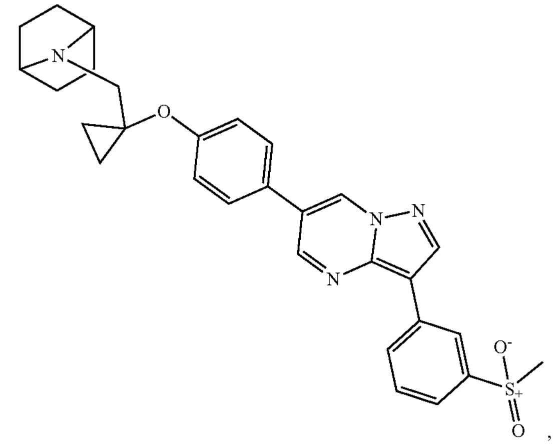

or a pharmaceutically acceptable salt thereof.

In some embodiments, the compound of Formula II has a structure of Formula II-184:

(II-184)

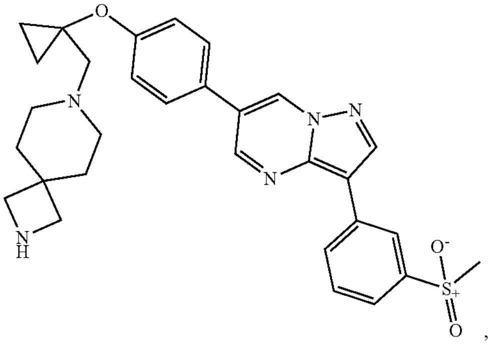

or a pharmaceutically acceptable salt thereof.

In some embodiments, the compound of Formula II has a structure of Formula II-185:

(II-185)

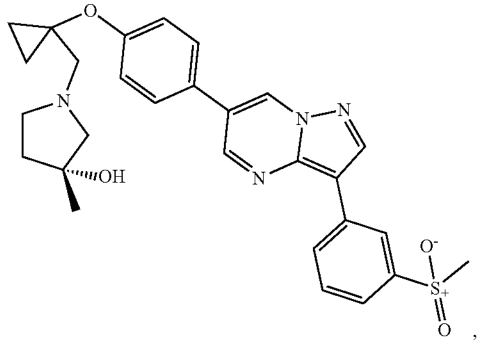

or a pharmaceutically acceptable salt thereof.

In some embodiments, the compound of Formula II has a structure of Formula II-186:

(II-186)

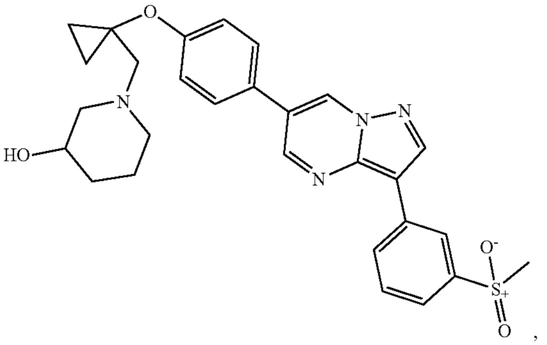

or a pharmaceutically acceptable salt thereof.

In some embodiments, the compound of Formula II has a structure of Formula II-187:

(II-187)

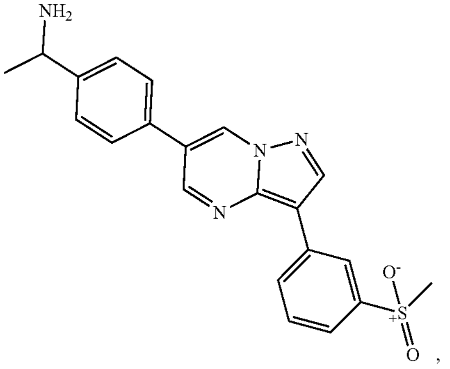

or a pharmaceutically acceptable salt thereof.

In some embodiments, the compound of Formula II has a structure of Formula II-188:

(II-188)

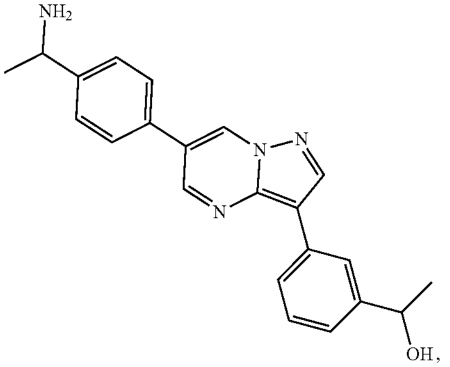

or a pharmaceutically acceptable salt thereof.

In some embodiments, the compound of Formula II has a structure of Formula II-189:

(II-189)

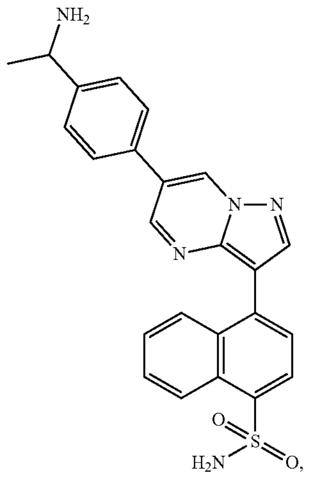

or a pharmaceutically acceptable salt thereof.

In some embodiments, the compound of Formula II has a structure of Formula II-190:

(II-190)

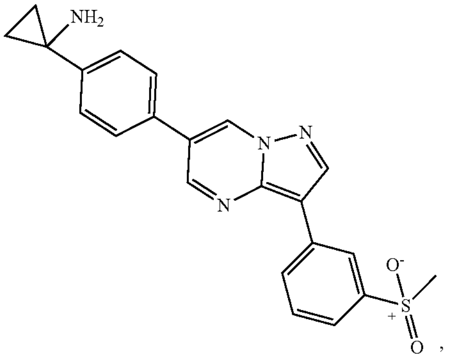

or a pharmaceutically acceptable salt thereof.

In some embodiments, the compound of Formula II has a structure of Formula II-191:

(II-191)

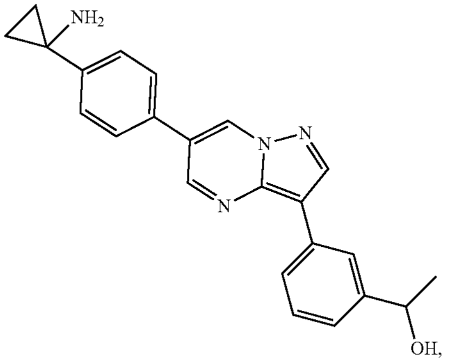

or a pharmaceutically acceptable salt thereof.

In some embodiments, the compound of Formula II has a structure of Formula II-192:

(II-192)

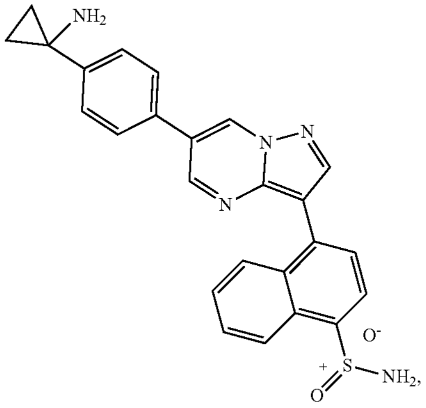

or a pharmaceutically acceptable salt thereof.

In some embodiments, the compound of Formula II has a structure of Formula II-193:

(II-193)

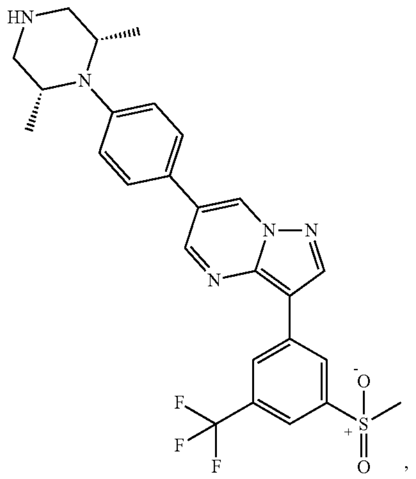

or a pharmaceutically acceptable salt thereof.

In some embodiments, the compound of Formula II has a structure of Formula II-194:

(II-194)

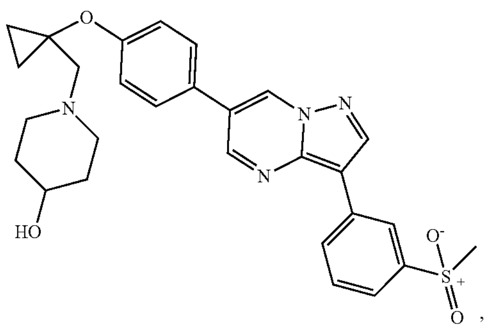

or a pharmaceutically acceptable salt thereof.

In some embodiments, the compound of Formula II has a structure of Formula II-195:

(II-195)

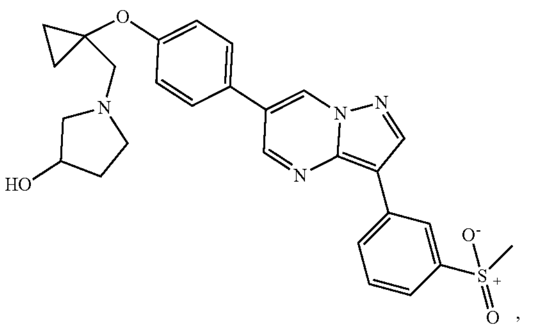

or a pharmaceutically acceptable salt thereof.

In some embodiments, the compound of Formula II has a structure of Formula II-196:

(II-196)

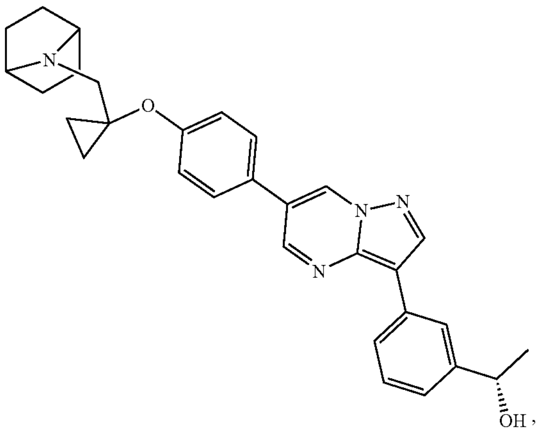

or a pharmaceutically acceptable salt thereof.

In some embodiments, the compound of Formula II has a structure of Formula II-197:

(II-197)

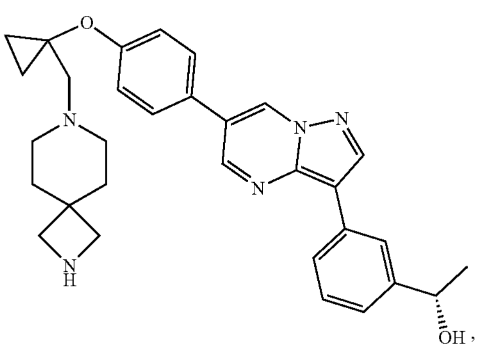

or a pharmaceutically acceptable salt thereof.

In some embodiments, the compound of Formula II has a structure of Formula II-198:

(II-198)

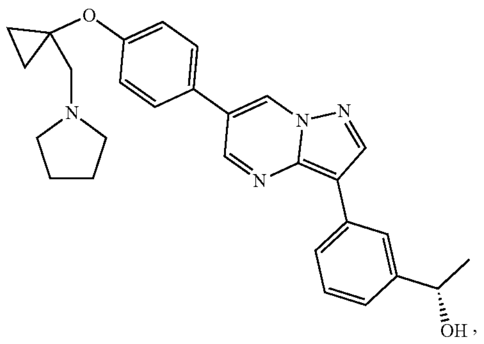

or a pharmaceutically acceptable salt thereof.

In some embodiments, the compound of Formula II has a structure of Formula II-199:

(II-199)

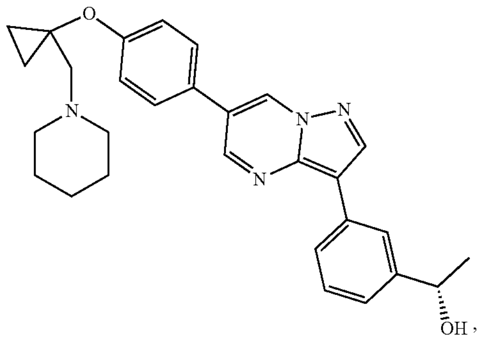

or a pharmaceutically acceptable salt thereof.

In some embodiments, the compound of Formula II has a structure of Formula II-200:

(II-200)

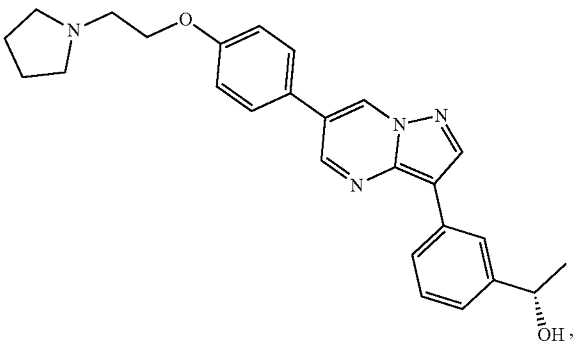

or a pharmaceutically acceptable salt thereof.

In some embodiments, the compound of Formula II has a structure of Formula II-201:

(II-201)

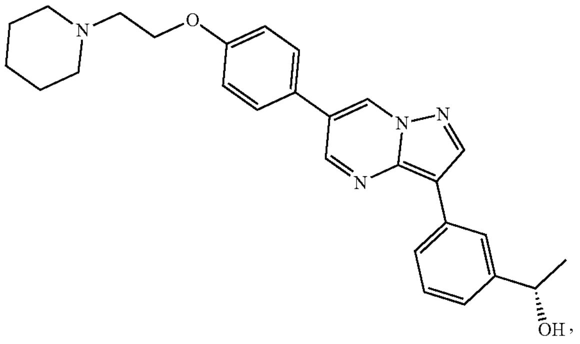

or a pharmaceutically acceptable salt thereof.

In some embodiments, the compound of Formula II has a structure of Formula II-202:

(II-202)

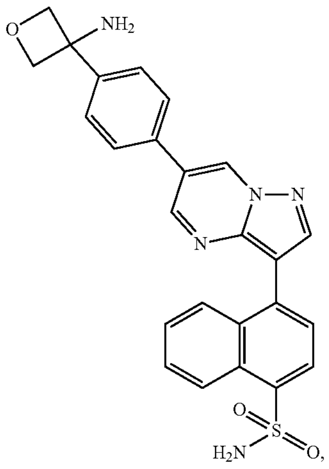

or a pharmaceutically acceptable salt thereof.

In some embodiments, the compound of Formula II has a structure of Formula II-203:

(II-203)

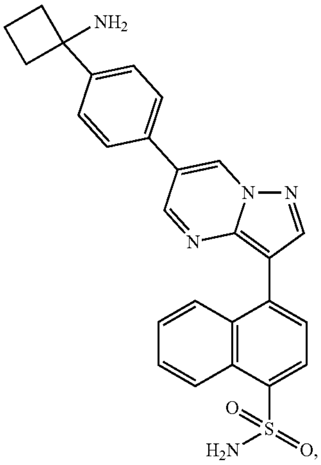

or a pharmaceutically acceptable salt thereof.

In some embodiments, the compound of Formula II has a structure of Formula II-204:

(II-204)

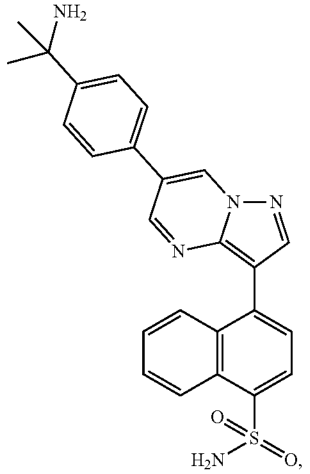

or a pharmaceutically acceptable salt thereof.

In some embodiments, the compound of Formula II has a structure of Formula II-205:

(II-205)

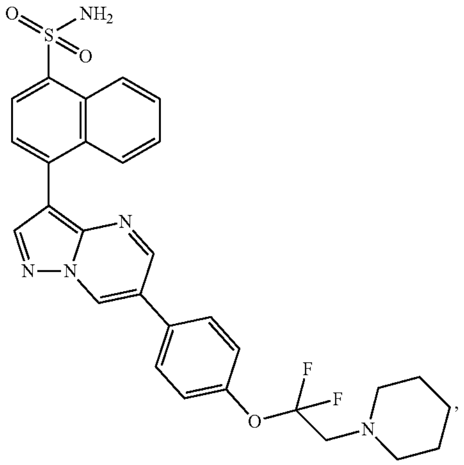

or a pharmaceutically acceptable salt thereof.

In some embodiments, the compound of Formula II has a structure of Formula II-206:

(II-206)

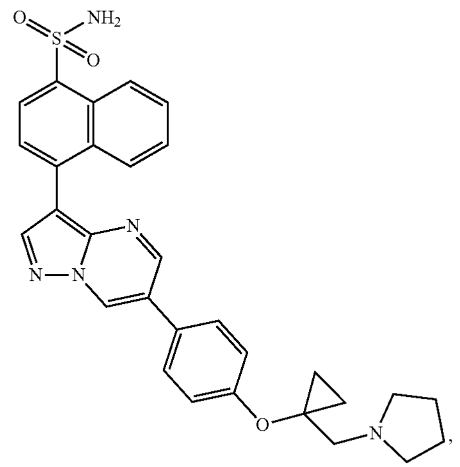

or a pharmaceutically acceptable salt thereof.

In some embodiments, the ALK2 inhibitor is a compound of Formula II or a pharmaceutically acceptable salt thereof, wherein X and Y are independently selected from $CR^{15}$ and N, preferably both N;

Z is selected from $CR^{3'}$ and N, preferably $CR^3$, most preferably CH;

Ar is a phenyl ring substituted with at least one non-protium ($^1H$) substituent or a substituted or unsubstituted heteroaryl ring;

$L_1$ is absent or selected from substituted or unsubstituted alkyl and heteroalkyl; and G, J, K, and M are all absent or, independently for each occurrence, are selected from $CR^{16}$ and N;

A, B, and E, independently for each occurrence, are selected from $CR^{16}$ and N; provided that no more than three (and preferably no more than two) of A, B, E, G, J, K, and M are N, and at least one of E and M is N, and that if G, J, K, and M are absent then the carbon atom adjacent to E and M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and $R^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, or sulfonamide.

In some embodiments, the ALK2 inhibitor is a compound of Formula II or a pharmaceutically acceptable salt thereof, wherein X and Y are independently selected from $CR^{15}$ and N, preferably both N;

Z is selected from $CR^{3'}$ and N, preferably $CR^{3'}$, most preferably CH;

Ar is selected from substituted or unsubstituted aryl and heteroaryl;

$L_1$ is absent or selected from substituted or unsubstituted alkyl and heteroalkyl; and G, J, K, and M are all absent or, independently for each occurrence, are selected from $CR^{16}$ and N;

A, B, and E, independently for each occurrence, are selected from $CR^{16}$ and N;

provided that no more than three (and preferably no more than two) of A, B, E, G, J, K, and M are N, and at least one of E and M is N, and that if G, J, K, and M are absent then the carbon atom adjacent to E and M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, or sulfonamido;

$R^7$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and $R^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide; wherein B is C—$R^{25}$ when E is N or K is C—$R^{25}$ when M is N or both such that at least one of B and K is C—$R^{25}$, where $R^{25}$ is selected from deuterium, halogen (preferably fluorine or chlorine), hydroxyl, lower alkyl (preferably methyl), and lower alkoxy (preferably methoxy), such as deuterium, fluorine, chlorine, methyl, ethyl, hydroxy, or methoxy.

In some embodiments, the ALK2 inhibitor is a compound of Formula II or a pharmaceutically acceptable salt thereof, wherein X and Y are independently selected from $CR^{15}$ and N;

Z is selected from $CR^{3'}$ and N;

Ar is selected from substituted or unsubstituted aryl and heteroaryl;

$L_1$ is absent or selected from substituted or unsubstituted alkyl and heteroalkyl;

G, J, K, and M are all absent or, independently for each occurrence, are selected from $CR^{16}$ and N;

A, B, and E, independently for each occurrence, are selected from $CR^{16}$ and N;

provided that:

no more than three of A, B, E, G, J, K, and M are N, at least one of E and M is N, and that if G, J, K, and M are absent, then the carbon atom drawn as connected to variable M is optionally substituted with $R^{16}$;

$R^{3'}$ is selected from H, halogen, cyano, and substituted or unsubstituted alkyl, cycloalkyl, acylamino, carbamate, sulfonyl, sulfoxido, sulfamoyl, and sulfonamido;

$R^7$ is selected from hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, and sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, and sulfonamido; and $R^{16}$, independently for each occurrence, is absent or is selected from H, OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide; provided that:

i) if Ar is a phenyl ring, it is substituted with at least one non-protium ($^1H$) substituent;

ii) B is C—$R^{25}$ when E is N, or K is C—$R^{25}$ when M is N, or both, such that at least one of B and K is C—$R^{25}$, wherein $R^{25}$ is selected from deuterium, halogen, hydroxyl, lower alkyl, and lower alkoxy; and/or iii) $R^7$ is

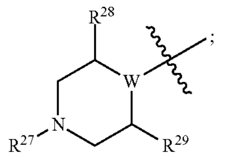

W is N, CH, or $CCH_3$;

$R^{27}$ is selected from H and substituted or unsubstituted alkyl, acyl, and ester; and $R^{28}$ and $R^{29}$ are each independently H or alkyl, or $R^{28}$ forms a one- or two-carbon bridge to the carbon atom adjacent to $R^{29}$ and $NR^{27}$; wherein either W is CH or $CCH_3$, or $R^{28}$ and $R^{29}$ are not both H.

Compounds of Formula II may be synthesized by methods known in the art, e.g., those described in U.S. Pat. Nos. 10,017,516 and 9,682,983, which are incorporated herein by reference.

In some embodiments, the compound of Formula II has a structure of Formula II-207:

(II-207)

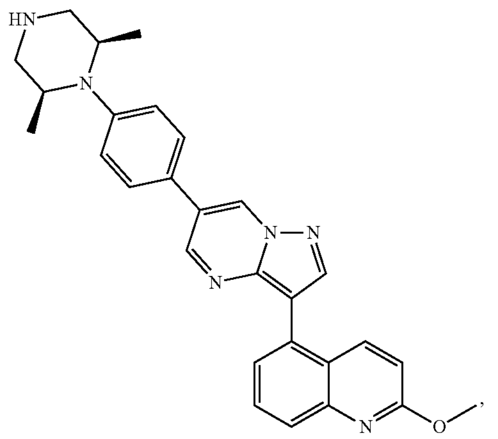

or a pharmaceutically acceptable salt thereof.

In some embodiments, the compound of Formula II has a structure of Formula II-208:

(II-208)

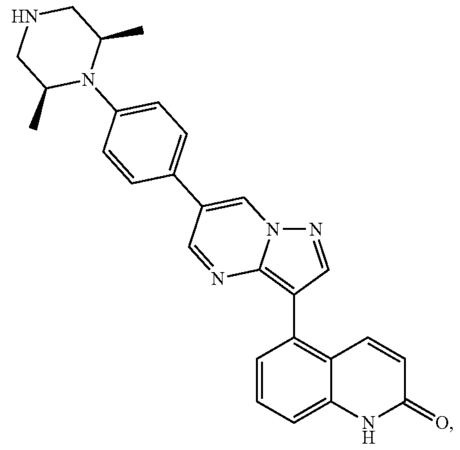

or a pharmaceutically acceptable salt thereof.

In some embodiments, the compound of Formula II has a structure of Formula II-209:

(II-209)

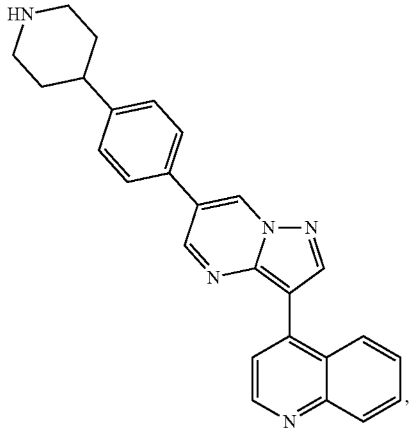

or a pharmaceutically acceptable salt thereof.

In some embodiments, the compound of Formula II has a structure of Formula II-210:

(II-210)

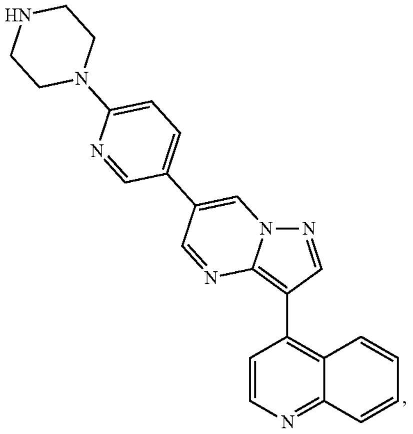

or a pharmaceutically acceptable salt thereof.

In some embodiments, the compound of Formula II has a structure of Formula II-211:

(II-211)

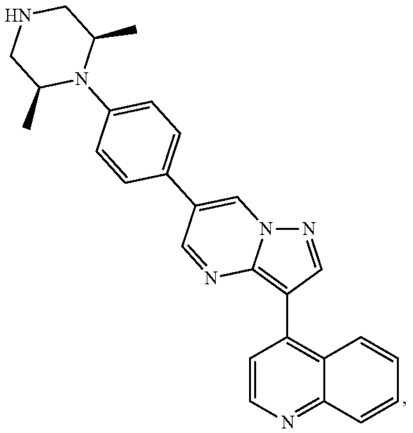

or a pharmaceutically acceptable salt thereof.

In some embodiments, the compound of Formula II has a structure of Formula II-212:

(II-212)

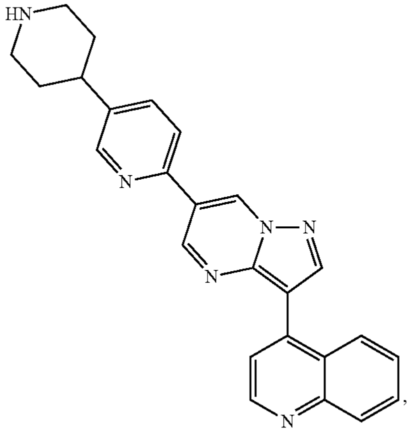

or a pharmaceutically acceptable salt thereof.

In some embodiments, the compound of Formula II has a structure of Formula II-213:

(II-213)

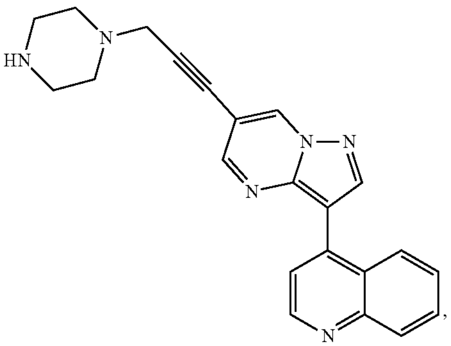

or a pharmaceutically acceptable salt thereof.

In some embodiments, the compound of Formula II has a structure of Formula II-214:

(II-214)

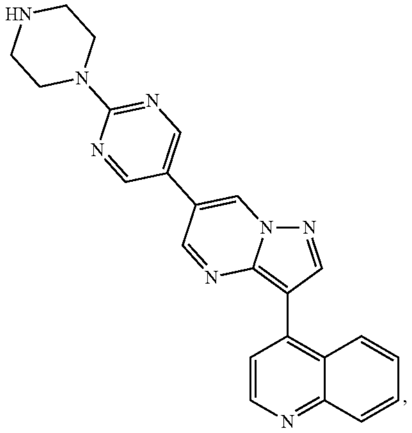

or a pharmaceutically acceptable salt thereof.

In some embodiments, the compound of Formula II has a structure of Formula II-215:

(II-215)

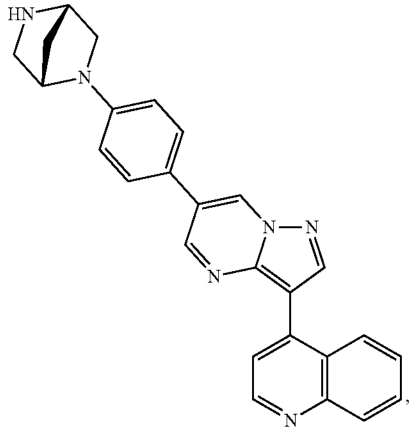

or a pharmaceutically acceptable salt thereof.

In some embodiments, the compound of Formula II has a structure of Formula II-216:

(11-216)

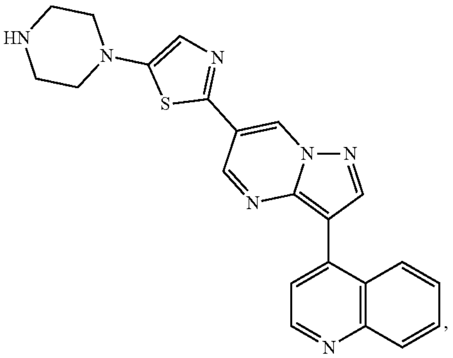

or a pharmaceutically acceptable salt thereof.

In some embodiments, the compound of Formula II has a structure of Formula II-217:

(II-217)

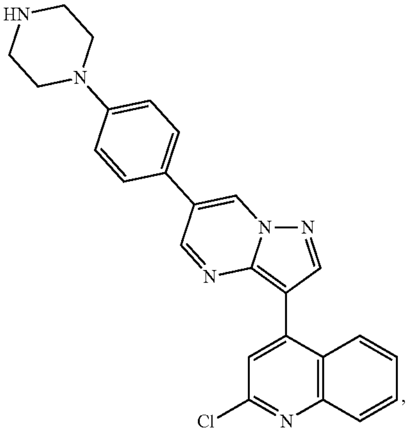

or a pharmaceutically acceptable salt thereof.

In some embodiments, the compound of Formula II has a structure of Formula II-218:

(II-218)

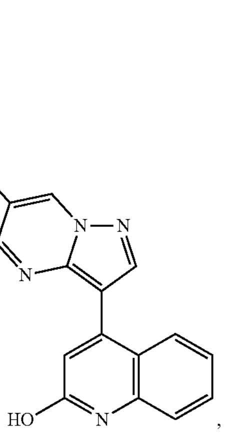

or a pharmaceutically acceptable salt thereof.

In some embodiments, the compound of Formula II has a structure of Formula II-219:

(II-219)

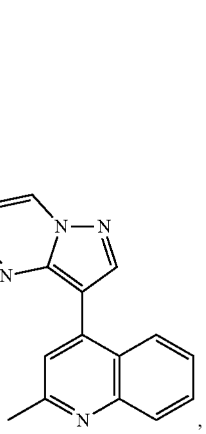

or a pharmaceutically acceptable salt thereof.

In some embodiments, the compound of Formula II has a structure of Formula II-220:

(II-219)

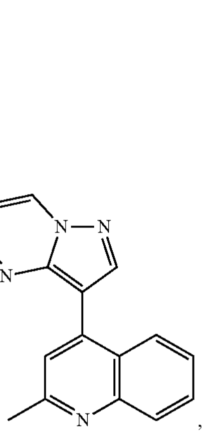

or a pharmaceutically acceptable salt thereof.

In some embodiments, the compound of Formula II has a structure of Formula II-221:

(II-221)

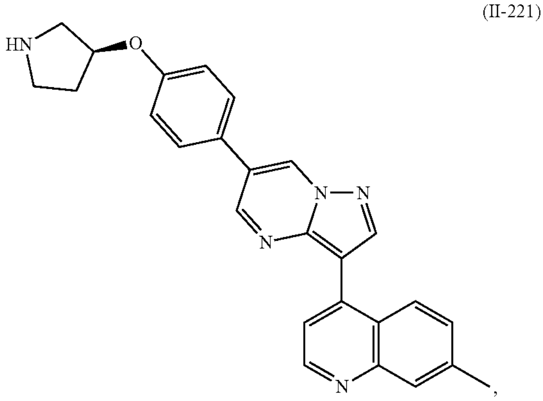 [SMILES: Cc1ccc2c(-c3cnn4cc(-c5ccc(O[C@H]6CCNC6)cc5)cnc34)ccnc2c1]

, or a pharmaceutically acceptable salt thereof.

In some embodiments, the compound of Formula II has a structure of Formula II-222:

(II-222)

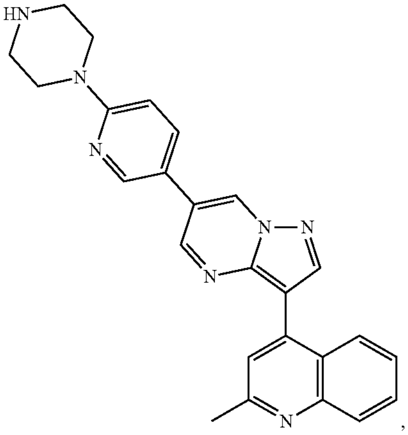

, or a pharmaceutically acceptable salt thereof.

In some embodiments, the compound of Formula II has a structure of Formula II-223:

(II-223)

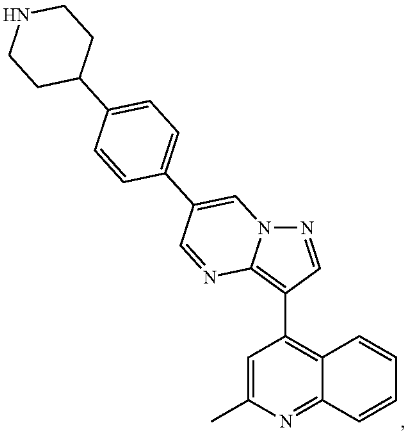

, or a pharmaceutically acceptable salt thereof.

In some embodiments, the compound of Formula II has a structure of Formula II-224:

(II-224)

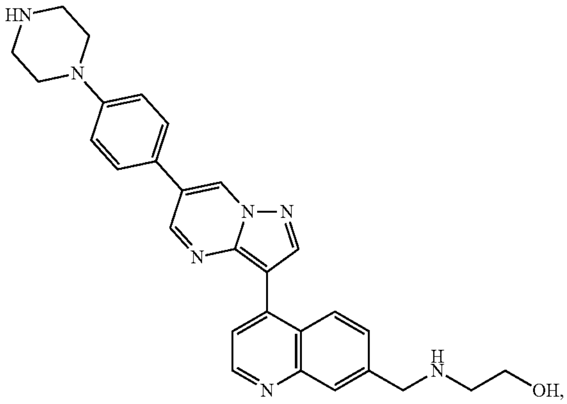

or a pharmaceutically acceptable salt thereof.

In some embodiments, the compound of Formula II has a structure of Formula II-225:

(II-225)

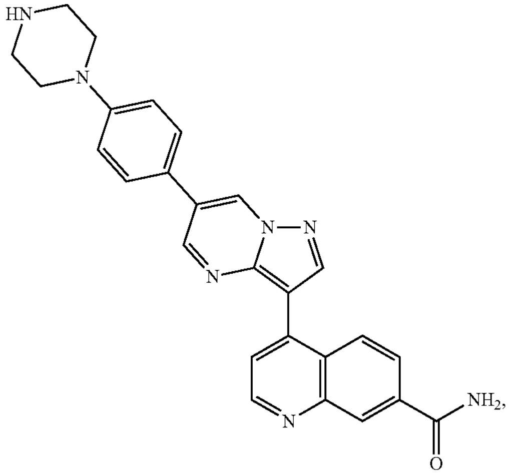

or a pharmaceutically acceptable salt thereof.

In some embodiments, the compound of Formula II has a structure of Formula II-226:

(II-225)

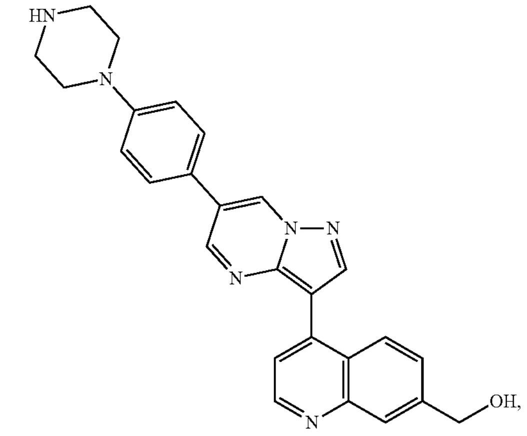

or a pharmaceutically acceptable salt thereof.

In some embodiments, the compound of Formula II has a structure of Formula II-227:

(II-227)

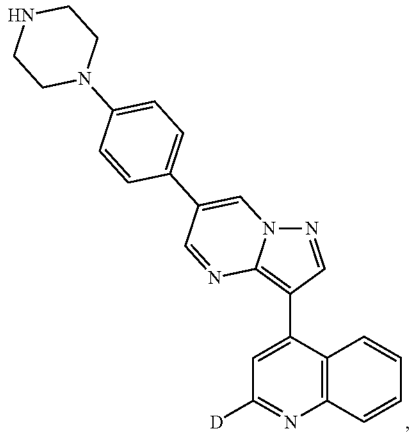

or a pharmaceutically acceptable salt thereof.

In some embodiments, the compound of Formula II has a structure of Formula II-228:

(II-228)

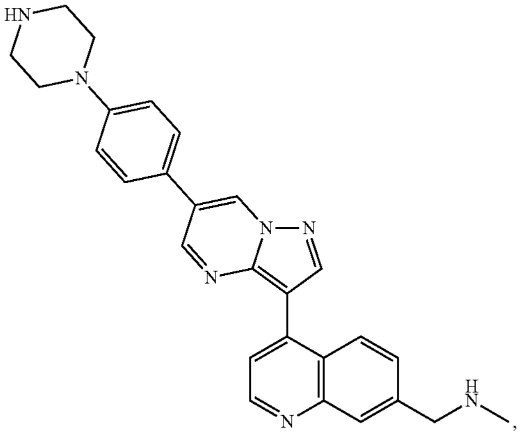

or a pharmaceutically acceptable salt thereof.

In some embodiments, the compound of Formula II has a structure of Formula II-229:

(II-229)

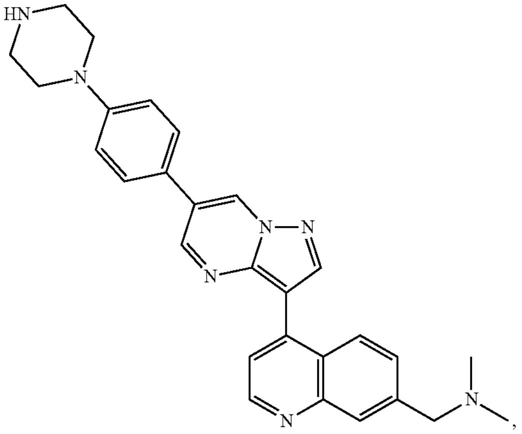

or a pharmaceutically acceptable salt thereof.

In some embodiments, the compound of Formula II has a structure of Formula II-230:

(II-230)

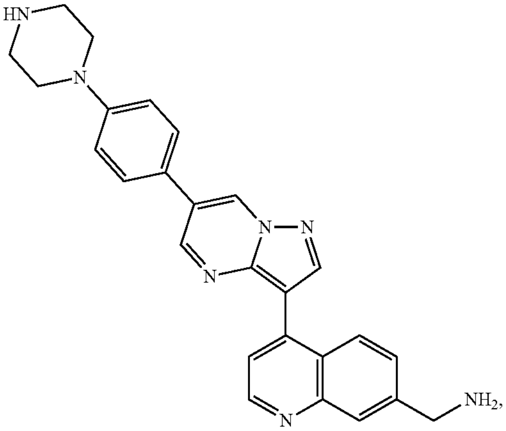

or a pharmaceutically acceptable salt thereof.

In some embodiments, the compound of Formula II has a structure of Formula II-231:

(II-231)

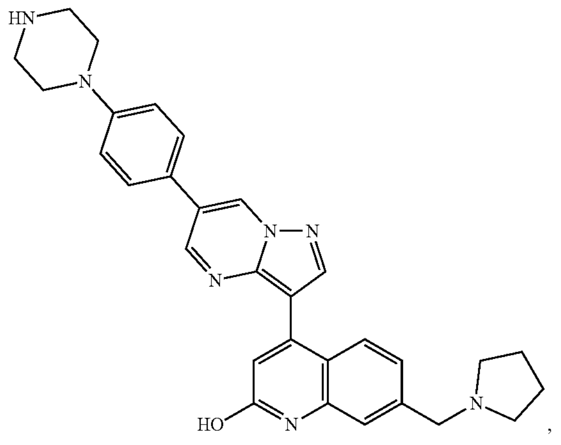

or a pharmaceutically acceptable salt thereof.

In some embodiments, the compound of Formula II has a structure of Formula II-232:

(II-232)

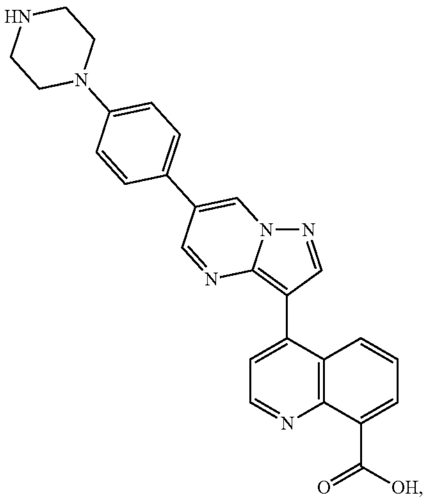

or a pharmaceutically acceptable salt thereof.

In some embodiments, the compound of Formula II has a structure of Formula II-233:

(II-233)

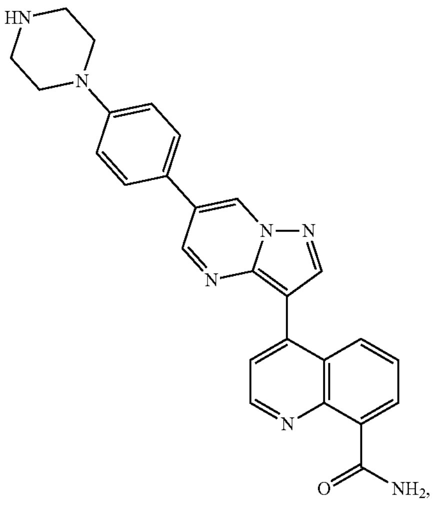

or a pharmaceutically acceptable salt thereof.

In some embodiments, the compound of Formula II has a structure of Formula II-234:

(II-234)

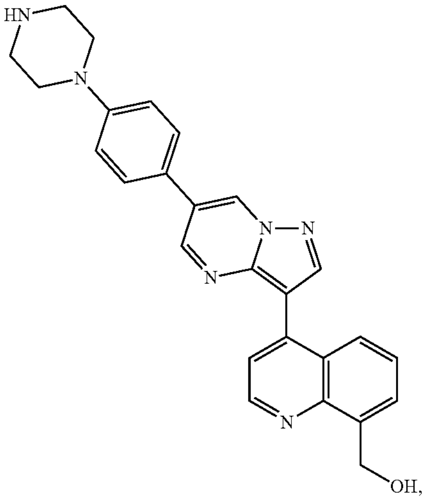

or a pharmaceutically acceptable salt thereof.

In some embodiments, the compound of Formula II has a structure of Formula II-235:

(II-235)

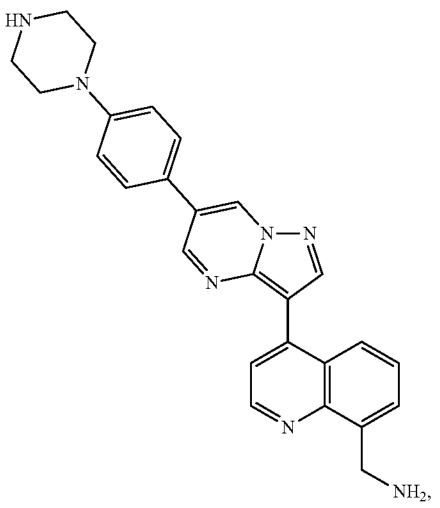

or a pharmaceutically acceptable salt thereof.

In some embodiments, the compound of Formula II has a structure of Formula II-236

(II-236)

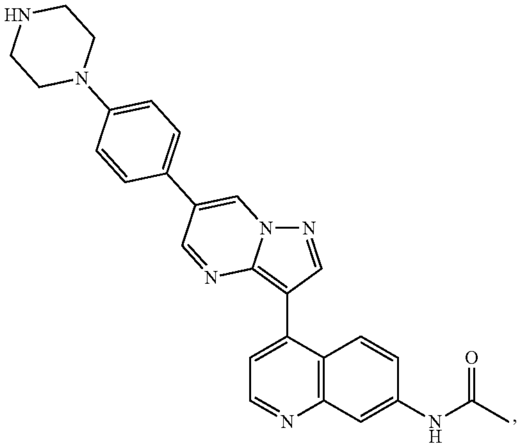

or a pharmaceutically acceptable salt thereof.

In some embodiments, the compound of Formula II has a structure of Formula II-237:

(II-237)

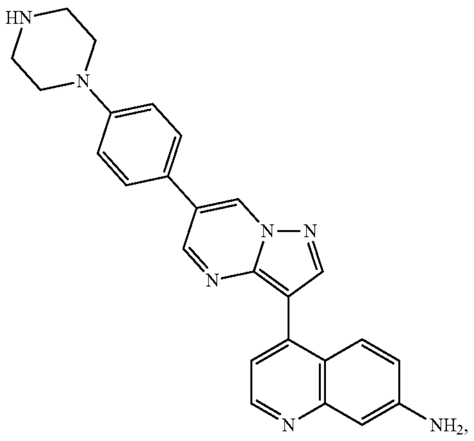

or a pharmaceutically acceptable salt thereof.

In some embodiments, the compound of Formula II has a structure of Formula II-238:

(II-238)

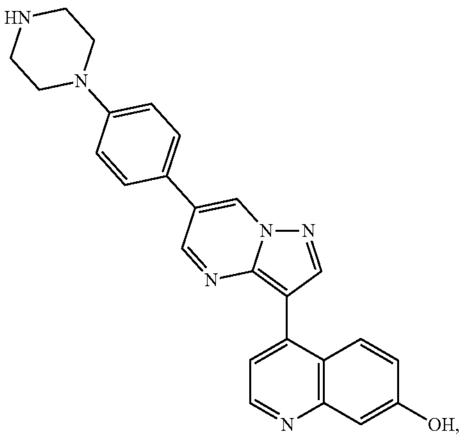

or a pharmaceutically acceptable salt thereof.

In some embodiments, the compound of Formula II has a structure of Formula II-239:

(II-239)

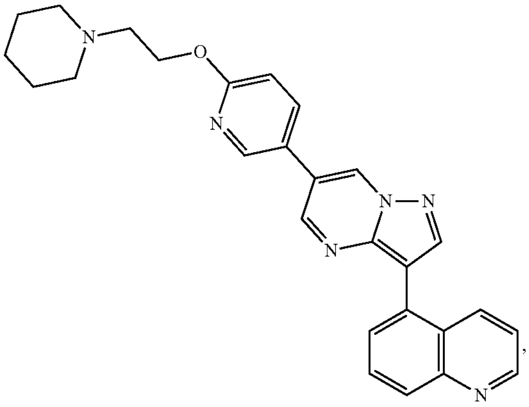

or a pharmaceutically acceptable salt thereof.

In some embodiments, the compound of Formula II has a structure of Formula II-240:

(II-240)

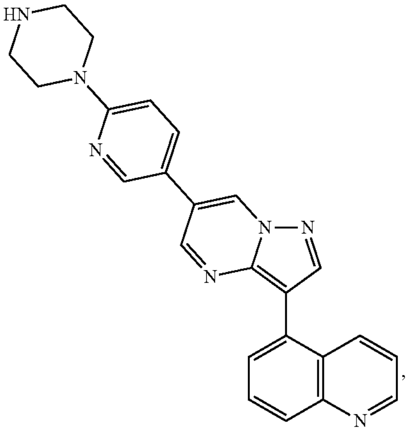

or a pharmaceutically acceptable salt thereof.

In some embodiments, the compound of Formula II has a structure of Formula II-241:

(II-241)

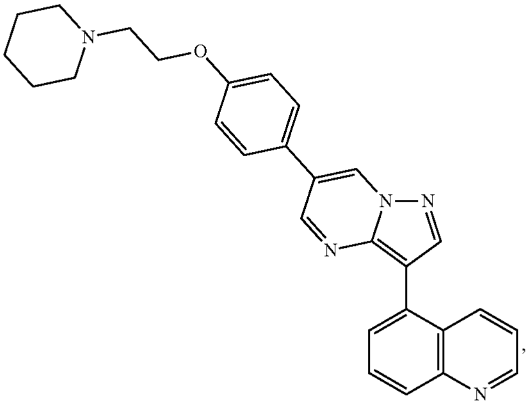

or a pharmaceutically acceptable salt thereof.

In some embodiments, the compound of Formula II has a structure of Formula II-242:

(II-242)

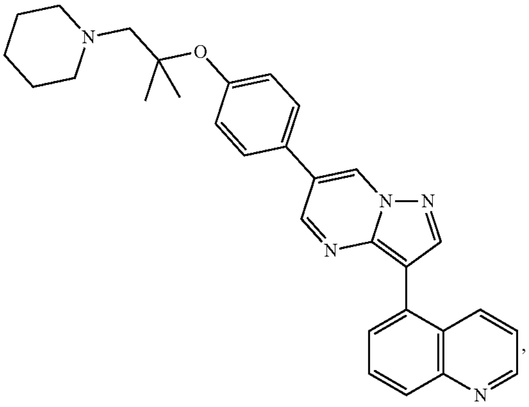

or a pharmaceutically acceptable salt thereof.

In some embodiments, the compound of Formula II has a structure of Formula II-243:

(II-243)

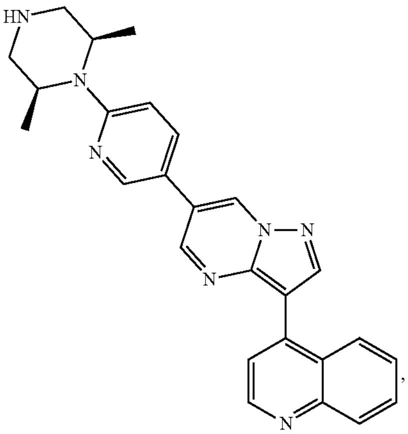

or a pharmaceutically acceptable salt thereof.

In some embodiments, the compound of Formula II has a structure of Formula II-244:

(II-244)

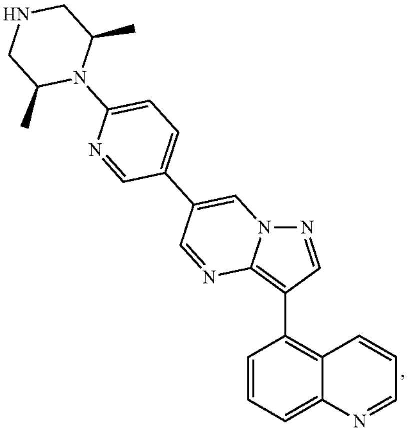

or a pharmaceutically acceptable salt thereof.

In some embodiments, the compound of Formula II has a structure of Formula II-245:

(II-245)

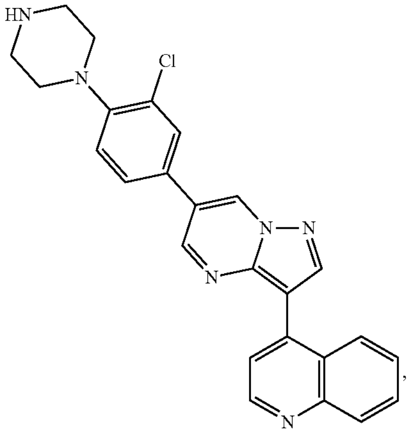

or a pharmaceutically acceptable salt thereof.

In some embodiments, the compound of Formula II has a structure of Formula II-246:

(II-246)

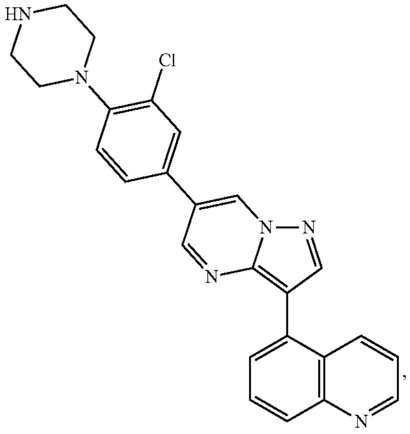

or a pharmaceutically acceptable salt thereof.

In some embodiments, the compound of Formula II has a structure of Formula II-247:

(II-247)

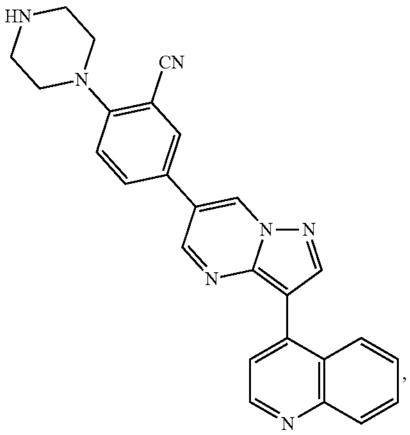

or a pharmaceutically acceptable salt thereof.

In some embodiments, the compound of Formula II has a structure of Formula II-248:

(II-248)

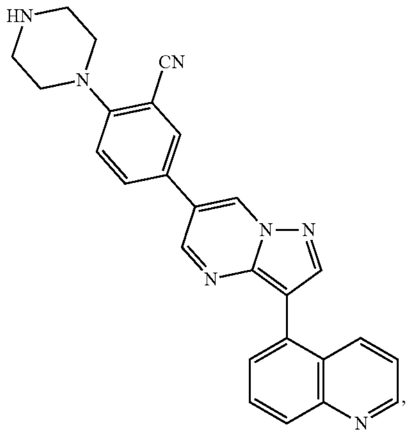

or a pharmaceutically acceptable salt thereof.

In some embodiments, the compound of Formula II has a structure of Formula II-249:

(II-249)

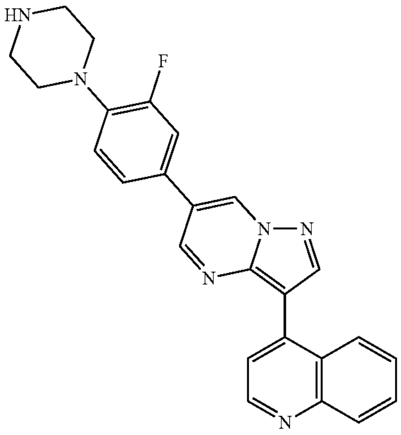

or a pharmaceutically acceptable salt thereof.

In some embodiments, the compound of Formula II has a structure of Formula II-250:

(II-250)

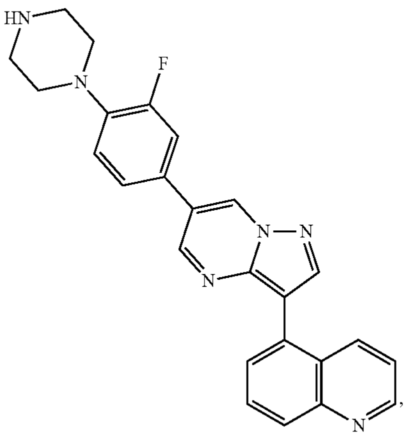

or a pharmaceutically acceptable salt thereof.

In some embodiments, the compound of Formula II has a structure of Formula II-251:

(II-251)

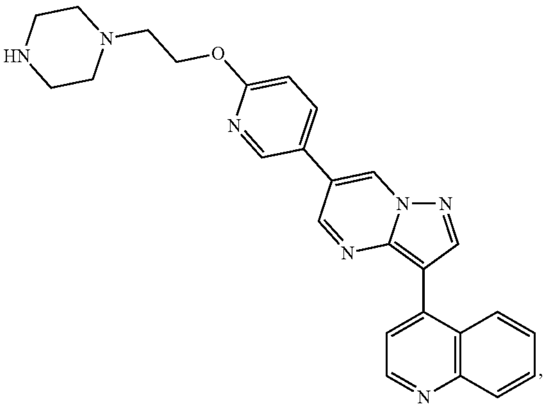

or a pharmaceutically acceptable salt thereof.

In some embodiments, the compound of Formula II has a structure of Formula II-252:

(II-252)

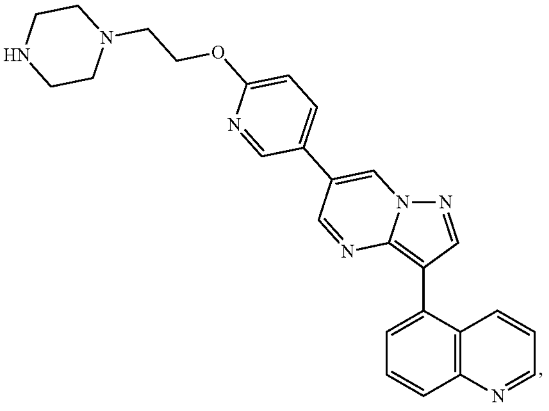

or a pharmaceutically acceptable salt thereof.

In some embodiments, the compound of Formula II has a structure of Formula II-253:

(II-253)

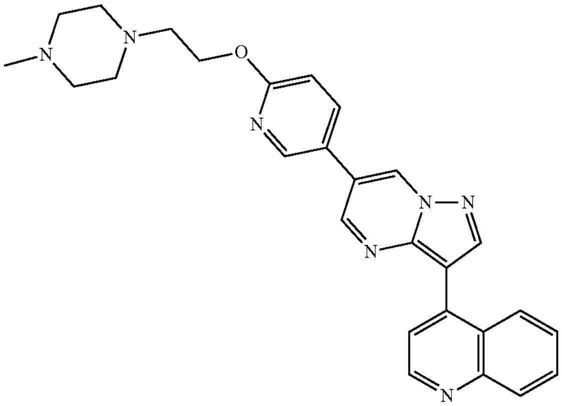

or a pharmaceutically acceptable salt thereof.

In some embodiments, the compound of Formula II has a structure of Formula II-254:

(II-254)

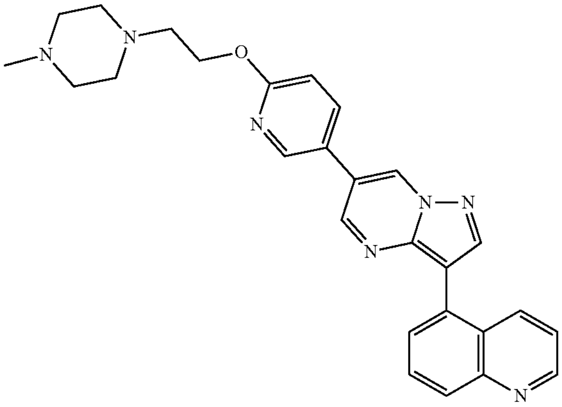

or a pharmaceutically acceptable salt thereof.

In some embodiments, the compound of Formula II has a structure of Formula II-255:

(II-255)

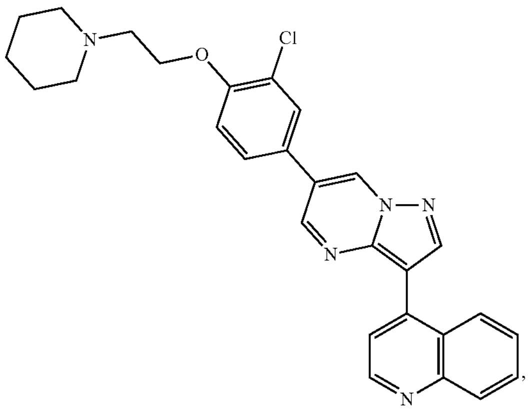

or a pharmaceutically acceptable salt thereof.

In some embodiments, the compound of Formula II has a structure of Formula II-256:

(II-256)

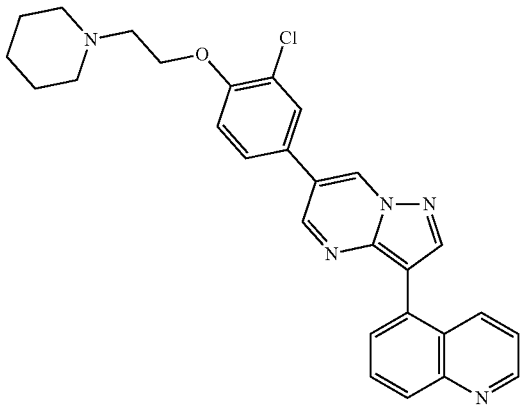

or a pharmaceutically acceptable salt thereof.

In some embodiments, the compound of Formula II has a structure of Formula II-257:

(II-257)

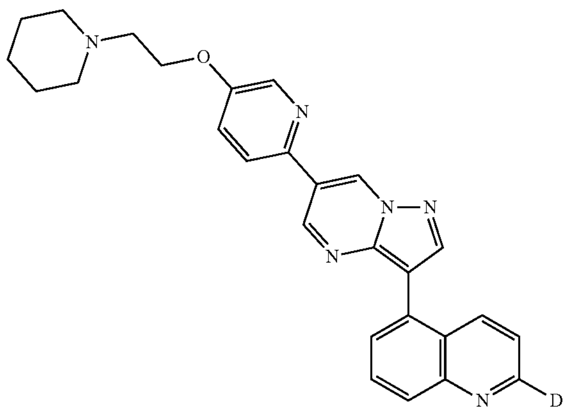

or a pharmaceutically acceptable salt thereof.

In some embodiments, the compound of Formula II has a structure of Formula II-258:

(II-258)

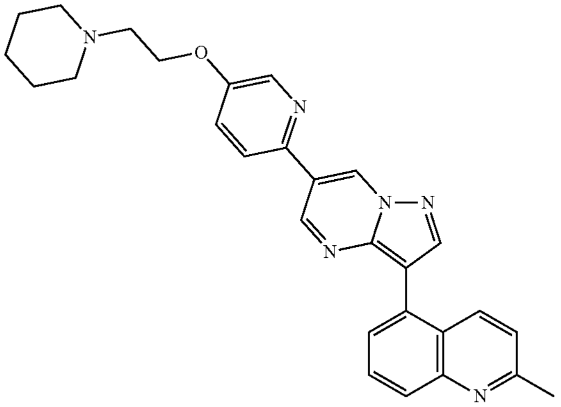

or a pharmaceutically acceptable salt thereof.

In some embodiments, the compound of Formula II has a structure of Formula II-259:

(II-259)

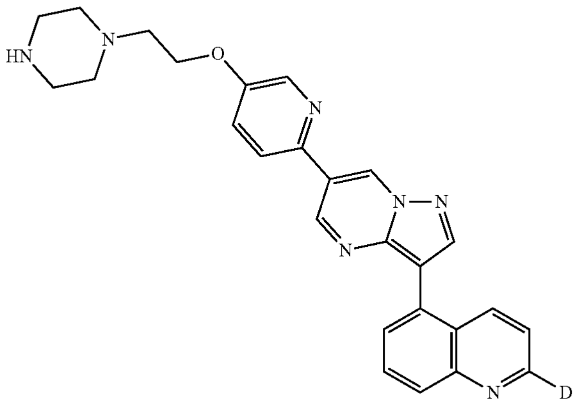

or a pharmaceutically acceptable salt thereof.

In some embodiments, the compound of Formula II has a structure of Formula II-260:

(II-260)

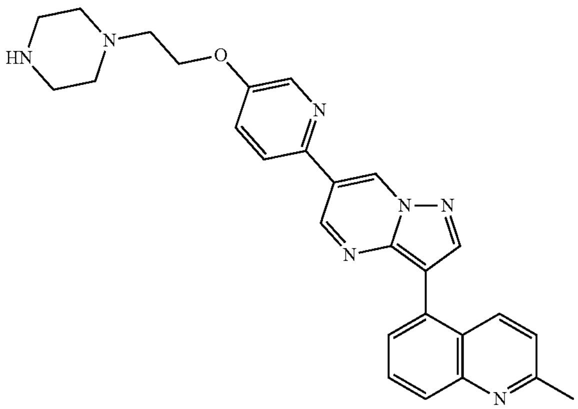

or a pharmaceutically acceptable salt thereof.

In some embodiments, the compound of Formula II has a structure of Formula II-261:

(II-261)

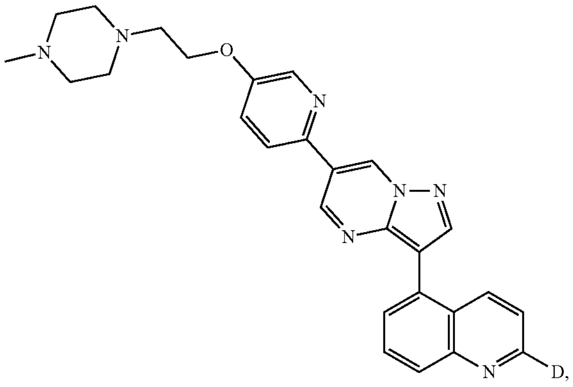

or a pharmaceutically acceptable salt thereof.

In some embodiments, the compound of Formula II has a structure of Formula II-262:

(II-262)

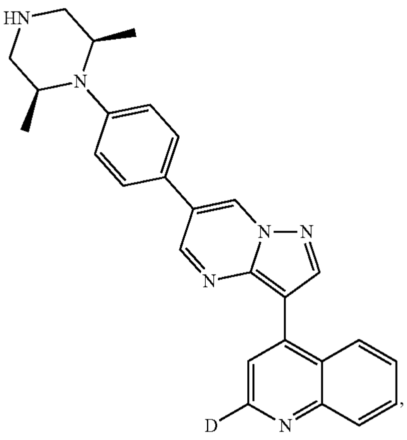

or a pharmaceutically acceptable salt thereof.

In some embodiments, the compound of Formula II has a structure of Formula II-263:

(II-263)

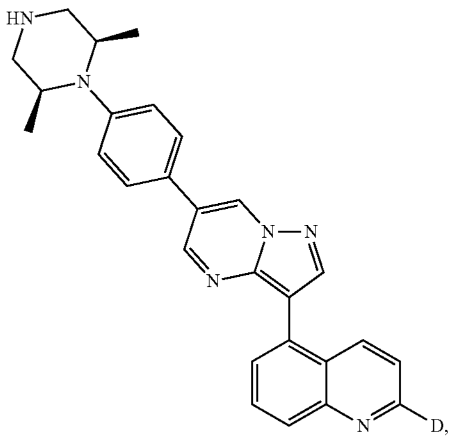

or a pharmaceutically acceptable salt thereof.

In some embodiments, the compound of Formula II has a structure of Formula II-264:

(II-264)

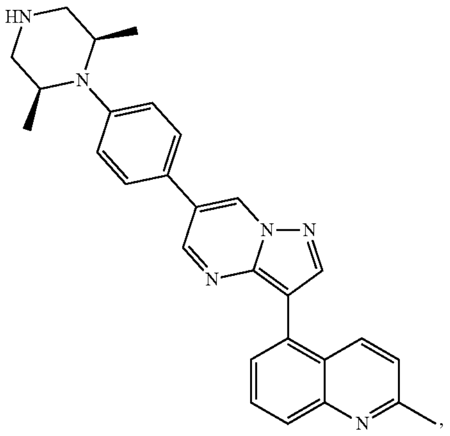

or a pharmaceutically acceptable salt thereof.

In some embodiments, the compound of Formula II has a structure of Formula II-265:

(II-265)

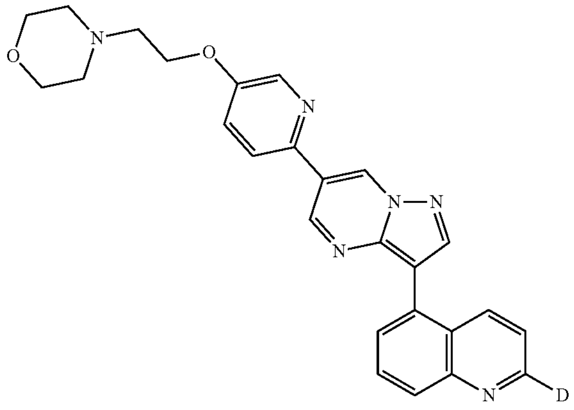

or a pharmaceutically acceptable salt thereof.

In some embodiments, the compound of Formula II has a structure of Formula II-266:

(II-266)

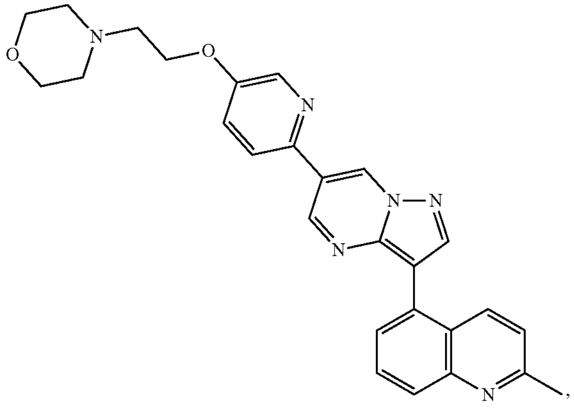

or a pharmaceutically acceptable salt thereof.

In some embodiments, the compound of Formula II has a structure of Formula II-267:

(II-267)

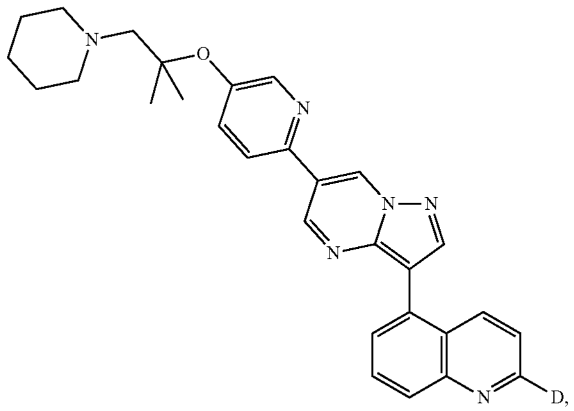

or a pharmaceutically acceptable salt thereof.

In some embodiments, the compound of Formula II has a structure of Formula II-268:

(II-268)

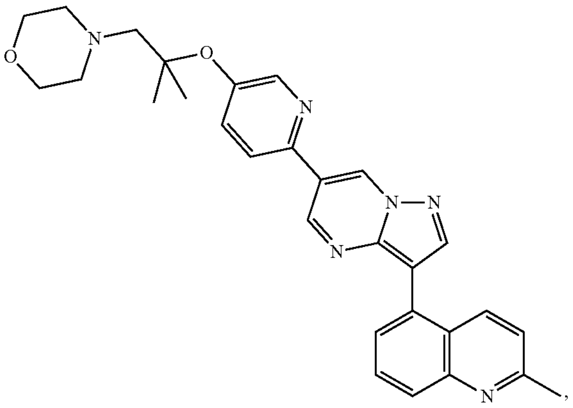

or a pharmaceutically acceptable salt thereof.

In some embodiments, the compound of Formula II has a structure of Formula II-269:

(II=269)

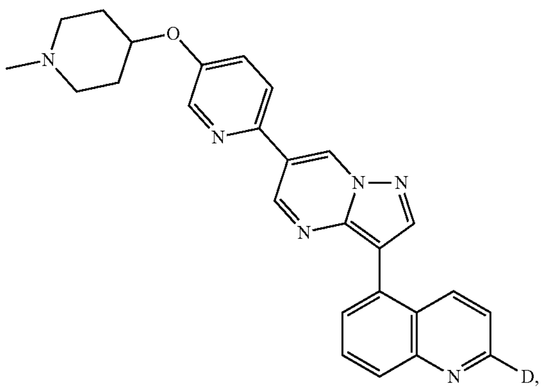

or a pharmaceutically acceptable salt thereof.

In some embodiments, the compound of Formula II has a structure of Formula II-270:

(II-270)

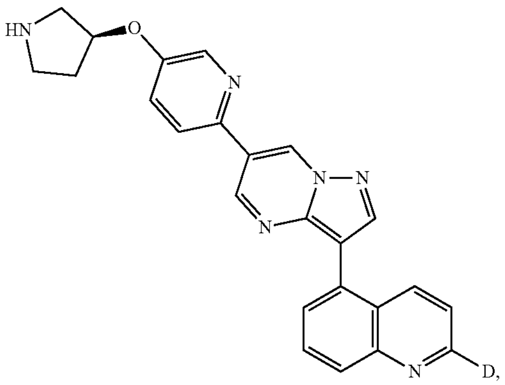

or a pharmaceutically acceptable salt thereof.

In some embodiments, the compound of Formula II has a structure of Formula II-271:

(II-271)

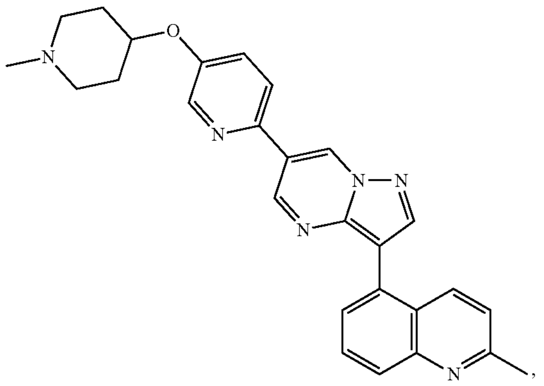

or a pharmaceutically acceptable salt thereof.

In some embodiments, the compound of Formula II has a structure of Formula II-272:

(II-272)

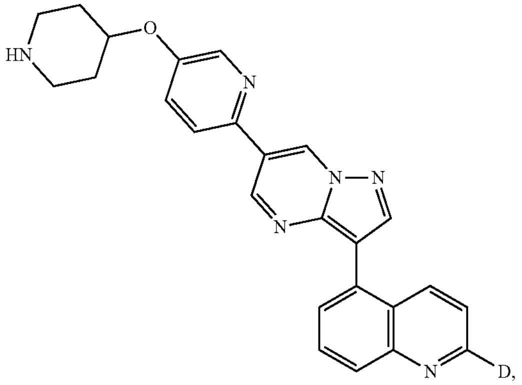

or a pharmaceutically acceptable salt thereof.

In some embodiments, the compound of Formula II has a structure of Formula II-273:

(II-273)

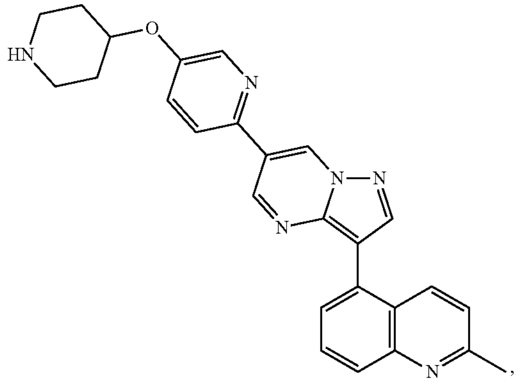

or a pharmaceutically acceptable salt thereof.

In some embodiments, the compound of Formula II has a structure of Formula II-274:

(II-274)

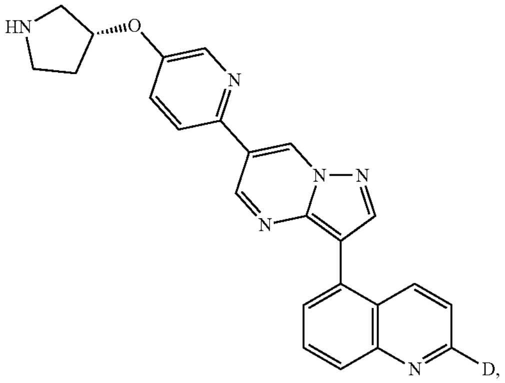

or a pharmaceutically acceptable salt thereof.

In some embodiments, the compound of Formula II has a structure of Formula II-275:

(II-275)

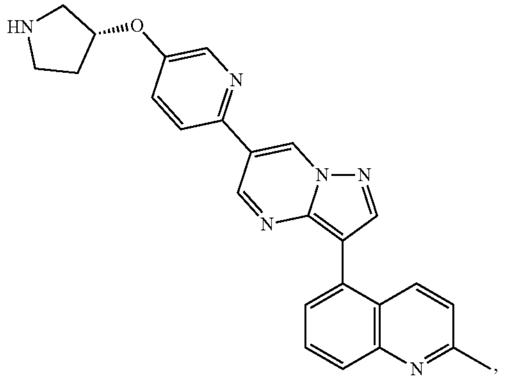

or a pharmaceutically acceptable salt thereof.

Additional compounds of Formula II are described U.S. Pat. Nos. 10,513,521, 10,017,516, and 9,682,983, and are incorporated herein by reference.

In some embodiments, the ALK2 inhibitor is a compound of Formula III:

Formula III

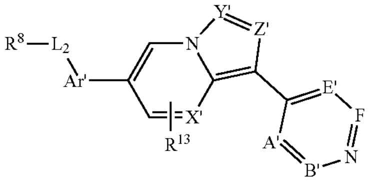

or a pharmaceutically acceptable salt thereof, wherein

X is selected from $CR^{15'}$ and N;

Y' is selected from $CR^{15'}$ and N;

Z' is selected from $CR^{26}$ and N;

Ar' is selected from substituted or unsubstituted aryl and heteroaryl, e.g., a six-membered ring, such as phenyl;

$L_2$ is absent or selected from substituted or unsubstituted alkyl and heteroalkyl;

A and B, independently for each occurrence, are selected from $CR^{16'}$ and N, preferably $CR^{16'}$, e.g., CH;

E and F, independently for each occurrence, are selected from $CR^{5'}$ and N, preferably $CR^{5'}$; preferably chosen such that no more than two of A, B, E, and F are N;

$R^{26}$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;

$R^8$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;

$R^{5'}$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^{5'}$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;

$R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably substituted or unsubstituted alkyl, heteroalkyl, halogen, hydroxyl, alkoxyl, alkylthio, acyloxy, acylamino, carbamate, or cyano;

$R^{15'}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;

$R^{16'}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

Compounds of Formula III may be synthesized by methods known in the art, e.g., those described in U.S. Pat. Nos. 8,507,501 and 9,045,484, which are incorporated herein by reference.

In some embodiments, a provided compound of Formula III has a structure of Formula III-a:

Formula III-a

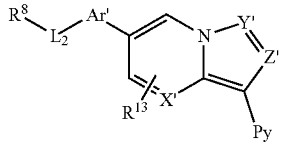

or a pharmaceutically acceptable salt thereof, wherein

X' is selected from $CR^{15'}$ and N;

Y' is selected from $CR^{15'}$ and N;

Z' is selected from $CR^{26}$ and N;

Ar' is selected from substituted or unsubstituted aryl and heteroaryl, e.g., a six-membered ring, such as phenyl;

$L_2$ is absent or selected from substituted or unsubstituted alkyl and heteroalkyl;

Py is substituted or unsubstituted 4-pyridinyl or 4-quinolinyl, e.g., optionally substituted with substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, amino, acylamino, carbamate, amido, amidino, cyano, sulfonyl, sulfoxido, sulfamoyl, or sulfonamido; and $R^{26}$ represents a substituent, e.g., selected from H and substituted or unsubstituted alkyl, heteroalkyl, cycloalkyl, halogen, hydroxyl, alkoxyl, alkylthio, acyloxy, acylamino, carbamate, cyano, sulfonyl, sulfoxido, sulfamoyl, or sulfonamido, e.g., lower alkyl;

$R^8$ is selected from substituted or unsubstituted alkyl, alkenyl, alkynyl, heteroalkyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido, e.g., substituted or unsubstituted alkenyl, alkynyl, cycloalkyl, heterocyclyl, aryl, heteroaryl, acyl, carboxyl, ester, acyloxy, amino, acylamino, carbamate, amido, amidino, sulfonyl, sulfoxido, sulfamoyl, or sulfonamido, preferably substituted or unsubstituted heterocyclyl or heteroaryl;

$R^5$, independently for each occurrence, represents a substituent, e.g., selected from H and substituted or unsubstituted alkyl, alkenyl, alkynyl, heteroalkyl, cycloalkyl, heterocyclyl, aryl, aralkyl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido (preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, amidino, or cyano), or two occurrences of $R^{26}$ taken together with the atoms to which they are attached form a substituted or unsubstituted 5- or 6-membered cycloalkyl, heterocycloalkyl, aryl, or heteroaryl ring, preferably an aryl or heteroaryl ring, e.g., a substituted or unsubstituted benzo ring;

$R^{13}$ is absent or represents 1-2 substituents on the ring to which it is attached and, independently for each occurrence, is selected from substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxide, sulfamoyl, or sulfonamido, preferably substituted or unsubstituted alkyl, heteroalkyl, halogen, hydroxyl, alkoxyl, alkylthio, acyloxy, acylamino, carbamate, or cyano;

$R^{15'}$, independently for each occurrence, represents a substituent, e.g., selected from H and substituted or unsubstituted alkyl, heteroalkyl, cycloalkyl, heterocyclyl, cycloalkylalkyl, heterocyclylalkyl, halogen, hydroxyl, alkoxyl, alkylthio, acyloxy, acylamino, carbamate, cyano, sulfonyl, sulfoxido, sulfamoyl, or sulfonamido, preferably H or substituted or unsubstituted alkyl, heteroalkyl, halogen, hydroxyl, alkoxyl, alkylthio, acyloxy, acylamino, carbamate, or cyano;

$R^{16'}$, independently for each occurrence, represents a substituent, e.g., selected from H and substituted or unsubstituted alkyl, alkenyl, alkynyl, heteroalkyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido, preferably H or substituted or unsubstituted alkyl, alkenyl, heteroalkyl, halogen, acyl, carboxyl, ester, hydroxyl, alkoxyl, alkylthio, acyloxy, amino, acylamino, carbamate, amido, or cyano.

In some embodiments, the compound of Formula III has a structure of Formula III-b:

Formula III-b

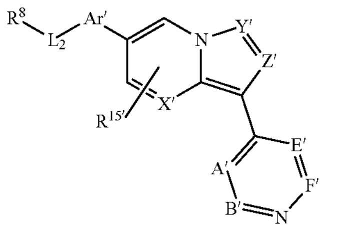

or a pharmaceutically acceptable salt thereof, wherein

X' and Y' are each N;

Z' is $CR^{26}$

Ar' is substituted or unsubstituted phenyl;

$L_2$ is absent or selected from substituted or unsubstituted alkyl and heteroalkyl;

A' and B' are both $CR^{16}$;

E' and F' are both $CR^{5'}$ and both occurrences of $R^{5'}$ taken together with E' and F' form a substituted or unsubstituted 5- or 6-membered cycloalkyl, heterocycloalkyl, aryl, or heteroaryl ring;

$R^{26}$ is selected from H and substituted or unsubstituted alkyl;

$R^8$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;

$R^{15'}$, independently for each occurrence, is selected from H and substituted or unsubstituted alkyl, cycloalkyl, heterocyclyl, cycloalkylalkyl, heterocyclylalkyl, halogen, acylamino, carbamate, cyano, sulfonyl, sulfoxido, sulfamoyl, or sulfonamido; and $R^{16'}$, independently for each occurrence, is absent or is selected from H and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In some embodiments, the compound of Formula III has a structure of Formula III-b, or a pharmaceutically acceptable salt thereof, wherein X' and Y' are each N;

Z' is $CR^{26}$;

Ar' is selected from substituted or unsubstituted aryl and heteroaryl;

$L_2$ is absent or selected from substituted or unsubstituted alkyl and heteroalkyl;

A' and B' are both $CR^{16'}$;

E' and F' are both $CR^{5'}$ and both occurrences of $R^{5'}$ taken together with E' and F' form a substituted or unsubstituted 5- or 6-membered cycloalkyl, heterocycloalkyl, aryl, or heteroaryl ring;

$R^{26}$ is selected from H and substituted or unsubstituted alkyl;

$R^8$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;

$R^{15'}$, independently for each occurrence, is selected from H and substituted or unsubstituted alkyl, cycloalkyl, heterocyclyl, cycloalkylalkyl, heterocyclylalkyl, halogen, acylamino, carbamate, cyano, sulfonyl, sulfoxido, sulfamoyl, or sulfonamido;

$R^{16'}$, independently for each occurrence, is absent or is selected from H and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, halogen, acyl, carboxyl, ester, hydroxyl, alkoxyl, alkylthio, acyloxy, amino, acylamino, carbamate, amido, amidino, cyano, sulfonyl, sulfoxido, sulfamoyl, or sulfonamido.

In some embodiments, the compound of Formula III has a structure of Formula III-1:

(III-1)

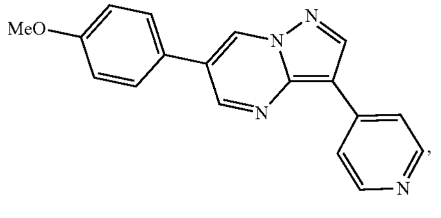

or a pharmaceutically acceptable salt thereof.

In some embodiments, the compound of Formula III has a structure of Formula III-2:

(III-2)

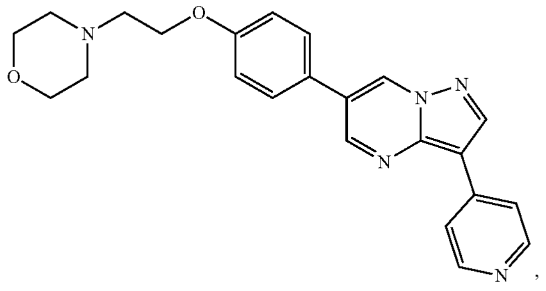

or a pharmaceutically acceptable salt thereof.

In some embodiments, the compound of Formula III has a structure of Formula III-3:

(III-3)

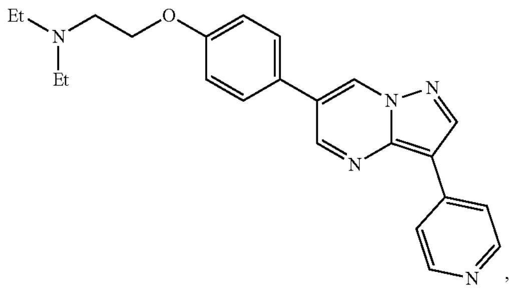

or a pharmaceutically acceptable salt thereof.

In some embodiments, the compound of Formula III has a structure of Formula III-4:

(III-4)

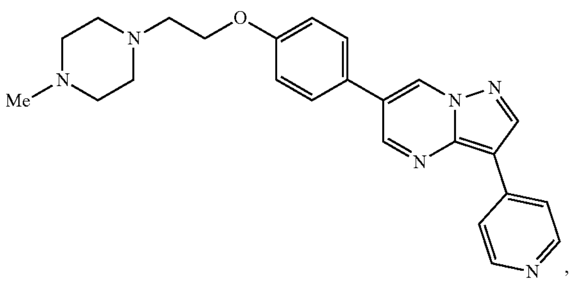

or a pharmaceutically acceptable salt thereof.

In some embodiments, the compound of Formula III has a structure of Formula III-5:

(III-5)

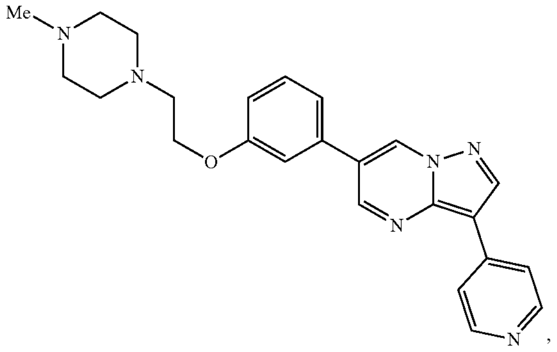

or a pharmaceutically acceptable salt thereof.

In some embodiments, the compound of Formula III has a structure of Formula III-6:

(III-6)

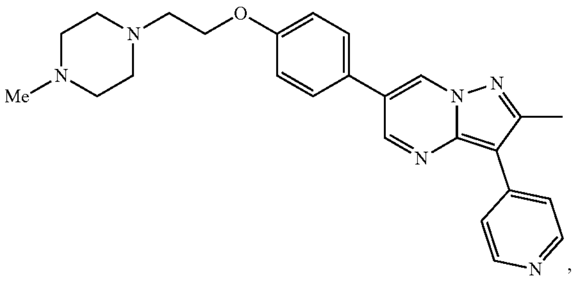

or a pharmaceutically acceptable salt thereof.

In some embodiments, the compound of Formula III has a structure of Formula III-7:

(III-7)

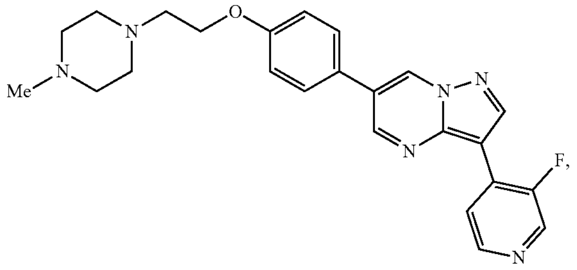

or a pharmaceutically acceptable salt thereof.

In some embodiments, the compound of Formula III has a structure of Formula III-8:

(III-8)

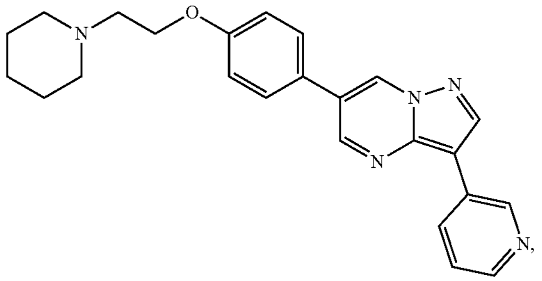

or a pharmaceutically acceptable salt thereof.

In some embodiments, the compound of Formula III has a structure of Formula III-9:

(III-9)

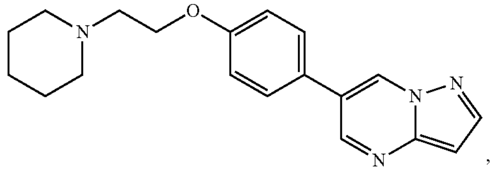

or a pharmaceutically acceptable salt thereof.

In some embodiments, the compound of Formula III has a structure of Formula III-10:

(III-10)

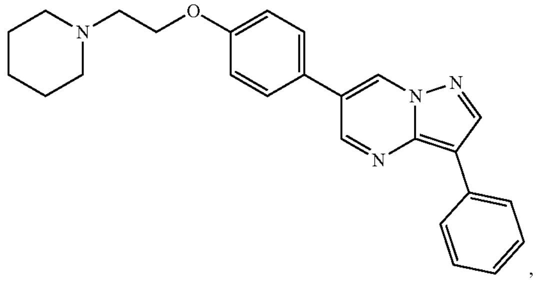

or a pharmaceutically acceptable salt thereof.

In some embodiments, the compound of Formula III has a structure of Formula III-11:

(III-11)

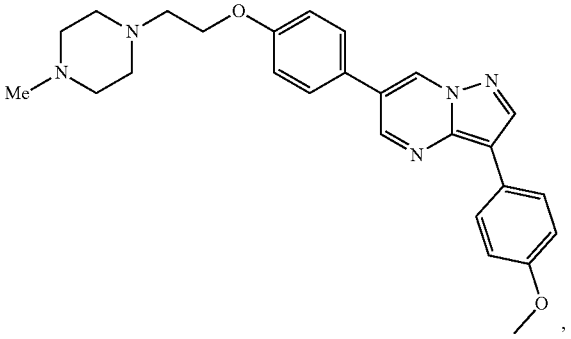

or a pharmaceutically acceptable salt thereof.

In some embodiments, the compound of Formula III has a structure of Formula III-12:

(III-12)

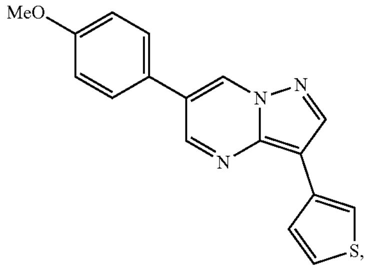

or a pharmaceutically acceptable salt thereof.

In some embodiments, the compound of Formula III has a structure of Formula III-13:

(III-13)

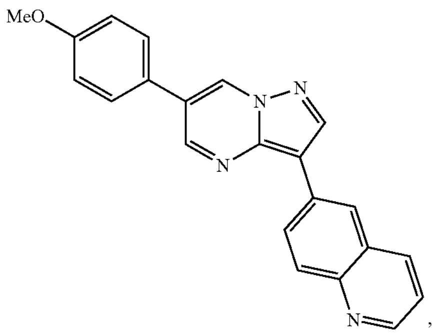

or a pharmaceutically acceptable salt thereof.

In some embodiments, the compound of Formula III has a structure of Formula III-14:

(III-14)

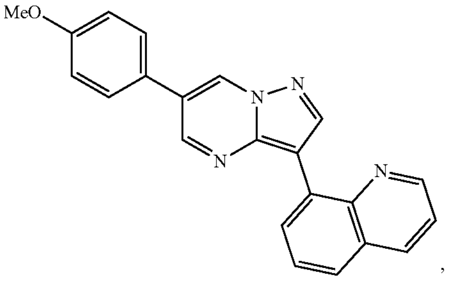

or a pharmaceutically acceptable salt thereof.

In some embodiments, the compound of Formula III has a structure of Formula III-15:

(III-15)

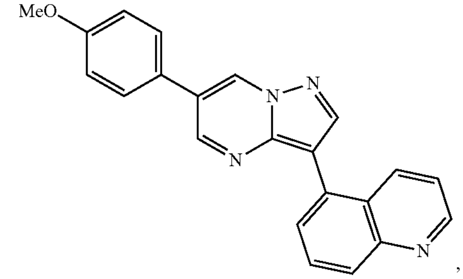
, or a pharmaceutically acceptable salt thereof.

In some embodiments, the compound of Formula III has a structure of Formula III-16:

(III-16)

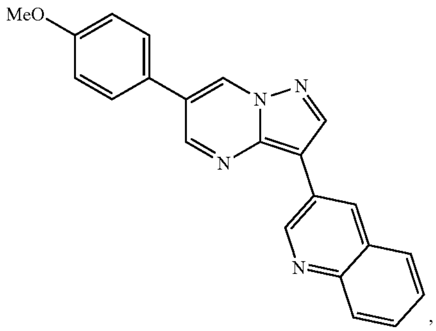
, or a pharmaceutically acceptable salt thereof.

In some embodiments, the compound of Formula III has a structure of Formula III-17:

(III-17)

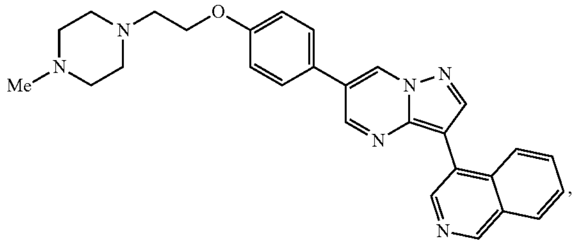
, or a pharmaceutically acceptable salt thereof.

In some embodiments, the compound of Formula III has a structure of Formula III-18:

(III-18)

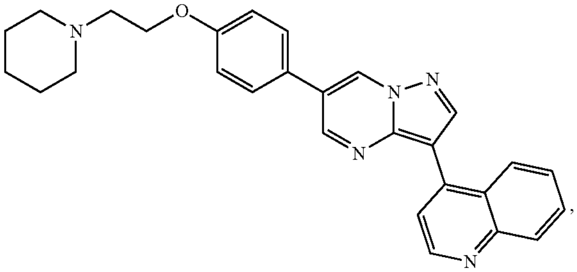
, or a pharmaceutically acceptable salt thereof.

In some embodiments, the compound of Formula III has a structure of Formula III-19:

(III-19)

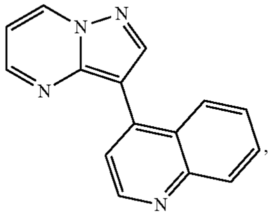
, or a pharmaceutically acceptable salt thereof.

In some embodiments, the compound of Formula III has a structure of Formula III-20:

(III-20)

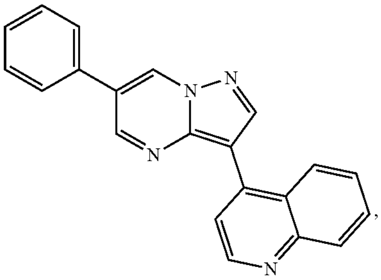
, or a pharmaceutically acceptable salt thereof.

In some embodiments, the compound of Formula III has a structure of Formula III-21:

(III-21)

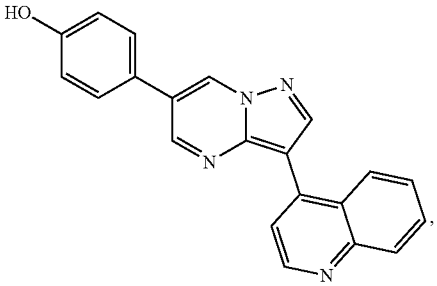
, or a pharmaceutically acceptable salt thereof.

In some embodiments, the compound of Formula III has a structure of Formula III-22:

(III-22)

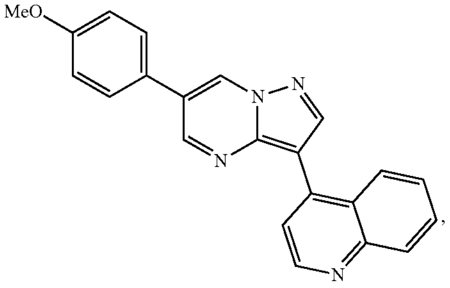

or a pharmaceutically acceptable salt thereof.

In some embodiments, the compound of Formula III has a structure of Formula III-23:

(III-23)

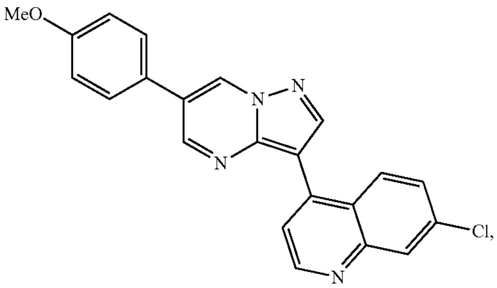

or a pharmaceutically acceptable salt thereof.

In some embodiments, the compound of Formula III has a structure of Formula III-24:

(III-24)

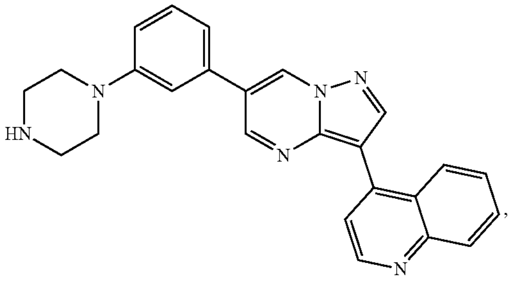

or a pharmaceutically acceptable salt thereof.

In some embodiments, the compound of Formula III has a structure of Formula III-25:

(III-25)

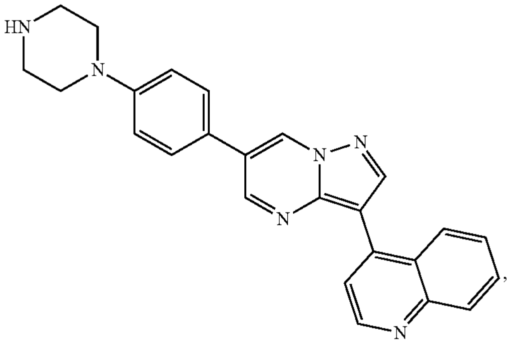

or a pharmaceutically acceptable salt thereof.

In some embodiments, the compound of Formula III has a structure of Formula III-26:

(III-26)

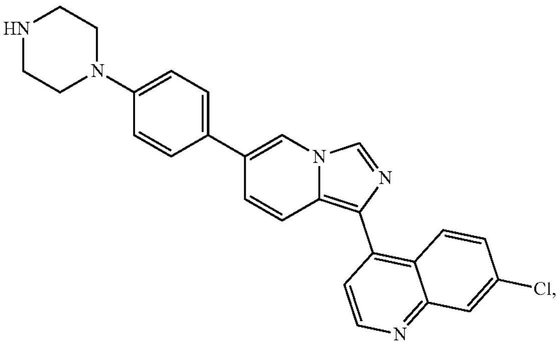

or a pharmaceutically acceptable salt thereof.

In some embodiments, the compound of Formula III has a structure of Formula III-27:

(III-27)

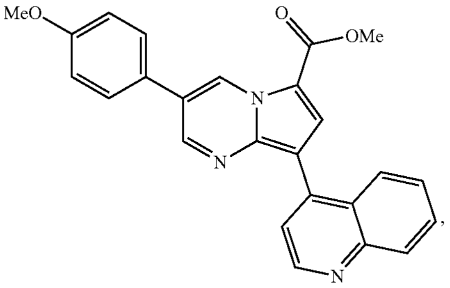

or a pharmaceutically acceptable salt thereof.

In some embodiments, the compound of Formula III has a structure of Formula III-28:

(III-28)

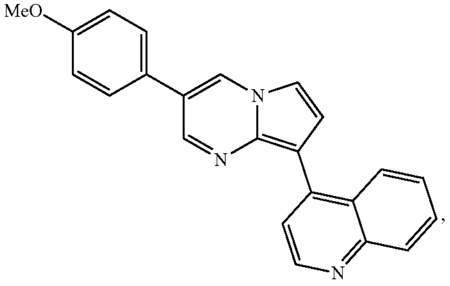

or a pharmaceutically acceptable salt thereof.

In some embodiments, the compound of Formula III has a structure of Formula III-29:

(III-29)

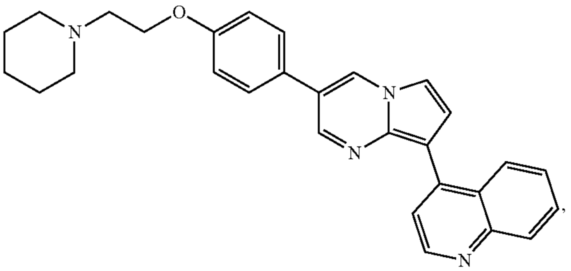

or a pharmaceutically acceptable salt thereof.

In some embodiments, the compound of Formula III has a structure of Formula III-30:

(III-30)

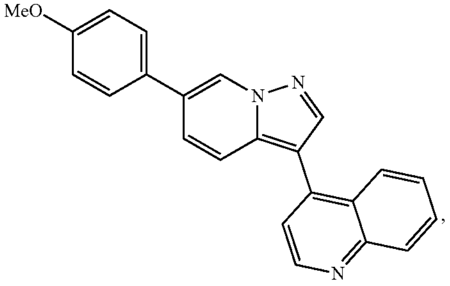

or a pharmaceutically acceptable salt thereof.

In some embodiments, the compound of Formula III has a structure of Formula III-31:

(III-31)

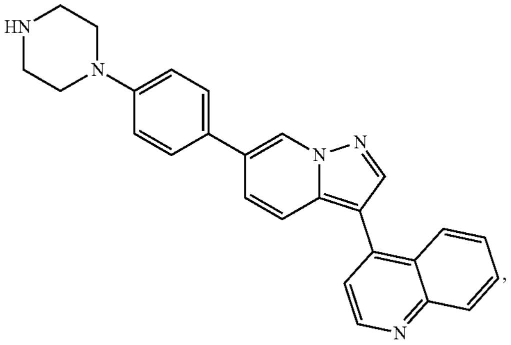

or a pharmaceutically acceptable salt thereof.

In some embodiments the compound of Formula III has a structure of Formula III-32:

(III-32)

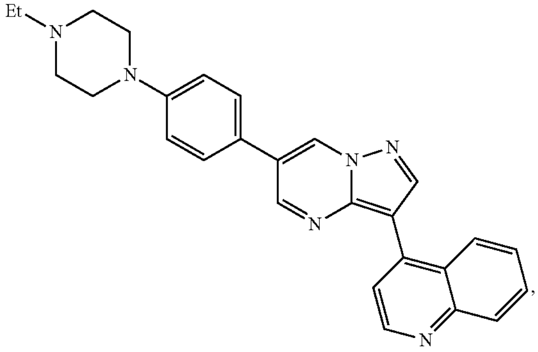

or a pharmaceutically acceptable salt thereof.

In some embodiments, the compound of Formula III has a structure of Formula III-33:

(III-33)

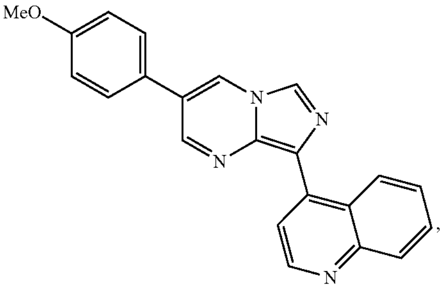

or a pharmaceutically acceptable salt thereof.

In some embodiments, the compound of Formula III has a structure of Formula III-34:

(III-34)

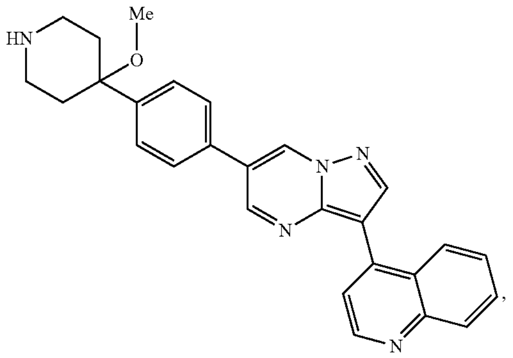

or a pharmaceutically acceptable salt thereof.

In some embodiments, the compound of Formula III has a structure of Formula III-35:

(III-35)

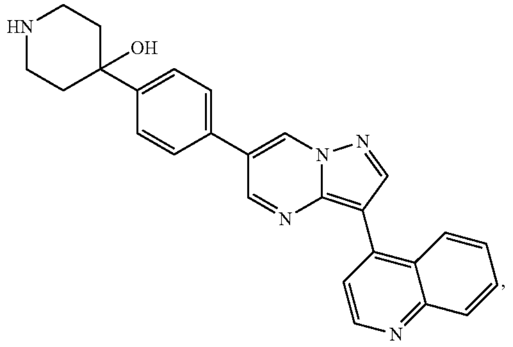

or a pharmaceutically acceptable salt thereof.

Additional compounds of Formula III are described U.S. Pat. Nos. 8,507,501 and 9,045,484, and are incorporated herein by reference.

In some embodiments, the ALK2 inhibitor is Compound 1:

(Compound 1)

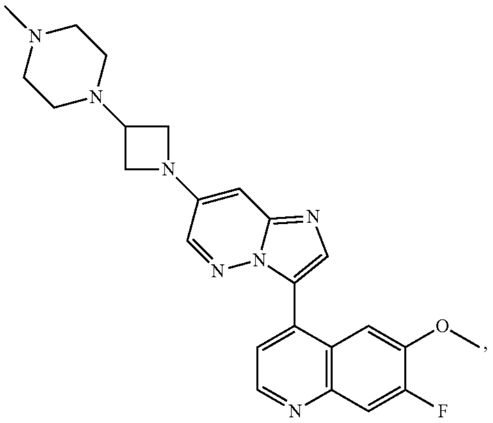

or a pharmaceutically acceptable salt thereof.

Compound 1 may be synthesized by methods known in the art, e.g., those described in US Patent Application Publication No. 2020/0179389, which is incorporated herein by reference.

In some embodiments, the ALK2 inhibitor is Compound 2:

(Compound 2)

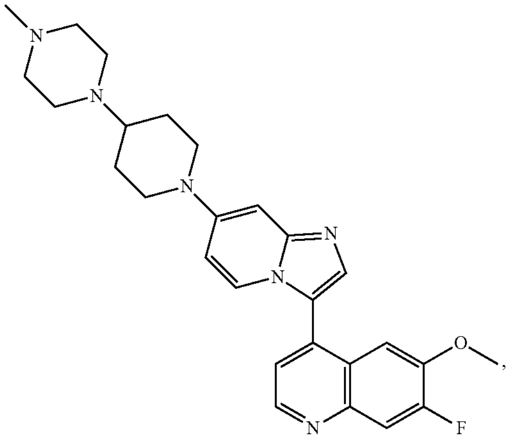

or a pharmaceutically acceptable salt thereof.

Compound 2 may be synthesized by methods known in the art, e.g., those described in US Patent Application Publication No. 2020/0179389, which is incorporated herein by reference.

In some embodiments, the ALK2 inhibitor is Compound 3:

(Compound 3)

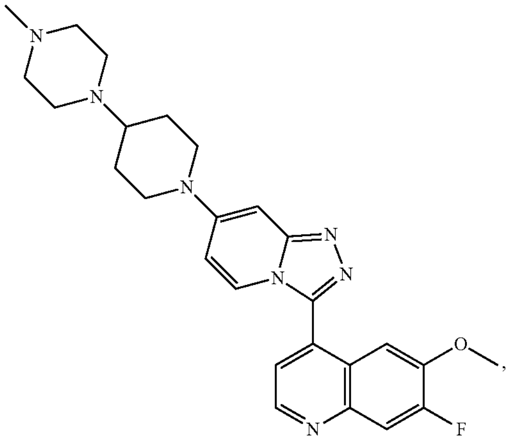

or a pharmaceutically acceptable salt thereof.

Compound 3 may be synthesized by methods known in the art, e.g., those described in US Patent Application Publication No. 2020/0179389, which is incorporated herein by reference.

In some embodiments, the ALK2 inhibitor is Compound 4:

(Compound 4)

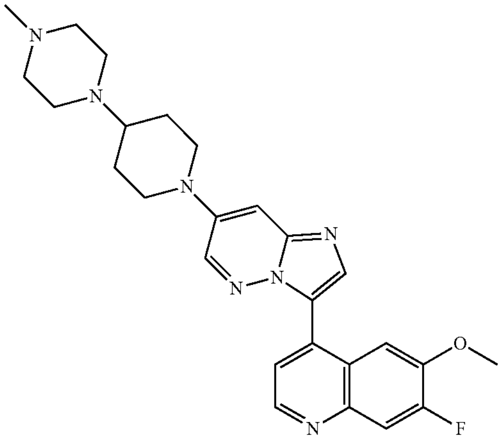

or a pharmaceutically acceptable salt thereof.

Compound 4 may be synthesized by methods known in the art, e.g., those described in US Patent Application Publication No. 2020/0179389, which is incorporated herein by reference.

In some embodiments, the ALK2 inhibitor is Compound 5:

(Compound 5)

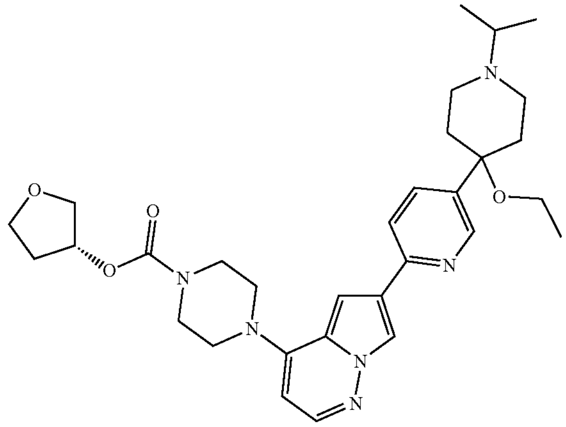

or a pharmaceutically acceptable salt thereof. Compound 5 may be synthesized by methods known in the art, e.g., those described in U.S. Pat. No. 10,233,186 and International Patent Application Publication No. WO2021067670A1, which are incorporated herein by reference. In some embodiments, the compound is a crystalline compound of Compound 5, or a salt thereof. Crystalline compounds of Compound 5 can be synthesized by methods known in the art, e.g., those described in International Patent Application Publication No. WO2021030386A1, which is incorporated herein by reference. In some embodiments, Compound 5 is administered as a succinate salt, a hydrochloride salt, or a fumarate salt, such as those described in International Patent Application Publication No. WO2021030386A1. Additional ALK2 inhibitors that can be used in the methods described herein are described in US Patent Application Publication No. 2020/0331908 and U.S. Pat. No. 10,233,186, which are incorporated herein by reference.

In some embodiments, the ALK2 inhibitor is Compound 6:

(Compound 6)

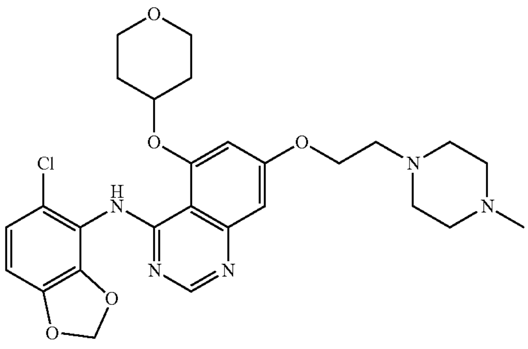

or a pharmaceutically acceptable salt thereof. Compound 6 is also known as Saracatinib and AZD530.

In some embodiments, the ALK2 inhibitor is Compound 7:

(Compound 7)

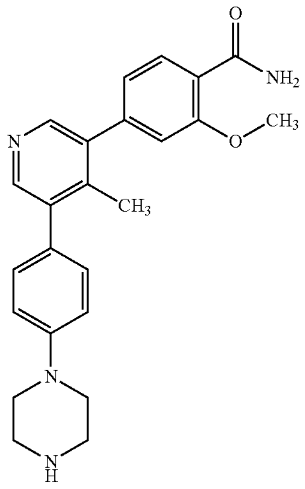

or a pharmaceutically acceptable salt thereof. Compound 7 is also known as M4K2149 and can be synthesized according to the methods described in Ensan et al., J. Med. Chem 63:4978-4996, 2020.

Additional ALK2 inhibitors that can be used in the methods described herein are BCX9250, INCB00928, and the ALK2 inhibitors described in International Patent Application Publication Nos. WO2018232094A1 and WO2020068729A1 and US Patent Application Publication No. US20200095250A1, which are incorporated herein by reference.

In some embodiments, the compound used in the methods and compositions described herein is a compound of Formula I-11:

(I-11)

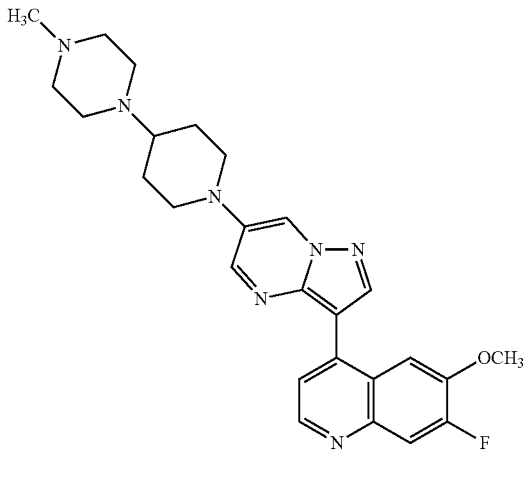

or a pharmaceutically acceptable salt thereof.

In some embodiments, the compound is a crystalline compound of Formula I-11, or a salt thereof. Crystalline compounds of Formula I-11 can be synthesized by methods known in the art, e.g., those described in International Patent Application Publication No. WO2020086963A1, which is incorporated herein by reference.

In certain embodiments, a crystalline compound of Formula I-11 is not solvated (e.g., the crystal lattice does not comprise molecules of a solvent). In certain such embodiments, the crystalline compound of Formula I-11 is anhydrous, or substantially anhydrous.

In certain embodiments, the compound of Formula I-11 is in the form of a salt with an anion selected from chloride, bromide, succinate, xinafoate, citrate, malate, hemi-malate, tartrate, malonate, mesylate, phosphate, tosylate, sulfate, and bis-sulfate. In preferred embodiments, the compound of Formula I-11 is in the form of a succinate salt, such as a mono-succinate salt.

The compound of Formula I-11 or any crystalline compound described herein may be used in the manufacture of a medicament for the treatment of any diseases or conditions disclosed herein.

The mono-succinate salt of the compound of Formula I-11 exists at least as "Form A," "Form B," "Form C," and "Form D," as described International Patent Application Publication No. WO2020086963A1. These different forms are understood as "polymorphs" herein.

A polymorph of the crystalline compound may be characterized by powder X-ray diffraction (XRPD). θ represents the diffraction angle, measured in degrees. In certain embodiments, the diffractometer used in XRPD measures the diffraction angle as two times the diffraction angle θ. Thus, in certain embodiments, the diffraction patterns described herein refer to X-ray intensity measured against angle 2θ.

In certain embodiments, a first anhydrous crystalline form of a compound of Formula I-11 mono-succinate salt has 2θ values of about 7.05 0.2, 15.16±0.2, 21.05 0.2, 21.26±0.2, and 24.47±0.2. In further embodiments, an anhydrous crystalline compound of Formula I-11 mono-succinate salt has 2θ values of about 3.58±0.2, 7.05±0.2, 13.8±0.2, 14.16±0.2, 15.16±0.2, 16.18±0.2, 16.80±0.2, 17.15±0.2, 17.69±0.2, 18.29±0.2, 18.84±0.2, 20.29±0.2, 21.05±0.2, 21.26±0.2, 22.68±0.2, 23.84±0.2, 24.47±0.2, 24.84±0.2, and 28.47±0.2. In yet further embodiments, the anhydrous crystalline compound of Formula I-11 mono-succinate salt has 2θ values of about 3.58±0.2, 7.05±0.2, 10.59±0.2, 10.75±0.2, 13.80±0.2, 14.16±0.2, 15.16±0.2, 15.68±0.2, 16.18±0.2, 16.80±0.2, 17.15±0.2, 17.69±0.2, 17.97±0.2, 18.29±0.2, 18.59±0.2, 18.84±0.2, 19.27±0.2, 20.29±0.2, 21.05±0.2, 21.26±0.2, 21.56±0.2, 21.78±0.2, 22.68±0.223840.2, 24.47±0.2, 24.84±0.2, 25.15±0.2, 26.10±0.2, 27.12±0.2, 27.78±0.2, 28.47±0.2, and 29.06±0.2.

In certain embodiments, a second anhydrous crystalline form of a compound of Formula I-11 mono-succinate salt has 2θ values of about 9.79±0.2, 13.05±0.2, 22.91±0.2, 23.60±0.2, and 26.25±0.2. In further embodiments, an anhydrous crystalline compound of Formula I-11 mono-succinate salt has 2θ values of about 3.25±0.2, 9.79±0.2, 13.05±0.2, 16.75±0.2, 19.50±0.2, 22.91±0.2, 23.60±0.2, and 26.25±0.2. In yet further embodiments, an anhydrous crystalline compound of Formula I-11 mono-succinate salt has 2θ values of about 3.25±0.2, 9.79±0.2, 13.05±0.2, 13.61±0.2, 14.39±0.2, 16.75±0.2, 18.50±0.2, 19.50±0.2, 22.91±0.2, 23.60±0.2, and 26.25±0.2.

In certain embodiments, the invention relates to a pharmaceutical composition comprising a crystalline compound of Formula I-11 mono-succinate salt and one or more pharmaceutically acceptable excipients. In certain embodiments, the pharmaceutical composition is selected from tablets, capsules, and suspensions.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

Uses of Small Molecule ALK2 Inhibitors

In various embodiments, the present invention provides compounds that inhibit the BMP signaling pathway, as well as methods to treat or prevent a disease or condition in a subject that would benefit by inhibition of BMP signaling. In various embodiments, compounds of the present invention include compounds of Formula I, Formula II, and Formula III and Compounds 1-7, BCX9250, and INCB00928, as disclosed herein and their salts (including pharmaceutically acceptable salts).

All references cited herein are incorporated by reference in their entirety as though fully set forth. Unless defined otherwise, technical and scientific terms used herein have the same meaning as commonly understood by one of ordinary skill in the art to which this invention belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, NY 2006); Smith, *March's Advanced Organic Chemistry* Reactions, Mechanisms and Structure $7^{th}$ ed., J. Wiley & Sons (New York, NY 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* $2^{nd}$ ed., Cold Spring Harbor Press (Cold Spring Harbor NY, 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy, Nature* 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

Unless stated otherwise, the terms "a," "an," and "the," and similar references used in the context of describing one or more embodiments of the application (especially in the context of claims), can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia and is used herein to indicate a non-limiting example. Thus, the abbreviation "e.g." is synonymous with the term "for example." No language in the specification should be construed as indicating any non-claimed element essential to the practice of the application.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic," as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

The term "alkenyl," as used herein, refers to an aliphatic group containing at least one double bond and is intended to include both "unsubstituted alkenyls" and "substituted alkenyls," the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl. Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino," as used herein, refers to an amino group substituted with at least one alkyl group.

The term "alkylthio," as used herein, refers to a thiol group substituted with an alkyl group and may be represented by the general formula alkylS—.

The term "alkynyl," as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Alkynyl groups include propynyl, butynyl, 3-methylpent-1-ynyl, and the like.

The term "amide," as used herein, refers to a group

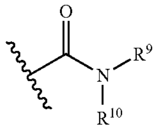

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

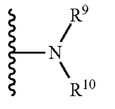

or

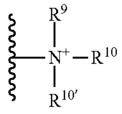

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl," as used herein, refers to an alkyl group substituted with an amino group.

The term "aralkyl," as used herein, refers to an alkyl group substituted with one or more aryl groups.

The term "aryl," as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

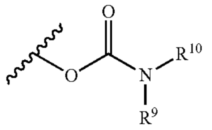

or

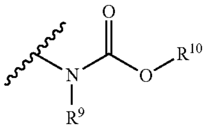

wherein $R^9$ and $R^{10}$ independently represent hydrogen or a hydrocarbyl group, such as an alkyl group.

The terms "carbocycle," "carbocyclyl," and "carbocyclic," as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl," as used herein, refers to an alkyl group substituted with a carbocycle group.

The term "carbonate" is art-recognized and refers to a group $—OCO_2—R^9$, wherein $R^9$ represents a hydrocarbyl group, such as an alkyl group.

The term "carboxy," as used herein, refers to a group represented by the formula $—CO_2H$. The term "cycloalkyl," as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester," as used herein, refers to a group $—C(O)OR^9$ wherein $R^9$ represents a hydrocarbyl group, such as an alkyl group or an aralkyl group.

The term "ether," as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen," as used herein, means halogen and includes chloro, fluoro, bromo, and iodo.

The term "heteroalkyl," as used herein, refers to a saturated or unsaturated chain of carbon atoms including at least one heteroatom (e.g., 0, S, or $NR^{50}$, such as where $R^{50}$ is H or lower alkyl), wherein no two heteroatoms are adjacent.

The terms "hetaralkyl" and "heteroaralkyl," as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms"heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom," as used herein, means an atom of any element other than carbon or hydrogen. Preferred heteroatoms are nitrogen, oxygen, and sulfur.

The terms "heterocyclyl," "heterocycle," and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl," as used herein, refers to an alkyl group substituted with a heterocycle group.

The term "hydrocarbyl," as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl," for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

As used herein, the term "pharmaceutically acceptable salt" means any pharmaceutically acceptable salt of a compound described herein. For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

The terms "polycyclyl," "polycycle," and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group $-OSO_3H$, or a pharmaceutically acceptable salt or ester thereof.

The term "sulfonamide" is art-recognized and refers to the group represented by the general formulae

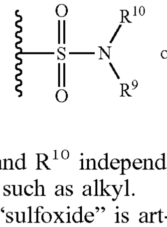
or
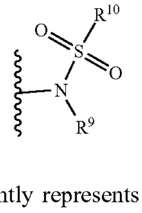

wherein $R^9$ and $R^{10}$ independently represents hydrogen or hydrocarbyl, such as alkyl.

The term "sulfoxide" is art-recognized and refers to the group $-S(O)-R^9$, wherein $R^9$ represents a hydrocarbyl, such as alkyl, aryl, or heteroaryl. The term "sulfonate" is art-recognized and refers to the group $-SO_3H$, or a pharmaceutically acceptable salt or ester thereof.

The term "sulfone" is art-recognized and refers to the group $-S(O)_2-R^9$, wherein $R^9$ represents a hydrocarbyl, such as alkyl, aryl, or heteroaryl.

The term "thioester," as used herein, refers to a group —C(O)S$R^9$ or —SC(O)$R^9$ wherein $R^9$ represents a hydrocarbyl, such as alkyl.

The term "thioether," as used herein, is equivalent to an ether, wherein the oxygen is replaced with a sulfur.

The term "urea" is art-recognized and may be represented by the general formula

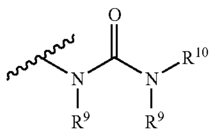

wherein $R^9$ and $R^{10}$ independently represent hydrogen or a hydrocarbyl, such as alkyl. At various places in the present specification substituents of compounds of the invention are disclosed in groups or in ranges. It is specifically intended that the invention include each and every individual sub-combination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

As used herein, the term "anemia resulting from iron imbalance" refers to anemia caused by insufficient red blood cell production as a result of lack of iron bioavailability, regardless of etiology.

As used herein, the term "soft tissue" is used to refer to tissues that connect, support, or surround other structures and organs of the body. The term "soft tissue" can refer to muscles, ligaments, tendons, fascia, skin, fibrous tissues, fat, synovial membranes, nerves and/or blood vessels.

As used herein, the term "abnormal bone formation" refers to the generation or bone in an area, such as a soft tissue, where bone normally does not exist.

The terms "patient," "subject," and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In some embodiments, the subject is human. In another embodiment, the subject is an experimental animal or animal substitute as a disease model. In another embodiment, the subject is a domesticated animal including companion animals (e.g., dogs, cats, rats, guinea pigs, hamsters etc.).

As used herein, the term "small molecule ALK2 inhibitor" refers to a small molecule that inhibits the activity of ALK2 (e.g., human ALK2) with an IC50 of 10 μM or lower (e.g., 1 μM, 500 nm, 100 nM. 50 nM, or lower, such as between 1 μM and 1 nM, 1 μM and 10 nM, 1 μM and 50 nM, 1 μM and 100 nM, 500 nM and 1 nM, 250 nM and 1 nM, 100 nM and 1 nM, and 50 nM and 1 nM). The small molecule ALK2 inhibitor may be selective for ALK2 (e.g., inhibits the activity of ALK2 with an IC50 that is lower by a factor of 5 or more (e.g., 5, 10, 25, 50, 100, 200, 300, 400, 500, 600, 800, 1000 or more) than its IC50 for inhibiting the activity of ALK3, ALK4, ALK5, or ALK6), or the ALK2 small molecule inhibitor may exhibit similar inhibitory effects on multiple BMP receptors (e.g., ALK2 and ALK3, ALK4, ALK5, or ALK6).

As used herein, the term "at risk of having abnormal bone formation" refers to a subject that has been exposed to conditions that are known to cause abnormal bone formation in a population of subjects. While not every subject exposed to such conditions will go on to have abnormal bone formation, but all subjects exposed to these conditions can be considered to be "at risk." Such conditions typically include a trauma, for example, a musculoskeletal trauma, a central nervous system injury or a spinal cord injury.

As used herein, the terms "multiple osteochondromas" and "MO" refer to a condition or disease associated with formation of osteochondromas on bones, e.g., at the ends of long bones or on flat bones, such as the arms, legs, digits, pelvis, and shoulder blade. Subjects with MO often carry a loss-of-function mutation in an exostosin gene, e.g., EXT1 or EXT2. MO is also known as multiple hereditary exostoses, Bessel-Hagen disease, diaphyseal aclasis, multiple cartilaginous exostoses, multiple congenital exostosis, hereditary multiple osteochondromas, multiple osteochondromatosis, multiple exostoses syndrome, EXT, multiple exostoses, and external chondromatosis syndrome.

As used herein, the term "osteochondroma" refers to a benign (noncancerous) bony tumor that develops during childhood or adolescence. It is an abnormal overgrowth of cartilage and bone that typically forms on the surface of a bone near a growth plate (e.g., near a metaphysis). Osteochondromas most often form on the long bones of the leg and arm and on flat bones such as the pelvis and shoulder blade (scapula).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The terms "decrease," "reduced," "reduction," and "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "enhance," and "activate" are all used herein to generally mean an increase of a property, level, or other parameter by a statically significant amount; for the avoidance of any doubt, the terms "increased," "increase," "enhance" and "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

The phrase "activity of ALK2" means ALK2 enzymatic activity (e.g., such as kinase activity; the ability of ALK2 to phosphorylate BMP-responsive SMAD proteins) and/or ALK2-mediated signaling (e.g., such as the ability of ALK2 to mediate downstream signal transduction and transcriptional activity following activation of ALK2 by binding of BMP ligands). In some embodiments, "activity of ALK2" means ALK2-mediated BMP signaling. In some embodiments, "activity of ALK2" means ALK2-mediated BMP-responsive gene transcription (e.g., transcriptional activity mediated by BMP/ALK2 signal transduction).

The phrase "activity of ALK5" means ALK5 enzymatic activity (e.g., such as kinase activity; the ability of ALK5 to phosphorylate TGF-β responsive SMAD proteins; the ability of ALK5 to phosphorylate SMAD2 or SMAD3) and/or ALK5-mediated signaling (e.g., such as the ability of ALK5 to mediate downstream signal transduction and transcriptional activity following activation of ALK5 by binding of TGF-β ligands). In some embodiments, "activity of ALK5" means ALK5-mediated TGF-β signaling. In some embodiments, "activity of ALK5" means ALK5-mediated TGF-β-responsive gene transcription (e.g., transcriptional activity mediated by TGF p/ALK5 signal transduction).

The phrase "activity of ALK1" means ALK1 enzymatic activity (e.g., such as kinase activity; the ability of ALK1 to phosphorylate BMP-responsive SMAD proteins) and/or ALK1-mediated signaling (e.g., such as the ability of ALK1 to mediate downstream signal transduction and transcriptional activity following activation of ALK1 by binding of BMP ligands). In some embodiments, "activity of ALK1" means ALK1-mediated BMP signaling. In some embodiments, "activity of ALK1" means ALK1-mediated BMP-responsive gene transcription (e.g., transcriptional activity mediated by BMP/ALK1 signal transduction).

The phrase "activity of ALK4" means ALK4 enzymatic activity (e.g., such as kinase activity; the ability of ALK4 to phosphorylate activin-responsive SMAD proteins; the ability of ALK4 to phosphorylate SMAD 2 or SMAD 3) and/or ALK4-mediated signaling (e.g., such as the ability of ALK4 to mediate downstream signal transduction and transcriptional activity following activation of ALK4 by binding of activin ligands). In some embodiments, "activity of ALK4" means ALK4-mediated activin signaling. In some embodiments, "activity of ALK4" means ALK4-mediated activin-responsive gene transcription (e.g., transcriptional activity mediated by activin/ALK4 signal transduction).

The phrase "activity of ALK6" means ALK6 enzymatic activity (e.g., such as kinase activity; the ability of ALK6 to phosphorylate BMP-responsive SMAD proteins) and/or ALK6-mediated signaling (e.g., such as the ability of ALK6 to mediate downstream signal transduction and transcriptional activity following activation of ALK6 by binding of BMP ligands). In some embodiments, "activity of ALK6" means ALK6-mediated BMP signaling. In some embodiments, "activity of ALK6" means ALK6-mediated GDF5 signaling. In some embodiments, "activity of ALK6" means ALK6-mediated BMP-responsive gene transcription (e.g., transcriptional activity mediated by BMP/ALK6 signal transduction).

Human ALK2 is a 509 amino acid protein. The protein sequence is published, for example, as GenBank accession number NP_001104537.1 (with corresponding nucleotide sequence at NM_001111067.2) and UniProt entry Q04771.

Human ALK5 has at least two isoforms: a 503 amino acid protein (isoform 1) and a 426 amino acid protein. The protein sequence for human ALK5 isoform 1 is published, for example, as GenBank accession number NP_004603.1 (with corresponding nucleotide sequence at NM_004612.2). The protein sequence for the 426 amino acid isoform is published, for example, as GenBank accession number NP_001124388.1 9f with corresponding nucleotide sequence at NM_001130916.1). Information regarding both isoforms is also published as UniProt entry P36897.

Human ALK1 is a 503 amino acid protein. The protein sequence is published, for example, as GenBank accession number NP_001070869.1 (with corresponding nucleotide sequence at NM_001077401.1; transcript variant 2) and NP_000011.2 (with corresponding nucleotide sequence at NM_000020.2; transcript variant 1), UniProt entry P37023.

Human ALK3 is a 532 amino acid protein. The protein sequence is published, for example as GenBank accession number NP_004320 (with corresponding nucleotide sequence at NM_004329.2), UniProt entry P36894.

Human ALK4 has at least three isoforms. Isoform a is a 505 amino acid protein. The protein sequence is published, for example, as GenBank accession number NP_004293 (with corresponding nucleotide sequence at NM_004302), UniProt entry P36896.

Isoform a of human ALK6 is a 532 amino acid protein and isoform b is a 502 amino acid protein. The protein sequence for human ALK6 isoform a is published, for example, as GenBank accession number NP_001243722 (with corresponding nucleotide sequence at NM_001256793.1). The protein sequence for human ALK6 isoform b is published, for example, as GenBank accession number NP_001194 (with corresponding nucleotide sequence at NM_01203.2).

Note that each of the foregoing proteins are further processed in vivo, such as by the cleaving of a signal sequence, to yield a mature form.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the embodiment.

"Optional" or "optionally" means that the subsequently described circumstance may or may not occur, so that the description includes instances where the circumstance occurs and instances where it does not.

Bone Morphogenetic Protein 6 (BMP6): A member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland, and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation, and neuronal maturation (Heikinheimo et al., *Cancer Res* 59:5815-5821, 1999). BMP6 is also known as vegetal related growth factor (TGFB-related), VGR, VGR1 and VG-1-related protein. Genomic, mRNA and protein sequences for BMP6 from a number of different species are publicly available, such as in the GenBank database from the National Center for Biotechnology Information.

Diagnosis: The process of identifying a disease by its signs, symptoms and/or results of various tests. The conclusion reached through that process is also called "a diagnosis." Forms of testing commonly performed include physical examination, blood tests, medical imaging, genetic analysis, urinalysis, and biopsy.

Diagnostically Significant Amount: In some embodiments, a "diagnostically significant amount" refers to an increase or decrease in the level of BMP6 (or any other gene or protein) in a biological sample that is sufficient to allow one to distinguish one patient population from another. In some examples, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold. RT-PCR is provided herein as one example of how BMP6 expression can be detected. Immunoassays, such as an ELISA, are another example of a method for detecting expression of BMP6. However, one of skill in the art will recognize that other methods exist to measure gene expression and variation in detected expression levels can occur depending on the method that is used. Thus, the diagnostically significant amount may vary if another method of detection is used. In other embodiments, a "diagnostically significant amount" refers to an increase or decrease in electrical potential of a salivary gland that is sufficient to allow one to distinguish one patient population from another. In some examples, the diagnostically significant increase or decrease is about 10%, about 20%, about 30%, about 40% or about 50%.

Immunosuppressive Drug: Includes any agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Inhibitor: Any chemical compound, nucleic acid molecule, small molecule, peptide, or polypeptide (such as an antibody) that can reduce activity of a gene product or interfere with expression of a gene. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization. In various embodiments of the present invention, an inhibitor is one or more compounds of Formula I, Formula II, and Formula III, Compounds 1-7, BCX9250, and INCB00928.

Inhibit Expression or Activity: As used herein, an agent that inhibits expression or activity of a gene (such as BMP6) is an agent that reduces the level of mRNA or protein expressed by the gene (such as BMP6) in a cell or tissue, or reduces (including eliminates) one or more activities of the gene or encoded protein (such as BMP6). Similarly, an agent that inhibits BMP signaling is any compound that inhibits, blocks, or prevents signaling events in the BMP signaling pathway, such as phosphorylation of downstream targets, for example phosphorylation of SMAD1/5/8.

Measuring the Level of Expression: Quantifying the amount of a gene product present in a sample. Quantification can be either numerical or relative. Detecting expression of the gene product (such as BMP6 mRNA or protein) can be achieved using any method known in the art or described herein, such as by RT-PCR, antibody-binding (e.g., ELISA), or immunohistochemistry. In some embodiments, the change detected is an increase or decrease in expression as compared to a control. In some examples, the detected increase or decrease is an increase or decrease of at least two-fold, at least three-fold or at least four-fold compared with the control. In other embodiments of the methods, the increase or decrease is of a diagnostically significant amount, which refers to a change of a sufficient magnitude to provide a statistical probability of the diagnosis.

Noggin (NOG): A secreted protein that binds and inactivates members of the transforming growth factor-beta (TGF-beta) superfamily signaling proteins, such as BMP4 and BMP6. By diffusing through extracellular matrices more efficiently than members of the TGF-beta superfamily, this protein may have a principal role in creating morphogenic gradients. The protein appears to have pleiotropic effect, both early in development as well as in later stages. Nucleotide and amino acid sequences of noggin are publicly available, such as in the GenBank database (see NCBI Gene ID 9241 for human noggin).

Non-Steroidal Anti-Inflammatory Drug (NSAID): A type of anti-inflammatory agent that works by inhibiting the production of prostaglandins. NSAIDS exert anti-inflammatory, analgesic, and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Therapeutically Effective Amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

Abbreviations

BMP6 bone morphogenetic protein 6

ELISA enzyme-linked immunosorbent assay

HO heterotopic ossification

IL interleukin

MO multiple osteochondromas

RT-PCR reverse transcriptase polymerase chain reaction

TGF transforming growth factor

Further, unless otherwise required by context, singular terms shall include pluralities and plural terms shall include the singular.

It should be understood that this invention is not limited to the particular methodologies, protocols, and reagents, etc., described herein and as such can vary therefrom. The terminology used herein is for the purpose of describing particular embodiments only and is not intended to limit the scope of the present invention, which is defined solely by the claims.

The methods and compositions provided herein are based, in part, on the discovery that the compounds of Formula I, Formula II, and Formula III, Compounds 1-7, BCX9250, and INCB00928 described herein act as BMP inhibitors by inhibiting signaling through ALK2, a BMP type I receptor. In addition, the compounds of Formula I described herein are shown herein to be effective in the treatment and/or prevention of anemia resulting from iron imbalance. Accordingly, provided herein are methods and compositions for the treatment of anemia resulting from iron imbalance, comprising treatment with a compound of Formula I, Formula II, or Formula III or any one of and Compounds 1-7, BCX9250, or INCB00928 or a pharmaceutically acceptable salt thereof.

In various embodiments, the present invention provides a method for treating the formation of abnormal bone in a soft tissue of a subject, the method comprising: administering a therapeutically effective amount of a compound of Formula I, Formula II, or Formula III or any one of and Compounds 1-7, BCX9250, or INCB00928. In some embodiments, the subject is determined to have or be at risk of having abnormal bone formation prior to treatment. In some embodiments, the subject has been subjected to a musculoskeletal trauma, a spinal cord injury or a central nervous system injury. In some embodiments, the formation of abnormal bone is associated with a heterotopic ossification disease. In some embodiments, the heterotopic ossification disease is selected from the group consisting of: acquired heterotopic ossification, fibrodysplasia ossificans progressiva, anklyosing spondylosis, traumatic heterotopic ossification, burn- or blast-injury associated heterotopic ossification, and joint replacement surgery associated heterotopic ossification. In some embodiments, the soft tissue comprises muscles, tendons, ligaments and/or fascia. In some embodiments, at least one additional agent is administered to the subject. In some embodiments, the at least one additional agent comprises a corticosteroid, a non-steroidal anti-inflammatory drug (NSAID), a lipoxygenase inhibitor, a leukotriene inhibitor, a mast cell stabilizing agent, an antihistamine, a TNF inhibitor, an IL-23 blocker, or an inhibitor of IL-1 signaling. In some embodiments, the therapeutically effective amount of a compound of Formula I, Formula II, or Formula III or of Compounds 1-7, BCX9250, or INCB00928 comprises a dose within the range of 5 mg/kg to 250 mg/kg. In some embodiments, the therapeutically effective amount of a compound of Formula I, Formula II, or Formula III or of Compounds 1-7, BCX9250, or INCB00928 does not cause weight loss greater than 20% of total body mass.

In various embodiments, the present invention provides a method for treating the formation of abnormal bone in a soft tissue of a subject, the method comprising: administering a therapeutically effective amount of an inhibitor of a BMP type I serine-threonine kinase receptor to the subject, wherein the inhibitor of a BMP type I serine-threonine kinase receptor is a compound of Formula I, Formula II, or Formula III or of Compounds 1-7, BCX9250, or INCB00928. In some embodiments, the BMP type I serine-threonine receptor is ALK2, ALK3, or ALK6. In some embodiments, the BMP type I serine-threonine receptor is ALK2 or ALK3.

In various embodiments, the present invention provides a method for treating the formation of abnormal bone in a soft tissue of a subject, the method comprising: administering a therapeutically effective amount of an inhibitor of a BMP type II serine-threonine kinase receptor to the subject, wherein the inhibitor of a BMP type II serine-threonine kinase receptor is a compound of Formula I, Formula II, or Formula III or of Compounds 1-7, BCX9250, or INCB00928. In some embodiments, the BMP type II serine-threonine receptor is ACVR2A, ACVR2B, BMPR2, or TGFβR2.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is a compound of Formula I, Formula II, or Formula III or of Compounds 1-7, BCX9250, or INCB00928. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5.

In various embodiments, the present invention provides a method for identifying one or more compounds for inhibiting a serine-threonine kinase receptor, the method comprising: a) providing a sample comprising the serine-threonine kinase receptor; b) contacting the sample with one or more compounds described herein; and c) performing an assay to identify the one or more compounds that inhibit the serine-threonine kinase receptor, wherein the assay is an in vitro assay, an in vivo assay, or an ex vivo assay. In some embodiments, the serine-threonine kinase receptor is a BMP type I receptor, a BMP type II receptor, or a TGF-β type I receptor. In some embodiments, the assay is an in vitro assay.

In various embodiments, the present invention provides a method for treating a subject having MO, preventing or reducing the formation of an osteochondroma in a subject having MO, reducing the size of an osteochondroma in a subject having MO, slowing or inhibiting the growth of an osteochondroma in a subject having MO, or reducing the number of osteochondromas in a subject having MO, comprising administering to the subject a therapeutically effective amount of a compound of Formula I, Formula II, or Formula III or of Compounds 1-7, BCX9250, or INCB00928 or a pharmaceutically acceptable salt thereof. In some embodiments, the MO is hereditary MO. In some embodiments, the MO is spontaneous MO. In some embodiments, the subject is determined to have MO prior to treatment (e.g., based on having a mutation in EXT1 or EXT2). In some embodiments, the preventing or reducing the formation of an osteochondroma in a subject having MO is in a subject identified as having MO (e.g., based on genetic testing) who has not yet developed an osteochondroma. In some embodiments, the preventing or reducing the formation of an osteochondroma in a subject having MO is in a subject identified as having MO (e.g., based on genetic testing) who has already developed one or more osteochondroma. In some embodiments, the osteochondroma is formed on a long bone. In some embodiments, the osteochondroma is formed on a flat bone. In some embodiments, the osteochondroma is formed on the growing end (metaphysis) of a bone. In some embodiments, the compound of Formula I, Formula II, or Formula III or of Compounds 1-7, BCX9250, or INCB00928 is administered in an amount sufficient to treat MO, prevent the formation of an osteochondroma, reduce the formation of an osteochondroma, reduce the size of an osteochondroma, reduce the growth of an osteochondroma, or reduce the number of osteochondromas in a subject having MO. The subject with MO may be an adult, a child, or an adolescent. In some embodiments, treatment with the compound of Formula I, Formula II, or Formula III or of Compounds 1-7, BCX9250, or INCB00928 reduces the need of a subject for surgical intervention to treat MO (e.g., the subject no longer requires surgery to treat MO or the subject requires fewer, less frequent, or less invasive surgical procedures to treat MO).

In various embodiments, the present invention provides a method for treating a subject having anemia resulting from iron imbalance, increasing serum iron in a subject in need thereof, increasing transferrin saturation in a subject in need thereof, increasing iron bioavailability (e.g., by mobilizing iron from storage tissue) in a subject in need thereof, increasing reticulocyte hemoglobin in a subject in need thereof, promoting the formation of hemoglobin-containing (e.g., hemoglobin-rich) red blood cells in a subject in need thereof, reestablishing iron homeostasis in a subject in need thereof, and/or reducing hepcidin in a subject in need thereof, comprising administering to the subject a therapeutically effective amount of a compound of Formula I, Formula II, or Formula III or of Compounds 1-7, BCX9250, or INCB00928 or a pharmaceutically acceptable salt thereof. In some embodiments, the subject in need thereof has anemia. In some embodiments, the subject in need thereof has anemia resulting from iron imbalance. In some embodiments, the anemia is iron deficiency anemia (IDA). In some embodiments, the anemia is iron-refractory iron deficiency anemia (IRIDA). In some embodiments, the anemia is associated with myelofibrosis or with myelofibrosis treatment (e.g., treatment with a JAK inhibitor, such as ruxolitinib or fedratinib). In some embodiments, the anemia is associated with a nutritional deficit (e.g., a vitamin deficiency, such as vitamin B-12 deficiency or folate deficiency), a bone marrow defect (e.g., paroxysmal nocturnal hemoglobinuria), adverse reaction to medication (e.g., to an anti-retroviral HIV drug), a myelodysplastic syndrome, a gastrointestinal condition (e.g., Crohn's disease or ulcerative colitis, celiac disease, gastric bypass surgery, *Helicobacter pylori* infection, or autoimmune gastritis), bone marrow transplantation, cancer (e.g., a solid tumor, such as breast cancer, lung cancer, or colon cancer; a tumor of the lymphatic system, such as chronic lymphocyte leukemia, non-Hodgkin's lymphoma, or Hodgkin's lymphoma; or a tumor of the hematopoietic system, such as leukemia or multiple myeloma), cancer treatment (e.g., radiation or chemotherapy, e.g., chemotherapy with a platinum-containing agent), dialysis, an inflammatory or autoimmune disease (e.g., rheumatoid arthritis, other inflammatory arthritides, ankylosing spondylitis, systemic lupus erythematosus (SLE), an acute or chronic skin disease (e.g. psoriasis), inflammatory bowel disease (e.g., Crohn's disease or ulcerative colitis), cystitis, or gastritis), acute or chronic renal disease (e.g., chronic kidney disease) or failure including idiopathic or congenital conditions, diabetes, acute or chronic liver disease, acute or chronic bleeding, an infection (e.g., malaria or osteomyelitis), splenomegaly, *Porphyria*, vasculitis, hemolysis, urinary tract infection, hemoglobinopathy (e.g., sickle cell disease), thalassemia (e.g., α- or β-thalassemia), Churg-Strauss syndrome, Felty syndrome, graft versus host disease, hematopoietic stem cell transplantation, pancytopenia, pure red-cell aplasia, purpura Schoenlein-Henoch, Shwachman syndrome (e.g., Shwachman-Diamond syndrome), drug use or abuse (e.g., alcohol abuse), or contraindication to transfusion (e.g., in a patient of advanced age, a patient with allo- or auto-antibodies, a pediatric patient, a patient with cardiopulmonary disease, or a patient who objects to transfusion for religious reasons (e.g., some Jehovah's Witnesses)). In some embodiments, the anemia is aplastic anemia, vitamin deficiency anemia, anemia of chronic disease (also called anemia of inflammation), anemia associated with bone marrow disease, hemolytic anemia, sickle cell anemia, microcytic anemia, hypochromic anemia, sideroblastic anemia (e.g., congenital sideroblastic anemia or acquired sideroblastic anemia), Diamond Blackfan anemia, Fanconi anemia, Pearson syndrome, dyskeratosis congenita, congenital dyserythropoietic anemia, anemia of prematurity, or refractory anemia with excess of blasts. The compositions and methods described herein can also be used to treat subjects that do not respond well to erythropoietin (EPO) or that are susceptible to an adverse effect of EPO (e.g., hypertension, headaches, vascular thrombosis, influenza-like syndrome, obstruction of shunts, and myocardial infarction). In some embodiments, the anemia may be due to blood loss, such as blood loss due to surgery, trauma, a wound, an ulcer, urinary tract bleeding, digestive tract bleeding, frequent blood donation, or heavy menstrual bleeding (e.g., menorrhagia). In some embodiments, the compound of Formula I, Formula II, or Formula III or of Compounds 1-7, BCX9250, or INCB00928 is administered in an amount sufficient to increase serum iron, increase transferrin saturation, increase iron bioavailability (e.g., by mobilizing iron from storage tissue), increase reticulocyte hemoglobin, promote the formation of hemoglobin-containing (e.g., hemoglobin-rich) red blood cells, reestablish iron homeostasis, and/or reduce hepcidin. In some embodiments, the compositions and methods described herein reduce the need of a subject for a blood transfusion (e.g., reduce transfusion burden, for example, the subject no longer needs blood transfusions, or the subject needs less frequent blood transfusion than before treatment with the compositions and methods described herein). Subjects without anemia can also be treated using the methods and compositions described herein to increase red blood cell levels so that blood can be drawn and stored for later use in transfusions (e.g., in preparation for surgery).

In various embodiments, the present invention provides a method for treating the formation of abnormal bone in a soft tissue of a subject, the method comprising: administering a therapeutically effective amount of an inhibitor of a TGF-β type I receptor serine-threonine kinase receptor to the subject, wherein the inhibitor of the TGF-β type I serine-threonine kinase receptor is a compound of Formula I, Formula II, or Formula III or of Compounds 1-7, BCX9250, or INCB00928. In some embodiments, the TGF-β type I receptor is ALK5.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is a compound of Formula I, Formula II, or Formula III or of Compounds 1-7, BCX9250, or INCB00928. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5.

Heterotopic Ossification Diseases

The term "heterotopic ossification" refers to the abnormal formation of bone in soft tissue where bone typically does not exist. Acquired heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis, and burns. Examples of musculoskeletal trauma include, but are not limited to, hip, knee, shoulder, or elbow arthroplasty; fractures; joint dislocations; or soft-tissue trauma, with the *musculus* quadriceps femoris and *musculus brachialis*. Acquired heterotopic ossification can also be associated with fever, swelling, and erythema (e.g., local, patchy reddening of the skin). In one embodiment, neurogenic heterotopic ossification is not associated with local trauma.

Genetic diseases fibrodysplasia ossificans progressiva (FOP) and progressive osseous heteroplasia (POH) are the most severe manifestations of heterotopic bone formation. FOP occurs rarely and is a result of a mutation in ACVR1, which encodes a bone morphogenetic protein type I receptor. Patients with POH have inactivating mutations of the GNAS gene, which also can give rise to Albright's hereditary osteodystrophy (AHO) when the mutations are inherited from the mother.

Myositis ossificans circumscripta is characterized by the intramuscular proliferation of fibroblasts, new bone, and/or cartilage.

HO typically occurs between 3 weeks and 12 weeks following an injury. Heterotopic ossification can be reliably diagnosed by computed tomography, bone scintigraphy and ultrasonography. Two to six weeks later, the abnormal bone formation has progressed to the point that it is detectable by radiography. Bony maturation typically occurs within six months.

Conventional treatment of Heterotopic ossification: Conventional treatment usually involves non-steroidal anti-inflammatory drugs (indomethecin, rofecoxib), or bisphosphonate (etidronate, pamidronate), Coumadin/warfarin, salicylates, and/or local radiation can also be administered. Often, surgery is the only option for treatment.

Outcome of treatment can be measured by a standard radiological grading system for HO, which includes measurements related to changes in range of motion in the affected joint measured by goniometry, mean length of time to objective improvement of HO-related clinical symptoms or signs, changes in standardized functional or joint-specific measures.

Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while other findings have suggested that in some contexts excess BMP signaling might be pathogenic (Waite et al. *Nat. Rev. Genet.* 4:763-773, 2005; Yu et. *J. Biol. Chem.* 280:24443-24450, 2003). The ability to modulate BMP signaling experimentally would provide a means for investigating therapy, and for determining the root causes of these conditions. The compounds of Formula I, Formula II, and Formula III and Compounds 1-7, BCX9250, and INCB00928 are inhibitors of ALK2, a BMP type 1 receptor and can be used to disrupt signaling through the BMP pathway.

Treatment of Anemia, Including Iron Deficiency and Anemia of Chronic Disease

For a review, see Weiss et al. *N. Engl. J. Med.* 352:1011-1023, 2005. Anemia of inflammation (also called anemia of chronic disease) can be seen in patients with chronic infections, autoimmune diseases (such as systemic lupus erythematosus and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J. Med.* 352:1011-1023, 2005). It has been shown that stimulating hepatoma cell lines with IL-6 induces hepcidin expression, while treatment with a BMP antagonist abrogates IL-6-induced hepcidin expression (Yu et al. *Nat. Chem. Biol.* 4:33-41, 2008). Moreover, BMP antagonists can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by the previous finding that BMP antagonists can inhibit hepcidin expression and raise serum iron levels in vivo (data not shown). Taken together these data indicate that iron- and inflammation-mediated regulation of hepcidin and circulating iron levels require BMP signaling. Thus, a compound of Formula I, Formula II, or Formula III or of Compounds 1-7, BCX9250, or INCB00928 which disrupts BMP signaling through ALK2 can be used to alter iron availability in diverse circumstances for therapeutic benefit.

Compounds and/or pharmaceutical compositions as described herein can be used in anemic states to (i) augment the efficacy of dietary iron or oral iron supplementation (which is safer than intravenous administration of iron) to increase serum iron concentrations; (ii) augment build-up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

The compounds of Formula I, Formula II, and Formula III and Compounds 1-7, BCX9250, and INCB00928 can be used to treat anemia resulting from iron imbalance. In some embodiments, the anemia is iron deficiency anemia (IDA). In some embodiments, the anemia is iron-refractory iron deficiency anemia (IRIDA). In some embodiments, the anemia is associated with myelofibrosis or with myelofibrosis treatment (e.g., treatment with a JAK inhibitors, such as ruxolitinib or fedratinib). In some embodiments, the anemia is associated with a nutritional deficit (e.g., a vitamin deficiency, such as vitamin B-12 deficiency or folate deficiency), a bone marrow defect (e.g., paroxysmal nocturnal hemoglobinuria), adverse reaction to medication (e.g., to an anti-retroviral HIV drug), a myelodysplastic syndrome, a gastrointestinal condition (e.g., Crohn's disease or ulcerative colitis, celiac disease, gastric bypass surgery, *Helicobacter pylori* infection, or autoimmune gastritis), bone marrow transplantation, cancer (e.g., a solid tumor, such as breast cancer, lung cancer, or colon cancer; a tumor of the lymphatic system, such as chronic lymphocyte leukemia, non-Hodgkin's lymphoma, or Hodgkin's lymphoma; or a tumor of the hematopoietic system, such as leukemia or multiple myeloma), cancer treatment (e.g., radiation or chemotherapy, e.g., chemotherapy with a platinum-containing agent), dialysis, an inflammatory or autoimmune disease (e.g., rheumatoid arthritis, other inflammatory arthritides, ankylosing spondylitis, systemic lupus erythematosus (SLE), an acute or chronic skin disease (e.g. psoriasis), inflammatory bowel disease (e.g., Crohn's disease or ulcerative colitis), cystitis, or gastritis), acute or chronic renal disease (e.g., chronic kidney disease) or failure including idiopathic or congenital conditions, diabetes, acute or chronic liver disease, acute or chronic bleeding, an infection (e.g., malaria or osteomyelitis), splenomegaly, *Porphyria*, vasculitis, hemolysis, urinary tract infection, hemoglobinopathy (e.g., sickle cell disease), thalassemia (e.g., α- or β-thalassemia), Churg-Strauss syndrome, Felty syndrome, graft versus host disease, hematopoietic stem cell transplantation, pancytopenia, pure red-cell aplasia, purpura Schoenlein-Henoch, Shwachman syndrome (e.g., Shwachman-Diamond syndrome), drug use or abuse (e.g., alcohol abuse), or contraindication to transfusion (e.g., in a patient of advanced age, a patient with allo- or auto-antibodies, a pediatric patient, a patients with cardiopulmonary disease, or a patient who objects to transfusion for religious reasons (e.g., some Jehovah's Witnesses)). The myelodysplastic syndrome may be myelodysplastic syndrome with unilineage dysplasia (MDS-SLD), myelodysplastic syndrome with multilineage dysplasia (MDS-MLD), myelodysplastic syndrome with ring sideroblasts (MDS-RS, which includes single lineage dysplasia (MDS-RS-SLD) and multilineage dysplasia (MDS-RS-MLD)), myelodysplastic syndrome associated with isolated del chromosome abnormality (MDS with isolated del(5q)), myelodysplastic syndrome with excess blasts (MDS-EB; which includes myelodysplastic syndrome with excess blasts—type 1 (MDS-EB-1) and myelodysplastic syndrome with excess blasts—type 2 (MDS-EB-2)), myelodysplastic syndrome, unclassifiable (MDS-U), or myelodysplastic syndrome/myeloproliferative neoplasm with ring sideroblasts and thrombocytosis (MDS/MPN-RS-T). In some embodiments, the anemia is aplastic anemia, vitamin deficiency anemia, anemia of chronic disease (also called anemia of inflammation), anemia associated with bone marrow disease, hemolytic anemia, sickle cell anemia, microcytic anemia, hypochromic anemia, sideroblastic anemia (e.g., congenital sideroblastic anemia or acquired sideroblastic anemia), Diamond Blackfan anemia, Fanconi anemia, Pearson syndrome, dyskeratosis congenita, congenital dyserythropoietic anemia, anemia of prematurity, or refractory anemia with excess of blasts. The compositions and methods described herein can also be used to treat subjects that do not respond well to erythropoietin (EPO) or that are susceptible to an adverse effect of EPO (e.g., hypertension, headaches, vascular thrombosis, influenza-like syndrome, obstruction of shunts, and myocardial infarction). In some embodiments, the anemia may be due to blood loss, such as blood loss due to surgery, trauma, a wound, an ulcer, urinary tract bleeding, digestive tract bleeding, frequent blood donation, or heavy menstrual bleeding (e.g., menorrhagia). In some embodiments, the methods described herein (e.g., treatment with a compound of Formula I, Formula II, or Formula III or of Compounds 1-7, BCX9250, or INCB00928) increase serum iron, increase transferrin saturation, increase iron bioavailability (e.g., by mobilizing iron from storage tissue), increase reticulocyte hemoglobin, promote the formation of hemoglobin-containing (e.g., hemoglobin-rich) red blood cells, reestablish iron homeostasis, and/or reduce serum hepcidin compared to measurements obtained prior to treatment or compared to measurements typically observed in untreated or placebo-treated subjects having the same disease or condition. By increasing iron bioavailability (e.g., increasing iron supply in the bone marrow), the methods described herein may promote or increase erythropoiesis or the production of functional red blood cells. In some embodiments, the compositions and methods described herein reduce the need of a subject for a blood transfusion (e.g., reduce transfusion burden, for example, the subject no longer needs blood transfusions, or the subject needs less frequent blood transfusion than before treatment with the compositions and methods described herein). Subjects without anemia can also be treated using the methods and compositions described herein to increase red blood cell levels so that blood can be drawn and stored for later use in transfusions (e.g., in preparation for surgery).

Treatment of Fibrodysplasia Ossificans Progressiva (FOP)

In various embodiments, the present disclosure relates to the treatment and/or prevention of a disease or disorder comprising abnormal bone growth in a soft tissue of a subject. Heterotopic ossification (HO) involves unwanted bone growth that may be characterized by inappropriate differentiation of cells into bone-forming cells. This condition leads to bone formation, usually near joints, where the bone formation often limits the mobility of the joint. HO may follow neurological injury and direct injury to soft tissue such as muscles or connective tissue around the joint in which HO later develops.

There are three recognized etiologies of HO: traumatic, neurogenic, and genetic. Traumatic HO typically follows fractures, dislocations, operative procedures, and severe burns. Most commonly, HO is seen around the hip after fracture and open reduction-internal fixation (ORIF) procedures or total hip arthroplasties (THA). As well, HO is often associated with pathologies such as traumatic brain injury (TBI), spinal cord injury (SCI), infections of the central nervous system (CNS), tumors, strokes, tetanus, polio, tabes dorsalis, multiple sclerosis, and selective posterior rhizotomy. The presence of idiopathic muscle spasticity is also associated with the development of HO.

Bone morphogenetic proteins (BMP) exhibit broad spectrum of biological activities in various tissues, including bone, cartilage, blood vessels, heart, kidney, neurons, liver, and lung. BMPs are members of the transforming growth factor-β (TGF-β) family that bind to type II and type I serine-threonine kinase receptors, and transduce signals through Smad and non-Smad signaling pathways. Fibrodysplasia ossificans progressiva (FOP), one type of heterotopic ossification disease, is an autosomal-dominant rare disease that affects one person in every 1-2 million. It is characterized by malformation of the great (big) toes during embryonic development and by progressive heterotopic endochondral ossification (HEO) postnatally, which leads to the formation of a second skeleton of heterotopic bone. Individuals with the classical features of FOP have the identical heterozygous activating mutation (R206H) in the gene encoding ACRV1 (also known as ALK2), a BMP type 1 receptor. No effective treatment currently exists for this rare and devastating disease. As such, there remains a need for compositions and methods for treating heterotopic ossification and heterotopic ossification diseases and disorders.

FOP is caused by the presence of a constitutively-active mutant form of ALK2 in affected individuals (Shore et al. *Nat. Genet.* 38:525-527, 2006). A specific inhibitor of BMP signaling such as a compound of Formula I, Formula II, or Formula III or any one of Compounds 1-7, BCX9250, or INCB00928 can be used to prevent excessive bone formation in response to trauma, musculoskeletal stress, or inflammation. Such compounds can also be used to aid in regression of pathologic bone. The compound of Formula I, Formula II, or Formula III or of Compounds 1-7, BCX9250, or INCB00928 can be administered systemically or locally to concentrate or limit effects to areas of trauma or inflammation.

The compound of Formula I, Formula II, or Formula III or of Compounds 1-7, BCX9250, or INCB00928 can be used as chronic therapy to suppress spontaneous bone formation in individuals who are highly susceptible. Transient therapy can be used to prevent abnormal bone formation in FOP individuals who develop osteomas or pathologic bone most frequently in association with trauma by administration before, during, or even after the traumatic incident. Transient therapy with BMP inhibitors (e.g., a compound of Formula I, Formula II, or Formula III or of Compounds 1-7, BCX9250, or INCB00928) can be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituximab, etanercept, or similar drugs) may increase the effectiveness of BMP antagonists in inhibiting heterotopic bone formation in this disorder. In some embodiments, the subject with FOP is an adult. In some embodiments, the subject with FOP is a child or an adolescent.

Provided herein are methods and compositions for the treatment and/or prevention of abnormal bone formation in a soft tissue. In certain embodiments, the methods and compositions treat and/or prevent a disease or disorder comprising abnormal bone formation in soft tissue. Exemplary diseases or disorders that can be treated with the methods and compositions described herein include, but are not limited to, heterotopic ossification diseases such as fibrodysplasia ossificans progressiva, anklyosing spondylosis, traumatic heterotopic ossification, burn- or blast-injury associated heterotopic ossification, and joint replacement surgery associated heterotopic ossification. In some embodiments, the methods described herein prevent or delay the development of new heterotopic ossification or the expansion of existing heterotopic ossification. In some embodiments, the compositions and methods described herein can be used to prevent or delay the regrowth of bone after surgical resection and new bone formation resulting from surgery-induced trauma.

Accordingly, provided herein in one aspect is a method for treating and/or preventing the formation of abnormal bone in a soft tissue of a subject, the method comprising: administering a therapeutically effective amount of a pharmaceutical composition comprising a compound of Formula I, Formula II, or Formula III or of Compounds 1-7, BCX9250, or INCB00928.

Treatment of Multiple Osteochondroma

A compound of Formula I, Formula II, or Formula III or of Compounds 1-7, BCX9250, or INCB00928 or a pharmaceutically acceptable salt thereof can be used to treat MO. MO is a rare genetic disorder characterized by the development of multiple benign (noncancerous) bone tumors called osteochondromas, often on the growing end (metaphysis) of the long bones of the legs, arms, and digits and on flat bones such as the hip and shoulder blade. These osteochondromas may lead to bone deformities, skeletal abnormalities, differences in limb length, short stature, pain, decreased range of motion, and pressure on nerves, blood vessels, the spinal cord, and tissues surrounding the osteochondromas. Hereditary MO is inherited in an autosomal dominant manner and is typically associated with mutations in EXT1 or EXT2. Current treatment options include a "watch and wait" approach (when no symptoms are present), surgical removal of the osteochondroma, corrective osteotomy, and growth plate arrest or limb-lengthening procedures.

Recent studies indicate that BMP signaling may regulate the formation of osteochondromas in MO. In Ext1 mutant mice, enhanced BMP signaling in perichondrial progenitor cells was found to lead to osteochondromagenesis. Moreover, treatment with a small molecule BMP inhibitor suppressed osteochondroma formation in two mouse models of MO. These data indicate that osteochondroma formation is amenable to therapeutic treatment with BMP inhibitors.

In some embodiments, a compound of Formula I, Formula II, or Formula III or of Compounds 1-7, BCX9250, or INCB00928 may be administered to a subject to treat MO, reduce or prevent the formation of an osteochondroma in a subject with MO, reduce the number of osteochondromas in a subject with MO, reduce the size of an osteochondroma in a subject with MO, or slow the growth of an osteochondroma in a subject with MO. The osteochondroma can be formed on the growing end (metaphysis) of a bone, on a long bone (e.g., a long bone of the leg, arm, or digit), and/or on a flat bone (e.g., a hip bone (pelvic bone), rib bone, or shoulder blade). In some embodiments, the MO is hereditary MO. In some embodiments, the MO is spontaneous MO. The compound of Formula I, Formula II, or Formula III or of Compounds 1-7, BCX9250, or INCB00928 may reduce or prevent the formation of an osteochondroma (e.g., prevent the formation of an osteochondroma in a subject with MO who has not yet developed osteochondroma or reduce or prevent the formation of an osteochondroma in a subject with MO who has already developed one or more osteochondroma), reduce the number of osteochondromas, reduce the size of an osteochondroma, or slow the growth of an osteochondroma compared to the formation of an osteochondroma, the number of osteochondromas, the size of an osteochondroma, or the growth of an osteochondroma in the subject prior to treatment or in an untreated subject with MO. The methods described herein may include a step of screening a subject for a mutation in EXT1 or EXT2 prior to treatment with or administration of the compound of Formula I, Formula II, or Formula III or of Compounds 1-7, BCX9250, or INCB00928. A subject can be screened for a genetic mutation using standard methods known to those of skill in the art (e.g., genetic testing). In some embodiments, the subject with MO is an adult. In some embodiments, the subject with MO is a child or an adolescent. In some embodiments, treatment with the compound of Formula I, Formula II, or Formula III or of Compounds 1-7, BCX9250, or INCB00928 reduces the need of a subject for surgical intervention to treat MO (e.g., the subject no longer requires surgery to treat MO or the subject requires fewer, less frequent, or less invasive surgical procedures to treat MO).

Ex Vivo Applications

In addition to being administered to patients in therapeutic methods, a compound of Formula I, Formula II, or Formula III or of Compounds 1-7, BCX9250, or INCB00928 can also be used to treat cells and tissues, as well as structural materials to be implanted into patients (see above), ex vivo. For example, a compound of Formula I, Formula II, or Formula III or of Compounds 1-7, BCX9250, or INCB00928 can be used to treat explanted tissues that may be used, for example, in transplantation.

Treatment of Hypercholesterolemia or Hyperlipoproteinemia

Treatment with small molecule or recombinant BMP inhibitors reduces vascular inflammation (via macrophage accumulation and cathepsin activity), atheroma formation, and vascular calcification in mice deficient in low-density lipoprotein receptor ($LDLR^{-/-}$). Without wishing to be bound by theory, as potential explanations for impact on vascular inflammation, oxidized LDL (oxLDL) has been found to increase BMP2 expression and induce the production of reactive oxygen species (ROS) in human aortic endothelial cells. ROS production induced by oxLDL appears to require BMP signaling, based on inhibition by small molecule or recombinant BMP inhibitors. Treatment with small molecule BMP inhibitors reduces plasma low-density lipoprotein levels without inhibiting HMG-CoA reductase activity, suggesting a role of BMP signaling in the regulation of LDL cholesterol biosynthesis. Small molecule BMP inhibitors have also been found to inhibit hepatosteatosis seen in LDLR-deficient mice fed a high-fat diet. Small molecule or recombinant BMP inhibitors inhibit the synthesis of ApoB-100 in hepatoma cells in vitro. These findings implicate BMP signaling in vascular calcification and atherogenesis and provide at least two novel mechanisms by which BMP signaling may contribute to the pathogenesis of atherosclerosis. These studies highlight the BMP signaling pathway as a therapeutic target in the treatment of atherosclerosis while identifying several novel functions of BMP signaling in the regulation of vascular oxidative stress, inflammation, and lipid metabolism.

In various embodiments, a compound of Formula I, Formula II, or Formula III or of Compounds 1-4 or a pharmaceutically acceptable salt thereof may be used for the reduction of circulating levels of ApoB-100 in patients. In various embodiments, a compound of Formula I, Formula II, or Formula III or of Compounds 1-4 or a pharmaceutically acceptable salt thereof may be used for the reduction of circulating levels of LDL in patients. In various embodiments, a compound of Formula I, Formula II, or Formula III or of Compounds 1-4 or a pharmaceutically acceptable salt thereof may be used for the treatment of hypercholesterolemia, hyperlipidemia, or hyperlipoproteinemia, including congenital or acquired hypercholesterolemia, hyperlipidemia, or hyperlipoproteinemia. In some embodiments, the congenital hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B).

In some embodiments, the acquired hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, end stage renal disease, hypothyroidism, iatrogenesis due to administration of thiazides, beta-blockers, retinoids, highly active antiretroviral agents, estrogen, progestins, or glucocorticoids. In various embodiments, a compound of Formula I, Formula II, or Formula III or of Compounds 1-4 may be used for the treatment of diseases, disorders, or syndromes associated with defects in lipid absorption or metabolism, such as sitosterolemia, cerebrotendinous xanthomatosis, or familial hypobetalipoproteinemia.

In various embodiments, a compound of Formula I, Formula II, or Formula III or of Compounds 1-4 or a pharmaceutically acceptable salt thereof may be used for the treatment of diseases, disorders, or syndromes caused by hyperlipidemia, such as coronary artery disease and its manifestations (e.g., myocardial infarction; angina pectoris; acute coronary artery syndromes, such as unstable angina pectoris; cardiac dysfunction, such as congestive heart failure, caused by myocardial infarction; or cardiac arrhythmia associated with myocardial ischemia/infarction), stroke due to occlusion of arteries supplying portions of the brain, cerebral hemorrhage, peripheral arterial disease (e.g., mesenteric ischemia; renal artery stenosis; limb ischemia and claudication; subclavian steal syndrome; abdominal aortic aneurysm; thoracic aortic aneurysm, pseudoaneurysm, intramural hematoma; or penetrating aortic ulcer, aortic dissection, aortic stenosis, vascular calcification, xanthoma, such as xanthoma affecting tendons or scleral and cutaneous xanthomas, xanthelasma, or hepatosteatosis.

In various embodiments, a compound of Formula I, Formula II, or Formula III or of Compounds 1-4 or a pharmaceutically acceptable salt thereof may be used for the treatment of the foregoing diseases, disorders, or syndromes regardless of circulating lipid levels, such as in individuals exhibiting normal circulating lipid levels or metabolism.

In various embodiments, a compound of Formula I, Formula II, or Formula III or of Compounds 1-4 or a pharmaceutically acceptable salt thereof may be used for the reduction of secondary cardiovascular events arising from coronary, cerebral, or peripheral vascular disease. In various embodiments, a compound of Formula I, Formula II, or Formula III or of Compounds 1-4 or a pharmaceutically acceptable salt thereof may be used to treat individuals regardless of lipid levels, such as used in the treatment of individuals exhibiting normal circulating cholesterol and lipid levels. In various embodiments, a compound of Formula I, Formula II, or Formula III or of Compounds 1-4 or a pharmaceutically acceptable salt thereof may be administered conjointly with a HMG-CoA reductase inhibitor.

In various embodiments, a compound of Formula I, Formula II, or Formula III or of Compounds 1-4 or a pharmaceutically acceptable salt thereof may be used for the prevention of cardiovascular disease, such as in individuals with elevated markers of cardiovascular risk (e.g., C-reactive protein) or, for example, an elevated Framingham Risk Score. In various embodiments, a compound of Formula I, Formula II, or Formula III or of Compounds 1-4 or a pharmaceutically acceptable salt thereof may be used to prevent cardiovascular disease in individuals exhibiting normal circulating cholesterol and lipid levels.

In various embodiments in which a compound of Formula I, Formula II, or Formula III or of Compounds 1-4 or a pharmaceutically acceptable salt thereof is used in the treatment or prevention of the foregoing diseases, disorders, or syndromes, the patient being treated is not diagnosed with and/or is not suffering from one or more of the following conditions: vascular inflammation associated with atherosclerosis, autoimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

In various embodiments in which a compound of Formula I, Formula II, or Formula III or of Compounds 1-4 or a pharmaceutically acceptable salt thereof is used in the treatment or prevention of the foregoing diseases, disorders, or syndromes (e.g., for the reduction of circulating levels of ApoB-100 and/or LDL in patients; for the treatment of hypercholesterolemia, hyperlipidemia, or hyperlipoproteinemia, including congenital or acquired hypercholesterolemia, hyperlipidemia, or hyperlipoproteinemia; for the treatment of diseases, disorders, or syndromes associated with defects in lipid absorption or metabolism; for the treatment of diseases, disorders, or syndromes caused by hyperlipidemia; for the reduction of secondary cardiovascular events arising from coronary, cerebral, or peripheral vascular disease; or for the reduction of secondary cardiovascular events arising from coronary, cerebral, or peripheral vascular disease), the patient being treated is also diagnosed with and/or is also suffering from one or more of the following conditions: vascular inflammation associated with atherosclerosis, autoimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events Treatment of Cartilage Defects The selective inhibition of specific BMP receptors enables cartilage formation by preventing calcification and mineralization of scaffolds produced by mesenchymal stem cells (Hellingman et al. Tissue Eng Part A. 2011 April; 17(7-8): 1157-67. Epub 2011 Jan. 17.) Accordingly, in some embodiments compounds of the invention as described herein may be useful to promote cartilage repair/regeneration in patients with cartilage injuries or defects, as well as in the ex vivo or in vitro production of cartilage tissue, e.g., for implantation, from appropriate cells, such as mesenchymal stem cells.

Application of Compounds with Varying Degrees of Selectivity: Compounds which Inhibit BMP Signaling Via Particular BMP Type I Receptors, or Compounds which Also Affect Signaling Via TGF-β, Activin, AMP Kinase, or VEGF Receptors.

In various embodiments several of the compounds of the present invention described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. Nat. Chem. Biol. 4:33-41, 2008). In such instances, in various embodiments compounds of the present invention as described herein which specifically antagonize the function of a subset of the BMP type I receptors may have the advantage of reduced toxicity or side effects, or greater effectiveness, or both.

In some embodiments compounds of the invention as described herein may have a high degree of selectivity for BMP vs. TGF-β, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g., decrease tumor size), when molecular phenotyping of specific patients' tumors reveals dysregulation of multiple pathways.

In some embodiments compounds of the invention as described herein (e.g., a compound of Formula I, Formula II, or Formula III or of Compounds 1-7, BCX9250, or INCB00928) have a high degree of selectivity for ALK2 versus ALK1 or ALK3 or ALK4 or ALK5 or ALK6. Selective inhibition of ALK2 versus ALK1 or ALK3 or ALK4 or ALK5 or ALK6 may minimize unwanted effects or toxicity. Chronic ALK3 inhibition might impair normal mucosal epithelial turnover due to known importance in intestinal crypt stem cell recycling, and implication of ALK3 function in juvenile familial polyposis. ALK1 inhibition might impair normal vascular remodeling and lead to complications similar to human hereditary telangiectasia syndrome type 2 (HHT2), such as leaky capillaries, AV malformations, and bleeding. Accordingly, compounds that selectively inhibit ALK2 relative to ALK3 and ALK1 may help avoid toxicities of this type that might be encountered through the use of an unselective inhibitor.

In certain embodiments, the invention provides a method of inhibiting the activity of ALK2 in a human, comprising administering to the human a compound of Formula I, Formula II, or Formula III or of Compounds 1-7, BCX9250, or INCB00928 or a pharmaceutically acceptable salt thereof that selectively inhibits the activity of human ALK2 relative to the activity of human ALK1. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of about 2 than its $IC_{50}$ for inhibiting the activity of human ALK1. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 5 than its $IC_{50}$ for inhibiting the activity of human ALK1. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 10 than its $IC_{50}$ for inhibiting the activity of human ALK1. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK1.

In certain embodiments, the invention provides a method of inhibiting the activity of ALK2 in a human, comprising administering to the human a compound of Formula I, Formula II, or Formula III or of Compounds 1-7, BCX9250, or INCB00928 or a pharmaceutically acceptable salt thereof that selectively inhibits the activity of human ALK2 relative to the activity of human ALK3. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 15 than its $IC_{50}$ for inhibiting the activity of human ALK3. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 20 than its $IC_{50}$ for inhibiting the activity of human ALK3. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 30 than its $IC_{50}$ for inhibiting the activity of human ALK3. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 50 or 100 or 200 or 300 or 400 or 500 or 600 or 800 or 1000 or 1500 or 2000 or 5000 or 10000 or 15,000 or 20,000 or 40,000 or 60,000 or 70,000 or 80,000 or 90,000 or 100,000 than its $IC_{50}$ for inhibiting the activity of human ALK3.

In certain embodiments, the invention provides a method of inhibiting the activity of ALK2 in a human, comprising administering to the human a compound of Formula I, Formula II, or Formula III or of Compounds 1-7, BCX9250, or INCB00928 or a pharmaceutically acceptable salt thereof that selectively inhibits the activity of human ALK2 relative to the activity of human ALK4. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 1000 than its $IC_{50}$ for inhibiting the activity of human ALK4. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 2000 than its $IC_{50}$ for inhibiting the activity of human ALK4. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 3000 than its $IC_{50}$ for inhibiting the activity of human ALK4. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK4.

In certain embodiments, the invention provides a method of inhibiting the activity of ALK2 in a human, comprising administering to the human a compound of Formula I, Formula II, or Formula III or of Compounds 1-7, BCX9250, or INCB00928 or a pharmaceutically acceptable salt thereof that selectively inhibits the activity of human ALK2 relative to the activity of human ALK6. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 2 than its $IC_{50}$ for inhibiting the activity of human ALK6. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 5 than its $IC_{50}$ for inhibiting the activity of human ALK6. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 10 than its $IC_{50}$ for inhibiting the activity of human ALK6. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK6

In one aspect, the invention provides a method of inhibiting the activity of ALK2 in a human, comprising administering to the human compound of Formula I, Formula II, or Formula III or of Compounds 1-7, BCX9250, or INCB00928 or a pharmaceutically acceptable salt thereof that selectively inhibits the activity of human ALK2 relative to the activity of human ALK5. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 1000 than its $IC_{50}$ for inhibiting the activity of human ALK5. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 2000 than its $IC_{50}$ for inhibiting the activity of human ALK5. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 3000 than its $IC_{50}$ for inhibiting the activity of human ALK5. In some such embodiments, the compound of Formula I, Formula II, or Formula III or of Compounds 1-7, BCX9250, or INCB00928 or a pharmaceutically acceptable salt thereof inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK5.

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

Combination Therapies

In certain instances a compound of Formula I, Formula II, or Formula III or of Compounds 1-7, BCX9250, or INCB00928 or a pharmaceutically acceptable salt thereof can be used in combination with other current or future drug therapies, because the effects of inhibiting BMP alone may be less optimal by itself, and/or can be synergistic or more highly effective in combination with therapies acting on distinct pathways which interact functionally with BMP signaling, or on the BMP pathway itself. In certain instances, conjoint administration of a BMP inhibitor as described herein (e.g., a compound of Formula I, Formula II, or Formula III or of Compounds 1-7, BCX9250, or INCB00928 or a pharmaceutically acceptable salt thereof) with an additional drug therapy reduces the dose of the additional drug therapy such that it is less than the amount that achieves a therapeutic effect when used in a monotherapy (e.g., in the absence of a BMP inhibitor as described herein).

Some non-limiting examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of a compound of Formula I, Formula II, or Formula III or of Compounds 1-7, BCX9250, or INCB00928. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

When used in combination, one or more compounds described herein can be administered separately or in different formulations from at least one additional agent as described herein or can be administered in a single formulation comprising one or more compounds described herein and the additional agent. A compound of Formula I, Formula II, or Formula III or of Compounds 1-7, BCX9250, or INCB00928 or a pharmaceutically acceptable salt thereof can be administered simultaneously or concurrently with the at least one additional agent. Administration of a compound of Formula I, Formula II, or Formula III or of Compounds 1-7, BCX9250, or INCB00928 or a pharmaceutically acceptable salt thereof can be administered using the same or different modes of administration (e.g., oral, intravenous, injection, etc.). Administration of a compound of Formula I, Formula II, or Formula III or of Compounds 1-7, BCX9250, or INCB00928 or a pharmaceutically acceptable salt thereof and the at least one additional agent can occur simultaneously, within 15 min, within 30 min, or can be separated by at least one hour (e.g., at least 2, at least 3, at least 4, at least 5, at least 6, at least 7, at least 8, at least 9, at least 10, at least 11, at least 12 or more hours). One of skill in the art can easily determine an appropriate dosing regimen for a combination treatment comprising a compound of Formula I, Formula II, or Formula III or of Compounds 1-7, BCX9250, or INCB00928 or a pharmaceutically acceptable salt thereof and at least one additional agent, for example, to reduce side effects, to prevent metabolic interference from one of the agents, to enhance activity of a compound of Formula I, Formula II, or Formula III or of Compounds 1-7, BCX9250, or INCB00928 or a pharmaceutically acceptable salt thereof, or to otherwise improve pharmacodynamic or pharmacokinetic factors.

It is contemplated herein that a combination of at least one additional agent as described above with a compound of Formula I, Formula II, or Formula III or of Compounds 1-7, BCX9250, or INCB00928 or a pharmaceutically acceptable salt thereof can produce a synergistic effect that is greater than the sum of the effects of each agent administered alone. In such embodiments, it is contemplated that a lower dose of a compound of Formula I, Formula II, or Formula III or of Compounds 1-7, BCX9250, or INCB00928 or a pharmaceutically acceptable salt thereof is administered in combination with a second agent than is required for a therapeutic effect when the compound of Formula I, Formula II, or Formula III or of Compounds 1-7, BCX9250, or INCB00928 or a pharmaceutically acceptable salt thereof is administered alone.

Dosage and Administration

In one aspect, the methods described herein provide a method for treating a disease or disorder comprising abnormal bone formation in a subject (e.g., a heterotopic ossification diseases). In another aspect, the methods described herein provide a method for treating anemia associated with iron imbalance. In another aspect, the methods described herein provide a method for treating MO. In one embodiment, the subject can be a mammal. In another embodiment, the mammal can be a human, although the approach is effective with respect to all mammals. The method comprises administering to the subject an effective amount of a pharmaceutical composition comprising a compound of Formula I, Formula II, or Formula III, or of Compounds 1-7, BCX9250, or INCB00928 or a pharmaceutically acceptable salt thereof.

The dosage range for the agent depends upon the potency, and includes amounts large enough to produce the desired effect, e.g., reduction in at least one symptom of abnormal bone formation, increase in serum iron, increase in transferrin saturation, increase in reticulocyte hemoglobin, increase in iron bioavailability, mobilization of iron from storage tissues, increase in functional red blood cells, reduction in hepcidin, or reduction in osteochondroma size, number, or the formation of new osteochondroma. The dosage should not be so large as to cause unacceptable adverse side effects. Generally, the dosage will vary with the type of inhibitor and with the age, condition, and sex of the patient. The dosage can be determined by one of skill in the art and can also be adjusted by the individual physician in the event of any complication. Typically, the dosage ranges from 0.1 mg/kg body weight to 1 g/kg body weight. In some embodiments, the dosage range is from 0.1 mg/kg body weight to 1 g/kg body weight, from 0.1 mg/kg body weight to 500 mg/kg body weight, from 0.1 mg/kg body weight to 250 mg/kg body weight, from 0.1 mg/kg body weight to 100 mg/kg body weight, from 0.1 mg/kg body weight to 50 mg/kg body weight, from 0.1 mg/kg body weight to 10 mg/kg body weight, from 0.1 mg/kg body weight to 5 mg/kg body weight, from 0.1 mg/kg body weight to 1 mg/kg body weight, from 1 mg/kg to 100 mg/kg, from 5 mg/kg to 100 mg/kg, from 10 mg/kg to 100 mg/kg, from 15 mg/kg to 100 mg/kg, from 20 mg/kg to 100 mg/kg, from 25 mg/kg to 100 mg/kg, from 30 mg/kg to 100 mg/kg, from 40 mg/kg to 100 mg/kg, from 50 mg/kg to 100 mg/kg, from 60 mg/kg to 100 mg/kg, from 70 mg/kg to 100 mg/kg, from 75 mg/kg to 100 mg/kg, from 25 mg/kg to 50 mg/kg, from 50 mg/kg to 200 mg/kg, from 75 mg/kg to 250 mg/kg, from 100 mg/kg to 300 mg/kg, from 100 mg/kg to 200 mg/kg, from 100 mg/kg to 400 mg/kg, from 100 mg/kg to 500 mg/kg, from 100 mg/kg to 750 mg/kg from 200 mg/kg to 1000 mg/kg, from 300 mg/kg to 1000 mg/kg, from 400 mg/kg to 1000 mg/kg, from 500 mg/kg to 1000 mg/kg, from 600 mg/kg to 1000 mg/kg, from 700 mg/kg to 1000 mg/kg, from 800 mg/kg to 1000 mg/kg, from 900 mg/kg to 1000 mg/kg, from 250 mg/kg to 750 mg/kg, from 300 mg/kg to 600 mg/kg, or any range there between.

In certain embodiments, the dose of the agent is at least 0.1 mg/kg/day; in other embodiments the dose of the agent is at least 1 mg/kg/day, at least 10 mg/kg/day, at least 20 mg/kg/day, at least 25 mg/kg/day, at least 30 mg/kg/day, at least 40 mg/kg/day, at least 50 mg/kg/day, at least 60 mg/kg/day, at least 70 mg/kg/day, at least 80 mg/kg/day, at least 90 mg/kg/day, at least 100 mg/kg/day, at least 125 mg/kg/day, at least 150 mg/kg/day, at least 175 mg/kg/day, at least 200 mg/kg/day, at least 250 mg/kg/day, at least 300 mg/kg/day, at least 400 mg/kg/day, at least 500 mg/kg/day or more.

In some embodiments, the dosage range of the agent for use in a human subject is from 1 mg/day to 500 mg/day, from 1 mg/day to 450 mg/day, from 1 mg/day to 350 mg/day, from 1 mg/day to 300 mg/day, from 3 mg/day to 250 mg/day, from 5 mg/day to 250 mg/day, from 10 mg/day to 250 mg/day, from 15 mg/day to 200 mg/day, from 20 mg/day to 200 mg/day, from 25 mg/day to 200 mg/day, from 25 mg/day to 175 mg/day, from 25 mg/day to 150 mg/day, from 25 mg/day to 125 mg/day, from 25 mg/day to 100 mg/day, from 25 mg/day to 75 mg/day, from 25 mg/day to 50 mg/day, from 50 mg/day to 200 mg/day, from 75 mg/day to 200 mg/day, from 100 mg/day to 200 mg/day, from 125 mg/day to 200 mg/day, from 150 mg/day to 200 mg/day, from 175 mg/day to 200 mg/day, from 50 mg/day to 200 mg/day, from 50 mg/day to 175 mg/day, from 50 mg/day to 150 mg/day, from 50 mg/day to 100 mg/day, from 50 mg/day to 75 mg/day, from 75 mg/day to 200 mg/day, from 75 mg/day to 175 mg/day, from 75 mg/day to 150 mg/day, from 75 mg/day to 125 mg/day, from 75 mg/day to 100 mg/day, from 100 mg/day to 200 mg/day, from 100 mg/day to 175 mg/day, from 100 mg/day to 125 mg/day, from 125 mg/day to 200 mg/day, from 125 mg/day to 175 mg/day, from 125 mg/day to 150 mg/day, from 150 mg/day to 200 mg/day, from 150 mg/day to 175 mg/day, from 175 mg/day to 200 mg/day, or any range there between. In some embodiments, the dosage of the agent for use in a human subject is 1 mg/day, 3 mg/day, 5 mg/day, 10 mg/day, 15 mg/day, 20 mg/day, 25 mg/day, 30 mg/day, 35 mg/day, 40 mg/day, 45 mg/day, 50 mg/day, 75 mg/day, 100 mg/day, 125 mg/day, 150 mg/day, 175 mg/day, 200 mg/day, 225 mg/day, 250 mg/day, 275 mg/day, 300 mg/day, 325 mg/day, 350 mg/day, 375 mg/day, 400 mg/day, 425 mg/day, 450 mg/day, 475 mg/day, or 500 mg/day.

In one embodiment, the dose of a compound of Formula I, Formula II, or Formula III or of Compounds 1-7, BCX9250, or INCB00928 or a pharmaceutically acceptable salt thereof used in humans for the treatment of abnormal bone formation in soft tissue is less than the dose of the compound of Formula I, Formula II, or Formula III or of Compounds 1-7, BCX9250, or INCB00928 or a pharmaceutically acceptable salt thereof typically used in treatment of oncologic diseases and cancers.

Administration of the doses recited above can be repeated for a limited period of time. In some embodiments, the doses are given once a day, or multiple times a day, for example but not limited to three times a day. In another embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of a cancer (see "Efficacy Measurement" below). Such effective amounts can be gauged in clinical trials as well as animal studies for a given agent.

Agents useful in the methods and compositions described herein can be administered systemically or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art.

In some embodiments, the pharmaceutically acceptable formulation used to administer the active compound provides sustained delivery, such as "slow-release" of the active compound to a subject. For example, the formulation can deliver the agent or composition for at least one, two, three, or four weeks after the pharmaceutically acceptable formulation is administered to the subject. Preferably, a subject to be treated in accordance with the methods described herein is treated with the active composition for at least 30 days (either by repeated administration or by use of a sustained delivery system, or both).

As used herein, the term "sustained delivery" is intended to include continual delivery of the composition in vivo over a period of time following administration, preferably at least several days, a week, several weeks, one month or longer. Sustained delivery of the active compound can be demonstrated by, for example, the continued therapeutic effect of the composition overtime (such as sustained delivery of the agents can be demonstrated by continued improvement or maintained improvement in cancer symptoms in a subject).

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., tumor site). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood or skeletal muscle tissue in the ranges specified for in vivo therapies are contemplated.

Efficacy Measurement

The efficacy of a given treatment for a disorder comprising abnormal bone growth or anemia associated with iron imbalance as described herein can be determined by the skilled clinician. However, a treatment is considered "effective treatment," as the term is used herein, if any one or all of the signs or symptoms of the disease or disorder is/are altered in a beneficial manner (e.g., reduced ossification, regression of abnormal bone growths, reduced pain, increased range of motion etc. for a disorder comprising abnormal bone growth, reduced number, the size, or growth of an osteochondroma for MO, or increased serum iron, increased transferrin saturation, increased reticulocyte hemoglobin, increased iron bioavailability, increased red blood cells, or decreased hepcidin for anemia associated with iron imbalance), other clinically accepted symptoms or markers of disease are improved, or even ameliorated, e.g., by at least 10% following treatment with an agent comprising one or more compounds described herein. Efficacy can also be measured by failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of abnormal bone growth; or (2) relieving the disease, e.g., causing regression of symptoms; and (3) preventing or reducing the likelihood of the development of a disease (e.g., ossification following trauma).

An effective amount for the treatment of a disease means that amount which, when administered to a mammal in need thereof, is sufficient to result in effective treatment as that term is defined herein, for that disease. Efficacy of an agent can be determined by assessing physical indicators of abnormal bone growth, such as e.g., reduced size of abnormal bone growth, slowed deposition of abnormal bone, regression of bone growth, improvement in mobility etc. Efficacy for the treatment of anemia can be determined by assessing parameters such as increased serum iron, increased transferrin saturation, increased reticulocyte hemoglobin, increased iron bioavailability, increased red blood cells, or decreased hepcidin. Efficacy for the treatment of MO can be determined by assessing parameters such as reduced number of osteochondromas, reduced size of osteochondromas, or reduced growth of an osteochondroma.

Pharmaceutical Compositions

In certain embodiments, the present invention relates to pharmaceutical compositions comprising a compound of Formula I, Formula II, or Formula III or of Compounds 1-7, BCX9250, or INCB00928 or a pharmaceutically acceptable salt thereof and one or more pharmaceutically acceptable excipients, as well as formulations prepared using such a compound and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient. In certain embodiments, the invention also relates to preparations suitable for nutraceutical, veterinary, and agriculturally-relevant uses.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage will vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The pharmaceutical compositions are administered in a manner compatible with the dosage formulation and in such amount as is therapeutically effective to result in an improvement or remediation of symptoms. The pharmaceutical compositions are administered in a variety of dosage forms, e.g., intravenous dosage forms, subcutaneous dosage forms, and oral dosage forms (e.g., ingestible solutions, drug release capsules). Pharmaceutical compositions that include an ALK2 inhibitor of the invention may be administered to a subject in need thereof, for example, one or more times (e.g., 1-10 times or more) daily, weekly, biweekly, monthly, bimonthly, quarterly, biannually, annually, or as medically necessary. Dosages may be provided in either a single or multiple dosage regimens. The timing between administrations may decrease as the medical condition improves or increase as the health of the patient declines.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues, or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an eye drop, through ophthalmic mucous membrane administration.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups, and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams, or spray formulations containing such carriers as are known in the art to be appropriate.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions, and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-30% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, or other metal salts.

The pharmaceutically acceptable acid addition salts can also exist as various solvates, such as with water, methanol, ethanol, dimethylformamide, dimethylsulfoxide, and the like. Mixtures of such solvates can also be prepared. The source of such solvate can be from the solvent of crystallization, inherent in the solvent of preparation or crystallization, or adventitious to such solvent. In some embodiments, a solvate of a disclosed compound can be a dimethylsulfoxide solvate.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention and are not intended to limit the invention.

EXAMPLES

Example 1—Effect of the Compound of Formula I-11 on Serum Iron, Transferrin Saturation, Reticulocyte Hemoglobin, and Serum Hepcidin in Human Subjects Subject Eligibility:

A total of 131 healthy, males aged 18 to 60 years and post-menopausal females aged 45 to 60 years, participated in this study.

Study Design:

The primary objectives of this study were to a) evaluate safety and tolerability of escalating doses of the compound of Formula I-11 administered as single and multiple oral doses in healthy male volunteers and healthy postmenopausal female volunteers and b) evaluate the PK parameters following escalating doses of the compound of Formula I-11 administered as single and multiple oral doses. The secondary objective of this study was to evaluate the pharmacodynamic (PD) parameters following escalating doses of the compound of Formula I-11 administered as single and multiple oral doses. This study was conducted in two parts.

Part 1, Single-ascending dose (SAD) Cohorts:

Part 1 included 80 participants (10 cohorts of 8 participants each). Male and female participants who met the eligibility criteria were randomly assigned, in a ratio of 3:1 to receive the compound of Formula I-11 or matching placebo, N=6 and 2 per dose cohort, respectively. Participant enrollment included 81.5% males and 12.5% females (post-menopausal). The IMP formulation used in Cohorts 1 through 6 was an oral capsule (doses of 1, 3, 10, 30, 100, or 300 mg capsule formulation). An oral liquid formulation was evaluated in Cohorts 7 through 10 (doses of 30, 100, 300 or 450 mg liquid formulation).

Participants in Part 1 received a single oral dose of the compound of Formula I-11 or placebo on Day 1 and serial PK samples were collected. Baseline assessments were performed on day −1 prior to dosing. Samples were collected for determination of pharmacodynamic parameters at pre-dose daily and up to 24 hours post dose (day 2) after a single oral dose of the compound of Formula I-11. Participants remained at the study site for observation for 24 hours post-dose through the PK sample collection on Day 2. Participants returned to the site for the 48, 72, and 120-hour post-dose sample collection on Days 3, 4, and 6. Safety was evaluated by a Safety Review Committee prior to escalation to the next dose level cohort.

Part 2, Multiple-ascending dose (MAD) Cohorts:

Part 2, Cohorts 1 through 4, included 41 participants (4 cohorts of 10 participants each and 1 additional placebo participant in Cohort 1). Male and female participants who met the eligibility criteria were randomly assigned at a ratio of 4:1 to receive either the compound of Formula I-11 oral liquid formulation or matching placebo, N=8 and 2 per dose cohort respectively. Forty (97.6%) males and 1 (2.4%) female (placebo) participant were enrolled.

Participants in Part 2, Cohorts 1 through 3, received a daily oral dose of the compound of Formula I-11 (50, 100, or 200 mg liquid formulation respectively) or placebo for 7 days. A daily oral dose of the compound of Formula I-11 or placebo in participants in Part 2, Cohort 4 (350 mg liquid formulation) was planned for 14 days but was discontinued early in all subjects, either by the Investigator because of AEs, or by the Sponsor. A decision was made by the Sponsor to discontinue dosing of the entire cohort based on the frequency of AEs and laboratory abnormalities after Day 9. In Cohort 4, participants on the compound of Formula I-11 received daily oral dosing of 350 mg for up to 7 days; one placebo participant received daily oral dosing for 9 days. Samples were collected for determination of pharmacodynamic parameters at pre-dose daily and to 24 hours post dose (day 8) while on drug. Daily trough PK samples were collected for the determination of steady-state from Day 2 to Day 12 or 13. Participants returned to the site on Day 30 for an end-of-study visit. Safety was evaluated by a Safety Review Committee prior to escalation to the next dose level cohort.

Part 2, MAD Cohort 5 (C5) participants received either the compound of Formula I-11, 100 mg (n=8) or placebo (n=2) on Days 1, 2, 3, 4, 5, 6, 7. The last dose was administered on the morning of Day 7. Serial PK sample collection for the determination of steady-state concentrations of the compound of Formula I-11 was done at pre-dose and up to 24 hours post-dose, beginning on Day 1, 4 and 7. Participants returned for follow-up visits on or 17, and Day 30 for an end-of-study visit.

Assessments and Endpoints:

Pharmacodynamic endpoints: Protocol-specified endpoints were assessed at baseline and regularly throughout the study period. These assessments included measurements of serum iron, transferrin saturation (calculated as serum iron/total iron-binding capacity), serum ferritin, serum hepcidin, and reticulocyte hemoglobin content, serum cholesterol, LDL, and HDL cholesterol. Measurements of all pharmacodynamic end points were made using standard clinical laboratory tests. Hepcidin analysis was performed using an ELISA kit from Intrinsic LifeSciences (Intrinsic Hepcidin IDx™ ELISA kit).

Statistical Methods

The sample size for this study was sufficient to evaluate safety, tolerability, and PK based on clinical considerations.

Results

The compound of Formula I-11 was well tolerated at dose levels up to 450 mg as a single dose, and up to 200 mg after 7 daily doses. There were no serious adverse events in either Part 1 or Part 2 of the study. In Part 1, 3 subjects discontinued the study; none discontinued due to AEs. In Part 2, 10 of 40 (25%) participants administered the compound of Formula I-11 and 1 of 11 (9.1%) participants administered placebo discontinued the study due to AEs. AEs that led to study drug discontinuation in three or more participants in the groups treated with the compound of Formula I-11 included lymphopenia and chills. In Part 2, 1/8 subjects administered 200 mg and 4/8 subjects administered 350 mg discontinued study drug due to AEs. The majority of AEs observed in subjects treated with the compound of Formula I-11 were mild or moderate in severity; severe AEs were reported in 1 of 8 (12.5%) participants in the 350 mg and 100 mg (Cohort 5) dose groups. AEs reported in ≥2 subjects treated with the compound of Formula I-11 and higher than placebo were: headache, nausea, vomiting, diarrhea, gastroenteritis, chills, pyrexia, myalgia, decreased appetite, lymphopenia, neutropenia, abdominal discomfort, abdominal pain (upper), dizziness, fatigue, rhinorrhea, tonsillitis, and liver enzyme increases. At the 200 mg dose 2/7 subjects, and at the 350 mg dose 7/8 subjects, had decreases in lymphocyte count below normal. Decreases in neutrophil count were also observed at 200 mg and 350 mg. Increases in ALT >2×ULN occurred in 3 subjects; these were not dose-related.

Mean AUC and $C_{max}$ of the compound of Formula I-11 increased linearly with greater than dose-proportional increases across multiple doses from 50-200 mg. Half-life values ranged from approximately 10 to 15 hours. Once-daily oral administration of the compound of Formula I-11 over 7 days resulted in robust decreases in baseline hepcidin when compared to placebo. The effect was similar at 50 mg, 100 mg, and 200 mg (hepcidin was not measured at 350 mg or in SAD cohorts) (FIG. 1). Cohort 5 demonstrated a decrease in hepcidin as early as 4 hours after administration of the first dose. These effects are consistent with inhibition of ALK2 signaling. The limited sampling scheme, variability of baseline serum hepcidin concentrations at Day 1, or limited dynamic range given the normally low baseline hepcidin levels seen in healthy participants may have precluded observation of dose- or exposure-related differences in hepcidin response. The timing of the effect of the compound of Formula I-11 on hepcidin was consistent with the observed $C_{max}$ of the compound of Formula I-11 at 6 hours post dose.

Figure 2A:
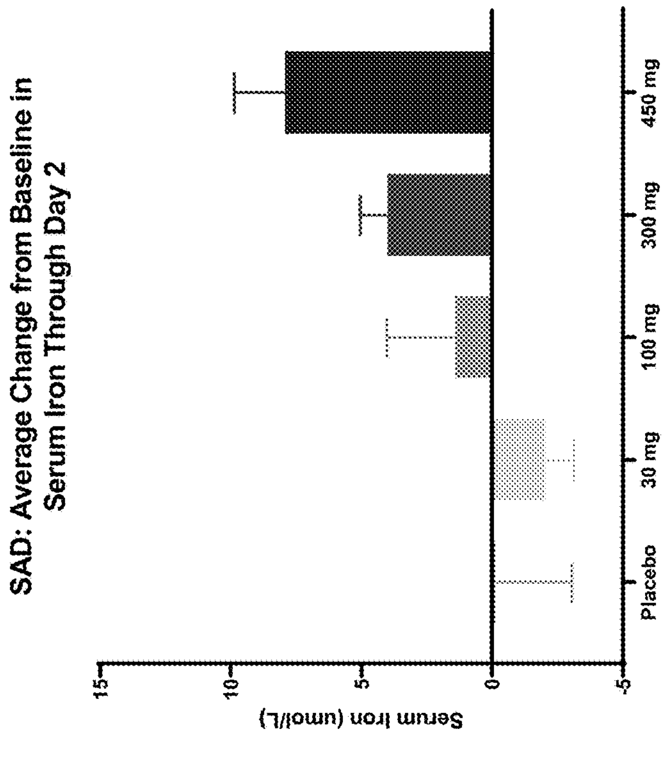
FIGS. 2A-2B are a series of graphs showing the effect of the compound of Formula I-11 on serum iron in healthy volunteers. Following single (SAD) or once-daily (MAD) oral administration to healthy participants, the compound of Formula I-11 elicited rapid, robust, and sustained dose-related increases in serum iron (FIGS. 2A-2B). Peak effect following a single dose was observed on Day 2, 24 hours post-dose, while serum iron increases were sustained in the multiple dose regimen, with peak serum iron concentrations typically observed on Day 3 or 4 of treatment. In some participants exhibiting large PD effects, serum iron concentrations had returned to baseline or below by Day 7.
Figure 2B:
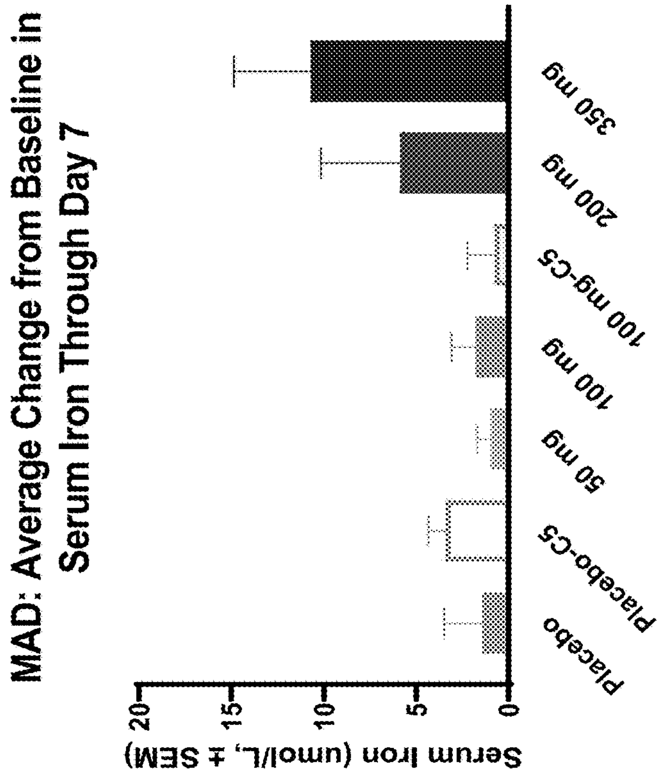
Figure 3B:
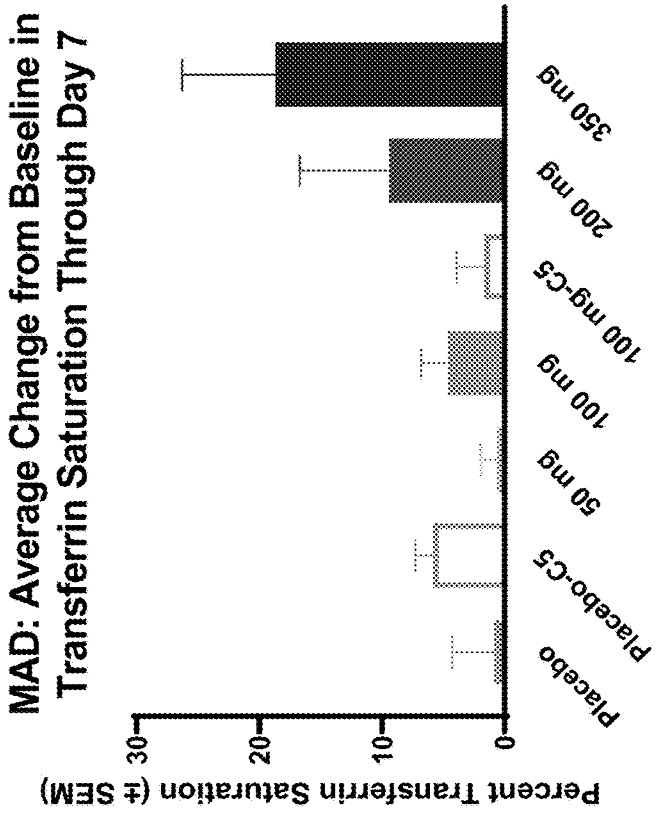
FIGS. 3A-3B are a series of graphs showing the effect of the compound of Formula I-11 on transferrin saturation (TSAT) in healthy volunteers. Administration of single (SAD) or repeated (MAD) oral doses of the compound of Formula I-11 produced robust changes in transferrin saturation. Consistent with observed changes in serum iron, administration of single or repeated oral doses of the compound of Formula I-11 produced robust changes in transferrin saturation. Single doses of 30 mg of the compound of Formula I-11 in the liquid formulation (FIG. 3A), and once-daily doses of 50 mg (FIG. 3B), were not substantially different from placebo in observed PD response; however, single or repeated doses of 100 mg or above produced sustained, dose-related increases in transferrin saturation.
Figure 3A:
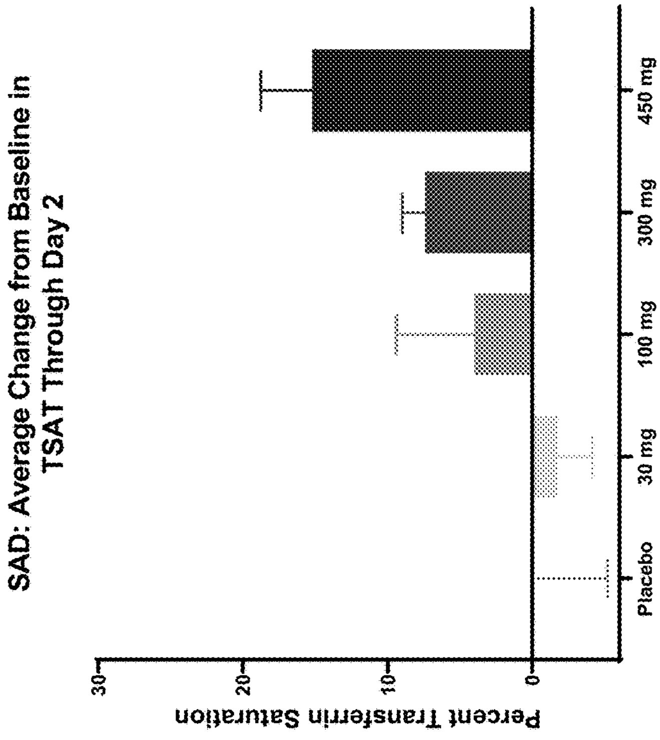

Administration of the compound of Formula I-11 resulted in dose-related increases in serum iron and transferrin saturation that were associated with decreases in hepcidin. Following single or once-daily oral administration to healthy participants, the compound of Formula I-11 elicited rapid, robust, and sustained dose-related increases in serum iron (FIGS. 2A-2B). Increases in serum iron were observed beginning on Day 2 after single doses. Peak effect following a single dose was observed on Day 2, 24 hours post-dose, while serum iron increases were sustained in the multiple dose regimen, with peak serum iron concentrations typically observed on Day 3 or 4 of treatment. In some participants exhibiting large PD effects on Day 4, serum iron concentrations had returned to baseline or below by Day 7, suggesting large mobilization of iron stores (e.g., mobilization of tissue iron). The mean change from baseline (μM/L), on Day 4 following administration of multiple ascending doses was 1.48, 0.59, 5.11, and 17.71, respectively, vs. 1.4 in placebo. Consistent with observed changes in serum iron, administration of single or repeated oral doses of the compound of Formula I-11 produced robust changes in transferrin saturation (FIGS. 3A-3B). Single doses of 30 mg of the compound of Formula I-11 in the liquid formulation, and once-daily doses of 50 mg of the compound of Formula I-11, were not substantially different from placebo in observed PD response; however, single or repeated doses of 100 mg or above produced sustained, dose-related increases in transferrin saturation. The mean percent change from baseline (μM/L) in transferrin saturation on Day 4 following administration of multiple ascending doses was 1.6%, 1.5%, 7.5%, and 30.1%, respectively, vs. 0.3% in placebo.

Figure 4B:
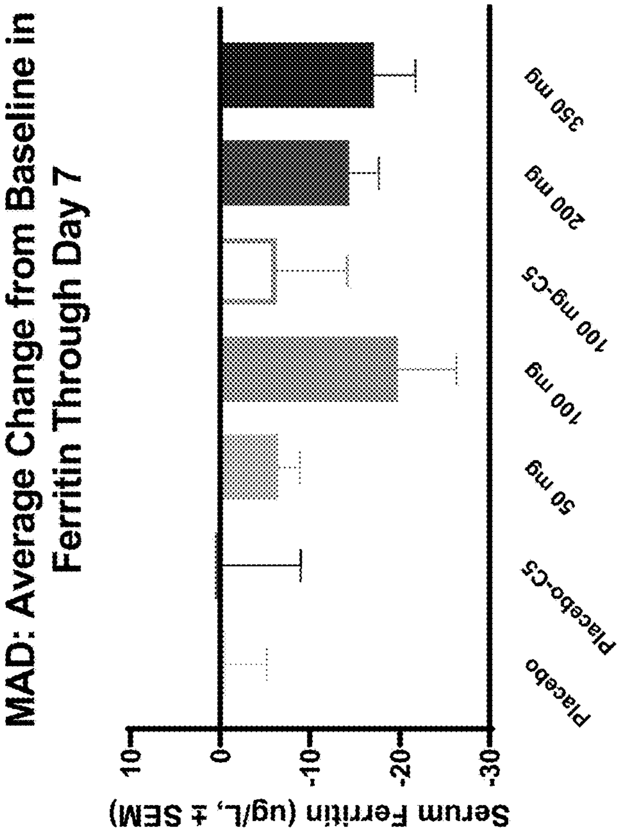
FIGS. 4A-4B are a series of graphs showing the effect of the compound of Formula I-11 on serum ferritin levels in healthy volunteers. While single doses of the compound of Formula I-11 were sufficient to produce a similar magnitude of effect in terms of serum iron and transferrin saturation change from baseline, the effect on serum ferritin was observed only after multiple doses (FIG. 4A). Upon administration of the compound of Formula I-11 in MAD cohort participants, decreases were observed in serum ferritin, indicating mobilization of iron stores (FIG. 4B).
Figure 4A:
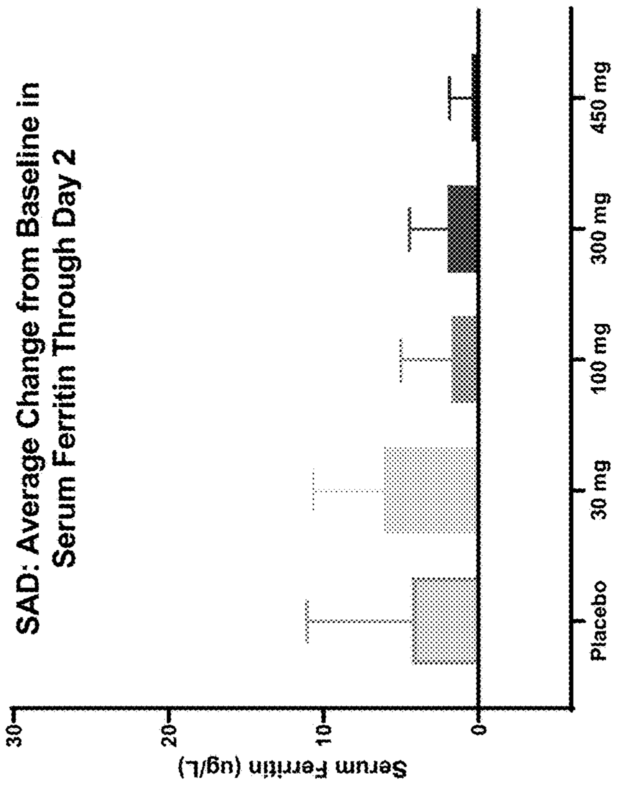

The increases in serum iron and transferrin saturation were followed by expected decrease in ferritin, consistent with mobilization of iron stores (e.g., mobilization of tissue iron into serum). While single doses of the compound of Formula I-11 were sufficient to produce a similar magnitude of effect in terms of serum iron and transferrin saturation change from baseline, the effect on serum ferritin was observed only after multiple doses (FIG. 4A). Administration of the compound of Formula I-11 in MAD cohort participants led to decreases in serum ferritin, indicating mobilization of iron stores (FIG. 4B).

Figure 5:
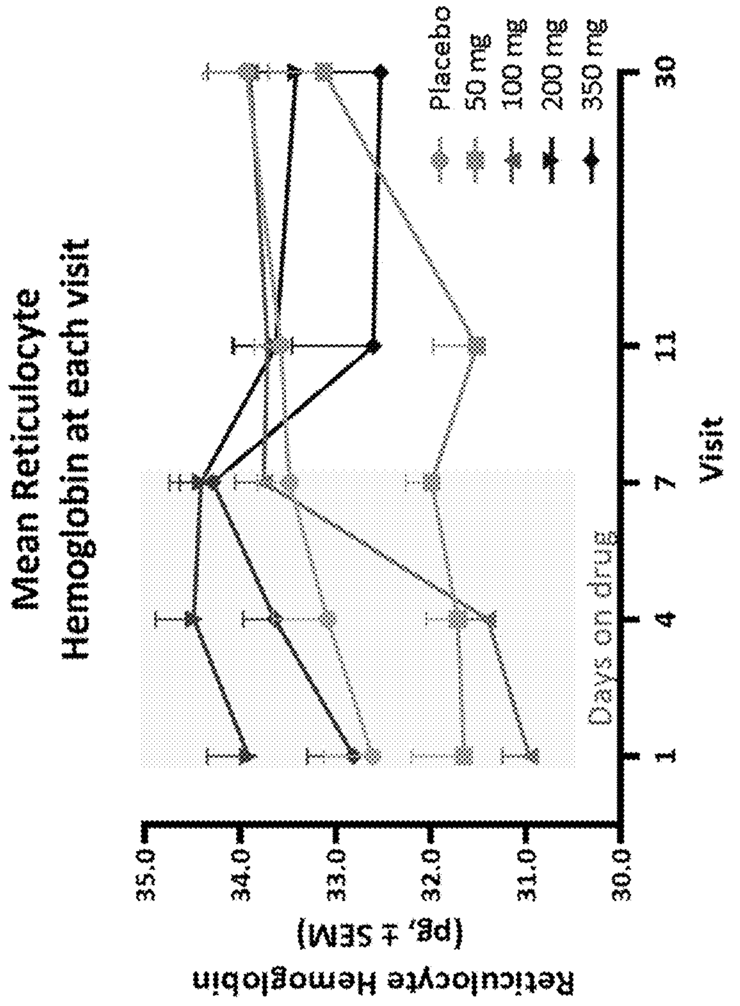
FIG. 5 is a graph showing the effect of multiple ascending doses of the compound of Formula I-11 on reticulocyte hemoglobin content. Repeated administration of the compound of Formula I-11 was associated with increases over baseline in the hemoglobin content of reticulocytes, an indicator of increased iron availability in bone marrow.

Repeated administration of the compound of Formula I-11 was also associated with increases over baseline in the hemoglobin content of reticulocytes, an indicator of increased iron availability in bone marrow (FIG. 5). An increase in reticulocyte hemoglobin content in MAD cohorts 1-4 was observed starting on day 4 post-dosing. Participants enrolled in this study had baseline reticulocyte hemoglobin content at the higher end of the normal range, which likely limited the ability to see a response at some doses. The magnitude of reticulocyte hemoglobin increase appeared to be more pronounced in the cohorts with less saturated reticulocyte hemoglobin content at baseline. Peak increase in reticulocyte hemoglobin content was seen at day 7, which is consistent with the timing of erythropoiesis induction and incorporation of iron into hemoglobin in the bone marrow. This supports a mechanism of action of the compound of Formula I-11 in increasing iron mobilization and availability (e.g., at the erythroblastic island) leading to its subsequent incorporation into hemoglobin in red blood cells.

Figure 6:
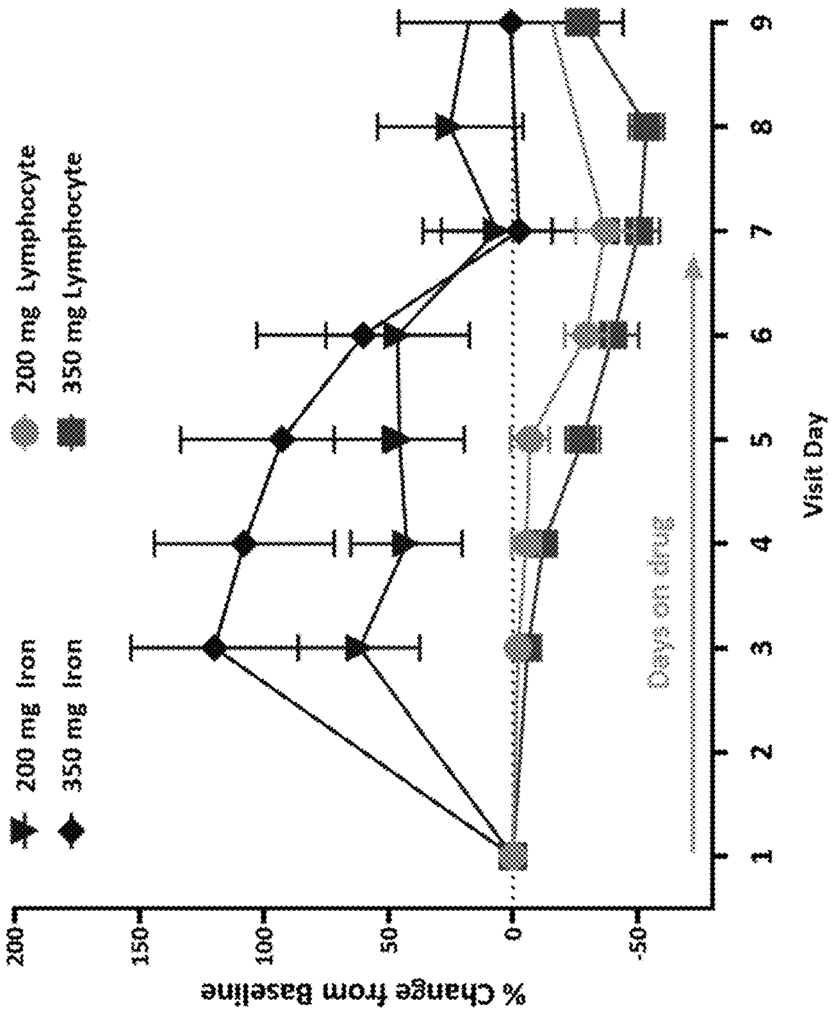
FIG. 6 is a graph showing the effect of multiple ascending doses of the compound of Formula I-11 on changes in lymphocytes and its association with serum iron levels. Onset of lymphopenia (% change in lymphocytes) was seen starting at day 5 post dose coinciding with the decline in serum iron levels (% change in serum iron). This lymphopenia was reversible and rapidly resolved after the treatment period ended.
Figure 7:
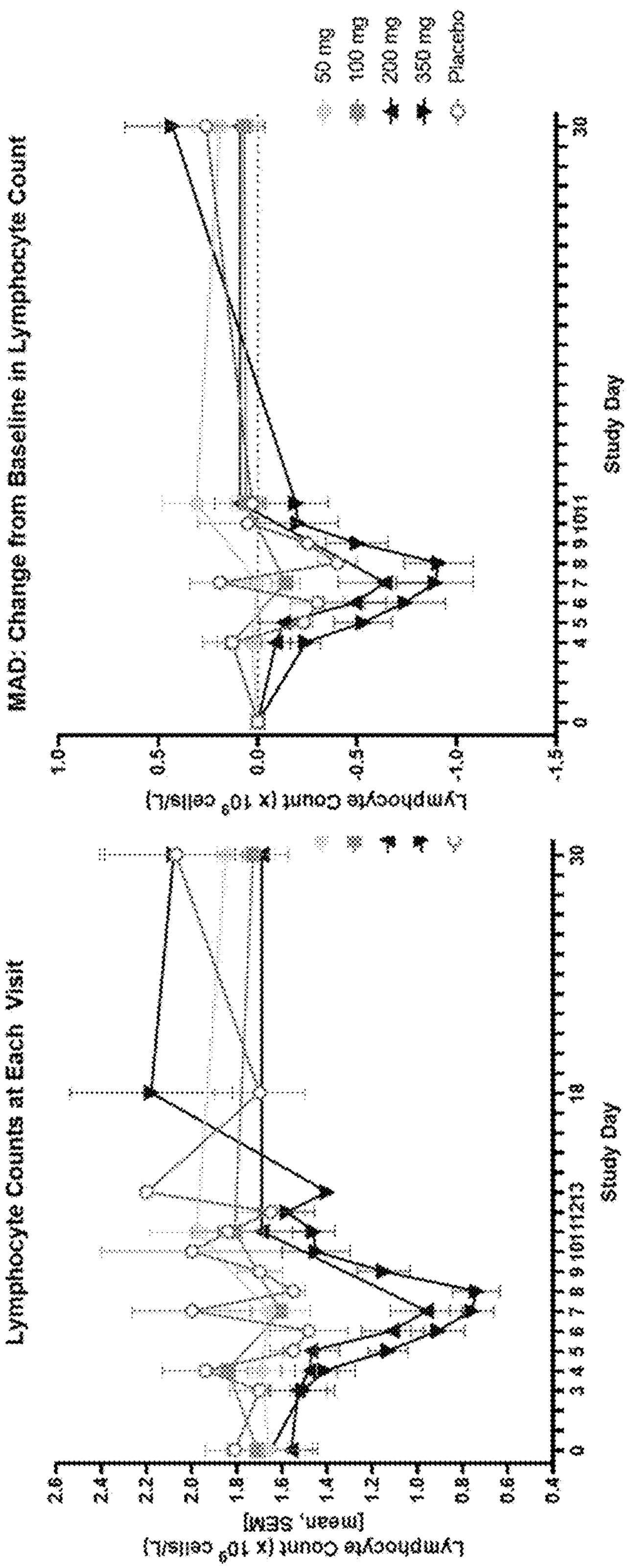
FIG. 7 is a series of graphs showing the effect of the compound of Formula I-11 on lymphocyte numbers. Repeated oral administration of the compound of Formula I-11 led to decreases in lymphocyte counts and development of lymphopenia. Decreases in lymphocyte counts were observed starting at day 5 post treatment, with lymphopenia (defined as lymphocyte counts <$1.0\times10^9$ cells/L) developing day 6 onward. Decreases were seen at the higher doses. These changes were reversible and lymphocyte counts returned to pre drug levels after the treatment period.
Figure 8B:
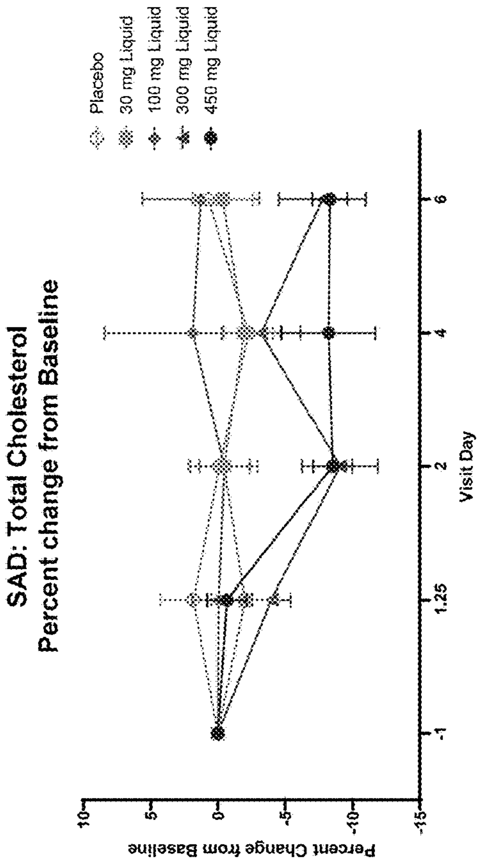
FIGS. 8A-8D are a series of graphs showing the effect of the compound of Formula I-11 on cholesterol. Single (FIGS. 8A-8B) or repeated (FIGS. 8C-8D) oral administration (Cohorts 1-4) of the compound of Formula I-11 led to decreases in total cholesterol, which were observed within 24 hours in the SAD cohorts and across the one-week dosing period in MAD cohorts.
Figure 8A:
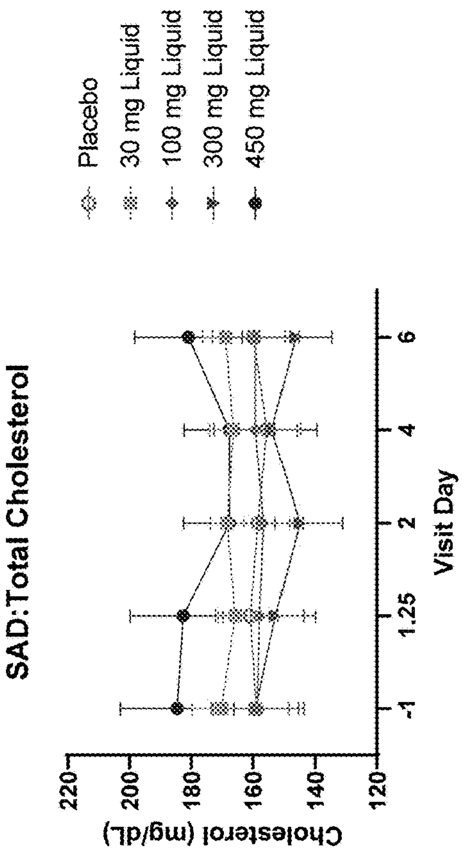
Figure 8C:
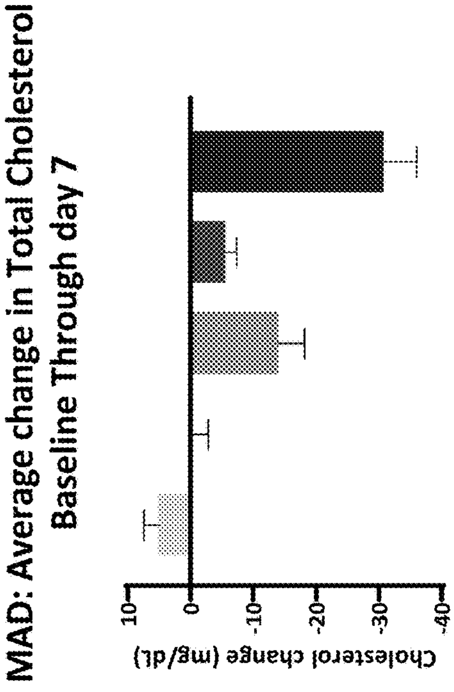
Figure 8D:
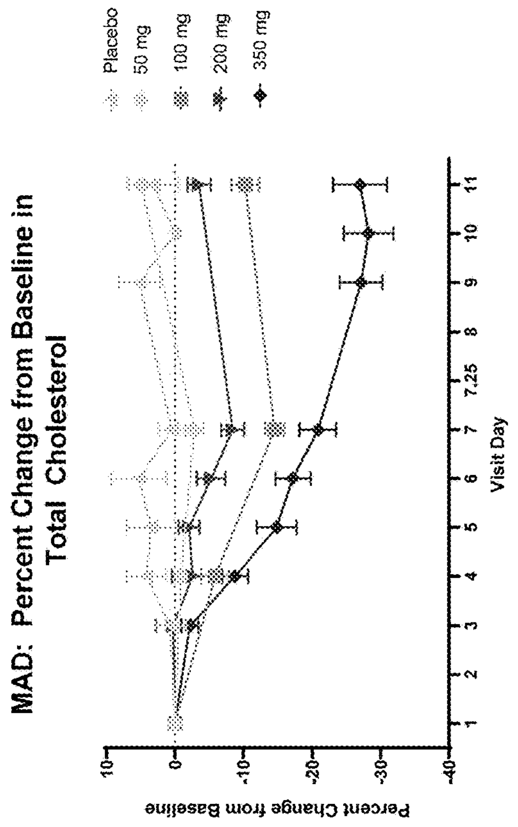

Repeated oral administration of the compound of Formula I-11 was also associated with changes in lymphocytes. Decreases in lymphocyte counts were observed starting at day 5 post treatment, with lymphopenia (defined as lymphocyte counts <1.0×$10^9$ cells/L) developing day 6 onward (FIG. 7). Decreases were seen at the higher doses. Onset of lymphopenia (% change in lymphocytes) was seen starting at day 5 post dose coinciding with the decline in serum iron levels (% change in serum iron) (FIG. 6). The lymphopenia was reversible and rapidly resolved after the treatment period ended, which lymphocyte counts returning to pre drug levels after the treatment period. Lymphopenia may be related to tissue iron depletion. Lymphopenia was observed in participants who had a large increase in serum iron by Day 4 that was not sustained through Day 7, and the onset of lymphopenia coincided with timing of loss of iron mobilization by the compound of Formula I-11. These participants also had a reduction in the hemoglobin content of reticulocytes suggestive of lower availability of iron in the bone marrow. Participants who had an increase in serum iron that was sustained through Day 7 did not develop lymphopenia. The dose-related decreases in lymphocytes observed following peak increases in serum iron at the highest doses are suggestive of excessive mobilization and subsequent depletion of iron.

Single or repeated oral administration (Cohorts 1-4) of the compound of Formula I-11 also led to decreases in total cholesterol, which were observed within 24 hours in the SAD cohorts and across the one-week dosing period in MAD cohorts (FIGS. 8A-8D).

Example 2—Effect of the Compound of Formula I-42 on Serum Iron, Hepcidin, Red Blood Cell Count, Hemoglobin, Hematocrit, and Reticulocyte Hemoglobin Content in a Mouse Model of Chronic Kidney Disease To induce chronic kidney disease (CKD), 6-week-old C57Bl/6 mice were dosed daily via PO administration with 50 mg/kg of adenine or vehicle. After six weeks of adenine administration, a representative group of mice were taken down and tested to confirm anemia. Concomitantly, the remainder of the CKD mice began dosing with either vehicle or the compound of Formula I-42 5 mg/kg PO daily. Mice were dosed with vehicle or the compound of Formula I-42 while still receiving daily adenine for 10 days. The study was terminated at 52 days and hematology (Heska, Element HT-5), serum hepcidin (Intrinsic Biosciences, Hepcidin Murine Compete), and serum iron (Bioassay Systems, QuantiChrom Kit) levels were assessed.

Figure 9A:
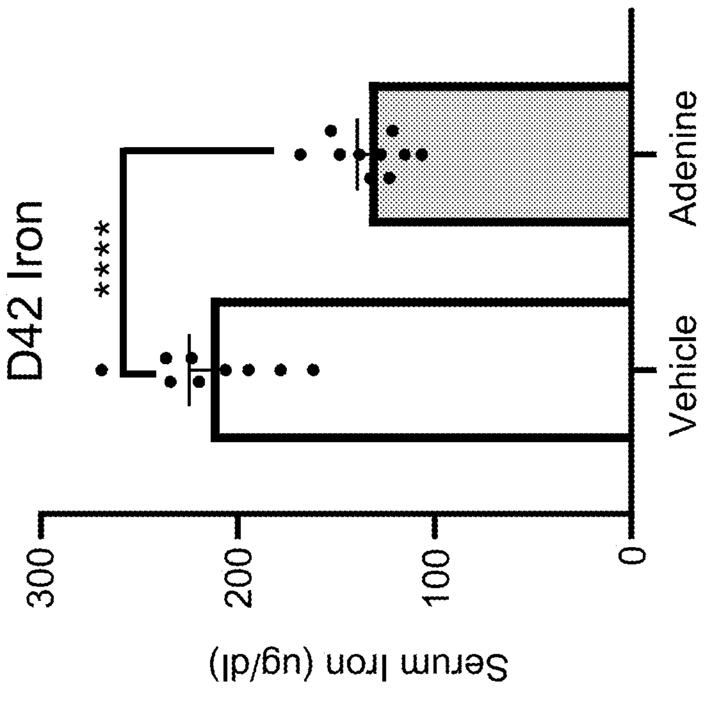
FIGS. 9A-9D are a series of graphs showing the effect of the compound of Formula I-42 on serum iron and serum hepcidin in a mouse model of chronic kidney disease (CKD). To induce CKD, 6-week-old C57Bl/6 mice were dosed daily via oral (PO) administration with 50 mg/kg of adenine or vehicle. After six weeks of adenine administration, a representative group of mice were taken down and tested to confirm anemia. At Day 42, adenine-induced kidney disease resulted in serum iron values 37.6% lower and serum hepcidin values 248.9% higher than vehicle treated mice (FIGS. 9A-9B). Concomitantly, the remainder of CKD mice began dosing with either vehicle or the compound of Formula I-42 5 mg/kg PO daily. Mice were dosed with vehicle or the compound of Formula I-42 while still receiving daily adenine for 10 days. The compound of Formula I-42 increased serum iron values 108.2% and reduced serum hepcidin values 85.4% after 10 days compared to vehicle treated mice receiving adenine and vehicle (FIGS. 9C-9B). *p≤0.05, p≤0.01, ** p≤0.0001 by two-way ANOVA. Data are shown as the mean±SEM.
Figure 9B:
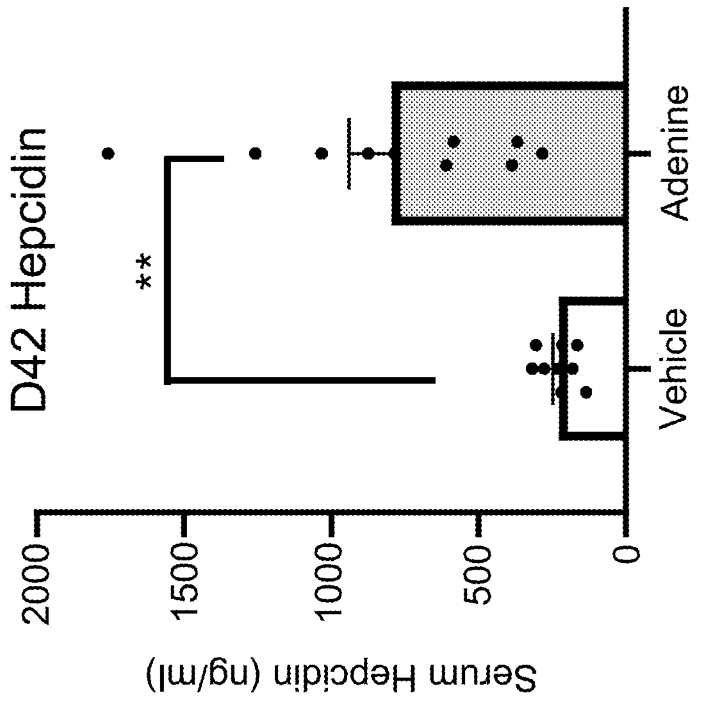
Figures 9C, 9D:
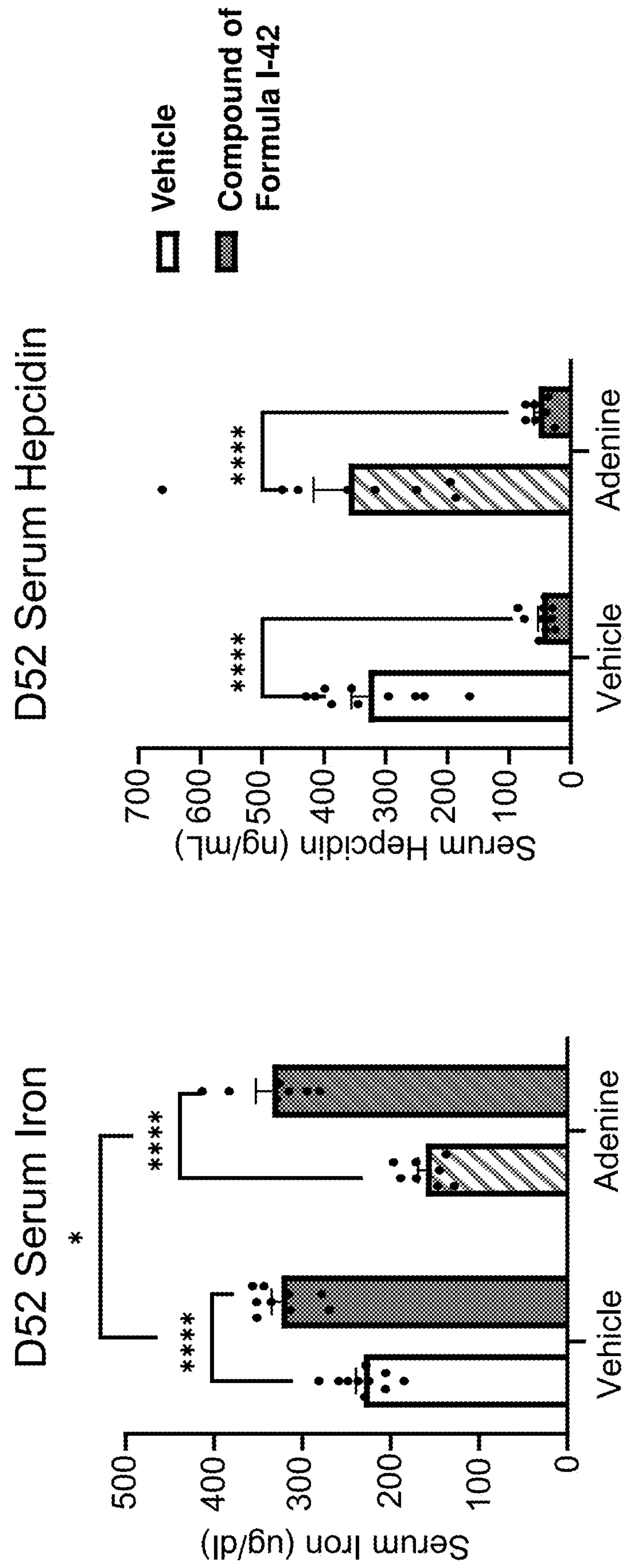
Figure 10A:
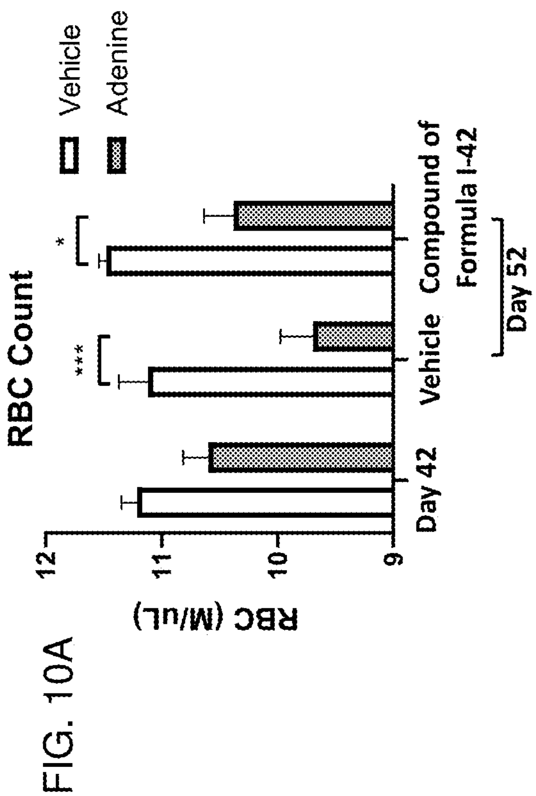
FIGS. 10A-10D are a series of graphs showing the effect of the compound of Formula I-42 on red blood cell count, hemoglobin, hematocrit, and reticulocyte hemoglobin content in a mouse model of chronic kidney disease (CKD). CKD was induced as described above and after six weeks of adenine administration, a representative group of mice were taken down and tested to confirm anemia. At Day 42, adenine-treated mice had reduced red blood cell count, hemoglobin, hematocrit, and reticulocyte hemoglobin content compared to vehicle treated mice (FIGS. 10A-10D, Day 42). Concomitantly, the remainder of CKD mice began dosing with either vehicle or the compound of Formula I-42 5 mg/kg PO daily. Mice were dosed with vehicle or the compound of Formula I-42 while still receiving daily adenine for 10 days. At study termination (Day 52), mice receiving adenine in combination with the compound of Formula I-42 had red blood cell counts, hemoglobin, hematocrit, and reticulocyte hemoglobin content that were 7.1%, 10.7%, 10.2% and 10.4% higher than the vehicle treated mice receiving adenine (FIGS. 10A-10D, Day 52). Data are shown as mean±SEM. Statistical analysis was performed using 2-way ANOVA with Tukey post test. * P±0.05, P<0.01, * P<0.001, and **** P<0.0001.
Figure 10B:
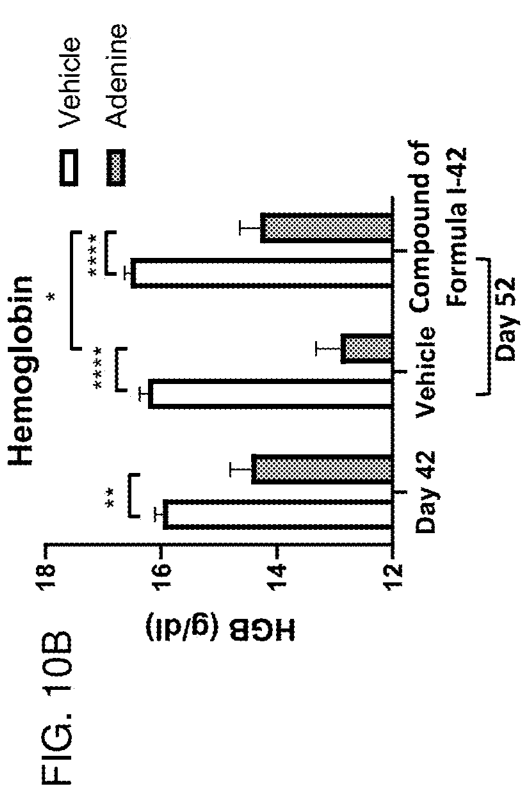
Figure 10C:
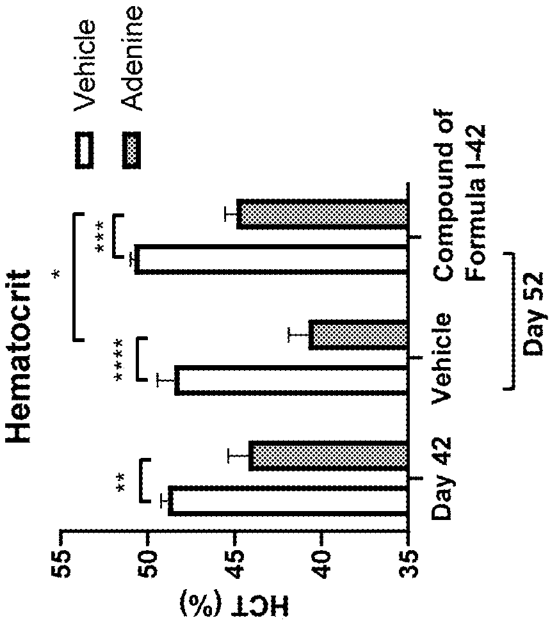
Figure 10D:
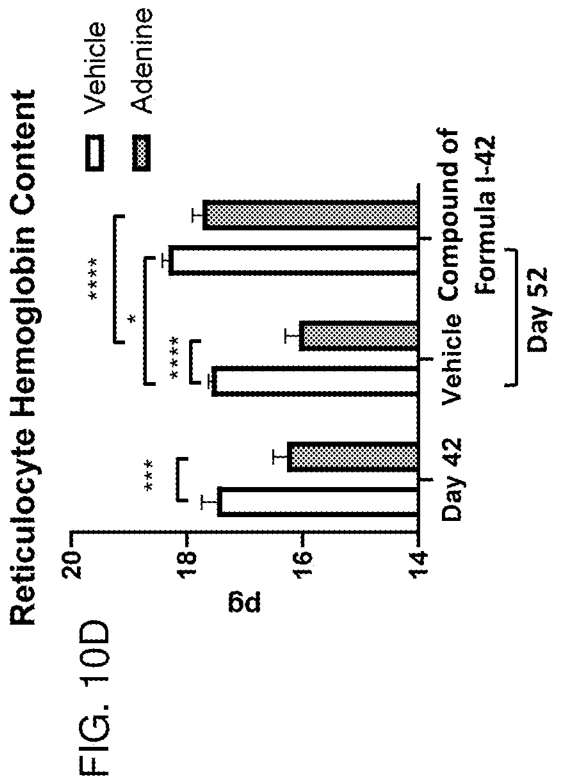

At Day 42, adenine-induced kidney disease resulted in serum iron values 37.6% lower and serum hepcidin values 248.9% higher than vehicle treated mice (FIGS. 9A-9B). The compound of Formula I-42 increased serum iron values 108.2% and reduced serum hepcidin values 85.4% after 10 days compared to the vehicle treated mice receiving adenine and vehicle (FIGS. 9C-9D). *$p \leq 0.05$, $p \leq 0.01$, **$p \leq 0.0001$ by two-way ANOVA. Data are shown as the mean±SEM. These data indicate that the compound of Formula I-42 can overcome low serum iron that results from increased hepcidin in a mouse model of chronic kidney disease.

At Day 42, adenine treated mice also had reduced red blood cell counts, hemoglobin, hematocrit, and reticulocyte hemoglobin content compared to vehicle-treated mice (FIGS. 10A-10D, Day 42). At study termination (Day 52), mice receiving adenine in combination with the compound of Formula I-42 had red blood cell counts, hemoglobin, hematocrit, and reticulocyte hemoglobin content that were 7.1%, 10.7%, 10.2% and 10.4% higher than the vehicle-treated mice receiving adenine (FIGS. 10A-10D, Day 52). Data are shown as mean±SEM. Statistical analysis was performed using 2-way ANOVA with Tukey post test. * $P \leq 0.05$, $P<0.01$, * $P<0.001$, and **** $P<0.0001$.

Example 3—Effect of the Compound of Formula I-42 on Serum Hepcidin and Hemoglobin in a Mouse Model of IRIDA To establish a murine model of IRIDA, eight-week-old male C57BL/6 mice were dosed intravenously with lipid encapsulated siRNA targeted against either Luciferase (control) or TMPRSS6 (0.75 mg/kg). Following confirmation of disease at day 8 post initial siRNA administration, once-daily oral dosing with the compound of Formula I-42 (5 mg/kg) or vehicle commenced. A second siRNA administration was given on day 10. Studies were terminated 18 days post initial siRNA administration. Hematological parameters, serum iron, and serum hepcidin were measured at the end of the study.

Figure 11A:
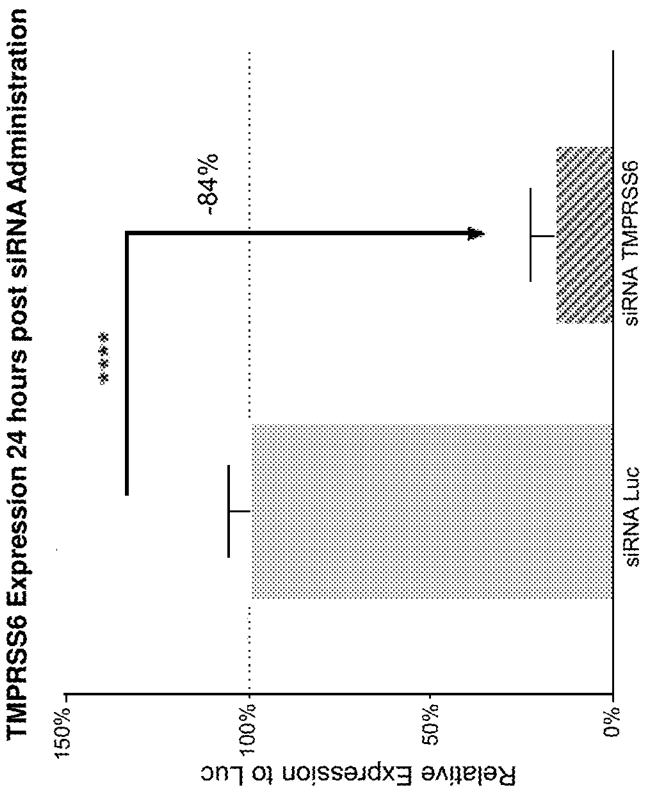
Figure 11B:
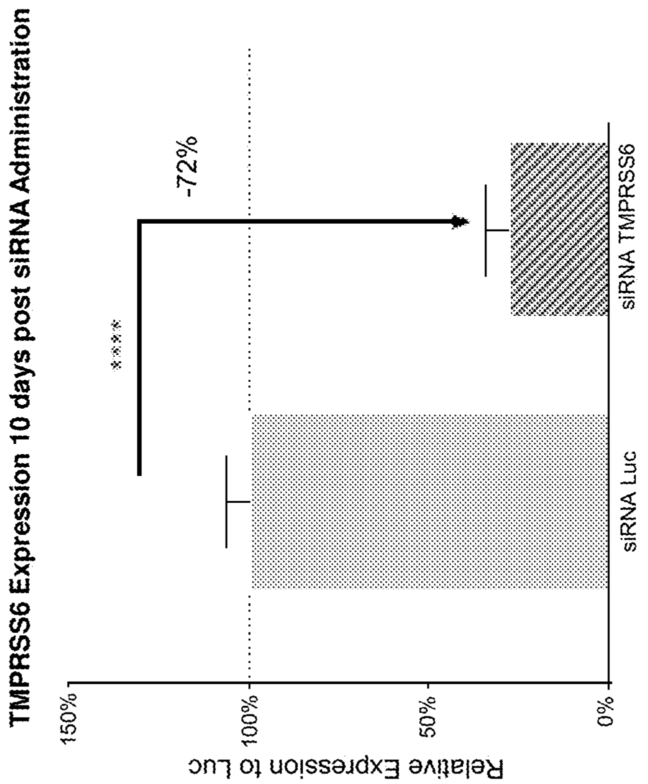
Figure 11C:
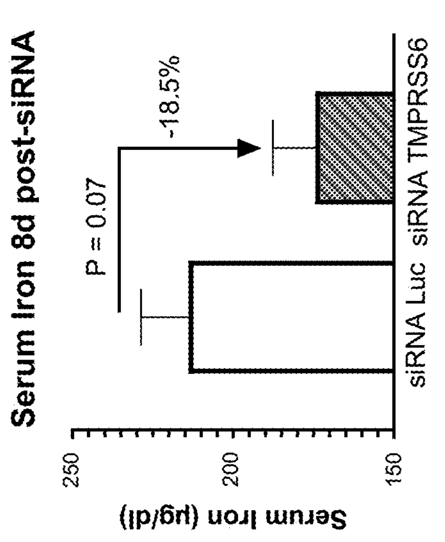
Figure 11D:
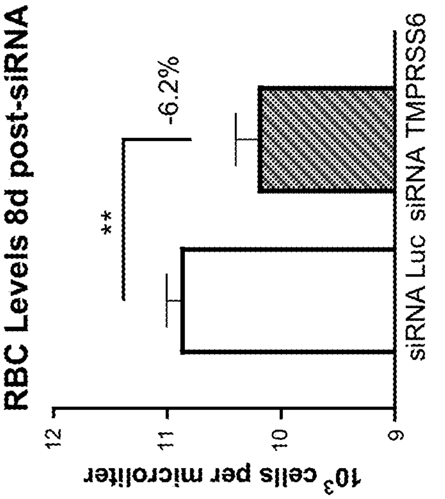
Figure 11E:
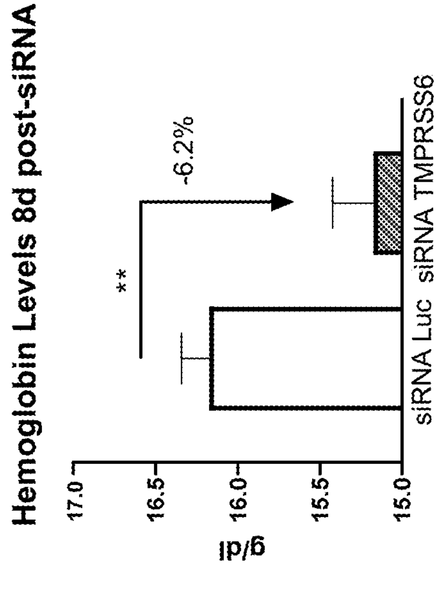
Figure 11F:
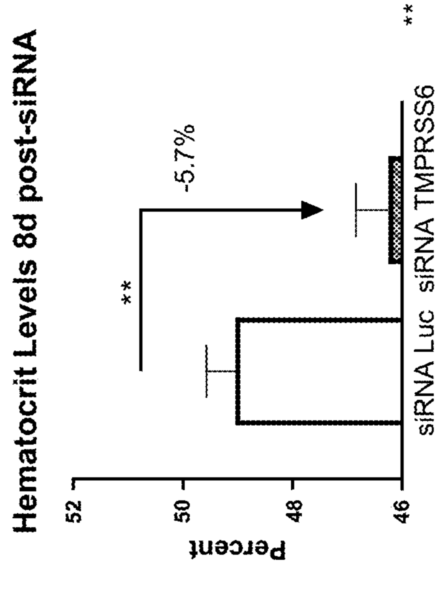

TMPRSS6 expression was reduced by >80% within 24 hours of administration and knockdown was confirmed to persist through 10 days following injection (FIGS. 11A-11B). ** $P<0.0001$ via unpaired two-tail t-test. Eight days after siRNA administration, an 18.5% drop in serum iron, a 6.2% drop in both red blood cell counts and hemoglobin, and a 5.7% drop in hematocrit were observed in mice receiving TMPRSS6 siRNA compared to mice receiving control siRNA (FIGS. 11C-11F).  $P<0.01$ via unpaired two-tail t-test. These changes persisted in the vehicle-treated TMPRSS6 siRNA cohort for the remaining 10 days of the study. At study termination, mice receiving TMPRSS6 siRNA in combination with the compound of Formula I-42 (ALK2 inhibitor) had an increase in hemoglobin levels, hematocrit, and red blood cell counts compared to vehicle-treated mice (FIGS. 11G-11I). Mice receiving TMPRSS6 siRNA in combination with the compound of Formula I-42 also exhibited decreased serum hepcidin and increased serum iron compared to vehicle-treated mice receiving TMPRSS6 siRNA (FIGS. 11J-11K). *$P<0.05$,  $P<0.01$, **$P<0.0001$ via two-way ANOVA. Data are shown as the mean±SEM. These data indicate that treatment with the compound of Formula I-42 rescued the disease phenotype.

Example 4—Treatment of Multiple Osteochondroma by Administration of an ALK2 Inhibitor According to the methods disclosed herein, a physician of skill in the art can treat a subject, such as a human patient, having or at risk of developing MO so as to prevent the formation of an osteochondroma, reduce the formation of an osteochondroma, reduce the size of an osteochondroma, reduce the growth of an osteochondroma, or reduce the number of osteochondromas in the subject. The method of treatment can include diagnosing or identifying a subject as a candidate for treatment based on genetic testing (e.g., for a mutation in an exostosin gene) or imaging (e.g., X-ray). To treat the subject, a physician of skill in the art can administer to the subject a composition containing an ALK2 inhibitor described herein (e.g., a compound of any one of Formulas I-III or any one of Compounds 1-7, BCX9250, or INCB00928, or a pharmaceutically acceptable salt thereof, such as a compound of Formula I-11 or a pharmaceutically acceptable salt thereof). The composition containing the ALK2 inhibitor may be administered to the subject, for example, by oral administration. The ALK2 inhibitor is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 inhibitor is administered bimonthly, once a month, once every two weeks, or at least once a week or more (e.g., 1, 2, 3, 4, 5, 6, or 7 times a week or more). The ALK2 inhibitor is administered in an amount sufficient to prevent the formation of an osteochondroma, reduce the formation of an osteochondroma, reduce the size of an osteochondroma, reduce the growth of an osteochondroma, or reduce the number of osteochondromas in the subject.

Following administration of the composition to a patient, a practitioner of skill in the art can monitor the patient's improvement in response to the therapy by a variety of methods. For example, the practitioner can perform imaging (e.g., an X-ray) to monitor osteochondromas in the subject. A finding that the patient exhibits reduced osteochondroma growth or number or does not exhibit any new osteochondromas following administration of the composition compared to test results prior to administration of the composition indicates that the patient is responding favorably to the treatment. Subsequent doses can be determined and administered as needed.

Example 5—Treatment of Anemia Resulting from Iron Imbalance by Administration of an ALK2 Inhibitor According to the methods disclosed herein, a physician of skill in the art can treat a subject, such as a human patient, having or at risk of developing anemia resulting from iron imbalance so as to increase serum iron, increase transferrin saturation, increase iron bioavailability, increase reticulocyte hemoglobin, promote the formation of hemoglobin-rich red blood cells, reestablish iron homeostasis, and/or reduce serum hepcidin. The method of treatment can include diagnosing or identifying a subject as a candidate for treatment based on a blood test to measure iron bioavailability. To treat the subject, a physician of skill in the art can administer to the subject a composition containing an ALK2 inhibitor (e.g., a compound of any one of Formulas I-III or any one of Compounds 1-7, BCX9250, or INCB00928, or a pharmaceutically acceptable salt thereof, such as a compound of Formula I-11 or a pharmaceutically acceptable salt thereof). The composition containing the ALK2 inhibitor may be administered to the subject, for example, by oral administration. The ALK2 inhibitor is administered in a therapeutically effective amount, such as from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg). In some embodiments, the ALK2 inhibitor is administered bimonthly, once a month, once every two weeks, or at least once a week or more (e.g., 1, 2, 3, 4, 5, 6, or 7 times a week or more). The ALK2 inhibitor is administered in an amount sufficient to increase serum iron, increase transferrin saturation, increase iron bioavailability, increase reticulocyte hemoglobin, promote the formation of hemoglobin-rich red blood cells, reestablish iron homeostasis, and/or reduce serum hepcidin.

Following administration of the composition to a patient, a practitioner of skill in the art can monitor the patient's improvement in response to the therapy by a variety of methods. For example, the practitioner can perform a blood test to measure serum iron, transferrin saturation, iron bioavailability, reticulocyte hemoglobin, hemoglobin-rich red blood cells, iron homeostasis, and/or serum hepcidin. A finding that the patient exhibits increased serum iron, increased transferrin saturation, increased iron bioavailability, increased reticulocyte hemoglobin, an increased number of hemoglobin-rich red blood cells, and/or reduced serum hepcidin following administration of the composition compared to test results prior to administration of the composition indicates that the patient is responding favorably to the treatment. Subsequent doses can be determined and administered as needed.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of treating anemia associated with a myelodysplastic syndrome, anemia associated with β-thalassemia, Diamond Blackfan anemia, aplastic anemia, hemolytic anemia, or sickle cell anemia in a human subject, comprising administering to the subject a therapeutically effective amount of a small molecule ALK2 inhibitor of Formula I (Formula 1)

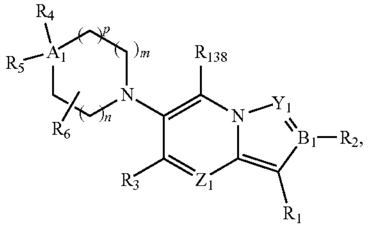

or a pharmaceutically acceptable salt thereof, wherein:

$R_1$ is hydrogen or an optionally substituted substituent;

$R_2$ is optionally absent, hydrogen, or an optionally substituted substituent;

$R_3$ is hydrogen or an optionally substituted substituent;

$R_4$ is optionally absent, hydrogen, or an optionally substituted substituent;

$R_5$ is optionally absent, hydrogen, or an optionally substituted substituent;

$R_{138}$ is hydrogen or an optionally substituted substituent;

$R_6$ is independently one or more of hydrogen or an optionally substituted substituent; $B_1$, is C or N; $Y_1$ is N or $CR_{139}$, wherein $R_{139}$ is hydrogen or an optionally substituted substituent; $Z_1$ is N or $CR_{140}$, wherein $R_{140}$ is hydrogen or an optionally substituted substituent; $A_1$ is C, N, O, C (O), S, SO, or $SO_2$; m is 0, 1, 2, or 3; n is 0, 1, 2, or 3; and p is 0 or 1; wherein optionally any two or more of $R_4$, $R_5$, or $R_6$ may be joined together to form one or more rings.
2. The method of claim 1, wherein the compound of Formula I is the compound of Formula I-11
(I-11)
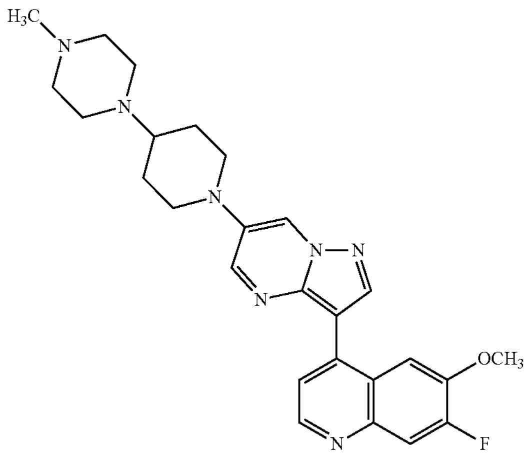
or a pharmaceutically acceptable salt thereof.
* * * * *